United States Patent
Karapetian et al.

(10) Patent No.: US 12,419,746 B2
(45) Date of Patent: Sep. 23, 2025

(54) VALVULAR INSUFFICIENCY REPAIR DEVICE AND METHOD

(71) Applicant: EDWARDS LIFESCIENCES CORPORATION, Irvine, CA (US)

(72) Inventors: Emil Karapetian, Huntington Beach, CA (US); Maria Charles Vija Stanislaus, Irvine, CA (US); Gregory Bak-Boychuk, San Clemente, CA (US); Christopher J. Olson, Lake Forest, CA (US); Cristobal R. Hernandez, Santa Ana, CA (US); William C. Brunnett, Mission Viejo, CA (US); Netanel Benichou, D.n. Hof Hacarmel (IL); Lauren R. Freschauf, Mission Viejo, CA (US); Alexander J. Siegel, Irvine, CA (US); Stanton J. Rowe, Newport Coast, CA (US); Alison S. Curtis, Colden, CO (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 18/172,806

(22) Filed: Feb. 22, 2023

(65) Prior Publication Data
US 2023/0190469 A1   Jun. 22, 2023

Related U.S. Application Data

(60) Division of application No. 16/735,352, filed on Jan. 6, 2020, now Pat. No. 11,589,988, which is a
(Continued)

(51) Int. Cl.
*A61F 2/24* (2006.01)
*A61F 2/07* (2013.01)
(Continued)

(52) U.S. Cl.
CPC ............ *A61F 2/246* (2013.01); *A61F 2/07* (2013.01); *A61F 2/2409* (2013.01);
(Continued)

(58) Field of Classification Search
CPC ............ A61F 2220/0016; A61F 2/2418; A61F 2/2436; A61F 2002/825; A61F 2/2409;
(Continued)

(56) References Cited

U.S. PATENT DOCUMENTS

| 3,409,013 A | 11/1968 | Berry |
| 3,472,230 A | 10/1969 | Fogarty |

(Continued)

FOREIGN PATENT DOCUMENTS

| CN | 1142351 A | 2/1997 |
| CN | 106175845 A | 12/2016 |

(Continued)

OTHER PUBLICATIONS

Al Zaibag et al., "Percutaneous Balloon Valvotomy in Tricuspid Stenosis", British Heart Journal, vol. 57, No. 1, Jan. 1987.
(Continued)

*Primary Examiner* — Katherine M Shi
(74) *Attorney, Agent, or Firm* — Klarquist Sparkman LLP

(57) ABSTRACT

This application relates to methods, systems, and apparatus for replacing native heart valves with prosthetic heart valves and treating valvular insufficiency. In a representative embodiment, a support frame configured to be implanted in a heart valve comprises a main body formed by formed by a plurality of inner members forming an inner clover and a plurality of outer members forming an outer clover. The support frame can include gaps located between inner members of the plurality of inner members and outer members of the plurality of outer members. The inner clover can be radially inside the outer clover, and the outer clover can have
(Continued)

larger dimensions than the inner clover. The support frames herein can be radially expandable and collapsible.

20 Claims, 74 Drawing Sheets

Related U.S. Application Data continuation of application No. 16/181,858, filed on Nov. 6, 2018, now Pat. No. 11,337,810, which is a continuation of application No. 15/482,555, filed on Apr. 7, 2017, now Pat. No. 10,507,106, which is a division of application No. 14/549,431, filed on Nov. 20, 2014, now Pat. No. 9,622,863.

(60) Provisional application No. 61/907,650, filed on Nov. 22, 2013.

(51) Int. Cl.
*A61F 2/88* (2006.01)
*A61F 2/82* (2013.01)
*A61F 2/91* (2013.01)
*A61F 2/958* (2013.01)

(52) U.S. Cl.
CPC .......... *A61F 2/2418* (2013.01); *A61F 2/2427* (2013.01); *A61F 2/2436* (2013.01); *A61F 2/2454* (2013.01); *A61F 2/2466* (2013.01); *A61F 2/88* (2013.01); *A61F 2002/077* (2013.01); *A61F 2002/825* (2013.01); *A61F 2/91* (2013.01); *A61F 2/958* (2013.01); *A61F 2210/0061* (2013.01); *A61F 2220/0016* (2013.01); *A61F 2230/001* (2013.01); *A61F 2230/0065* (2013.01); *A61F 2230/0091* (2013.01); *A61F 2250/0004* (2013.01); *A61F 2250/0063* (2013.01)

(58) Field of Classification Search
CPC ...... A61F 2/2427; A61F 2/243; A61F 2/2433; A61F 2/2439; A61F 2/2466
See application file for complete search history.

(56) References Cited

U.S. PATENT DOCUMENTS

| | | |
|---|---|---|
| 3,548,417 A | 12/1970 | Kisher |
| 3,570,014 A | 3/1971 | Hancock |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,340,091 A | 7/1982 | Skelton et al. |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,491,986 A | 1/1985 | Gabbay |
| 4,501,030 A | 2/1985 | Lane |
| 4,506,669 A | 3/1985 | Blake, III |
| 4,535,483 A | 8/1985 | Klawitter et al. |
| 4,574,803 A | 3/1986 | Storz |
| 4,590,937 A | 5/1986 | Deniega |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,693,248 A | 9/1987 | Failla |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,803,983 A | 2/1989 | Siegel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,125,895 A | 6/1992 | Buchbinder et al. |
| 5,141,494 A | 8/1992 | Danforth et al. |
| 5,152,771 A | 10/1992 | Sabbaghian et al. |
| 5,163,953 A | 11/1992 | Vince |
| 5,167,628 A | 12/1992 | Boyles |
| 5,171,252 A | 12/1992 | Friedland |
| 5,192,297 A | 3/1993 | Hull |
| 5,195,962 A | 3/1993 | Martin et al. |
| 5,232,446 A | 8/1993 | Arney |
| 5,266,073 A | 11/1993 | Wall |
| 5,282,847 A | 2/1994 | Trescony et al. |
| 5,292,326 A | 3/1994 | Green et al. |
| 5,295,958 A | 3/1994 | Shturman |
| 5,327,905 A | 7/1994 | Avitall |
| 5,332,402 A | 7/1994 | Teitelbaum |
| 5,360,444 A | 11/1994 | Kusuhara |
| 5,363,861 A | 11/1994 | Edwards et al. |
| 5,370,685 A | 12/1994 | Stevens |
| 5,389,077 A | 2/1995 | Melinyshyn et al. |
| 5,397,351 A | 3/1995 | Pavcnik et al. |
| 5,411,522 A | 5/1995 | Trott |
| 5,411,552 A | 5/1995 | Andersen et al. |
| 5,443,446 A | 8/1995 | Shturman |
| 5,450,860 A | 9/1995 | O'Connor |
| 5,456,674 A | 10/1995 | Bos et al. |
| 5,474,057 A | 12/1995 | Makower et al. |
| 5,478,353 A | 12/1995 | Yoon |
| 5,480,424 A | 1/1996 | Cox |
| 5,487,746 A | 1/1996 | Yu et al. |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,565,004 A | 10/1996 | Christoudias |
| 5,571,175 A | 11/1996 | Vanney et al. |
| 5,591,195 A | 1/1997 | Taheri et al. |
| 5,599,305 A | 2/1997 | Hermann et al. |
| 5,607,462 A | 3/1997 | Imran |
| 5,607,464 A | 3/1997 | Trescony et al. |
| 5,609,598 A | 3/1997 | Laufer et al. |

(56) References Cited

U.S. PATENT DOCUMENTS

| | | |
|---|---|---|
| 5,609,626 A | 3/1997 | Quijano et al. |
| 5,611,794 A | 3/1997 | Sauer et al. |
| 5,626,607 A | 5/1997 | Malecki et al. |
| 5,639,274 A | 6/1997 | Fischell et al. |
| 5,665,115 A | 9/1997 | Cragg |
| 5,695,504 A | 12/1997 | Gifford, III et al. |
| 5,716,417 A | 2/1998 | Girard et al. |
| 5,727,569 A | 3/1998 | Benetti et al. |
| 5,728,068 A | 3/1998 | Leone et al. |
| 5,741,297 A | 4/1998 | Simon |
| 5,749,890 A | 5/1998 | Shaknovich |
| 5,756,476 A | 5/1998 | Epstein et al. |
| 5,769,812 A | 6/1998 | Stevens et al. |
| 5,782,746 A | 7/1998 | Wright |
| 5,797,960 A | 8/1998 | Stevens et al. |
| 5,800,508 A | 9/1998 | Goicoechea et al. |
| 5,836,311 A | 11/1998 | Borst et al. |
| 5,840,081 A | 11/1998 | Andersen et al. |
| 5,843,076 A | 12/1998 | Webster, Jr. et al. |
| 5,855,597 A | 1/1999 | Jayaraman |
| 5,855,601 A | 1/1999 | Bessler et al. |
| 5,855,602 A | 1/1999 | Angell |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,925,063 A | 7/1999 | Khosravi |
| 5,944,738 A | 8/1999 | Amplatz et al. |
| 5,957,835 A | 9/1999 | Anderson et al. |
| 5,957,949 A | 9/1999 | Leonhardt et al. |
| 5,968,068 A | 10/1999 | Dehdashtian et al. |
| 5,972,020 A | 10/1999 | Carpentier et al. |
| 5,980,534 A | 11/1999 | Gimpelson |
| 5,980,570 A | 11/1999 | Simpson |
| 5,984,959 A | 11/1999 | Robertson et al. |
| 6,004,329 A | 12/1999 | Myers et al. |
| 6,010,531 A | 1/2000 | Donlon et al. |
| 6,017,358 A | 1/2000 | Yoon et al. |
| 6,027,525 A | 2/2000 | Suh et al. |
| 6,042,607 A | 3/2000 | Williamson, IV et al. |
| 6,086,600 A | 7/2000 | Kortenbach |
| 6,120,496 A | 9/2000 | Whayne et al. |
| 6,132,370 A | 10/2000 | Furnish et al. |
| 6,132,473 A | 10/2000 | Williams et al. |
| 6,162,239 A | 12/2000 | Manhes |
| 6,165,183 A | 12/2000 | Kuehn et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,228,032 B1 | 5/2001 | Eaton et al. |
| 6,231,602 B1 | 5/2001 | Carpentier et al. |
| 6,241,743 B1 | 6/2001 | Levin et al. |
| 6,245,040 B1 | 6/2001 | Inderbitzen et al. |
| 6,245,102 B1 | 6/2001 | Jayaraman |
| 6,269,819 B1 | 8/2001 | Oz et al. |
| 6,269,829 B1 | 8/2001 | Chen et al. |
| 6,299,637 B1 | 10/2001 | Shaolian et al. |
| 6,302,906 B1 | 10/2001 | Goicoechea et al. |
| 6,312,447 B1 | 11/2001 | Grimes |
| 6,350,277 B1 | 2/2002 | Kocur |
| 6,379,372 B1 | 4/2002 | Dehdashtian et al. |
| 6,419,696 B1 | 7/2002 | Ortiz et al. |
| 6,425,916 B1 | 7/2002 | Garrison et al. |
| 6,432,134 B1 | 8/2002 | Anson et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,366 B1 | 10/2002 | Seguin |
| 6,461,382 B1 | 10/2002 | Cao |
| 6,468,285 B1 | 10/2002 | Hsu et al. |
| 6,468,660 B2 | 10/2002 | Ogle et al. |
| 6,482,228 B1 | 11/2002 | Norred |
| 6,488,704 B1 | 12/2002 | Connelly et al. |
| 6,508,806 B1 | 1/2003 | Hoste |
| 6,508,825 B1 | 1/2003 | Selmon et al. |
| 6,527,979 B2 | 3/2003 | Constantz et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,569,196 B1 | 5/2003 | Vesely |
| 6,582,462 B1 | 6/2003 | Andersen et al. |
| 6,605,112 B1 | 8/2003 | Moll et al. |
| 6,626,930 B1 | 9/2003 | Allen et al. |
| 6,629,534 B1 | 10/2003 | St. Goar et al. |
| 6,652,578 B2 | 11/2003 | Bailey et al. |
| 6,719,767 B1 | 4/2004 | Kimblad |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,764,510 B2 | 7/2004 | Vidlund et al. |
| 6,767,362 B2 | 7/2004 | Schreck |
| 6,770,083 B2 | 8/2004 | Seguin |
| 6,797,002 B2 | 9/2004 | Spence et al. |
| 6,830,584 B1 | 12/2004 | Seguin |
| 6,837,867 B2 | 1/2005 | Kortelling |
| 6,855,137 B2 | 2/2005 | Bon |
| 6,869,444 B2 | 3/2005 | Gabbay |
| 6,878,162 B2 | 4/2005 | Bales et al. |
| 6,893,460 B2 | 5/2005 | Spenser et al. |
| 6,908,481 B2 | 6/2005 | Cribier |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,018,406 B2 | 3/2006 | Seguin et al. |
| 7,018,408 B2 | 3/2006 | Bailey et al. |
| 7,037,334 B1 | 5/2006 | Hlavka et al. |
| 7,048,754 B2 | 5/2006 | Martin et al. |
| 7,077,861 B2 | 7/2006 | Spence |
| 7,101,395 B2 | 9/2006 | Tremulis et al. |
| 7,125,421 B2 | 10/2006 | Tremulis et al. |
| 7,160,322 B2 | 1/2007 | Gabbay |
| 7,276,078 B2 | 10/2007 | Spenser et al. |
| 7,276,084 B2 | 10/2007 | Yang et al. |
| 7,318,278 B2 | 1/2008 | Zhang et al. |
| 7,371,210 B2 | 5/2008 | Brock et al. |
| 7,374,571 B2 | 5/2008 | Pease et al. |
| 7,381,210 B2 | 6/2008 | Zarbatany et al. |
| 7,393,360 B2 | 7/2008 | Spenser et al. |
| 7,462,191 B2 | 12/2008 | Spenser et al. |
| 7,509,959 B2 | 3/2009 | Oz et al. |
| 7,510,575 B2 | 3/2009 | Spenser et al. |
| 7,527,646 B2 | 5/2009 | Rahdert et al. |
| 7,563,280 B2 | 7/2009 | Anderson et al. |
| 7,569,062 B1 | 8/2009 | Kuehn et al. |
| 7,579,381 B2 | 8/2009 | Dove |
| 7,585,321 B2 | 9/2009 | Cribier |
| 7,618,446 B2 | 11/2009 | Andersen et al. |
| 7,618,449 B2 | 11/2009 | Tremulis et al. |
| 7,621,948 B2 | 11/2009 | Herrmann et al. |
| 7,655,034 B2 | 2/2010 | Mitchell et al. |
| 7,708,775 B2 | 5/2010 | Rowe et al. |
| 7,731,706 B2 | 6/2010 | Potter |
| 7,737,060 B2 | 6/2010 | Strickler et al. |
| 7,748,389 B2 | 7/2010 | Salahieh et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,785,366 B2 | 8/2010 | Maurer et al. |
| 7,803,185 B2 | 9/2010 | Gabbay |
| 7,824,443 B2 | 11/2010 | Salahieh et al. |
| 7,887,580 B2 | 2/2011 | Randall et al. |
| 7,951,195 B2 | 5/2011 | Antonsson et al. |
| 7,959,672 B2 | 6/2011 | Salahieh et al. |
| 7,988,724 B2 | 8/2011 | Salahieh et al. |
| 7,993,394 B2 | 8/2011 | Hariton et al. |

(56) References Cited

U.S. PATENT DOCUMENTS

| | | |
|---|---|---|
| 8,007,992 B2 | 8/2011 | Tian et al. |
| 8,029,556 B2 | 10/2011 | Rowe |
| 8,052,750 B2 | 11/2011 | Tuval et al. |
| 8,096,985 B2 | 1/2012 | Legaspi et al. |
| 8,104,149 B1 | 1/2012 | McGarity |
| 8,105,375 B2 | 1/2012 | Navia et al. |
| 8,147,542 B2 | 4/2012 | Maisano et al. |
| 8,167,932 B2 | 5/2012 | Bourang et al. |
| 8,172,856 B2 | 5/2012 | Eigler et al. |
| 8,206,437 B2 | 6/2012 | Bonhoeffer et al. |
| 8,313,525 B2 | 11/2012 | Tuval et al. |
| 8,323,335 B2 | 12/2012 | Rowe et al. |
| 8,348,963 B2 | 1/2013 | Wilson |
| 8,377,115 B2 | 2/2013 | Thompson |
| 8,398,704 B2 | 3/2013 | Straubinger et al. |
| 8,398,708 B2 | 3/2013 | Meiri et al. |
| 8,425,404 B2 | 4/2013 | Wilson et al. |
| 8,449,599 B2 | 5/2013 | Chau et al. |
| 8,449,605 B2 | 5/2013 | Lichtenstein et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,540,767 B2 | 9/2013 | Zhang |
| 8,652,202 B2 | 2/2014 | Alon et al. |
| 8,657,872 B2 | 2/2014 | Seguin |
| 8,663,322 B2 | 3/2014 | Keranen |
| 8,668,733 B2 | 3/2014 | Haug et al. |
| 8,672,998 B2 | 3/2014 | Lichtenstein et al. |
| 8,734,507 B2 | 5/2014 | Keranen |
| 8,747,463 B2 | 6/2014 | Fogarty et al. |
| 8,771,347 B2 | 7/2014 | DeBoer et al. |
| 8,778,017 B2 | 7/2014 | Eliasen et al. |
| 8,834,564 B2 | 9/2014 | Tuval et al. |
| 8,840,663 B2 | 9/2014 | Salahieh et al. |
| 8,945,177 B2 | 2/2015 | Dell et al. |
| 9,034,032 B2 | 5/2015 | McLean et al. |
| 9,078,747 B2 | 7/2015 | Conklin |
| 9,095,434 B2 | 8/2015 | Rowe |
| 9,119,718 B2 | 9/2015 | Keranen |
| 9,198,757 B2 | 12/2015 | Schroeder et al. |
| 9,220,507 B1 | 12/2015 | Patel et al. |
| 9,237,886 B2 | 1/2016 | Seguin et al. |
| 9,259,317 B2 | 2/2016 | Wilson et al. |
| 9,282,972 B1 | 3/2016 | Patel et al. |
| 9,308,360 B2 | 4/2016 | Bishop et al. |
| 9,364,326 B2 | 6/2016 | Yaron |
| 9,387,071 B2 | 7/2016 | Tuval et al. |
| 9,427,327 B2 | 8/2016 | Parrish |
| 9,439,763 B2 | 9/2016 | Geist et al. |
| 9,463,268 B2 | 10/2016 | Spence |
| 9,474,599 B2 | 10/2016 | Keranen |
| 9,510,946 B2 | 12/2016 | Chau et al. |
| 9,572,660 B2 | 2/2017 | Braido et al. |
| 9,597,205 B2 | 3/2017 | Tuval |
| 9,622,863 B2 | 4/2017 | Karapetian et al. |
| 9,700,445 B2 | 7/2017 | Martin et al. |
| 9,775,963 B2 | 10/2017 | Miller |
| D809,139 S | 1/2018 | Marsot et al. |
| 10,076,327 B2 | 9/2018 | Ellis et al. |
| 10,076,415 B1 | 9/2018 | Metchik et al. |
| 10,099,050 B2 | 10/2018 | Chen et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 10,575,841 B1 | 3/2020 | Paulos |
| 2001/0005787 A1 | 6/2001 | Oz et al. |
| 2001/0021872 A1 | 9/2001 | Bailey et al. |
| 2002/0013571 A1 | 1/2002 | Goldfarb et al. |
| 2002/0032481 A1 | 3/2002 | Gabbay |
| 2002/0107531 A1 | 8/2002 | Schreck et al. |
| 2002/0107535 A1 | 8/2002 | Wei et al. |
| 2002/0173811 A1 | 11/2002 | Tu et al. |
| 2002/0173842 A1 | 11/2002 | Buchanan |
| 2002/0183787 A1 | 12/2002 | Wahr et al. |
| 2003/0050694 A1 | 3/2003 | Yang et al. |
| 2003/0074628 A1 | 4/2003 | Lee |
| 2003/0100939 A1 | 5/2003 | Yodfat et al. |
| 2003/0144573 A1 | 7/2003 | Heilman et al. |
| 2003/0158597 A1 | 8/2003 | Quiachon et al. |
| 2003/0187467 A1 | 10/2003 | Schreck |
| 2003/0208231 A1 | 11/2003 | Williamson et al. |
| 2003/0212454 A1 | 11/2003 | Scott et al. |
| 2003/0225420 A1 | 12/2003 | Wardle |
| 2004/0003819 A1 | 1/2004 | St. Goar et al. |
| 2004/0030382 A1 | 2/2004 | St. Goar et al. |
| 2004/0034365 A1 | 2/2004 | Lentz et al. |
| 2004/0039436 A1 | 2/2004 | Spenser et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0111006 A1 | 6/2004 | Alferness et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0133263 A1 | 7/2004 | Dusbabek et al. |
| 2004/0147943 A1 | 7/2004 | Kobayashi |
| 2004/0181135 A1 | 9/2004 | Drysen |
| 2004/0181206 A1 | 9/2004 | Chiu et al. |
| 2004/0181238 A1 | 9/2004 | Zarbatany et al. |
| 2004/0186563 A1 | 9/2004 | Lobbi |
| 2004/0186565 A1 | 9/2004 | Schreck |
| 2004/0210307 A1 | 10/2004 | Khairkhahan |
| 2004/0220593 A1 | 11/2004 | Greenhalgh |
| 2004/0260389 A1 | 12/2004 | Case et al. |
| 2005/0010287 A1 | 1/2005 | Macoviak et al. |
| 2005/0049618 A1 | 3/2005 | Masuda et al. |
| 2005/0070926 A1 | 3/2005 | Ortiz |
| 2005/0096736 A1 | 5/2005 | Osse et al. |
| 2005/0096739 A1 | 5/2005 | Cao |
| 2005/0119682 A1 | 6/2005 | Nguyen et al. |
| 2005/0119735 A1 | 6/2005 | Spence et al. |
| 2005/0137690 A1 | 6/2005 | Salahieh et al. |
| 2005/0137691 A1 | 6/2005 | Salahieh et al. |
| 2005/0143767 A1 | 6/2005 | Kimura et al. |
| 2005/0149160 A1 | 7/2005 | McFerran |
| 2005/0165429 A1 | 7/2005 | Douglas et al. |
| 2005/0182486 A1 | 8/2005 | Gabbay |
| 2005/0203614 A1 | 9/2005 | Forster et al. |
| 2005/0203617 A1 | 9/2005 | Forster et al. |
| 2005/0216039 A1 | 9/2005 | Lederman |
| 2005/0234546 A1 | 10/2005 | Nugent et al. |
| 2005/0251177 A1 | 11/2005 | Saadat et al. |
| 2005/0251183 A1 | 11/2005 | Buckman et al. |
| 2005/0288766 A1 | 12/2005 | Plain et al. |
| 2005/0288786 A1 | 12/2005 | Chanduszko |
| 2006/0020275 A1 | 1/2006 | Goldfarb et al. |
| 2006/0025857 A1 | 2/2006 | Bergheim et al. |
| 2006/0058872 A1 | 3/2006 | Salahieh et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0142837 A1 | 6/2006 | Haverkost et al. |
| 2006/0149350 A1 | 7/2006 | Patel et al. |
| 2006/0173251 A1 | 8/2006 | Govari et al. |
| 2006/0178700 A1 | 8/2006 | Quinn |
| 2006/0224169 A1 | 10/2006 | Weisenburgh et al. |
| 2006/0229719 A1 | 10/2006 | Marquez et al. |
| 2006/0259135 A1 | 11/2006 | Navia et al. |
| 2006/0259137 A1 | 11/2006 | Artof et al. |
| 2007/0005131 A1 | 1/2007 | Taylor |
| 2007/0010800 A1 | 1/2007 | Weitzner et al. |

(56) References Cited

U.S. PATENT DOCUMENTS

| | | |
|---|---|---|
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0027534 A1 | 2/2007 | Bergheim et al. |
| 2007/0032807 A1 | 2/2007 | Ortiz et al. |
| 2007/0088431 A1 | 4/2007 | Bourang et al. |
| 2007/0093857 A1 | 4/2007 | Rogers et al. |
| 2007/0093890 A1 | 4/2007 | Eliasen et al. |
| 2007/0112422 A1 | 5/2007 | Dehdashtian |
| 2007/0156197 A1 | 7/2007 | Root et al. |
| 2007/0156224 A1 | 7/2007 | Cioanta et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0203503 A1 | 8/2007 | Salahieh et al. |
| 2007/0203575 A1 | 8/2007 | Forster et al. |
| 2007/0260305 A1 | 11/2007 | Drews et al. |
| 2007/0265700 A1 | 11/2007 | Eliasen et al. |
| 2007/0270943 A1 | 11/2007 | Solem et al. |
| 2007/0282414 A1 | 12/2007 | Soltis et al. |
| 2007/0293808 A1 | 12/2007 | Williams et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0033542 A1 | 2/2008 | Antonsson et al. |
| 2008/0039743 A1 | 2/2008 | Fox et al. |
| 2008/0039953 A1 | 2/2008 | Davis et al. |
| 2008/0065011 A1 | 3/2008 | Marchand et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0114442 A1 | 5/2008 | Mitchell et al. |
| 2008/0125853 A1 | 5/2008 | Bailey et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0154355 A1 | 6/2008 | Benichou et al. |
| 2008/0161911 A1 | 7/2008 | Revuelta et al. |
| 2008/0167713 A1 | 7/2008 | Bolling |
| 2008/0177300 A1 | 7/2008 | Mas et al. |
| 2008/0208330 A1 | 8/2008 | Keranen |
| 2008/0208332 A1 | 8/2008 | Lamphere et al. |
| 2008/0215144 A1 | 9/2008 | Ryan et al. |
| 2008/0221672 A1 | 9/2008 | Lamphere et al. |
| 2008/0255427 A1 | 10/2008 | Satake et al. |
| 2008/0255661 A1 | 10/2008 | Straubinger et al. |
| 2008/0281411 A1 | 11/2008 | Berreklouw |
| 2008/0287862 A1 | 11/2008 | Weitzner et al. |
| 2008/0294230 A1 | 11/2008 | Parker |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0157175 A1 | 6/2009 | Benichou |
| 2009/0163934 A1 | 6/2009 | Raschdorf, Jr. et al. |
| 2009/0164005 A1 | 6/2009 | Dove et al. |
| 2009/0166913 A1 | 7/2009 | Guo et al. |
| 2009/0171456 A1 | 7/2009 | Kveen et al. |
| 2009/0177266 A1 | 7/2009 | Powell et al. |
| 2009/0234280 A1 | 9/2009 | Tah et al. |
| 2009/0275902 A1 | 11/2009 | Heeps et al. |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0287304 A1 | 11/2009 | Dahlgren et al. |
| 2009/0319037 A1 | 12/2009 | Rowe et al. |
| 2010/0022823 A1 | 1/2010 | Goldfarb et al. |
| 2010/0049313 A1 | 2/2010 | Alon et al. |
| 2010/0057192 A1 | 3/2010 | Celermajer |
| 2010/0069834 A1 | 3/2010 | Schultz |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0145440 A1 | 6/2010 | Keranen |
| 2010/0198347 A1 | 8/2010 | Zakay et al. |
| 2010/0204781 A1 | 8/2010 | Alkhatib |
| 2010/0249497 A1 | 9/2010 | Peine et al. |
| 2010/0249915 A1* | 9/2010 | Zhang ................ A61F 2/2436 |
| | | 623/2.37 |
| 2010/0262233 A1 | 10/2010 | He |
| 2010/0298929 A1 | 11/2010 | Thornton et al. |
| 2010/0312333 A1 | 12/2010 | Navia et al. |
| 2010/0318184 A1 | 12/2010 | Spence |
| 2010/0324595 A1 | 12/2010 | Linder et al. |
| 2011/0015729 A1 | 1/2011 | Jimenez et al. |
| 2011/0082538 A1 | 4/2011 | Dahlgren et al. |
| 2011/0098802 A1 | 4/2011 | Braido et al. |
| 2011/0137397 A1* | 6/2011 | Chau ................ A61F 2/2412 |
| | | 623/2.37 |
| 2011/0137410 A1 | 6/2011 | Hacohen |
| 2011/0208297 A1 | 8/2011 | Tuval et al. |
| 2011/0245855 A1 | 10/2011 | Matsuoka et al. |
| 2011/0257723 A1 | 10/2011 | McNamara |
| 2011/0264206 A1 | 10/2011 | Tabor |
| 2011/0295281 A1 | 12/2011 | Mizumoto et al. |
| 2011/0295363 A1 | 12/2011 | Girard et al. |
| 2012/0022633 A1* | 1/2012 | Olson ................ A61F 2/2433 |
| | | 623/2.11 |
| 2012/0059458 A1 | 3/2012 | Buchbinder et al. |
| 2012/0089125 A1 | 4/2012 | Scheibe et al. |
| 2012/0101567 A1* | 4/2012 | Jansen ................ A61F 2/2412 |
| | | 623/1.36 |
| 2012/0109160 A1 | 5/2012 | Martinez et al. |
| 2012/0116419 A1 | 5/2012 | Sigmon, Jr. |
| 2012/0123529 A1 | 5/2012 | Levi et al. |
| 2012/0209318 A1 | 8/2012 | Qadeer |
| 2012/0277853 A1 | 11/2012 | Rothstein |
| 2012/0283820 A1 | 11/2012 | Tseng et al. |
| 2013/0023985 A1 | 1/2013 | Khairkhahan et al. |
| 2013/0035759 A1 | 2/2013 | Gross et al. |
| 2013/0041314 A1 | 2/2013 | Dillon |
| 2013/0046373 A1 | 2/2013 | Cartledge et al. |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0190798 A1 | 7/2013 | Kapadia |
| 2013/0190861 A1 | 7/2013 | Chau et al. |
| 2013/0204359 A1 | 8/2013 | Thubrikar et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0317598 A1 | 11/2013 | Rowe et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0074299 A1 | 3/2014 | Endou et al. |
| 2014/0081394 A1 | 3/2014 | Keranen et al. |
| 2014/0094903 A1 | 4/2014 | Miller et al. |
| 2014/0135685 A1 | 5/2014 | Kabe et al. |
| 2014/0172070 A1 | 6/2014 | Seguin |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |

(56) References Cited

U.S. PATENT DOCUMENTS

| | | |
|---|---|---|
| 2014/0358222 A1 | 12/2014 | Gorman, III et al. |
| 2014/0371843 A1 | 12/2014 | Wilson et al. |
| 2014/0379074 A1 | 12/2014 | Spence et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0230921 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0282931 A1 | 10/2015 | Brunnett et al. |
| 2015/0313592 A1 | 11/2015 | Coillard-Lavirotte et al. |
| 2015/0335428 A1 | 11/2015 | Keranen |
| 2015/0335430 A1 | 11/2015 | Loulmet et al. |
| 2015/0351904 A1 | 12/2015 | Cooper et al. |
| 2015/0366666 A1 | 12/2015 | Khairkhahan et al. |
| 2015/0374493 A1 | 12/2015 | Yaron et al. |
| 2016/0008129 A1 | 1/2016 | Siegel |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0067038 A1* | 3/2016 | Park ............... A61F 2/2412 623/2.18 |
| 2016/0074164 A1 | 3/2016 | Naor |
| 2016/0074165 A1 | 3/2016 | Spence et al. |
| 2016/0095705 A1 | 4/2016 | Keranen et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0184095 A1 | 6/2016 | Spence et al. |
| 2016/0199177 A1 | 7/2016 | Spence et al. |
| 2016/0242906 A1 | 8/2016 | Morriss et al. |
| 2016/0256276 A1 | 9/2016 | Yaron |
| 2016/0287387 A1 | 10/2016 | Wei |
| 2016/0302811 A1 | 10/2016 | Rodriguez-Navarro et al. |
| 2016/0317290 A1 | 11/2016 | Chau et al. |
| 2016/0331523 A1 | 11/2016 | Chau et al. |
| 2016/0354082 A1 | 12/2016 | Oz et al. |
| 2017/0007399 A1 | 1/2017 | Keranen |
| 2017/0007402 A1 | 1/2017 | Zerkowski et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100119 A1 | 4/2017 | Baird et al. |
| 2017/0100236 A1 | 4/2017 | Robertson et al. |
| 2017/0217385 A1 | 8/2017 | Rinkleff et al. |
| 2017/0224955 A1 | 8/2017 | Douglas et al. |
| 2017/0239048 A1 | 8/2017 | Goldfarb et al. |
| 2017/0252154 A1 | 9/2017 | Tubishevitz et al. |
| 2017/0266413 A1 | 9/2017 | Khuu et al. |
| 2017/0273788 A1 | 9/2017 | O'Carroll et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |
| 2018/0078361 A1 | 3/2018 | Naor et al. |
| 2018/0092661 A1 | 4/2018 | Prabhu |
| 2018/0126124 A1 | 5/2018 | Winston et al. |
| 2018/0133008 A1 | 5/2018 | Kizuka et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0185154 A1 | 7/2018 | Cao |
| 2018/0206074 A1 | 7/2018 | Tanasa et al. |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0117113 A1 | 4/2019 | Curran |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0192296 A1 | 6/2019 | Schwartz et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0314155 A1 | 10/2019 | Franklin et al. |
| 2019/0321166 A1 | 10/2019 | Freschauf et al. |
| 2020/0113683 A1 | 4/2020 | Dale et al. |
| 2020/0138569 A1 | 5/2020 | Basude et al. |
| 2020/0205979 A1 | 7/2020 | O'Carroll et al. |
| 2020/0237512 A1 | 7/2020 | McCann et al. |
| 2020/0337842 A1 | 10/2020 | Metchik et al. |
| 2020/0352717 A1 | 11/2020 | Kheradvar et al. |
| 2020/0360054 A1 | 11/2020 | Walsh et al. |
| 2020/0360132 A1 | 11/2020 | Spence |
| 2020/0368016 A1 | 11/2020 | Pesce et al. |
| 2021/0022850 A1 | 1/2021 | Basude et al. |
| 2021/0059680 A1 | 3/2021 | Lin et al. |
| 2021/0169650 A1 | 6/2021 | Dai et al. |
| 2021/0186698 A1 | 6/2021 | Abunassar et al. |
| 2021/0251757 A1 | 8/2021 | Siegel et al. |
| 2021/0259835 A1 | 8/2021 | Tyler, II et al. |
| 2021/0267781 A1 | 9/2021 | Metchik et al. |
| 2021/0307900 A1 | 10/2021 | Hacohen |
| 2021/0330456 A1 | 10/2021 | Hacohen et al. |
| 2021/0338418 A1 | 11/2021 | Feld |
| 2021/0361238 A1 | 11/2021 | Bak-Boychuk et al. |
| 2021/0361416 A1 | 11/2021 | Stearns |

(56) References Cited

U.S. PATENT DOCUMENTS

| | | |
|---|---|---|
| 2021/0361428 A1 | 11/2021 | Dixon |
| 2021/0378818 A1 | 12/2021 | Manash et al. |
| 2021/0401434 A1 | 12/2021 | Tien et al. |
| 2022/0039943 A1 | 2/2022 | Phan |
| 2022/0039954 A1 | 2/2022 | Nia et al. |
| 2022/0071767 A1 | 3/2022 | Dixon et al. |
| 2022/0133327 A1 | 5/2022 | Zhang et al. |
| 2022/0142780 A1 | 5/2022 | Zhang et al. |
| 2022/0142781 A1 | 5/2022 | Zhang et al. |
| 2022/0226108 A1 | 7/2022 | Freschauf et al. |
| 2022/0233312 A1 | 7/2022 | Delgado et al. |
| 2022/0257196 A1 | 8/2022 | Massmann |
| 2022/0287841 A1 | 9/2022 | Freschauf et al. |
| 2022/0296248 A1 | 9/2022 | Abunassar et al. |
| 2022/0313433 A1 | 10/2022 | Ma et al. |
| 2023/0014540 A1 | 1/2023 | Metchik et al. |
| 2023/0149170 A1 | 5/2023 | Giese et al. |
| 2023/0218291 A1 | 7/2023 | Zarbatany et al. |
| 2023/0270549 A1 | 8/2023 | Guidotti et al. |

FOREIGN PATENT DOCUMENTS

| | | | |
|---|---|---|---|
| CN | 106491245 A | 3/2017 | |
| CN | 107789017 A | 3/2018 | |
| CN | 109953779 A | 7/2019 | |
| CN | 110338857 A | 10/2019 | |
| CN | 110495972 A | 11/2019 | |
| CN | 110537946 A | 12/2019 | |
| CN | 110664515 A | 1/2020 | |
| CN | 209996540 U | 1/2020 | |
| CN | 211243911 U | 8/2020 | |
| CN | 211723546 U | 10/2020 | |
| CN | 111870398 A | 11/2020 | |
| CN | 111904660 A | 11/2020 | |
| CN | 112120831 A | 12/2020 | |
| CN | 112168427 A | 1/2021 | |
| CN | 112190367 A | 1/2021 | |
| CN | 212346813 U | 1/2021 | |
| CN | 212415988 U | 1/2021 | |
| CN | 212490263 U | 2/2021 | |
| CN | 113476182 A | 10/2021 | |
| CN | 113855328 A | 12/2021 | |
| CN | 215019733 U | 12/2021 | |
| DE | 19532846 A1 | 3/1997 | |
| DE | 19907646 A1 | 8/2000 | |
| DE | 10049813 C1 | 4/2002 | |
| DE | 19546692 C2 | 11/2002 | |
| DE | 10049812 B4 | 6/2004 | |
| DE | 19857887 B4 | 5/2005 | |
| DE | 10049815 B4 | 10/2005 | |
| DE | 10049814 B4 | 10/2006 | |
| DE | 20 2007 005491 U1 | 6/2007 | |
| EP | 0098100 A2 | 1/1984 | |
| EP | 0103546 A1 | 3/1984 | |
| EP | 0144167 A2 | 6/1985 | |
| EP | 0592410 A1 | 4/1994 | |
| EP | 0597967 A1 | 5/1994 | |
| EP | 0850607 A1 | 7/1998 | |
| EP | 1057460 A1 | 12/2000 | |
| EP | 1088529 A2 | 4/2001 | |
| EP | 1432369 A1 | 6/2004 | |
| EP | 1570809 A1 | 9/2005 | |
| EP | 1296618 B1 | 1/2008 | |
| EP | 1827314 B1 | 12/2010 | |
| EP | 2620125 A1 | 7/2013 | |
| EP | 2726018 A2 | 5/2014 | |
| EP | 2806829 A2 | 12/2014 | |
| FR | 2146050 A5 | 2/1973 | |
| FR | 9711600 | 3/1997 | |
| FR | 2788217 A1 | 7/2000 | |
| FR | 2815844 B1 | 1/2003 | |
| GB | 2056023 B | 8/1983 | |
| SU | 1271508 A1 | 11/1986 | |
| WO | 9117720 A1 | 11/1991 | |
| WO | 9217118 A1 | 10/1992 | |
| WO | 9640008 A1 | 12/1996 | |
| WO | 9724080 A1 | 7/1997 | |
| WO | 9829057 A1 | 7/1998 | |
| WO | 9930646 A1 | 6/1999 | |
| WO | 9933414 A1 | 7/1999 | |
| WO | 9940964 A1 | 8/1999 | |
| WO | 9947075 A1 | 9/1999 | |
| WO | 0018333 A1 | 4/2000 | |
| WO | 0041652 A1 | 7/2000 | |
| WO | 0042950 A2 | 7/2000 | |
| WO | 0047139 A1 | 8/2000 | |
| WO | 0128459 A1 | 4/2001 | |
| WO | 0135878 A2 | 5/2001 | |
| WO | 0149213 A2 | 7/2001 | |
| WO | 0154624 A1 | 8/2001 | |
| WO | 0154625 A1 | 8/2001 | |
| WO | 0162189 A1 | 8/2001 | |
| WO | 0164137 A1 | 9/2001 | |
| WO | 0176510 A2 | 10/2001 | |
| WO | 0222054 A1 | 3/2002 | |
| WO | 0236048 A1 | 5/2002 | |
| WO | 0241789 A2 | 5/2002 | |
| WO | 0243620 A1 | 6/2002 | |
| WO | 0247575 A2 | 6/2002 | |
| WO | 0249540 A2 | 6/2002 | |
| WO | 03028558 A2 | 4/2003 | |
| WO | 03047468 A1 | 6/2003 | |
| WO | 2005034812 A1 | 4/2005 | |
| WO | 2005084595 A1 | 9/2005 | |
| WO | 2005087140 A1 | 9/2005 | |
| WO | 2005102015 A2 | 11/2005 | |
| WO | 2006011127 A2 | 2/2006 | |
| WO | 2006014233 A2 | 2/2006 | |
| WO | 2006034008 A2 | 3/2006 | |
| WO | 2006108090 A2 | 10/2006 | |
| WO | 2006111391 A1 | 10/2006 | |
| WO | 2006113906 A1 | 10/2006 | |
| WO | 2007047488 A2 | 4/2007 | |
| WO | 2007067942 A1 | 6/2007 | |
| WO | 2008005405 A2 | 1/2008 | |
| WO | 2008091515 A2 | 7/2008 | |
| WO | WO-2008100600 A1 * | 8/2008 | ........... A61F 2/2409 |
| WO | 2009033469 A1 | 3/2009 | |
| WO | 2009155561 A2 | 12/2009 | |
| WO | 2010112076 A1 | 10/2010 | |
| WO | 2010121076 A2 | 10/2010 | |
| WO | 2013037519 A1 | 3/2013 | |
| WO | 2013110722 A2 | 8/2013 | |
| WO | 2013114214 A2 | 8/2013 | |
| WO | 2014064694 A2 | 5/2014 | |
| WO | 2015023579 A1 | 2/2015 | |
| WO | 2015023862 A2 | 2/2015 | |
| WO | 2015198125 A1 | 12/2015 | |
| WO | 2016038017 A1 | 3/2016 | |
| WO | 2016040881 A1 | 3/2016 | |
| WO | 2016130820 A1 | 8/2016 | |
| WO | 2017015632 A1 | 1/2017 | |
| WO | 2018013856 A1 | 1/2018 | |
| WO | 2018050200 A1 | 3/2018 | |
| WO | 2018050203 A1 | 3/2018 | |
| WO | 2020168081 A1 | 8/2020 | |
| WO | 2021196580 A1 | 10/2021 | |
| WO | 2021227412 A1 | 11/2021 | |
| WO | 2022006087 A2 | 1/2022 | |
| WO | 2022036209 A1 | 2/2022 | |
| WO | 2022051241 A1 | 3/2022 | |
| WO | 2022052506 A1 | 3/2022 | |
| WO | 2022068188 A1 | 4/2022 | |
| WO | 2022101817 A1 | 5/2022 | |
| WO | 2022140175 A1 | 6/2022 | |
| WO | 2022153131 A1 | 7/2022 | |
| WO | 2022155298 A2 | 7/2022 | |
| WO | 2022157592 A1 | 7/2022 | |
| WO | 2022212172 A1 | 10/2022 | |
| WO | 2023003755 A1 | 1/2023 | |
| WO | 2023004098 A1 | 1/2023 | |

(56) References Cited

FOREIGN PATENT DOCUMENTS

| WO | 2023278663 A2 | 1/2023 |
|---|---|---|
| WO | 2023288003 A1 | 1/2023 |

OTHER PUBLICATIONS

Al-Khaja et al., "Eleven Years' Experience with Carpentier-Edwards Biological Valves in Relation to Survival and Complications", European Journal of Cardio-thoracic Surgery 3: pp. 305-311, 1989.

Almagor et al., "Balloon Expandable Stent Implantation in Stenotic Right Heart Valved Conduits", Journal of the American College of Cardiology, vol. 16, No. 6, pp. 1310-1314, Nov. 15, 1990.

Andersen, et al., "Transluminal implantation of artificial heart valves. Description of a new expandable aortic valve and initial results with implantation by catheter technique in closed chest pigs", European Heart Journal, vol. 13, No. 5, pp. 704-708, May 1, 1992, The European Society of Cardiology, Oxford University Press, United Kingdom.

Andersen, H.R. "History of Percutaneous Aortic Valve Prosthesis," Herz, vol. 34., No. 5, pp. 343-346, Aug. 2009, Urban & Vogel, Germany.

Batista RJ et al., "Partial left ventriculectomy to treat end-stage heart disease", Ann Thorac Surg., vol. 64, Issue-3, pp. 634-638, Sep. 1997.

Beall AC Jr. et al.,"Clinical experience with a dacron velour-covered teflon-disc mitral-valve prosthesis", Ann Thorac Surg., vol. 5, Issue 5, pp. 402-410, May 1968.

Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, No. 30, pp. 654-670, Nov. 1, 1964, Lippincott Williams & Wilkins, Philadelphia, PA.

Fucci et al., "Improved results with mitral valve repair using new surgical techniques", Eur J Cardiothorac Surg. 1995;Issue 9, vol. 11, pp. 621-626.

Grasso et al., "The Pascal transcatheter mitral valve repair system for the treatment of mitral regurgitation: another piece to the puzzle of edge-to-edge technique", Journal of Thoracic Disease, vol. 9, No. 12, pp. 4856-4859, Dec. 2017, doi: 10.21037/jtd.2017.10.156, AME Publishing Company, Hong Kong, China.

Henning Rud Andersen, "History of Percutaneous Aortic Valve Prosthesis", Herz 34, Urban and Vogel, pp. 343-346, 2009.

Inoue et al., "Clinical Application of Transvenous Mitral Commissurotomy by a New Balloon Catheter", The Journal of Thoracic and Cardiovascular Surgery, vol. 87, No. 3, pp. 394-402, 1984.

Kolata, Gina "Device That Opens Clogged Arteries Gets a Failing Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faili . . . .

Lawrence, Jr., et al., "Percutaneous Endovascular Graft: Experimental Evaluation", Cardiovascular Radiology 163, pp. 357-360, May 1987.

Maisano F et al., 'The edge-to-edge technique: a simplified method to correct mitral insufficiency', Eur J Cardiothorac Surg., vol. 13, Issue-3, pp. 240-245, Mar. 1998.

Pavcnik et al., "Development and Initial Experimental Evaluation of a Prosthetic Aortic Valve for a Transcatheter Placement: Work in Progress", Cardiovascular Radiology; 183, pp. 151-154, Apr. 1992.

Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.

Praz et al., "Compassionate use of the Pascal transcatheter mitral valve repair system for patients with severe mitral regurgitation: a multicentre, prospective, observational, first-in-man study," The Lancet, vol. 390, Issue 10096, pp. 773-780, Aug. 19, 2017, Lancet, United States.

Rashkind et al., "Creation of an Atrial Septal Defect Without Thoracotomy: A Pallative Approach to Complete Transposition of the Great Arteries", The Journal of the American Medical Association, vol. 196, No. 11, pp. 173-174, Jun. 13, 1956.

Rashkind et al., "Historical Aspects of Interventional Cardiology: Past, Present, and Future", Texas Heart Institute Journal, Interventional Cardiology, vol. 13, No. 4, pp. 363-367, Dec. 1986.

Reul RM et al., "Mitral valve reconstruction for mitral insufficiency", Prog Cardiovasc Dis., vol. 39, Issue-6, May-Jun. 1997.

Ross, D.N, "Aortic Valve Surgery", Surgery of the Aortic Valves, Guy's Hospital, London, pp. 192-197.

Rösch et al., "The Birth, Early Years and Future of Interventional Radiology," Journal of Vascular and Interventional Radiology, vol. 14, No. 7, pp. 841-853, Jul. 1, 2003, Elsevier, United States.

Rösch et al., "The Birth, Early Years, and Future of Interventional Radiology", JVIR, vol. 14, No. 7, pp. 841-853, Jul. 2003.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology, vol. 176, No. 2, pp. 535-538, Jul. 31, 1990, Radiological Society of North America, Oak Brook, IL.

Selby et al., "Experience with New Retrieval Forceps for Foreign Body Removal in the Vascular, Urinary, and Biliary Systems", Radiology: 176. pp. 535-538, 1990.

Serruys et al., "Stenting of Coronary Arteries. Are we the Sorcerer's Apprentice?", European Heart Journal, 10, 774-782, pp. 37-45, 1989.

Serruys et al., "Stenting of coronary arteries. Are we the sorcerer's apprentice?", European Heart Journal, vol. 10, No. 9 pp. 774-782, Sep. 1, 1989, The European Society of Cardiology, Oxford University Press, United Kingdom.

Sigwart, Ulrich, "An Overview of Intravascular Stents: Old and New," Textbook of Interventional Cardiology, Second Edition, chapter 48, pp. 803-815, © 1994, W.B. Saunders Company, Philadelphia, PA.

Uchida et al., "Modifications of Gianturco Expandable Wire Stents", Technical Note, American Roentgen Ray Society, pp. 1185-1187, May 1988.

Ulrich Sigwart, "An Overview of Intravascular Stents: Old and New", Textbook of Interventional Cardiology, Secon Edition, pp. 803-815, 1990.

Umaña JP et al., Bow-tie' mitral valve repair: an adjuvant technique for ischemic mitral regurgitation', Ann Thorac Surg., vol. 66, Issue-6, pp. 1640-1646, Nov. 1998.

Urban, Philip MD, "Coronary Artery Stenting", pp. 5-47, © 1991, ISBN: 2-88049-054-5, Editions Medecine et Hygiene, Geneva, Switzerland.

Watt et al., "Intravenous adenosine in the treatment of supraventricular rachycardia: a dose-ranging study and interaction with dipyridamole", British Journal of Clinical Pharmacology, vol. 21, No. 2, pp. 227-230, Feb. 1986, British Pharmacological Society, London, United Kingdom.

Watt et al., "Intravenous Adenosine in the Treatment of Supraventricular Tachycardia: A Dose-Ranging Study and Interaction with Dipyridamole", Br. J. Clin. Pharmac. 21, pp. 227-230, 1986.

Wheatley, David J., "Valve Prosthesis", Rob & Smith's Operative Surgery, pp. 415-424, 1986.

Wheatley, David J., "Valve Prosthesis", Rob & Smith's Operative Surgery—Cardiac Surgery, vol. 91, No. 2, pp. 415-424, Feb. 1, 1987, Butterworth Scientific, London, UK.

* cited by examiner

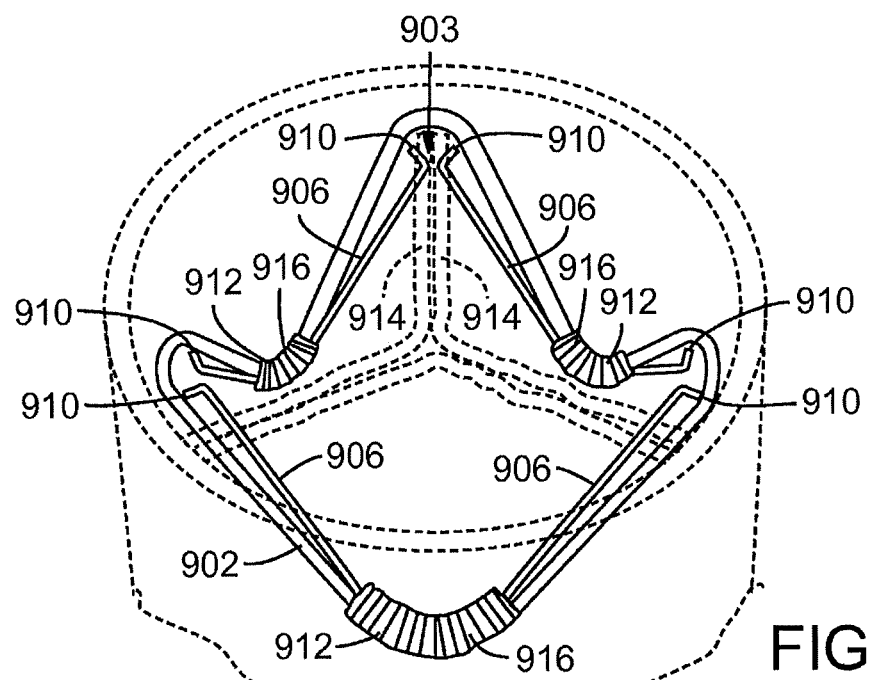
FIG. 43
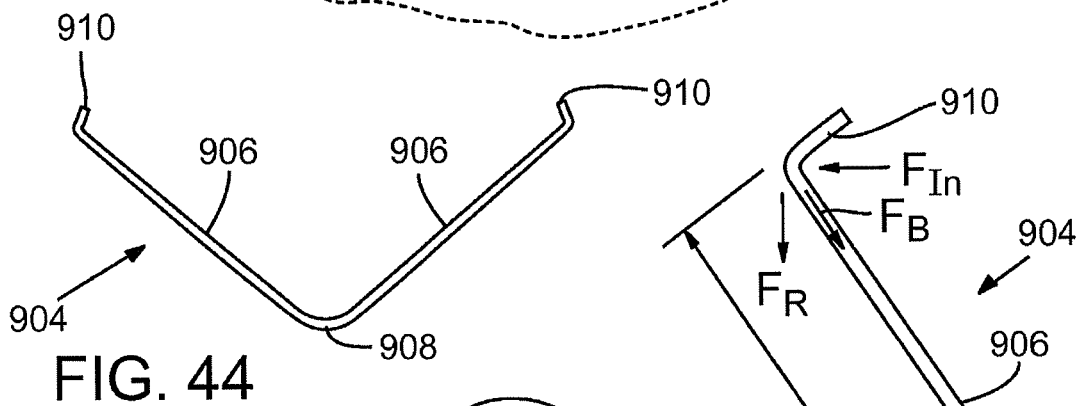
FIG. 44
FIG. 46
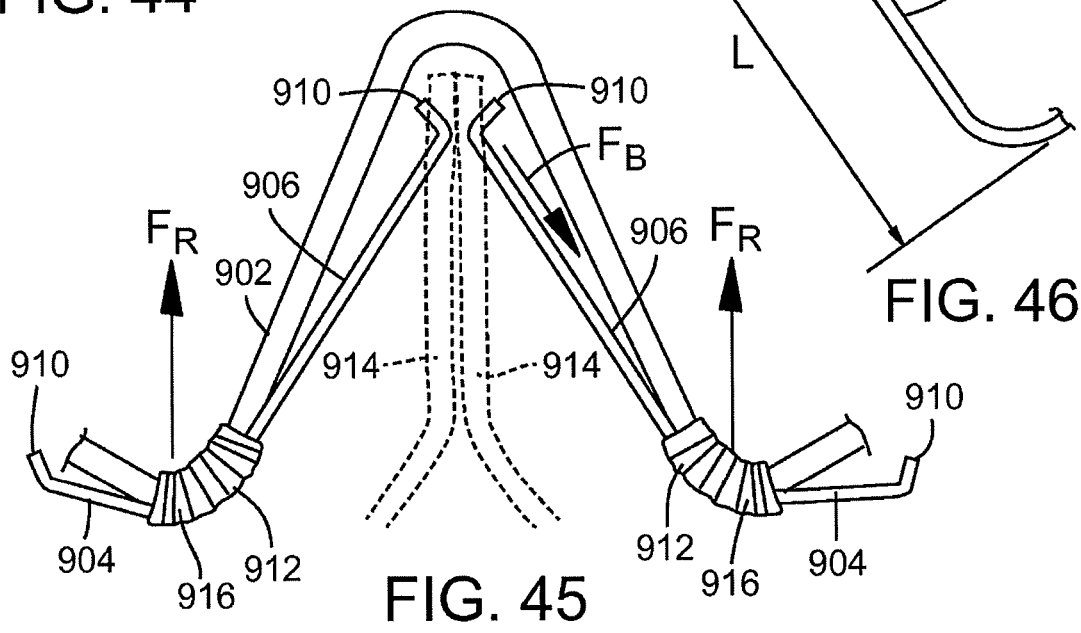
FIG. 45

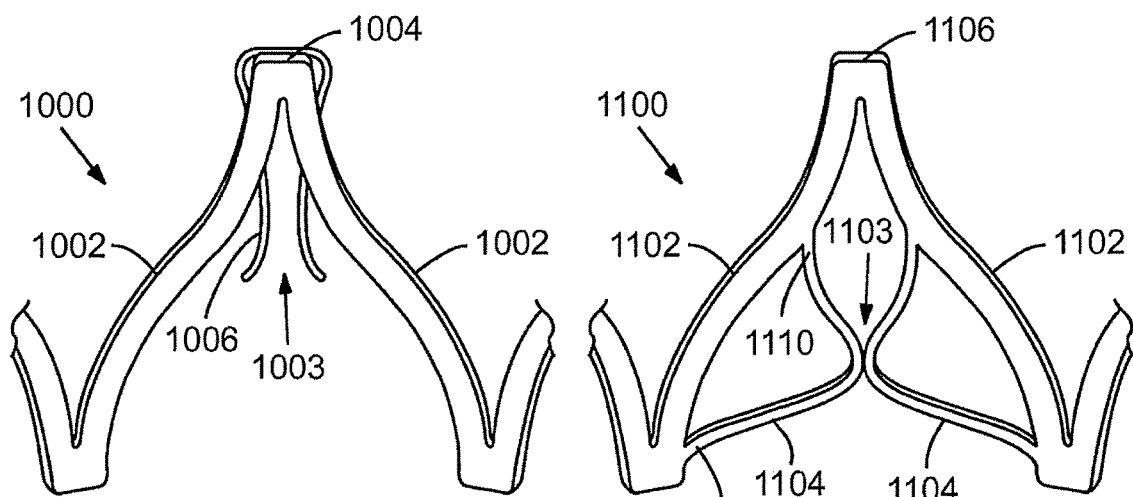
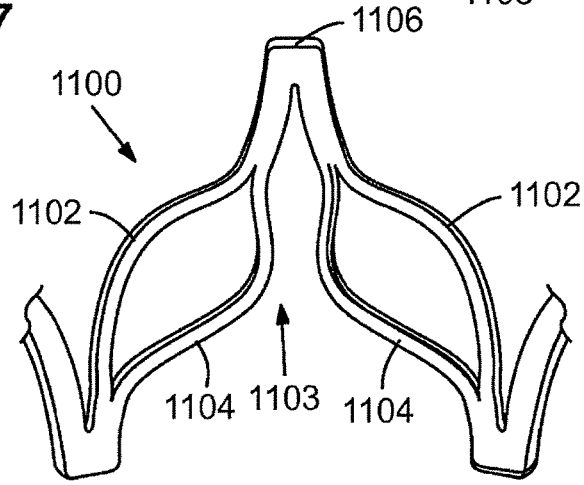
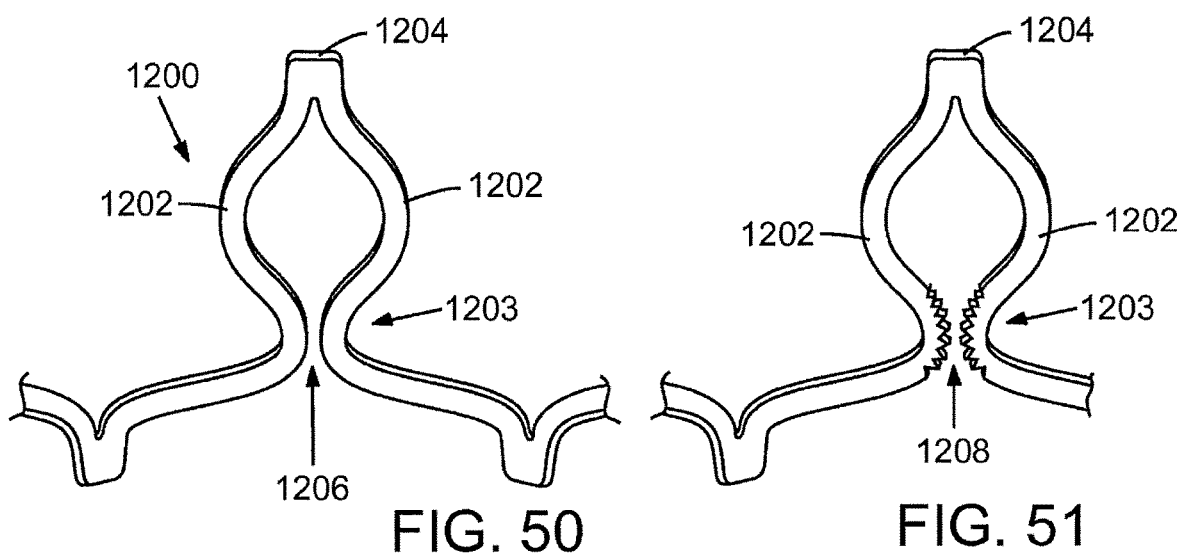
FIG. 47   FIG. 48   FIG. 49   FIG. 50   FIG. 51

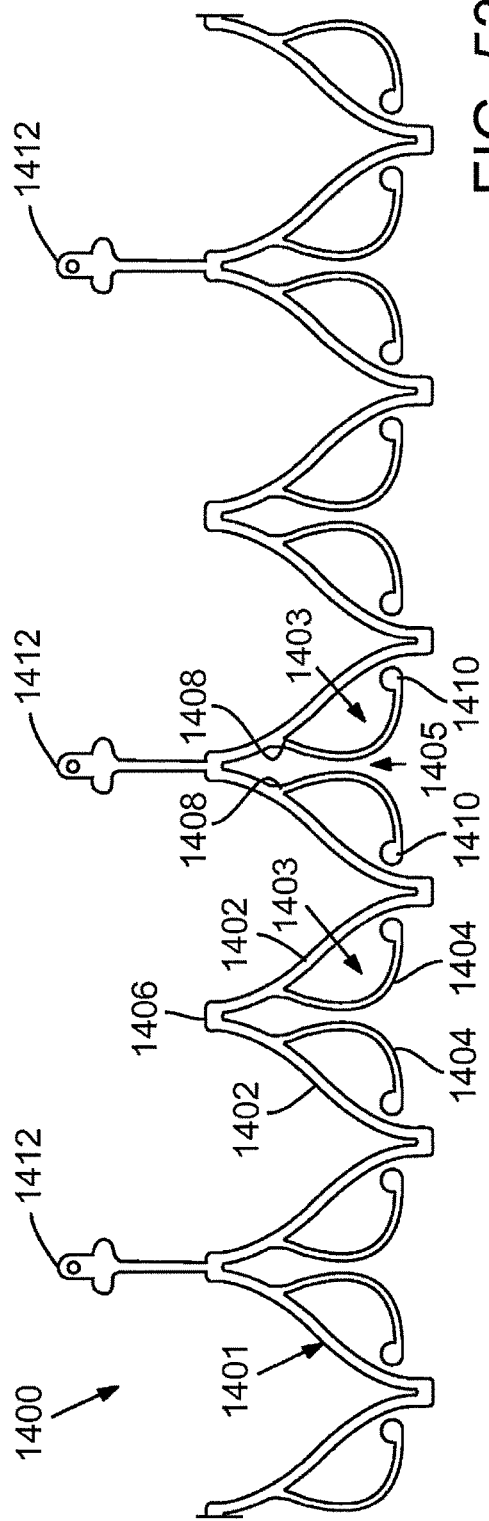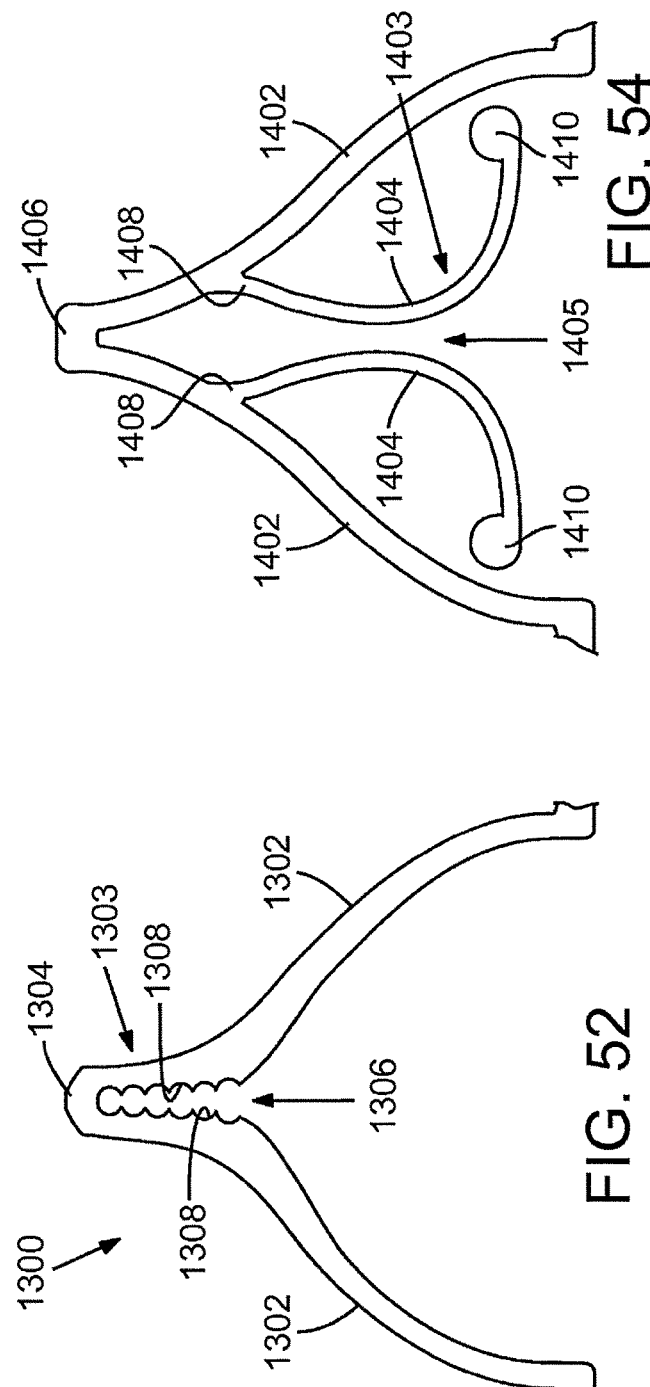

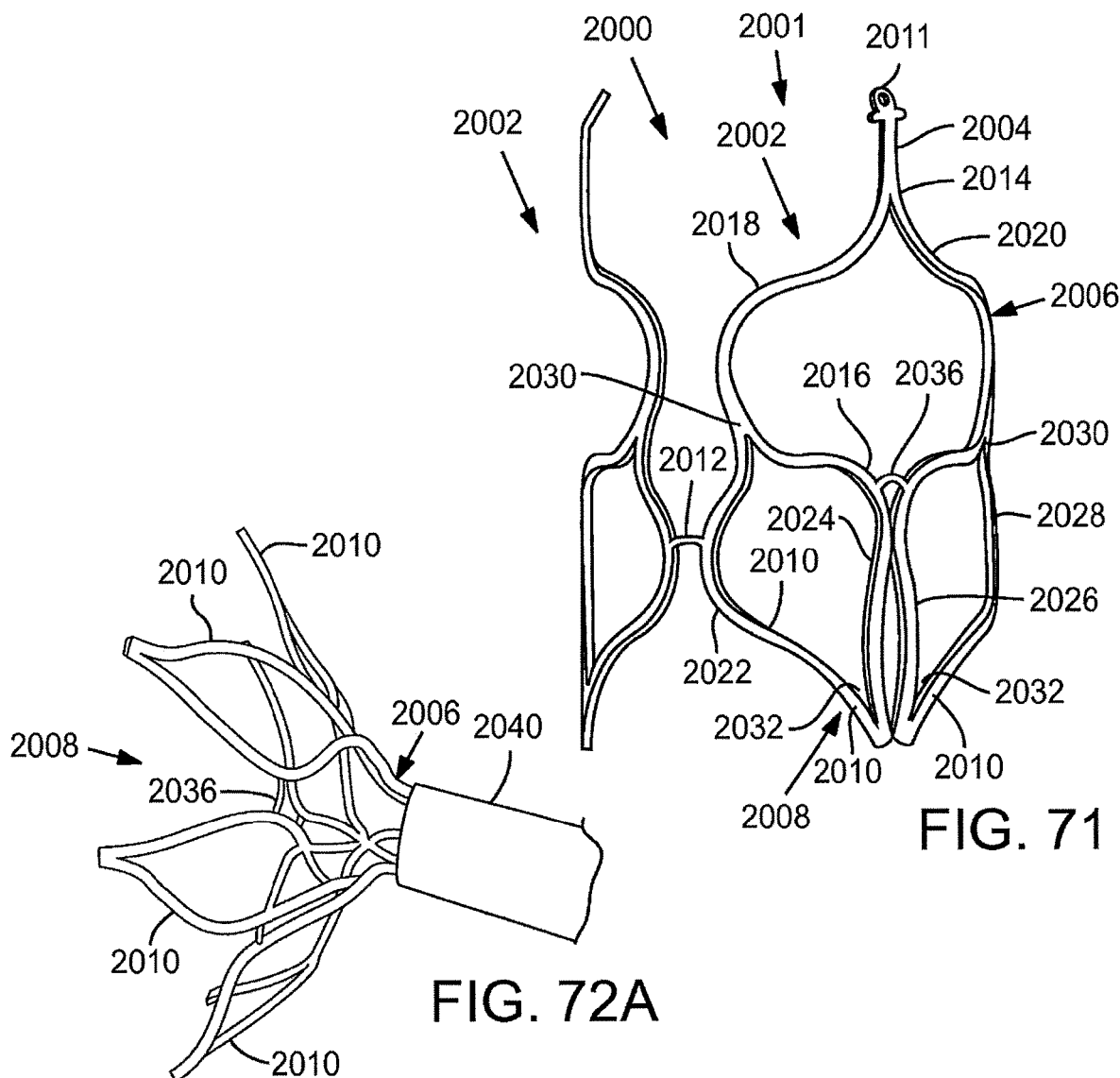
FIG. 71
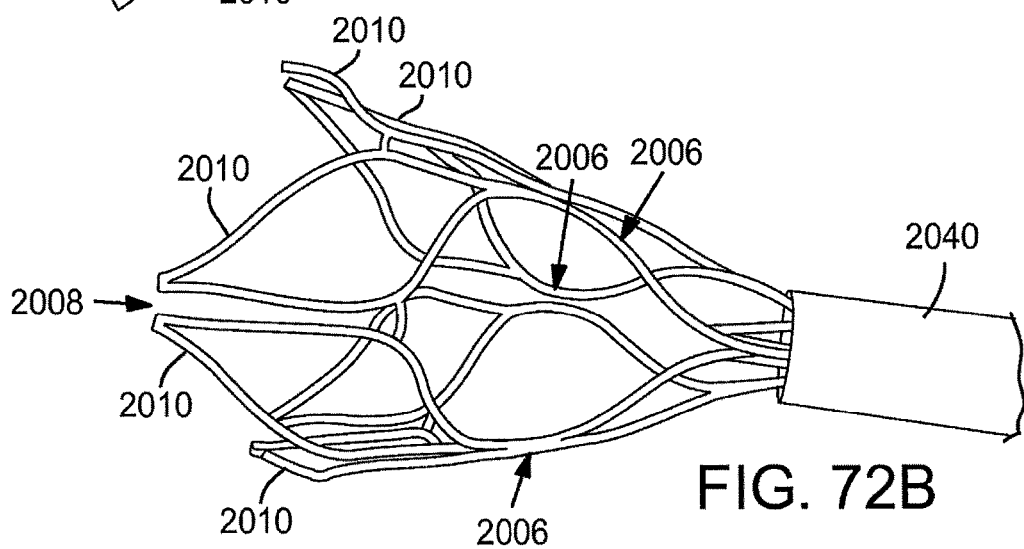
FIG. 72A
FIG. 72B

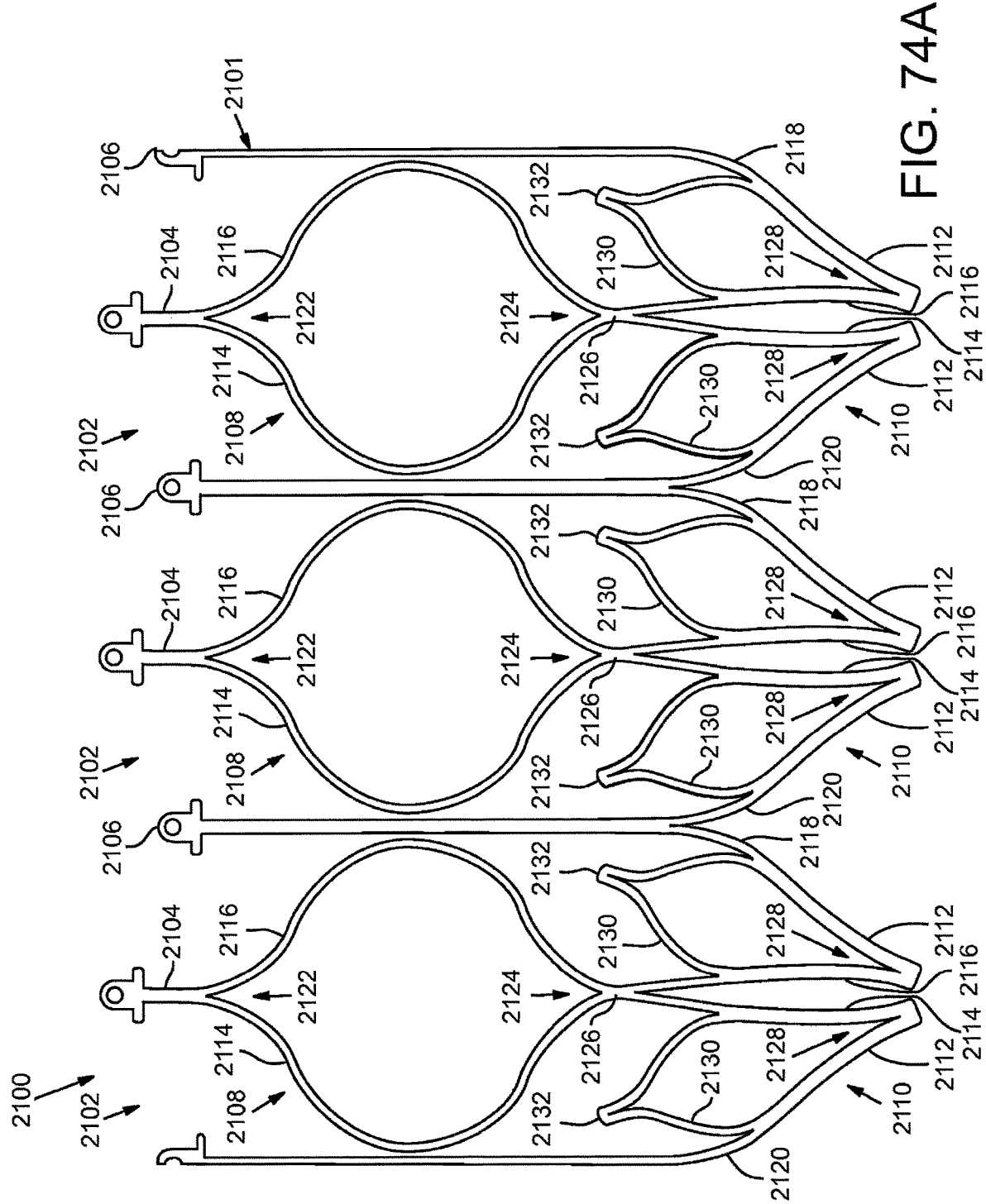

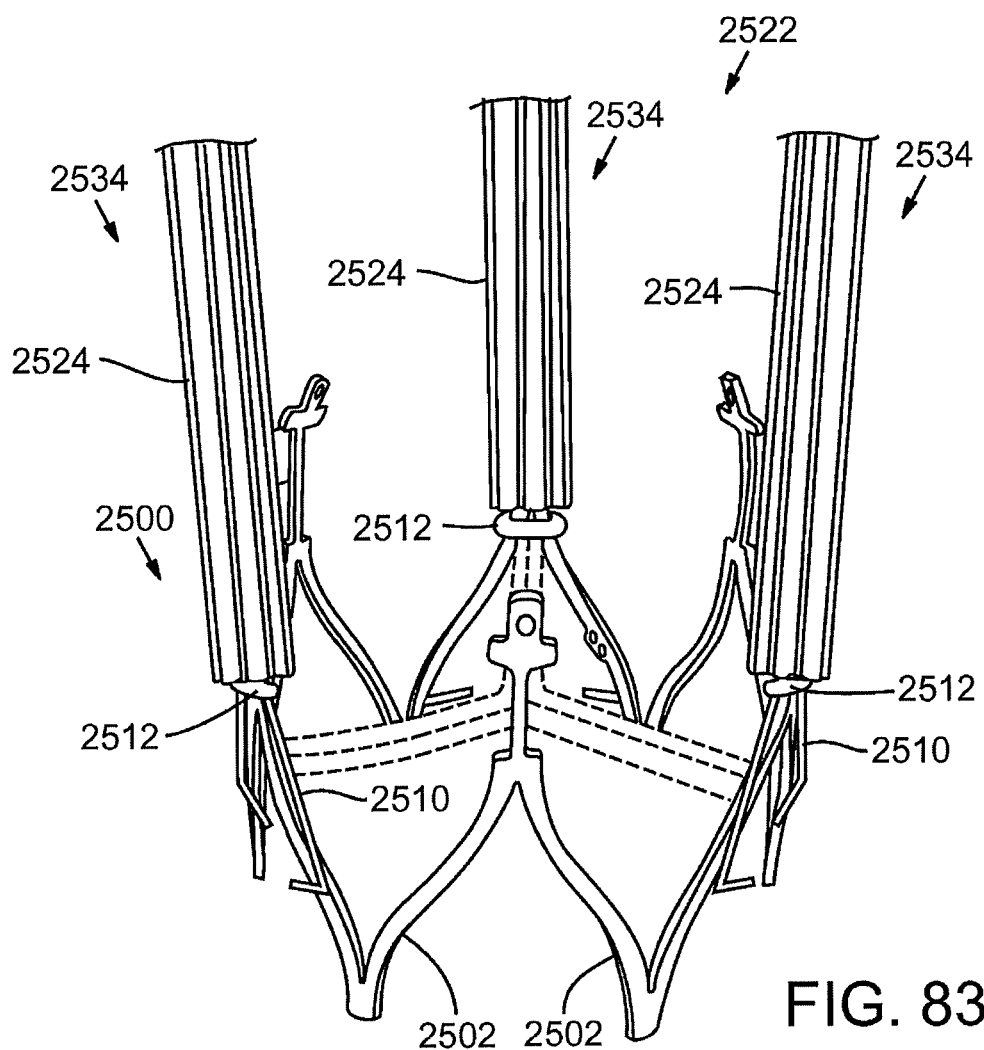
FIG. 83
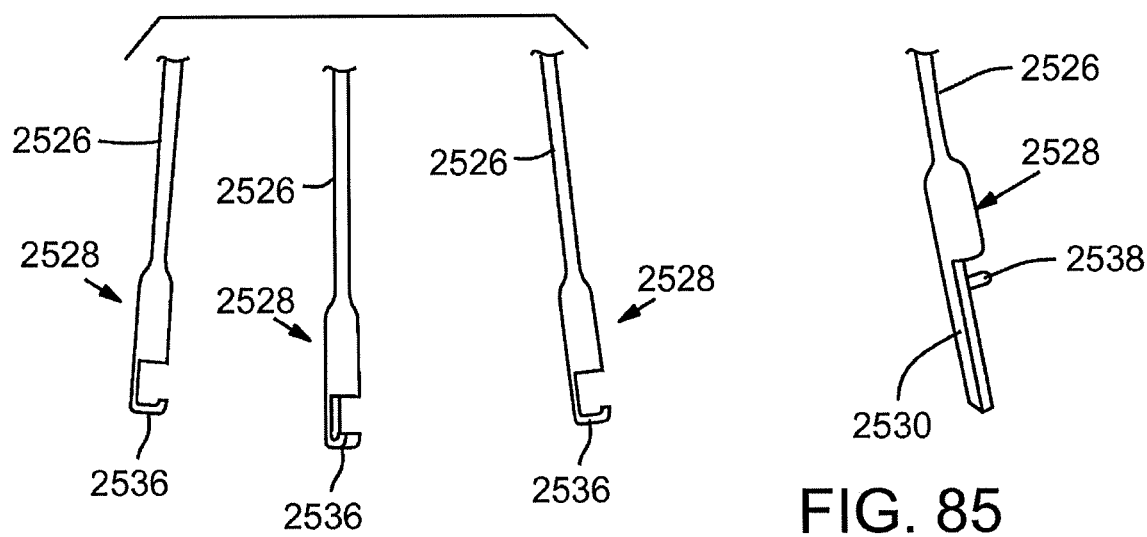
FIG. 84
FIG. 85

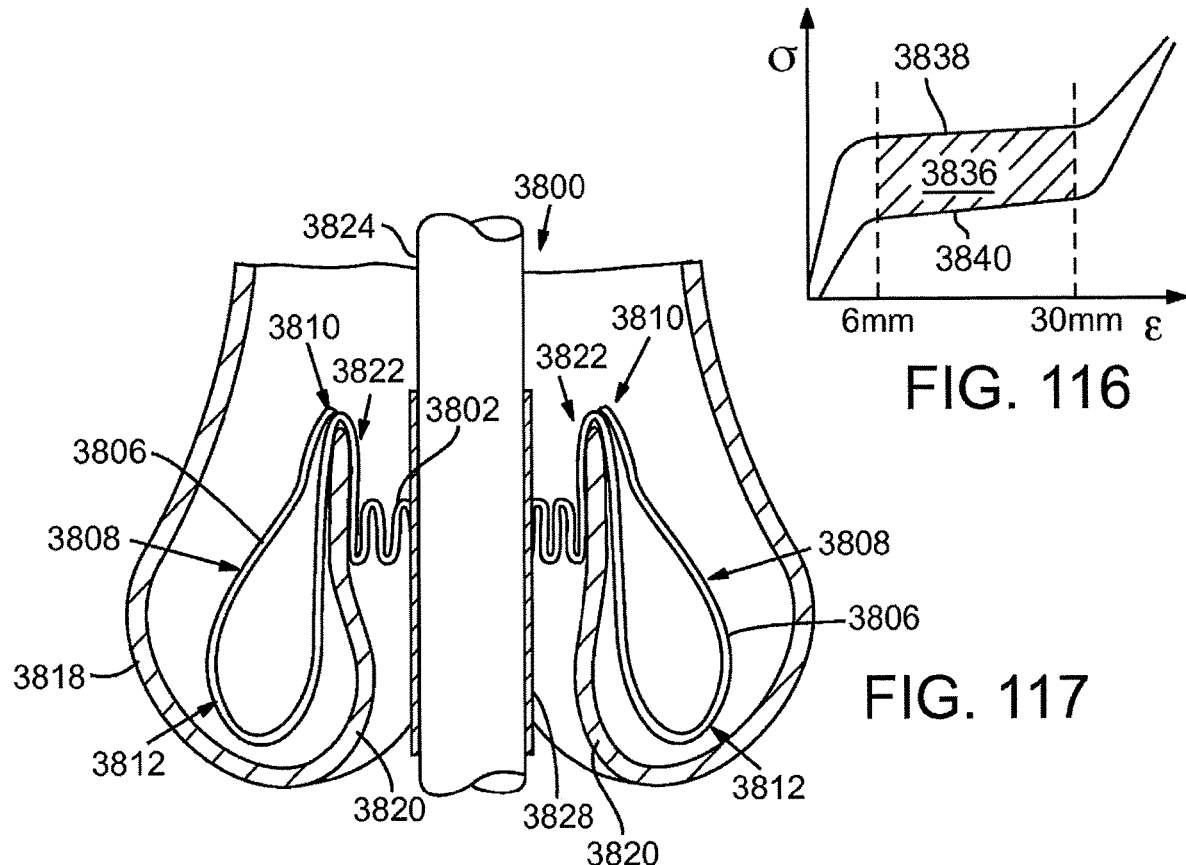
FIG. 116
FIG. 117
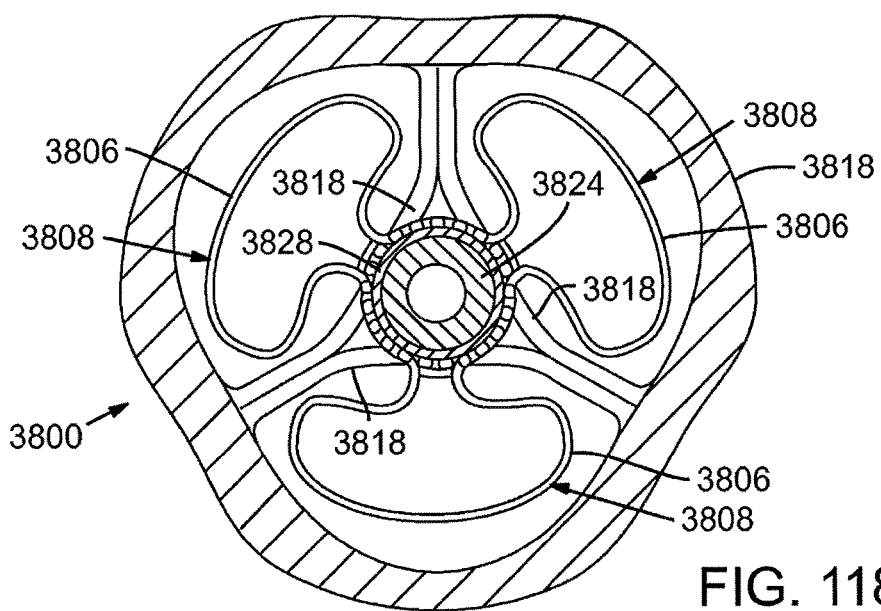
FIG. 118

VALVULAR INSUFFICIENCY REPAIR DEVICE AND METHOD

CROSS REFERENCE TO RELATED APPLICATIONS

This application is a divisional of U.S. patent application Ser. No. 16/735,352, filed Jan. 6, 2020, now U.S. Pat. No. 11,589,988, which is a continuation of U.S. patent application Ser. No. 16/181,858, filed Nov. 6, 2018, now U.S. Pat. No. 11,337,810, which is a continuation of U.S. patent application Ser. No. 15/482,555, filed Apr. 7, 2017, now U.S. Pat. No. 10,507,106, which is a divisional of U.S. patent application Ser. No. 14/549,431, filed Nov. 20, 2014, now U.S. Pat. No. 9,622,863, which claims priority to and the benefit of U.S. Provisional Patent Application No. 61/907,650, filed Nov. 22, 2013, all of which are incorporated herein by reference in their entirety.

FIELD

This application relates to methods, systems, and apparatus for safely replacing native heart valves with prosthetic heart valves.

BACKGROUND

Prosthetic heart valves have been used for many years to treat cardiac valvular disorders. The native heart valves (such as the aortic, pulmonary, tricuspid and mitral valves) serve critical functions in assuring the forward flow of an adequate supply of blood through the cardiovascular system. These heart valves can be rendered less effective by congenital, inflammatory, or infectious conditions. Such conditions can eventually lead to serious cardiovascular compromise or death. For many years the definitive treatment for such disorders was the surgical repair or replacement of the valve during open heart surgery.

More recently a transvascular technique has been developed for introducing and implanting a prosthetic heart valve using a flexible catheter in a manner that is less invasive than open heart surgery. In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve, such as by inflating a balloon on which the valve is mounted. Alternatively, the valve can have a resilient, self-expanding stent or frame that expands the valve to its functional size when it is advanced from a delivery sheath at the distal end of the catheter.

Balloon-expandable valves are commonly used for treating heart valve stenosis, a condition in which the leaflets of a valve (e.g., an aortic valve) become hardened with calcium. The hardened leaflets provide a good support structure on which the valve can be anchored within the valve annulus. Further, the catheter balloon can apply sufficient expanding force to anchor the frame of the prosthetic valve to the surrounding calcified tissue. There are several heart conditions, however, that do not involve hardened valve leaflets but which are still desirably treated by valve replacement. For example, aortic insufficiency (or aortic regurgitation) occurs when an aortic valve does not close properly, allowing blood to flow back into the left ventricle. One cause for aortic insufficiency is a dilated aortic annulus, which prevents the aortic valve from closing tightly. In such cases, the leaflets are usually too soft to provide sufficient support for a balloon-expandable prosthetic valve. Additionally, the diameter of the aortic annulus may continue to vary over time, making it dangerous to install a prosthetic valve that is not reliably secured in the valve annulus. Mitral insufficiency (or mitral regurgitation) involves these same conditions but affects the mitral valve.

Self-expanding prosthetic valves are sometimes used for replacing defective native valves with non-calcified leaflets. Self-expanding prosthetic valves, however, suffer from a number of significant drawbacks. For example, once a self-expanding prosthetic valve is placed within the patient's defective heart valve (e.g., the aorta or mitral valve), it continues to exert an outward force on the valve annulus. This continuous outward pressure can cause the valve annulus to dilate further, exacerbating the condition the valve was intended to treat. Additionally, when implanting a self-expanding valve, the outward biasing force of the valve's frame tends to cause the valve to be ejected very quickly from the distal end of a delivery sheath.

The size of the prosthetic valve to be implanted into a patient can also be problematic when treating aortic or mitral insufficiency. Specifically, the size of a prosthetic valve used to treat aortic or mitral insufficiency is typically larger than a prosthetic valve used to treat aortic or mitral stenosis. This larger valve size makes the delivery procedure much more difficult.

Additionally, many prosthetic heart valves are retained by a stent or frame (i.e., a "pinch") placed in the aortic annulus prior to implantation of the valve, with the valve being configured to pinch the native valve leaflets against the frame. However, such frames typically require attachment to the delivery apparatus to hold the frame in place before and/or during implantation of the prosthetic heart valve. This requires that the frame delivery apparatus remain in the patient during implantation of the prosthetic heart valve, which can complicate implantation of the valve.

Accordingly, there exists a need for improved methods, systems, and apparatus for delivering expandable prosthetic heart valves (e.g., balloon-expandable prosthetic valves). Embodiments of the methods, systems, and apparatus desirably can be used to replace native heart valves that do not have calcified leaflets (e.g., aortic valves suffering from aortic insufficiency). Furthermore, embodiments of the methods, systems, and apparatus desirably enable precise and controlled delivery of the prosthetic valves.

SUMMARY

An aortic insufficiency repair device improves aortic valve function by reducing a diameter of the aortic valve annulus, either an actual diameter and/or effective diameter. Embodiments of the device comprise a percutaneous or minimally invasively implantable ring-shaped or annular support structure that is deployable and anchorable on the downstream side of the aortic valve. Some embodiments of the device clip onto the native leaflets of the aortic valve at or near the commissures, thereby reducing the effective diameter of the valve annulus. Some embodiments of the device are secured in an over-expanded state and reduce the actual diameter of the aortic valve when the device springs back towards its default size.

Also disclosed below are representative embodiments of methods, systems, and apparatus used to replace deficient native heart valves with prosthetic heart valves. Embodiments of the disclosed methods, systems, and apparatus can be used, for example, to replace an aortic valve suffering from aortic insufficiency or a mitral valve suffering from mitral insufficiency. These embodiments are not limiting, however, as the disclosed methods, systems, and apparatus can be more generally applied to replace any heart valve.

In another representative embodiment a support frame configured to be implanted in a heart valve comprises an annular main body formed by a plurality of angled struts, the main body including a plurality of peaks formed by the intersection of respective adjacent struts. The support frame further comprises one or more leaflet-engaging mechanisms located beneath respective peaks of the support frame. Each of the one or more leaflet-engaging mechanisms defines a leaflet-receiving space between two opposing surfaces for engaging portions of adjacent leaflets therebetween, wherein the leaflet-receiving space can be adjustable to facilitate placement of the portions of the adjacent leaflets within the leaflet-engaging mechanism. The support frame can be radially expandable and collapsible.

In particular embodiments, the one or more leaflet-engaging mechanisms can comprise one or more pairs of leaflet clipping arms located beneath respective peaks of the support frame, wherein each clipping arm comprises a fixed end portion and a free end portion, the free end portions of each pair being configured to engage portions of adjacent leaflets therebetween. In some embodiments, the fixed end portion of each leaflet clipping arm is connected to a respective strut at a location below a respective peak and the leaflet clipping arm extends from the fixed end portion to the free end portion in a direction toward the peak. In other embodiments, the fixed end portion of each leaflet clipping arm is connected to a respective strut at a location below a respective peak and the leaflet clipping arm extends from the fixed end portion to the free end portion in a direction away from the peak.

In some embodiments, the free end portions of each pair of leaflet clipping arms can be curved or bent away from each other.

In some embodiments, the one or more leaflet-engaging mechanisms can be movable between an open position and a closed position. In some embodiments, the support frame is configured such that when the support frame is partially deployed from a delivery catheter the one or more leaflet-engaging mechanisms are in the open position. In some embodiments, the support frame is configured such that when the support frame is fully deployed from the delivery catheter the one or more leaflet-engaging mechanisms move to the closed position.

In some embodiments, the support frame further comprises one or more leaflet-engaging subunits.

In some embodiments, the one or more leaflet-engaging mechanisms are configured to be positioned over one or more commissures formed by the leaflets of the heart valve. In some embodiments, the one or more leaflet-engaging mechanisms comprise three leaflet-engaging mechanisms configured to engage the commissures of the aortic valve.

In some embodiments, the support frame further comprises one or more retaining arms coupled to the one or more of the peaks, the one or more retaining arms being configured to engage a delivery device.

In some embodiments, the support frame is configured to reduce the orifice area of the heart valve after implantation.

In another representative embodiment, a method of treating valvular insufficiency comprises inserting a delivery catheter into the vasculature of a heart proximate a heart valve, the delivery catheter carrying a support frame in a radially collapsed state. The method can further comprise positioning the delivery catheter such that one or more leaflet-engaging mechanisms of the support frame are aligned with commissures of the heart valve. Each of the one or more leaflet-engaging mechanisms is located below a respective apex of the support frame and defines a leaflet-receiving space between two opposing surfaces, wherein the leaflet-receiving space is adjustable. The method further comprises at least partially deploying the support frame from the delivery catheter to allow the support frame to radially expand to at least a partially deployed state, and engaging one or more of the commissures of the heart valve with the one or more leaflet-engaging mechanisms.

In some embodiments, the act of at least partially deploying the support frame causes the one or more leaflet-engaging mechanisms to move to open position to increase the leaflet-receiving space.

In some embodiments, the method further comprises fully deploying the support frame from the delivery catheter such that the one or more leaflet-engaging mechanisms move from the open position to a closed position.

In some embodiments, engaging one or more of the commissures of the heart valve with the one or more leaflet-engaging mechanisms is effective to reduce the orifice area of the heart valve.

In some embodiments, the method further comprises releasing the support frame from the delivery catheter and allowing the leaflets to regulate the flow of blood through the heart valve.

In some embodiments, the method further comprises, after releasing the support frame from the delivery catheter and allowing the leaflets to regulate the flow of blood through the heart valve, deploying a prosthetic heart valve within the leaflets such that the leaflets are captured between the support frame and the prosthetic heart valve.

In some embodiments, the act of engaging comprises actuating one or more leaflet-engaging mechanisms from an open position to a closed position such that the leaflet-engaging mechanisms engage the commissures of the heart valve.

In another representative embodiment, a support frame configured to be implanted in a heart valve comprises an annular main body formed by a plurality of angled struts, the main body including a plurality of peaks formed by the intersection of respective adjacent struts. In lieu of or in addition to one or more leaflet-engaging mechanisms, the support frame can have one or more frame-retaining mechanisms configured to restrain movement of the support frame in the heart by engaging one or more portions of the aortic root and/or the aorta. The support frame can be radially expandable and collapsible.

The foregoing and other objects, features, and advantages of the invention will become more apparent from the following detailed description, which proceeds with reference to the accompanying figures.

BRIEF DESCRIPTION OF THE DRAWINGS

FIG. 3 shows the delivery system before the support structure is deployed, and FIG. 4 shows the delivery system after the support structure is deployed.

FIG. 43 is a partial side elevation view of another embodiment of a support frame including a plurality of clipping members.

FIG. 44 is a side elevation view of a clipping arm of the support frame of FIG. 43

FIG. 45 is a partial side elevation view of the clipping members of the support frame of FIG. 43 illustrating the clipping members engaging leaflets of a native valve.

FIG. 46 is a side elevation view of a portion of a clipping member of FIG. 43 illustrating forces applied to the clipping member.

FIG. 47 is a partial side elevation view another embodiment of a support frame including one or more commissure clips.

FIG. 48 is a partial side elevation view of another embodiment of a support frame including one or more pairs of curved leaflet-engaging members.

FIG. 49 is a partial side elevation view of another embodiment of the support frame of FIG. 48 including one or more pairs of leaflet-engaging members defining a gap therebetween.

FIG. 50 is a partial side elevation view of another embodiment of a support frame including a plurality of curved struts that define a leaflet engagement region therebetween.

FIG. 51 is a partial side elevation view of another embodiment of the support frame of FIG. 50 wherein the curved struts comprise serrations.

FIG. 52 is a partial side elevation view of another embodiment of a support frame including a plurality of struts which define leaflet capture regions beneath select apices.

FIG. 53 is a side elevation view of another embodiment of a support frame in a flattened state including pairs of spring members.

FIG. 54 is a partial side elevation view of the support frame of FIG. 53.

FIG. 71 is a side elevation view of another embodiment of a support frame comprising a plurality of branching members defining leaflet-engaging mechanisms.

FIG. 72A is a perspective view of the support frame of FIG. 71 partially deployed from a delivery device with the leaflet-engaging mechanisms in the open position.

FIG. 72B is a perspective view of the support frame of FIG. 71 partially deployed from a delivery device with the leaflet-engaging mechanisms in the closed position.

FIG. 74A is a side elevation view of another embodiment of a support frame in a flattened state comprising a plurality of subunits, the subunits defining leaflet-engaging mechanisms.

FIG. 83 is a perspective view illustrating the support frame of FIG. 78 coupled to a delivery device.

FIG. 84 is a side elevation view of a portion of an alternative embodiment of an actuator member.

FIG. 85 is a side elevation view of a portion of another alternative embodiment of an actuator member.

FIG. 109 is a perspective view of another embodiment of a support frame including a semi-annular member supported by vertical members shape set such that the semi-annular member has a diameter greater than the diameter of the ascending aorta.

FIG. 110 is a side elevation view of the support frame of FIG. 109 located in a cross-section of the aortic root.

FIG. 111 is a perspective view of an alternative embodiment of the support frame of FIG. 109 including a semi-annular member shape set to have a diameter greater than the diameter of the ascending aorta such that vertical members supporting the semi-annular member remain vertical in an unconstrained configuration.

FIG. 112 is a side elevation view of the support frame of FIG. 111 located in a cross-section of the aortic root.

FIG. 113 is a perspective view of another embodiment of a another embodiment of a support frame including a plurality of retaining loops.

FIG. 114 is a side elevation view illustrating the loading of the support frame of FIG. 113 onto a delivery device.

FIG. 115 is a partial cross-sectional view of a delivery device illustrating the support frame of FIG. 113 loaded thereon.

FIG. 116 is a plot of stress versus strain for the support frame of FIG. 113 illustrating the stress exerted by the support frame on a transcatheter heart valve crimped beneath the support frame on a delivery device as the support frame and the transcatheter heart valve are expanded from a radially collapsed state to a radially expanded state.

FIG. 117 is a cross-sectional side elevation view of the support frame of FIG. 113 located in the aortic root.

FIG. 118 is a plan view of the support frame of FIG. 113 located in a cross-section of the aortic root.

FIG. 119 is a cross-sectional side elevation view of the support frame of FIG. 113 located in the aortic root and being expanded by a balloon catheter.

FIG. 120 is a cross-sectional side-elevation view of the support frame of FIG. 113 located in the aortic root and surrounding a transcatheter heart valve.

Figure 113:
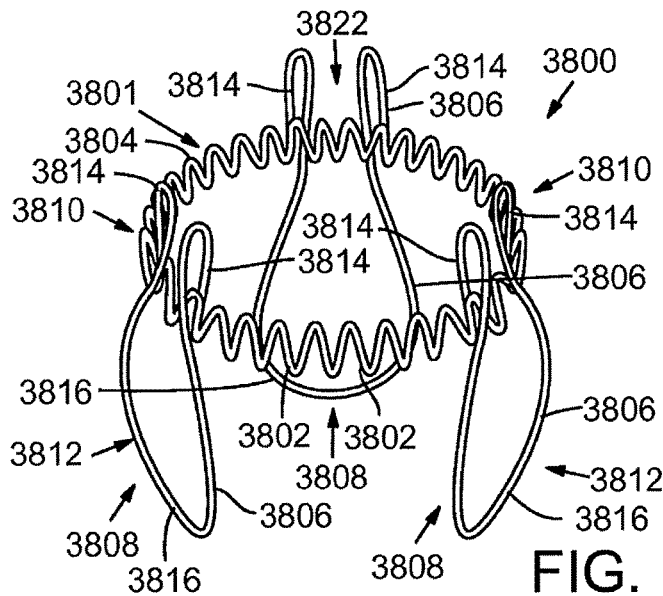
Figure 121:
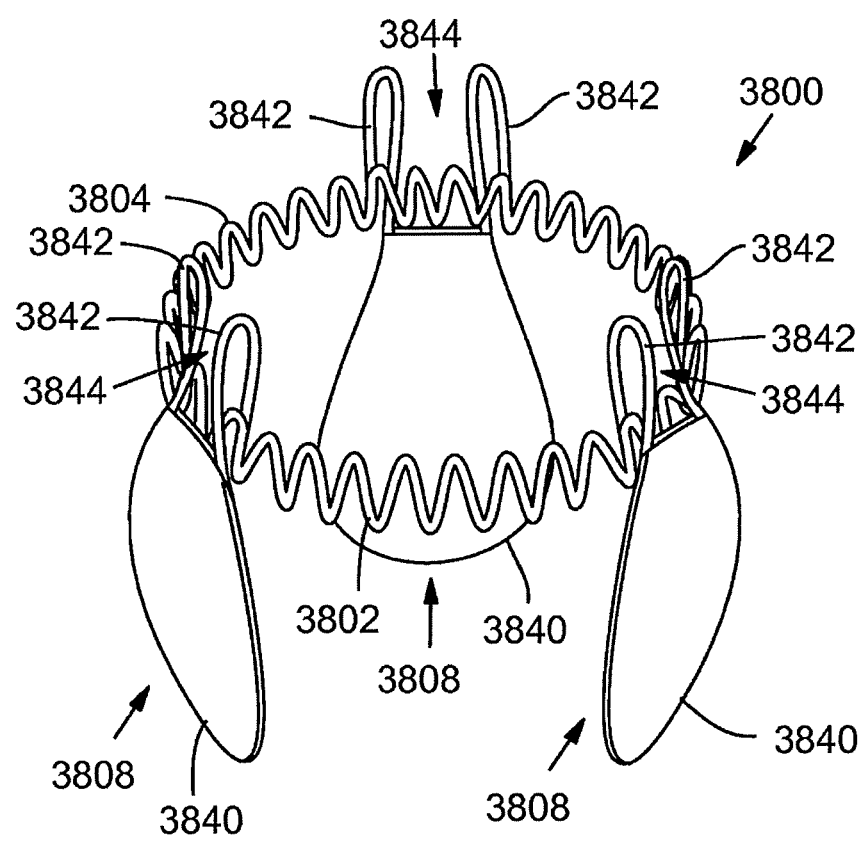

FIG. 121 is a perspective view of another embodiment of the support frame of FIG. 113 including a plurality of planar members.

Figure 122:
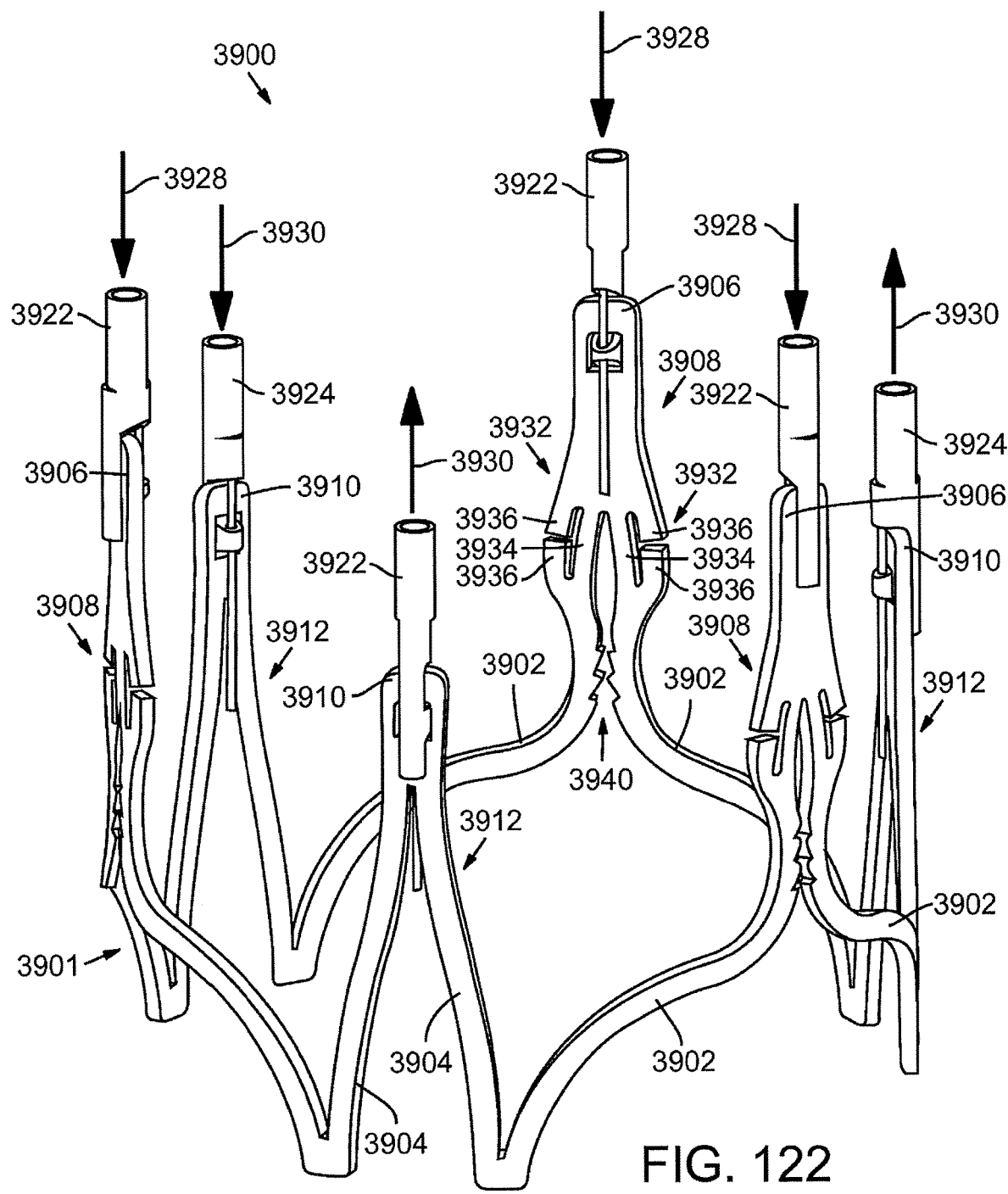

FIG. 122 is a perspective view of another embodiment of a support frame including a plurality of leaflet-engaging mechanisms and a plurality of actuator mechanisms.

Figure 123:
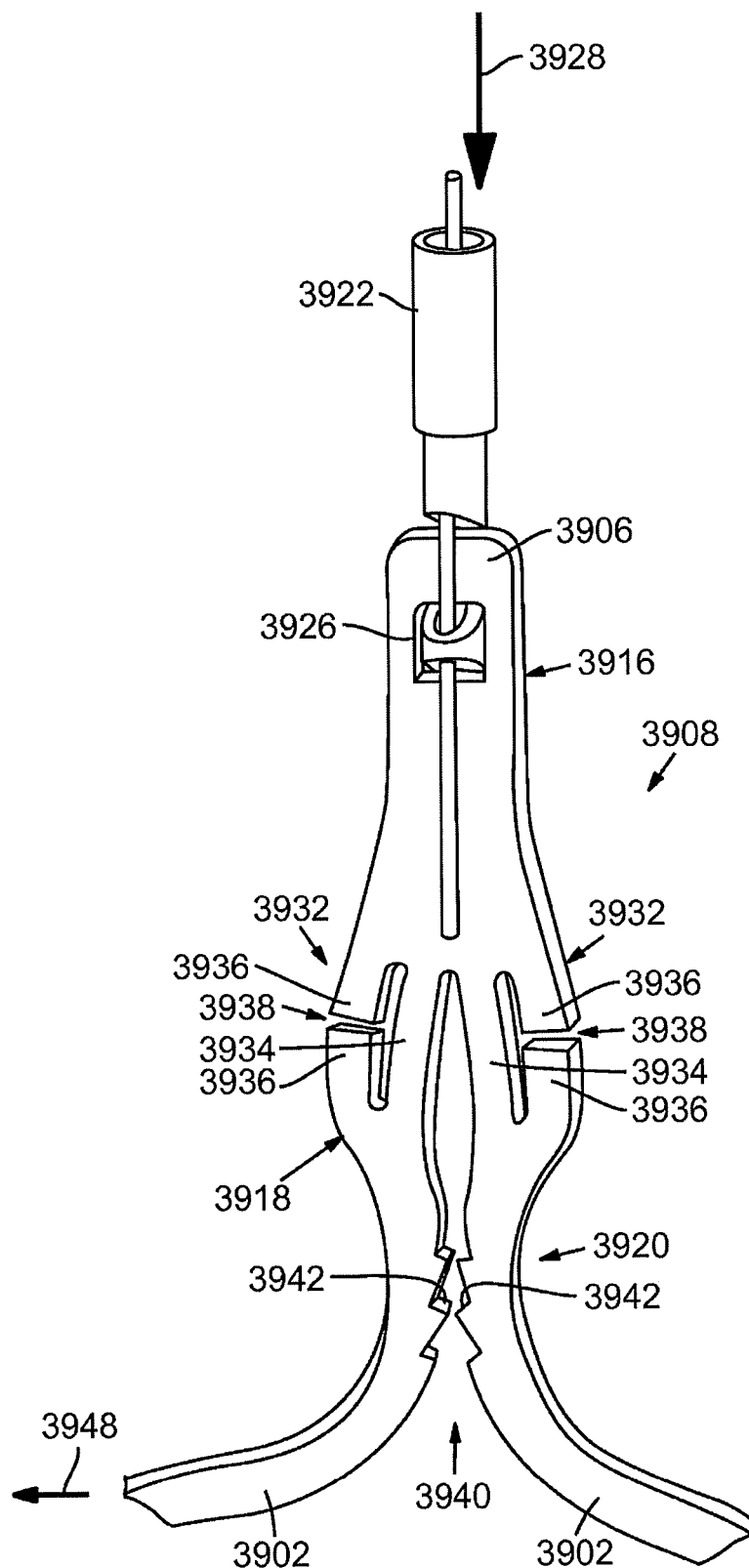

FIG. 123 is a side elevation view of a portion of a leaflet-engaging mechanism of the support frame of FIG. 122.

Figure 124:
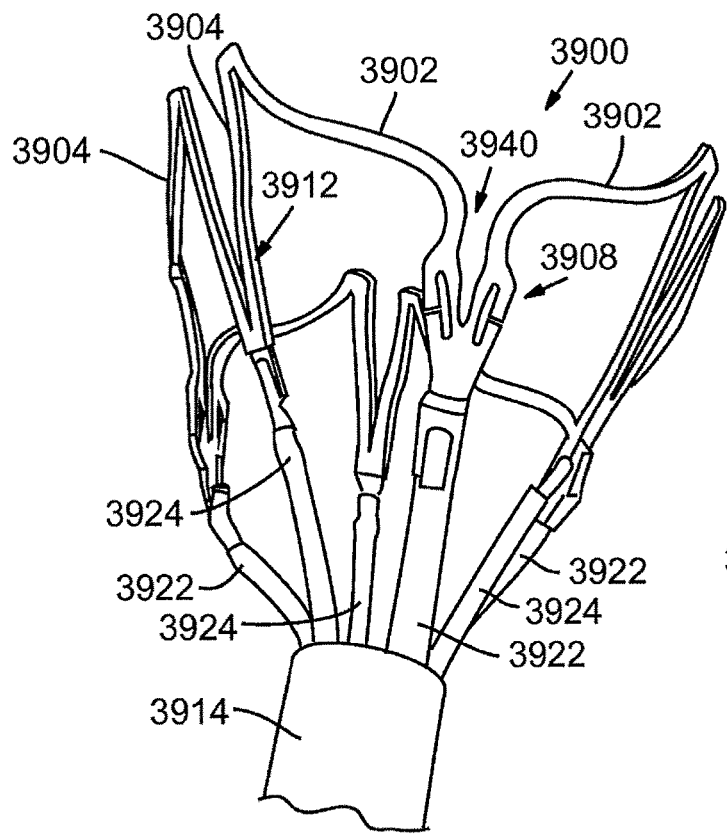

FIG. 124 is a perspective view of the support frame of FIG. 122 coupled to a delivery device and illustrating the support frame in the open position.

Figure 125:
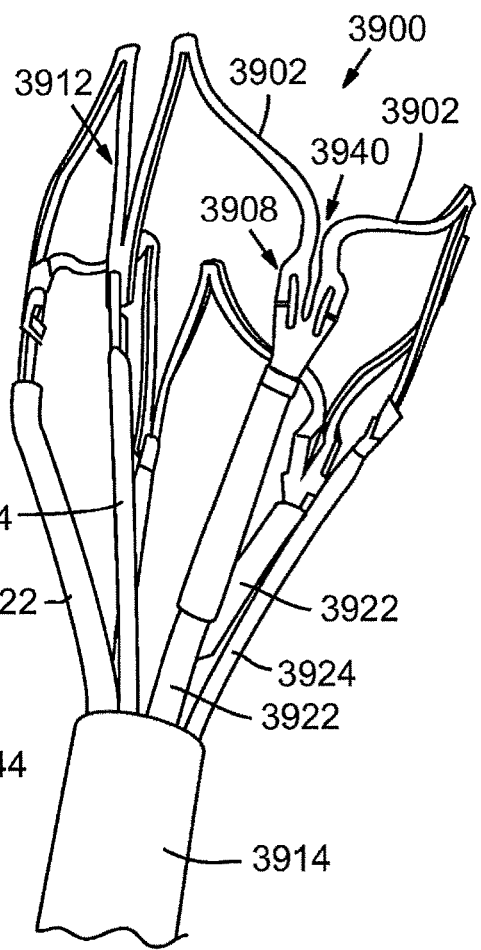

FIG. 125 is a perspective view of the support frame of FIG. 122 coupled to a delivery device and illustrating the support frame in the closed position.

Figure 126:
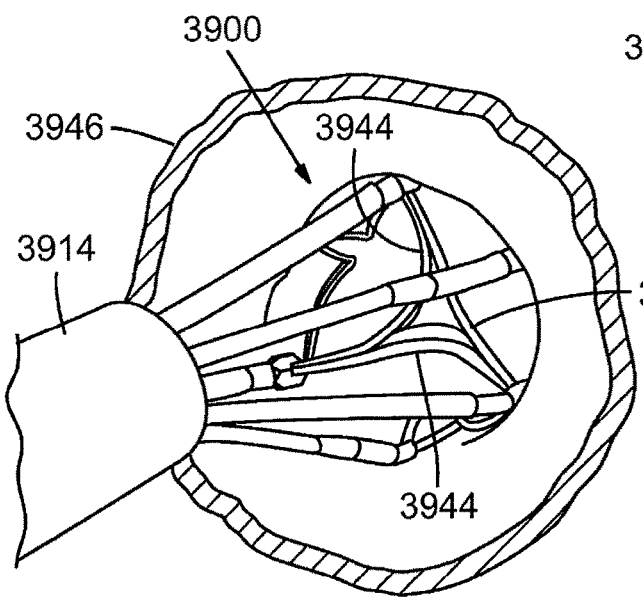

FIG. 126 is a perspective view of the support frame of FIG. 122 being implanted in a cross-section of the aortic root.

Figure 127:
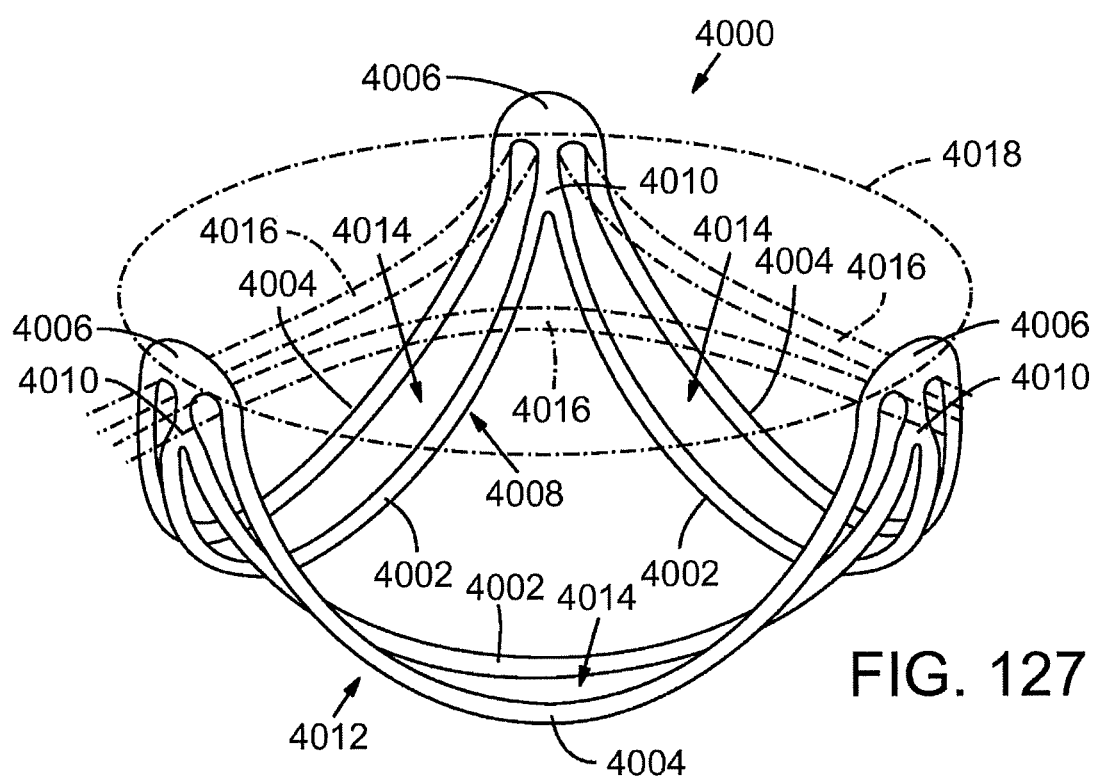

FIG. 127 is a perspective view of another embodiment of a support frame including an inner clover and an outer clover configured to pinch the leaflets of a native valve therebetween.

Figure 128:
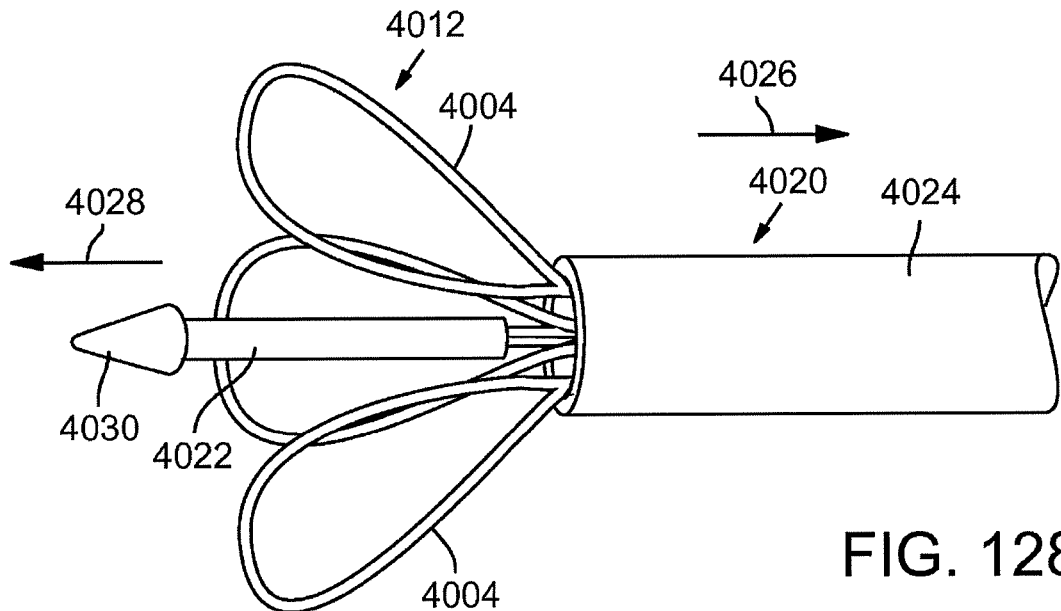

FIG. 128 is a side elevation view of the support frame of FIG. 127 partially deployed from a delivery device.

Figure 129:
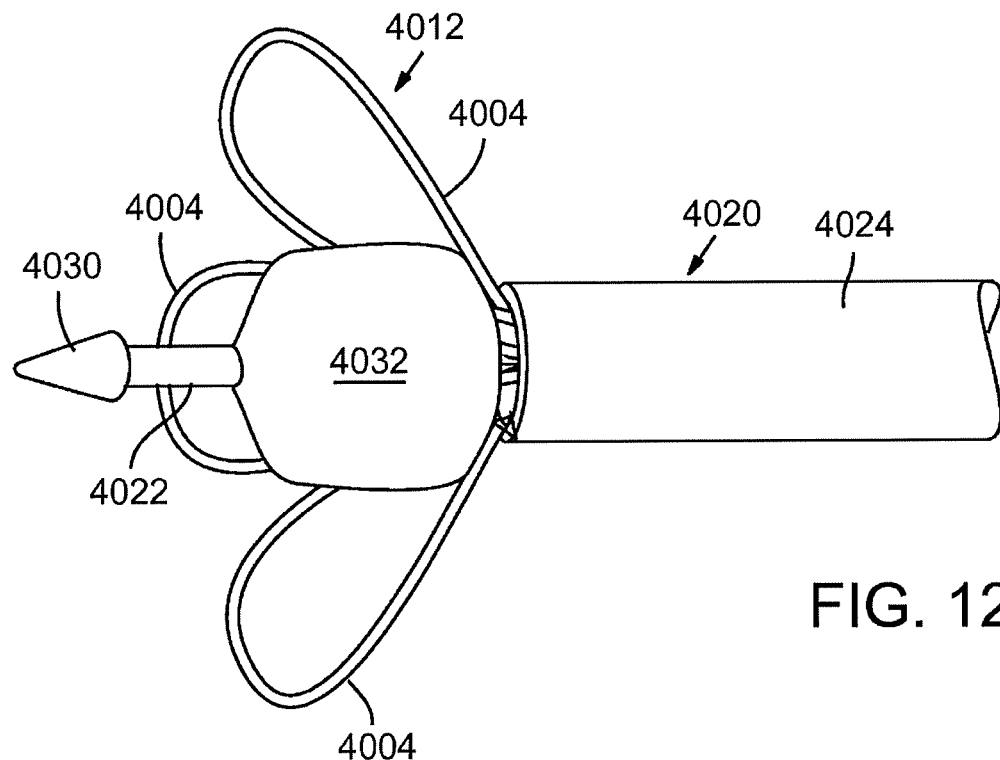

FIG. 129 is a side elevation view of the support frame of FIG. 127 partially deployed from an alternative embodiment of a delivery device including a balloon.

Figure 130:
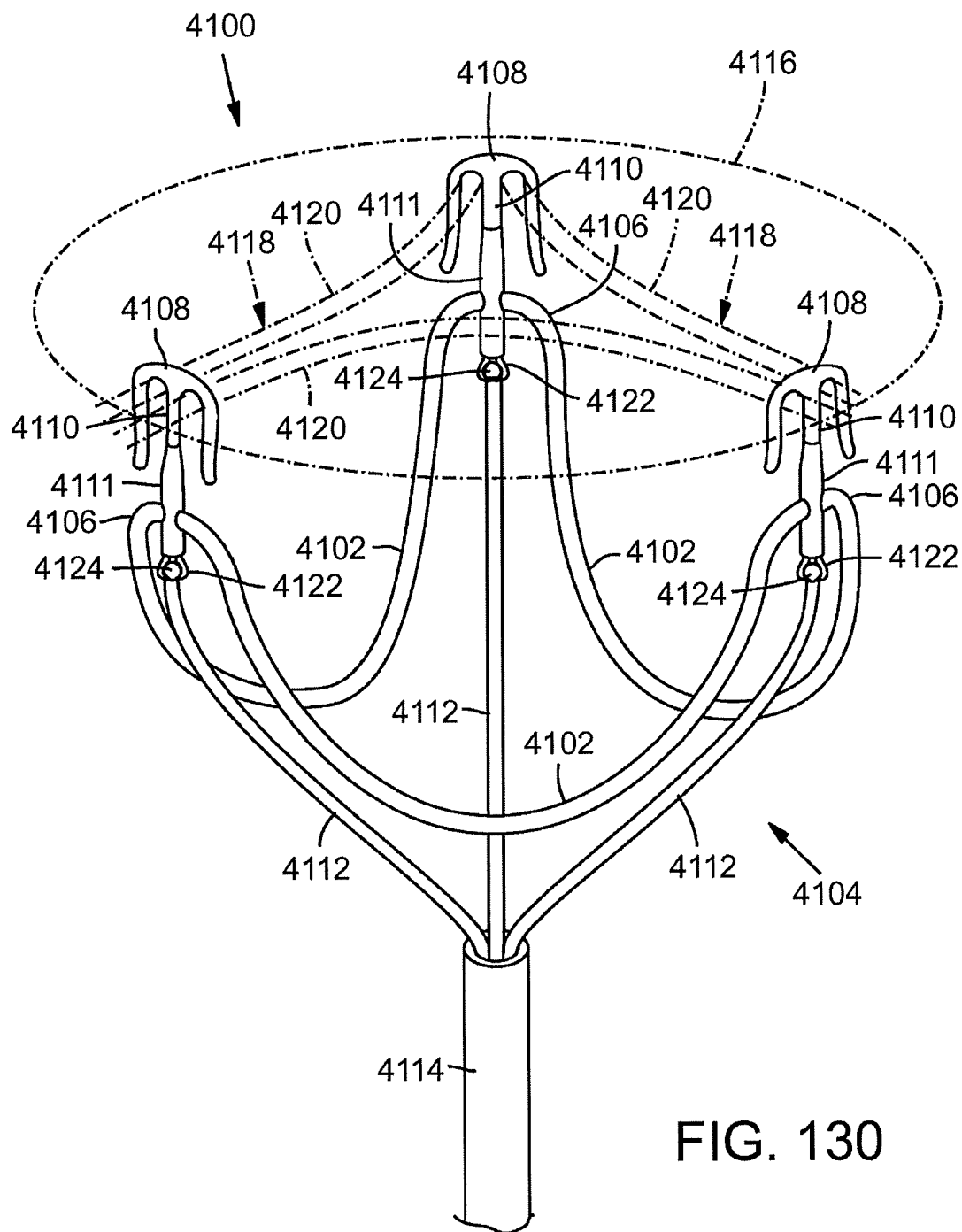

FIG. 130 is a perspective view of the support frame of FIG. 130 coupled to a delivery device.

DETAILED DESCRIPTION

General Considerations

Disclosed below are representative embodiments of a support structure (sometimes referred to as a "support stent," "support frame," "support band," or "support loop") that can be used to secure a prosthetic heart valve within a native heart valve or reduce the orifice area of a native heart valve. For illustrative purposes, embodiments of the support structure are described as being used to secure a transcatheter heart valve ("THV") in the aortic valve or the mitral valve of a heart. It should be understood that the disclosed support structure and THV can be configured for use with any other heart valve as well. Also disclosed herein are exemplary methods and systems for deploying the support structure and corresponding THV. Although the exemplary methods and systems are mainly described in connection with replacing an aortic or mitral valve, it should be understood that the disclosed methods and systems can be adapted to deliver a support structure and THV to any heart valve. Further, as used herein, the term "coupled" encompasses mechanical as well as other practical ways of coupling or linking items together, and does not exclude the presence of intermediate elements between the coupled items.

For illustrative purposes, certain embodiments of the support structure are described as being used in connection with embodiments of the balloon-expandable THV described in U.S. Patent Application Publication Nos. 2007/0112422 (U.S. application Ser. No. 11/280,063) and 2010/0049313 (U.S. application Ser. No. 12/429,040), which is hereby expressly incorporated herein by reference. It should be understood, however, that this particular usage is for illustrative purposes only and should not be construed as limiting. Instead, embodiments of the disclosed support structure can be used to secure a wide variety of THVs delivered through a variety of mechanisms (e.g., self-expanding heart valves, other balloon-expanding heart valves, and the like). For instance, any of the embodiments described in U.S. Pat. No. 6,730,118 can be used with embodiments of the disclosed support structure. U.S. Pat. No. 6,730,118 is hereby expressly incorporated herein by reference.

The specification and claims sometimes refer to a first catheter being "advanced" relative to a second catheter. It should be noted that this language not only encompasses situations where the first catheter is physically moved by an operator relative to the second catheter but also encompasses situations where the second catheter is physically moved by the operator relative to the first catheter (e.g., the second catheter is withdrawn over the first catheter, thereby causing the first catheter to be advanced relative to the second catheter). Likewise, the specification and claims sometimes refer to a first catheter being "withdrawn" relative to a second catheter. It should be noted that this language not only encompasses situations where the first catheter is physically moved by an operator relative to the second catheter but also encompasses situations where the second catheter is physically moved by the operator relative to the first catheter (e.g., the second catheter is advanced over the first catheter, thereby causing the first catheter to be withdrawn relative to the second catheter).

The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

Repairing Aortic Insufficiency

Embodiments of the support structures, stents, or frames disclosed herein are suitable for repairing aortic valve insufficiency or aortic valve regurgitation in which the native aortic valve leaflets no longer coapt properly or completely, allowing blood to leak or backflow through the aortic valve during diastole. Some of the support structures described below can repair or improve aortic insufficiency by reducing a diameter of the aortic valve annulus, either an actual diameter or an effective diameter. Some embodiments of the support structures clip together the native aortic valve leaflets at or near the commissures, thereby reducing the effective diameter of the annulus. Some embodiments pull the annulus of the valve radially inwards, thereby reducing the actual diameter by radially overexpanding the support structure, engaging the support structure with one or more structures of the aortic valve, for example, the native leaflets and/or valve annulus, and allowing the support structure to radially contract to the default size, thereby reducing the diameter of the valve annulus. Some embodiments do both.

In some cases, the support structure will by itself repair or ameliorate aortic insufficiency by itself. If the function of the valve deteriorates, for example, over the course of months or years, a THV is then deployed, using the support structure as a dock therefor, as described in detail below.

Exemplary Embodiments for Replacing Aortic Valves

Figure 1:
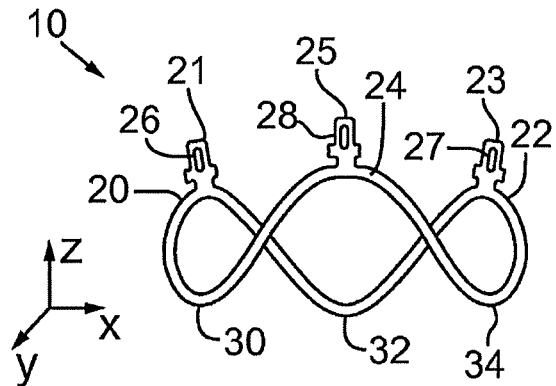
FIG. 1 is a perspective view of an exemplary embodiment of a support structure according to the disclosed technology.

FIG. 1 is a perspective view showing an exemplary embodiment of a support stent or frame 10. Support stent 10 has a generally annular or toroidal body formed from a suitable shape-memory metal or alloy, such as spring steel, cobalt-chromium alloy (Elgiloy®), or nitinol. Desirably, the material from which the support stent 10 is fabricated allows the support stent to automatically expand to its functional size and shape when deployed but also allows the support stent to be radially compressed to a smaller profile for delivery through the patient's vasculature. In other embodiments, however, the stent is not self expanding. In these embodiments, and as more fully explained below, other mechanisms for expanding the stent can be used (e.g., a balloon catheter).

In the illustrated embodiment, the projection of the support stent 10 onto an x-y plane has a generally annular or toroidal shape. The illustrated support stent 10 further defines a number of peaks and valleys (or crests and troughs) along its circumference. For example, the support stent 10 is sinusoidally shaped in the z direction. In other embodiments, the support stent 10 is shaped differently in the z direction (e.g., sawtooth-shaped, ringlet-shaped, square-wave shaped, or otherwise shaped to include peaks and valleys).

The illustrated support stent 10 includes three peaks 20, 22, 24 and three valleys 30, 32, 34. In the illustrated embodiment, the peaks 20, 22, 24 are positioned above the valleys 30, 32, 34 in the z direction. In some embodiments, the peaks have greater radii than the valleys 30, 32, 34, or vice versa. For instance, in some embodiments, the projection of the support stent 10 onto an x-y plane forms a closed shape having a variable radius (e.g., a starfish shape).

The size of the support stent 10 can vary from implementation to implementation. In particular embodiments, the support stent 10 is sized such that the support stent can be positioned within the aorta of a patient at a location adjacent to the aortic valve, thereby circumscribing the aortic valve. Furthermore, in order to frictionally secure a prosthetic heart valve in its interior, certain embodiments of the support stent 10 have a diameter that is equal to or smaller than the diameter of the prosthetic heart valve when fully expanded. In particular embodiments, for instance, the support stent can have an inner or outer diameter between 10 and 50 mm (e.g., between 17 and 28 mm) and a height between 5 and 35 mm (e.g., between 8 and 18 mm). Furthermore, the thickness of the annular body of the support stent 10 may vary from embodiment to embodiment, but in certain embodiments is between 0.3 and 1.2 mm.

Figure 2:
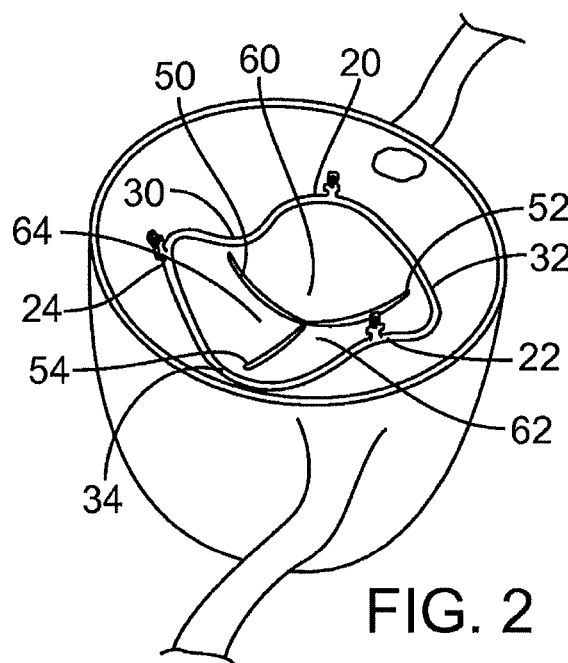
FIG. 2 is a cross-sectional view of a native aortic valve with the support structure of FIG. 1 positioned therein.

FIG. 2 is a perspective view of the exemplary support stent 10 positioned on the surface of an outflow side of a native aortic valve and further illustrates the shape of the support stent. In particular, it can be seen from FIG. 2 that the valleys 30, 32, 34 of the support stent 10 are shaped so that they can be placed adjacent to commissures 50, 52, 54 of the native leaflets 60, 62, 64 of the aortic valve. Furthermore, in the illustrated embodiment, the peaks 20, 22, 24 are shaped so that they generally approximate or minor the size and shape of the leaflets 60, 62, 64 but are slightly smaller and lower than the height of the leaflets 60, 62, 64 at their tips when the aortic valve is fully opened. In other embodiments, the peaks 20, 22, 24 are oriented so that they are adjacent to the commissures 50, 52, 54 of the native leaflets 60, 62, 64 and the valleys are opposite the apexes of the leaflets 60, 62, 64. The support stent 10 can be positioned in any other orientation within the aortic valve as well.

It should be understood that the shape of the support stent or frame 10 can vary from implementation to implementation. For example, in some embodiments, the support stent is not sinusoidal or otherwise shaped in the z-plane. In other embodiments, the support stent is shaped as a cylindrical band or sleeve. In general, the support stent or frame can be any shape that defines an interior through which a THV can be inserted, thereby causing the native leaflets of the aortic valve (or other heart valve) to be pinched or securely held between the support stent and the THV. Furthermore, the support stent can have a more complex structure. For example, although the support stent illustrated in FIGS. 1 and 2 is formed from a single annular member (or strut), the support stent can comprise multiple annular elements that interlock or are otherwise connected to one another (e.g., via multiple longitudinal members).

Returning to FIG. 1, the illustrated support stent 10 also include retaining arms 21, 23, 25 that can be used to help position and deploy the support stent 10 into its proper location relative to the native aortic valve. The retaining arms 21, 23, 25 can have respective apertures 26, 27, 28. An exemplary deployment system and procedure for deploying the support stent 10 using the retaining arms 21, 23, 25 are described in more detail below. The support stent 10 can also have one or more barbs located on its surface. Such barbs allow the support stent 10 to be more securely affixed to the tissue surrounding the stent or the leaflets of the aorta.

Figure 3:
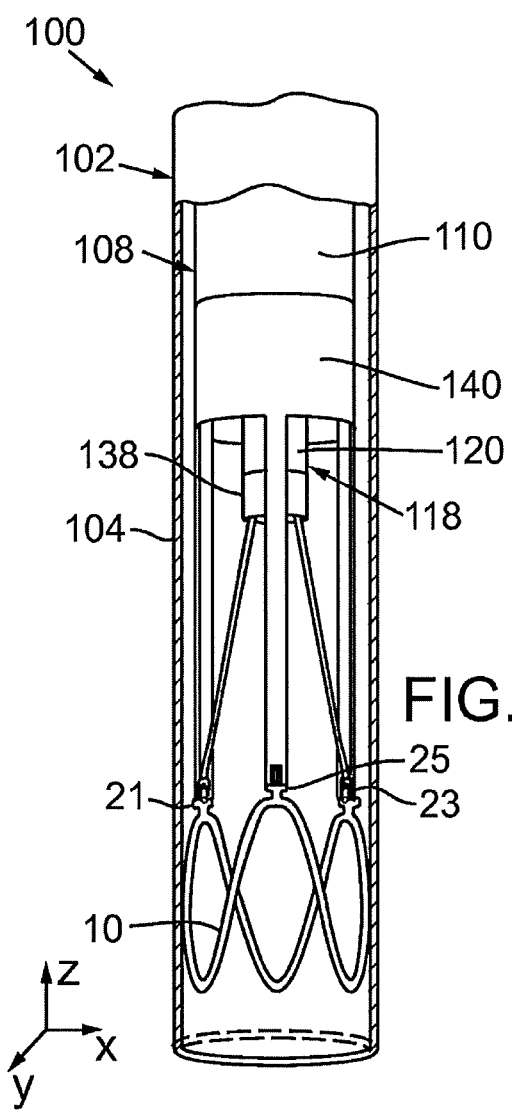
FIGS. 3 and 4 are perspective views of an exemplary delivery system for the support structure of FIG. 1. In particular.
Figure 4:
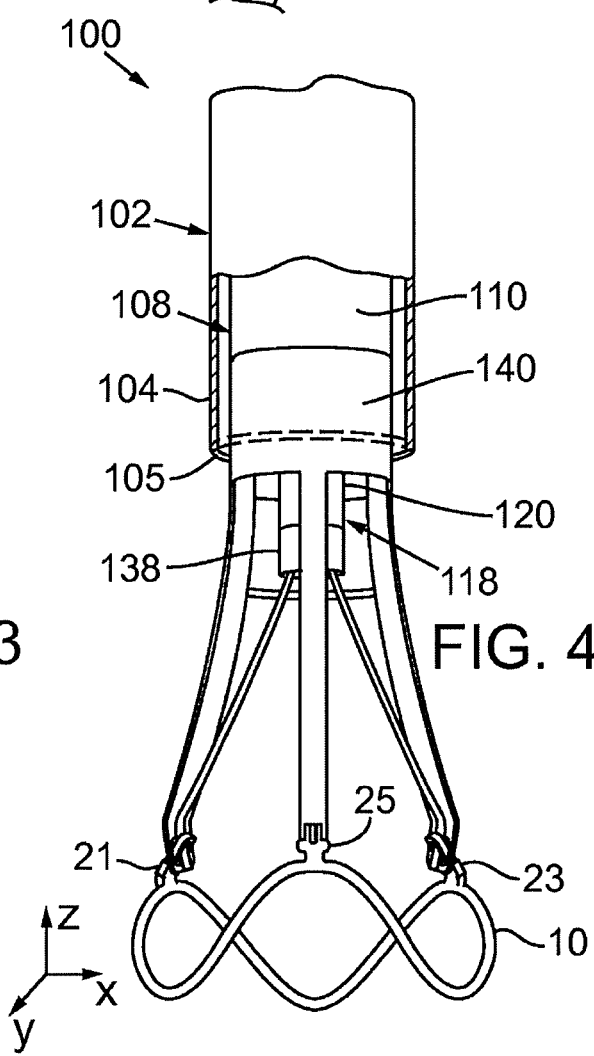

FIGS. 3 and 4 are side views of the distal end portion of an exemplary delivery apparatus 100 for delivering the support stent 10 to its location adjacent the native aortic valve through a patient's vasculature. In particular, FIG. 3 shows the delivery apparatus when the support stent 10 is in a compressed, predeployed state, whereas FIG. 4 shows the delivery apparatus when the support stent 10 is in a decompressed, deployed state. The delivery apparatus 100 comprises a guide catheter 102 having an elongated shaft 104, whose distal end 105 is open in the illustrated embodiment. In other embodiments, the distal end 105 of the guide catheter 102 can be tapered into a conical shape comprising multiple "flaps" forming a protective nose cone that can be urged apart when the support stent 10 and any interior catheters are advanced therethrough. Furthermore, for illustrative purposes, the guide catheter 102 is shown as being partially cut away, thus revealing the catheters in its interior.

A proximal end (not shown) of the guide catheter 102 is connected to a handle of the delivery apparatus 100. During delivery of a support stent, the handle can be used by a clinician to advance and retract the delivery apparatus through the patient's vasculature. In a particular use, the delivery apparatus 100 is advanced through the aortic arch of a patient's heart in the retrograde direction after having been percutaneously inserted through the femoral artery. The guide catheter can be configured to be selectively steerable or bendable to facilitate advancement of the delivery system 100 through the patient's vasculature. An exemplary steerable guide catheter as can be used in embodiments of the disclosed technology is described in detail in U.S. Patent Application Publication No. 2007/0005131 (U.S. patent application Ser. No. 11/152,288), which is hereby expressly incorporated herein by reference.

The delivery apparatus 100 also includes a stent delivery catheter 108 positioned in the interior of the guide catheter 102. The stent delivery catheter 108 has an elongated shaft 110 and an outer fork 140 connected to a distal end portion of the shaft 110. The shaft 110 of the stent delivery catheter 108 can be configured to be moveable axially relative to the shaft 104 of the guide catheter 102. Furthermore, the shaft 110 of the stent delivery catheter 108 can be sized so that its exterior wall is adjacent to or in contact with the inner wall of the shaft 104 of the guide catheter 102.

The delivery apparatus 100 can also include an inner catheter 118 positioned in the interior of the stent deliver catheter 108. The inner catheter 118 can have an elongated shaft 120 and an inner fork 138 secured to the distal end portion of the shaft 120. The shaft 120 of the inner catheter 118 can be configured to be moveable axially relative to the shaft 104 of the guide catheter 102 and relative to the shaft 110 of the stent delivery catheter 108. Furthermore, the shaft 120 of the inner catheter 118 can be sized so that its exterior wall is adjacent to or in contact with the inner wall of the shaft 110 of the stent delivery catheter 108. A guide wire (not shown) can be inserted into the interior of the inner catheter 118. The guide wire can be used, for example, to help ensure proper advancement of the guide catheter 102 and its interior catheters through the vasculature of a patient.

Figure 5:
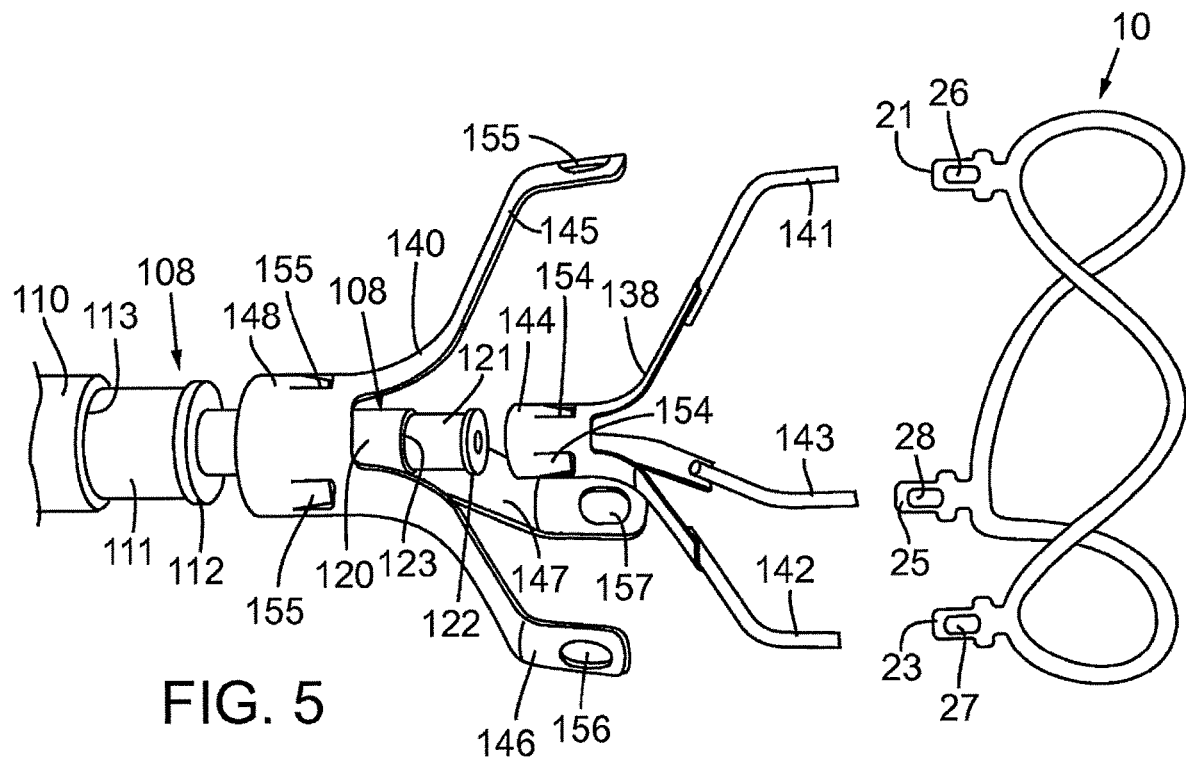
FIG. 5 is an exploded view of the components of the exemplary delivery system shown in FIGS. 3 and 4.

As best shown in FIG. 5, a stent retaining mechanism is formed from the inner fork 138 attached to the distal end portion of the shaft 120 of the inner catheter 118 and the outer fork 140 attached to the distal end portion of the shaft 110 of the stent delivery catheter 108. The inner fork 138 includes a plurality of flexible inner prongs 141, 142, 143 (three in the illustrated embodiment) at is distal end corresponding to the retaining arms 21, 23, 25 of the support stent 10, and a head portion 144 at its proximal end. The outer fork 140 includes a plurality of flexible outer prongs 145, 146, 147 (three in the illustrated embodiment) at its distal end corresponding to the retaining arms 21, 23, of the stent 10, and a head portion 148 at its proximal end. The distal end portions of the outer prongs 145, 146, 147 are formed with respective apertures 155, 156, 157 sized to receive the retaining arms 21, 23, 25.

Figure 6:
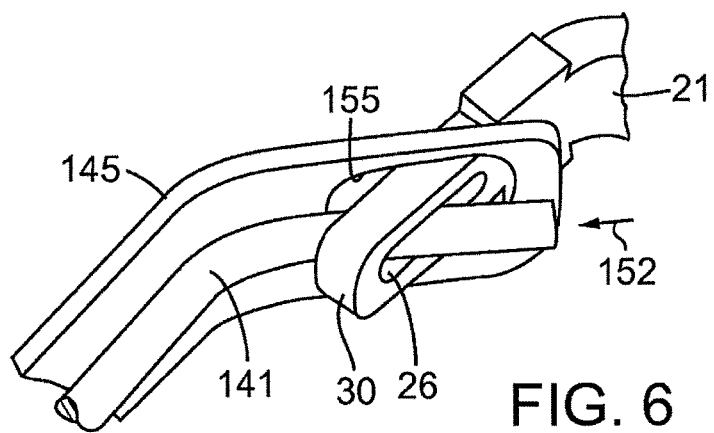
FIG. 6 is a zoomed-in perspective view showing the mechanism for releasably connecting the support structure to the exemplary delivery system of FIGS. 3 and 4.

FIG. 6 is a zoomed-in view of one of the retaining arms 21, 23, 25 as it interfaces with corresponding prongs of the outer fork 140 and the inner fork 138. In this example, retaining arm 21 is shown, though it should be understood that the retaining mechanism is similarly formed for the retaining arms 23, 25. The distal end portion of the outer prong 145 is formed with the aperture 155. When assembled, the retaining arm 21 of the stent is inserted through the aperture 155 of the prong 145 of the outer fork and the prong 141 of the inner fork is inserted through the aperture 26 of the retaining arm 21 so as to retain the retaining arm 21 in the aperture 155.

Retracting the inner prong 141 proximally (in the direction of arrow 152) to remove the prong from the aperture 26 allows the retaining arm 21 to be removed from the aperture 155, effectively releasing the retaining arm from the retaining mechanism. For instance, the outer prong 145 and the retaining arm 21 can be formed such that when the inner prong 141 is withdrawn from the aperture 26, the outer prong 145 flexes radially inward (downward in FIG. 7) and/or the retaining arm 21 of the support stent flexes radially outward (upward in FIG. 7), thereby causing the retaining arm 21 to be removed from the aperture 155. In this manner, the retaining mechanism formed by the inner fork 138 and the outer fork 140 create a releasable connection with the support stent 10 that is secure enough to retain the support stent to the stent delivery catheter 108 and to allow the user to adjust the position of the support stent after it is deployed. When the support stent 10 is positioned at the desired location adjacent to the leaflets of the aortic valve, the connection between the support stent and the retaining mechanism can be released by retracting the inner fork 138 relative to the outer fork 140, as further described below. In other embodiments, the function of the inner fork and the outer fork can be reversed. For example, the prongs of the inner fork can be formed with apertures sized to receive the corresponding retaining arms of the support stent and the prongs of the outer fork can be inserted through the apertures of the retaining arms when the retaining arms are placed through the apertures of the prongs of the inner fork.

As best shown in the exploded view in FIG. 5, the head portion 144 of the inner fork can be connected to the distal end portion of the shaft 120 of the inner catheter 118. In the illustrated embodiment, for example, the head portion 144 of the inner fork is formed with a plurality of angularly spaced, inwardly biased retaining flanges 154. An end piece of the shaft 120 can be formed as a cylindrical shaft having an annular groove 121. On the distal side of the annular groove 121, the shaft 120 can have a collar 122 with an outer diameter that is slightly greater than the diameter defined by the inner free ends of the flanges 154. Thus, the inner fork 138 can be secured to the end piece by inserting head portion 144 of the inner fork onto the end piece of the shaft 120 until the flanges 154 flex inwardly into the annular groove 121 adjacent the collar 122, thereby forming a snap-fit connection between the head portion 144 and the shaft 120. The head portion 144 can have a proximal end that engages an annular shoulder 123 of the shaft 120 that is slightly larger in diameter so as to prevent the head portion from sliding longitudinally along the shaft 120 in the proximal direction.

The head portion 148 of the outer fork can be secured to a distal end portion of the shaft 110 of the stent delivery catheter 108 in a similar manner. As shown in FIG. 5, the head portion 148 can be formed with a plurality of angularly spaced, inwardly biased retaining flanges 155. An end piece of the shaft 110 can be formed as a cylindrical shaft having an annular groove 111. On the distal side of the annular groove 111, the shaft 110 can have a collar 112 with an outer diameter that is slightly greater than the diameter defined by the free ends of the flanges 155. Thus, the outer fork 140 can be secured to the end piece of the shaft 110 by inserting the shaft 110 onto the head portion 148 until the flanges flex inwardly into the groove 111, thereby forming a snap-fit connection between the head portion 148 and the shaft 110. The head portion 148 can have a proximal end that engages an annular shoulder 123 of the shaft 110 that is slightly larger so as to prevent the head portion from sliding longitudinally along the shaft 110 in the proximal direction.

In FIG. 3, the support stent 10 is shown in a radially compressed state in the interior of the elongated shaft 104 of the guide catheter 102. In the radially compressed state, the distance along the z axis between a peak and an adjacent valley of the support stent is greater than the distance along the z axis between the peak and the adjacent valley when the support stent is in it uncompressed state. The distal end portion of the shaft 104 can also be referred to as a delivery sheath for the stent 10. In this undeployed and compressed state, the prongs of the outer fork 140 and the inner fork 138 of the stent delivery catheter 108 and the inner catheter 118 engage the retaining arms 21, 23, 25 of the support stent 10 in the manner described above with respect to FIGS. 5 and 6. To deploy the support stent 10 in the illustrated embodiment (advance the stent from the delivery system), the stent delivery catheter 108 and the inner catheter 118 are advanced toward the distal end 105 of the guide catheter 102 using one or more control handles or mechanisms (not shown) located at the proximal end of the guide catheter 102. This action causes the support stent 10 to be advanced outwardly through the distal end 105 of the guide catheter 102 and expand into its relaxed, uncompressed state (shown, for example, in FIGS. 1 and 2).

FIG. 4 is a perspective view showing the support stent 10 after it has been advanced from the distal end of the guide catheter 102. As seen in FIG. 4, the support stent 10 now assumes its relaxed, uncompressed shape but remains connected to the outer fork 140 and the inner fork 138 at its retaining arms 21, 23, 25. In this configuration, the support stent 10 can be rotated (in the clockwise or counter-clockwise directions) or repositioned (in the proximal and distal directions and/or into a different position in the x-y plane) into a proper orientation adjacent to its intended target area. For example, the support stent 10 can be positioned against the upper surfaces of leaflets of the aortic valve in the manner illustrated in FIG. 2 while the support stent 10 remains connected to the delivery system 100 via the retaining arms 21, 23, 25. As more fully illustrated below in FIGS. 7-12, a prosthetic valve (e.g., a THV) can be delivered to the aortic valve through a transapical approach (e.g., through the apex of the heart and through the left ventricle) and deployed within the native valve such that the prosthetic valve is secured in place by frictional engagement between the support stent, the native leaflets, and the prosthetic valve.

In particular embodiments, the support stent 10 is shaped so that the THV can be positioned in the interior of the support stent along with the native leaflets of the aortic valve. More specifically, the support stent 10 can be shaped such that the native leaflets become trapped or pinched between the support stent 10 and the exterior of the THV when the THV is installed. For instance, the diameter of the support stent 10 can be equal to or smaller than the maximum diameter of the THV when fully expanded, thus causing the THV to be frictionally fit to the leaflets of the aortic valve and the support stent 10. This friction fit creates a solid foundation for the THV that is independent of the state or condition of the leaflets in the aortic valve. For example, THVs are most commonly used for treating aortic stenosis, a condition in which the leaflets of the aortic valve become hardened with calcium. The hardened leaflets typically provide a good support structure for anchoring the THV within the aortic annulus. Other conditions may exist, however, in which it is desirable to implant a THV into the aortic valve and which do not result in a hardening of the leaflets of the aortic valve. For instance, the support stent 10 can be used as a foundation for a THV when treating patients with aortic insufficiency. Aortic insufficiency results when the aortic annulus dilates such that the aortic valve does not close tightly. With this condition, the aortic annulus is larger than normal and would otherwise require a large THV. Using a support stent or frame (such as the support stent or frame 10), however, a smaller THV can be used, thereby making the THV delivery process easier and safer. Furthermore, the use of a support stent protects against displacement of the THV if there is any further dilation of the aortic valve.

A support stent can be used to secure a THV in any situation in which the aorta or aortic valve may not be in condition to help support the THV and is not limited to cases of aortic insufficiency. For example, a support stent 10 can be used in cases in which the aortic annulus is too dilated or in which the leaflets of the aorta are too weak or soft. The support stent can be used to create an anchor for the THV, for instance, in cases in which the native leaflet tissue is too soft because of excess collagen in the aorta.

Figure 7:
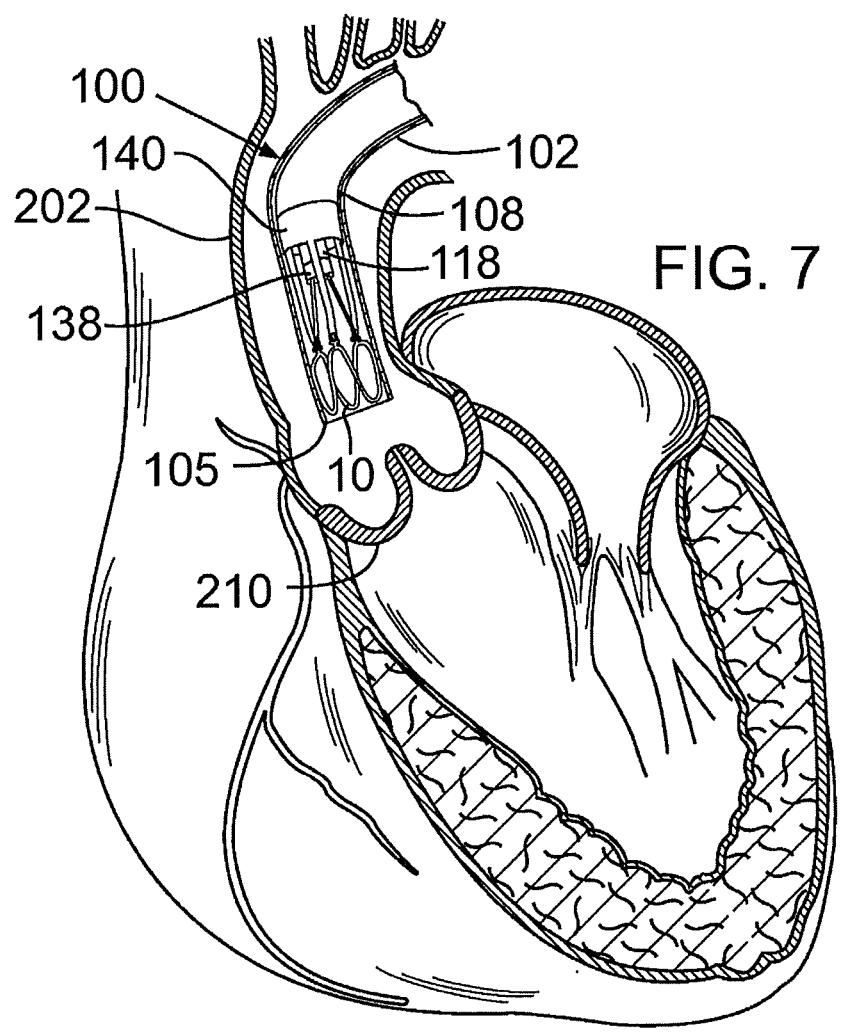
FIGS. 7 and 8 are cross-sectional views of a patient's heart illustrating how the delivery system of FIGS. 3 and 4 can operate to deploy the support structure of FIG. 1 to a desired position on the patient's aortic valve.
Figure 8:
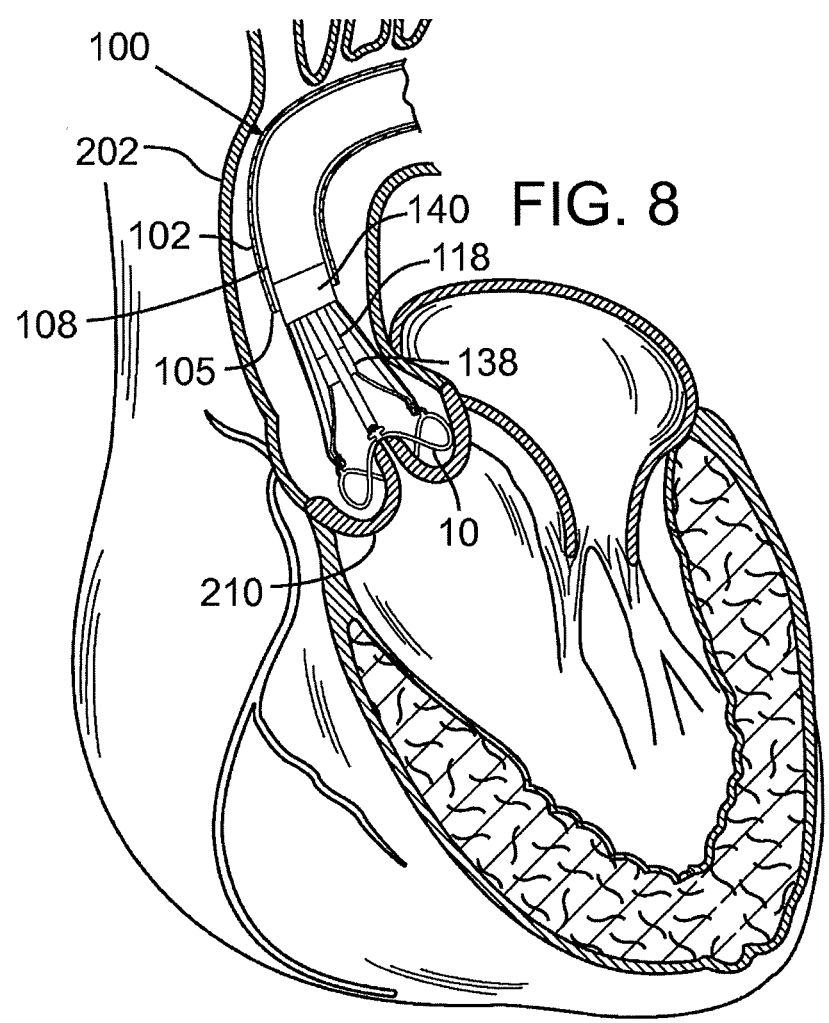

FIGS. 7-13 illustrate one exemplary procedure for deploying the support stent and securing a THV to the support stent. In particular, FIGS. 7-8 are cross-sectional views through the left side of a patient's heart showing the acts performed in delivering the support stent 10 through the aortic arch to the aortic valve. FIGS. 9-13 are cross-sectional views through the left side of a patient's heart showing the acts performed in deploying a THV 250 and having it engage the support stent 10. In order to better illustrate the components of the delivery system 100, the guide catheter 102 is shown partially cut away in FIGS. 7-13. For the sake of brevity, certain details concerning the delivery system of the THV 250 are omitted. Additional details and alternative embodiments of the delivery system for the THV 250 that may be used with the support stent described herein are discussed in U.S. Patent Application Publication No. 2007/0112422 (U.S. application Ser. No. 11/280,063), which is hereby expressly incorporated herein by reference.

FIG. 7 shows the guide catheter 102 of the delivery system 100 as it is advanced through the aortic arch 202 into a position near the surface of the outflow side of the aortic valve 210. The delivery system 100 can be inserted through the femoral artery of the patient and advanced into the aorta in the retrograde direction. FIG. 7 also shows the stent delivery catheter 108, the inner catheter 118, and the support stent 10. In FIG. 7, the support stent 10 is in its radially compressed, predeployment state. Also seen in FIG. 7 are the outer fork 140 and the inner fork 138, which couple the radially compressed support stent 10 to the distal ends of the stent delivery catheter 108 and the inner catheter 118, respectively.

FIG. 8 shows the support stent 10 after it has been advanced through the distal end of the guide catheter 102 and assumes its final, uncompressed shape in a position above and adjacent to the aortic valve 210. The support stent 10 can also be placed directly on the surface of the outflow side of the aortic valve. FIG. 8 shows that the stent delivery catheter 108 and the inner catheter 118 have been advanced though the distal end of the guide catheter 102, thereby pushing the support stent 10 out of the guide catheter and allowing it to expand into its natural shape. In particular embodiments, the support stent 10 is rotated and positioned as necessary so that the support stent generally circumscribes the aortic valve and so that the peaks of the support stent are aligned with the tips of the natural leaflets of the aortic valve 210. Therefore, when the THV is inserted and expanded within the aortic valve 210, the leaflets of the aortic valve will engage at least the majority of the surface in the interior of the support stent 10. This alignment will create an overall tighter fit between the support stent 10 and the THV. In other embodiments, the support stent 10 is rotated and positioned as necessary so that the peaks of the support stent 10 are aligned with the commissures or other portions of the aortic valve. The position of the guide catheter 102 and the support stent 10 relative to the aortic valve 210, as well as the position of other elements of the system, can be monitored using radiopaque markers and fluoroscopy, or using other imaging systems such as transesophageal echo, transthoracic echo, intravascular ultrasound imaging ("IVUS"), or an injectable dye that is radiopaque.

Also seen in FIG. 8 are the prongs of the outer fork 140 and the prongs of the inner fork 138. In the exemplary procedure, the prongs of the outer fork 140 and the inner fork 138 remain secured to the support stent 10 until the THV is deployed and frictionally engaged to the support stent. The inner and outer forks desirably form a connection between the stent 10 and the delivery system that is secure and rigid enough to allow the clinician to hold the stent 10 at the desired implanted position against the flow of blood while the THV is being implanted.

In FIG. 8, the support stent 10 is self-expanding. In other embodiments, however, the support stent may not be self-expanding. In such embodiments, the support stent can be made of a suitable ductile material, such as stainless steel. In addition, a mechanism for expanding the support stent can be included as part of the delivery system 100. For example, the support stent can be disposed around a balloon of a balloon catheter in a compressed state. The balloon catheter can have a shaft that is interior to the inner catheter 118. Because the stent 10 is not self-expanding, the distal end portion of the guide catheter 102 need not extend over the compressed support stent. During delivery of the support stent, the support stent, balloon catheter, inner catheter 118, and stent delivery catheter 108 can be advanced from the distal end of the guide catheter 102. The balloon portion of the balloon catheter can be inflated, causing the support stent to expand. The balloon portion can subsequently be deflated and the balloon catheter withdrawn into the delivery system 100 to remove the balloon from the interior of the support stent while the support stent remains connected to the inner catheter for positioning of the support stent. The delivery of the support stent otherwise proceeds as in the illustrated embodiment using the self-expanding support stent 10.

Figure 9:
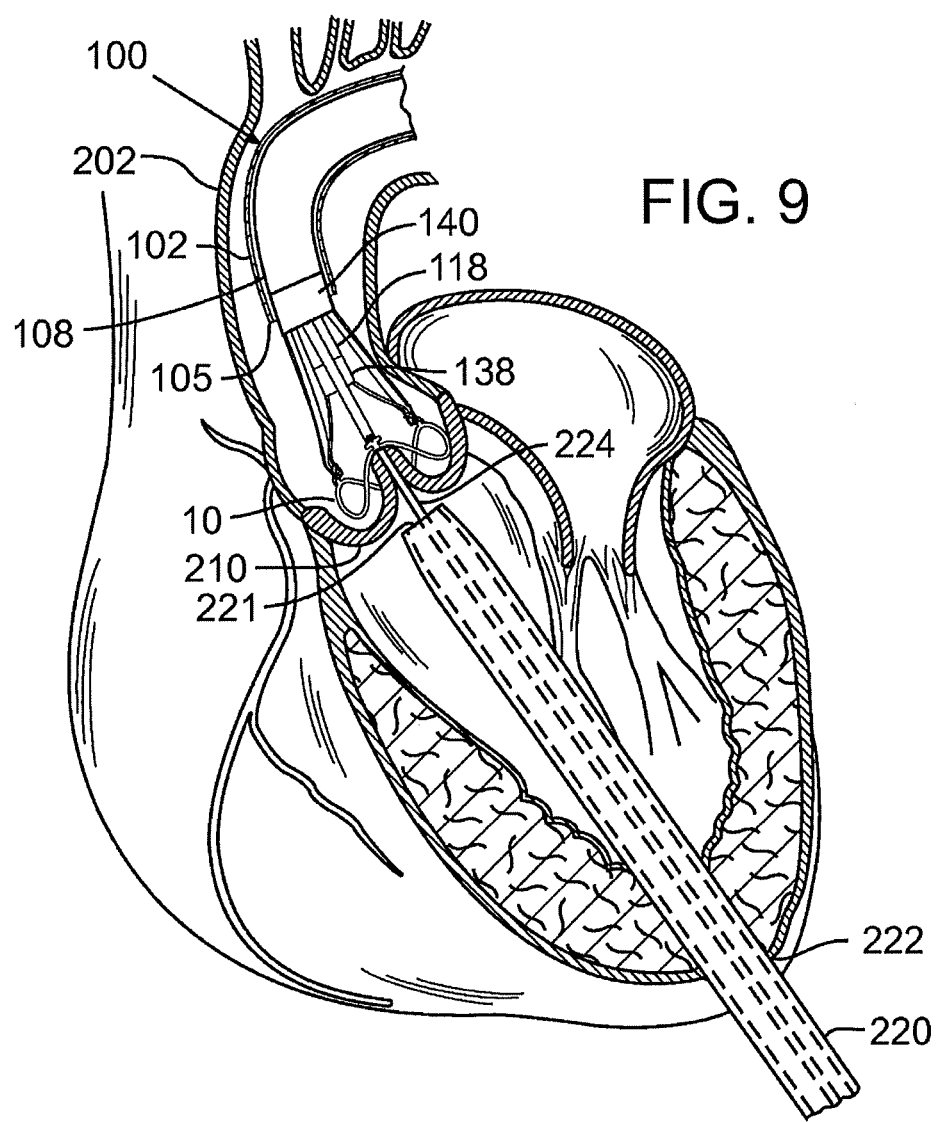
FIGS. 9-13 are cross-sectional views of a patient's heart illustrating how an exemplary transcatheter heart valve ("THV") can be deployed to the patient's aortic valve and frictionally secured to the native leaflets using the support structure of FIG. 1.

FIG. 9 shows an introducer sheath 220 passing into the left ventricle through a puncture 222 and over a guidewire 224 that extends upward through the aortic valve 210. The clinician locates a distal tip 221 of the introducer sheath 220 just to the inflow side of the aortic valve 210. The position of the introducer sheath 220 relative to the aortic valve 210, as well as the position of other elements of the system, can be monitored using radiopaque markers and fluoroscopy, or using other imaging systems.

Figure 10:
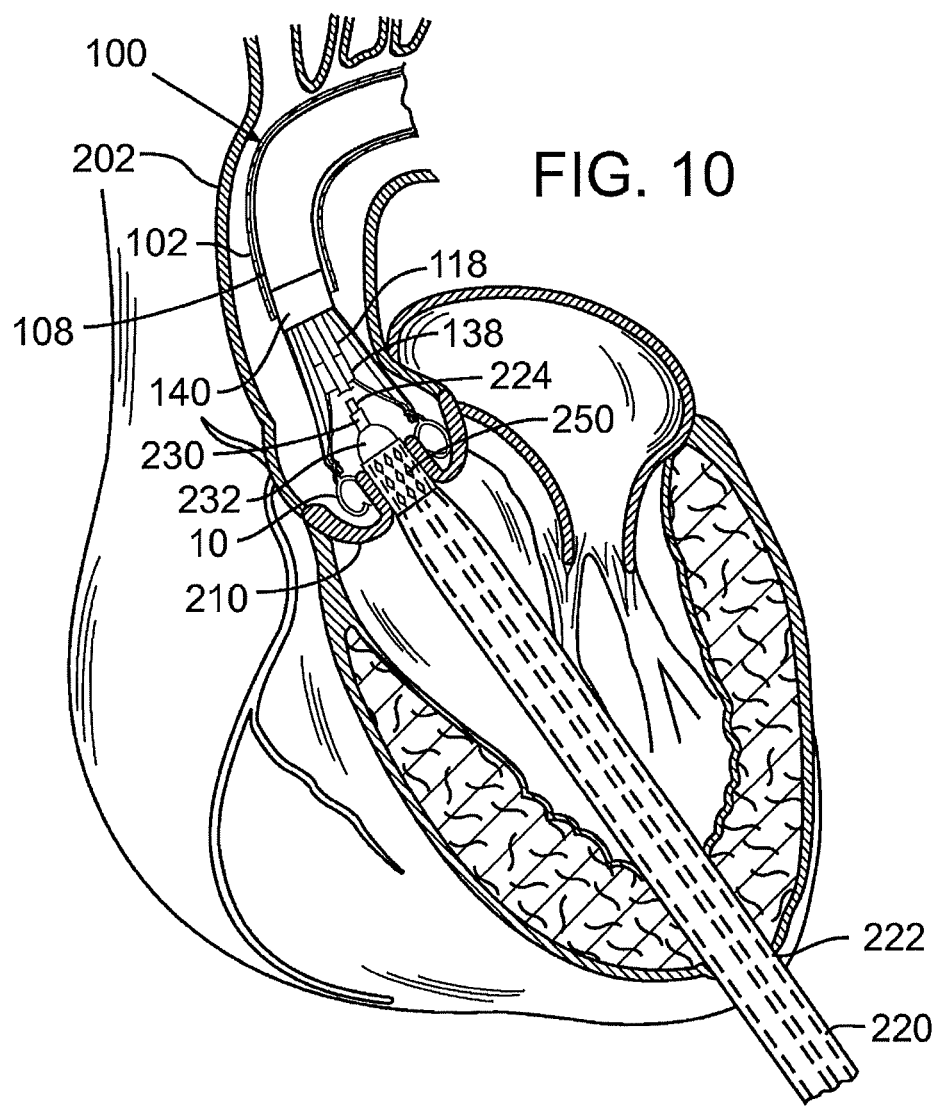
Figure 11:
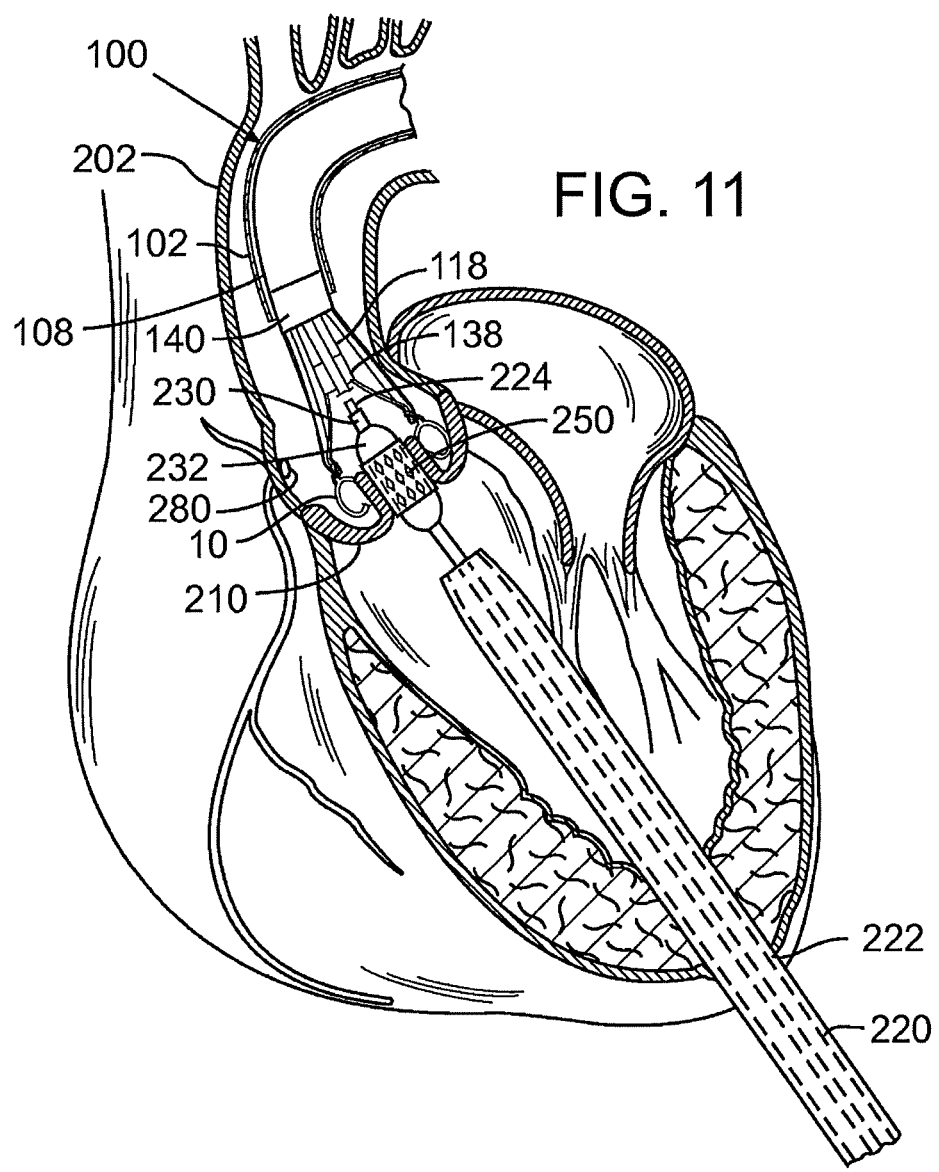
Figure 12:
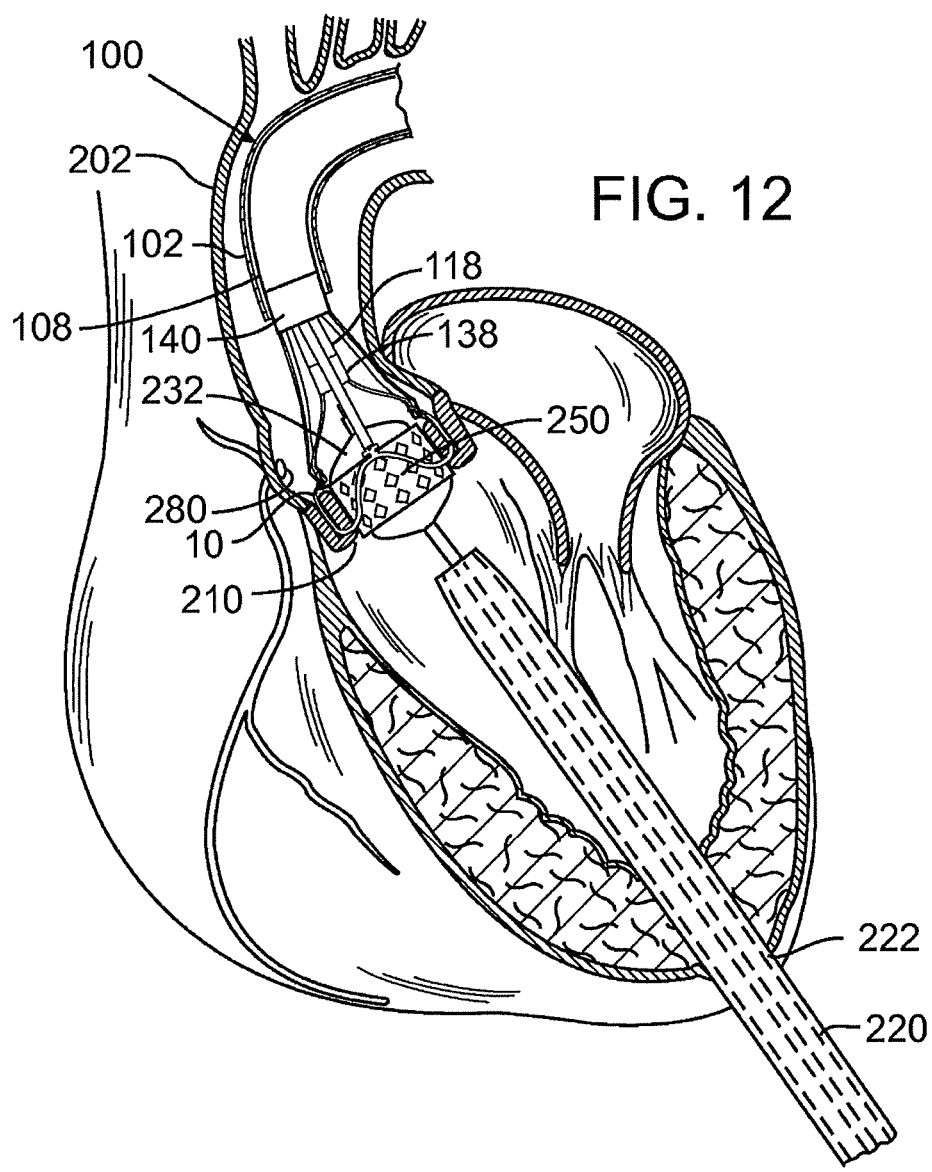
Figure 13:
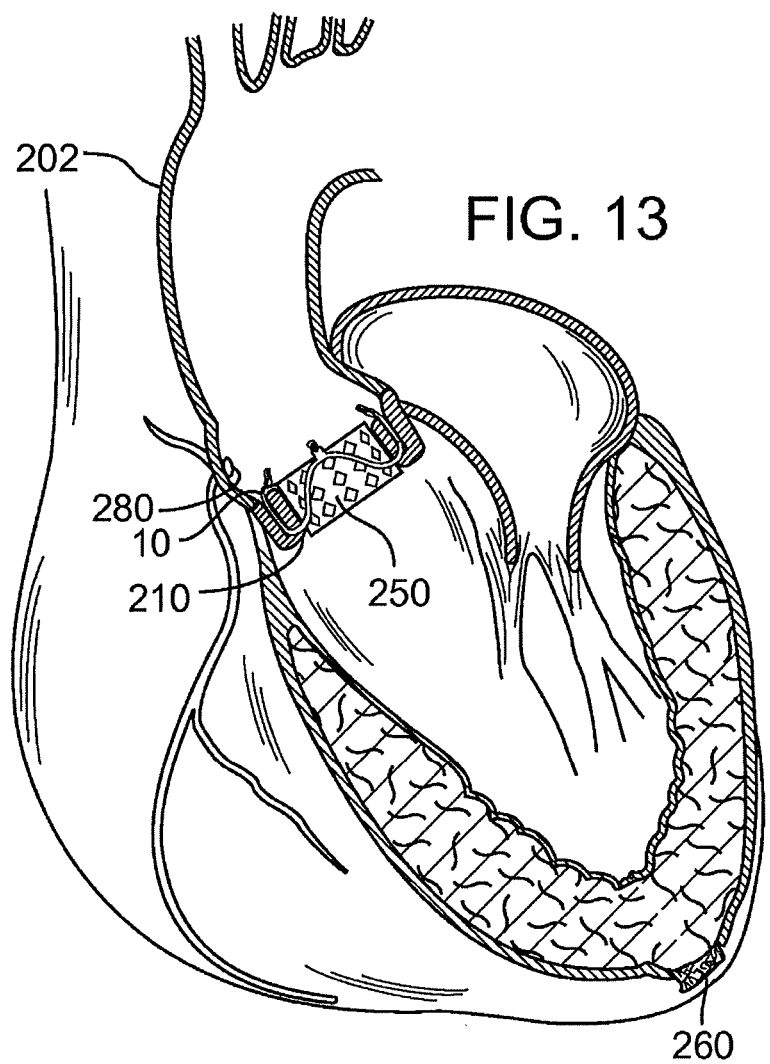

FIG. 10 shows the advancement of the balloon catheter 230 over the guidewire 224 and through the introducer sheath 220. Ultimately, as seen in FIG. 11, the THV 250 is located at the aortic annulus and between the native aortic leaflets. FIG. 11 also illustrates retraction of the introducer sheath 220 from its more distal position in FIG. 10. Radiopaque markers may be provided on the distal end of the introducer sheath 220 to more accurately determine its position relative to the valve 210 and balloon 232. In order to better illustrate the components of the delivery system for the THV, FIGS. 10-11 do not show the front third of the support stent 10 or the corresponding outer and inner prong of the outer fork and the inner fork, respectively. Furthermore, for purpose of illustrating the relative position of the support stent 10 on the THV 250, FIGS. 12-13 show the front third of the support stent 10 and the front of the THV 250, but do not show the portions of the native heart valve that would be secured by the front of the support stent 10. It is to be understood, however, that a corresponding leaflet of the native heart valve would be secured between the support stent 10 and the THV 250.

Again, the precise positioning of the THV 250 may be accomplished by locating radiopaque markers on its distal and proximal ends. In some embodiments, the clinician can adjust the position of the valve 250 by actuating a steering or deflecting mechanism within the balloon catheter 230. Furthermore, the rotational orientation of the valve 250 can be adjusted relative to the cusps and commissures of the native aortic valve by twisting the balloon catheter 230 from its proximal end and observing specific markers on the valve (or balloon catheter) under fluoroscopy. One of the coronary ostia 280 opening into one of the sinuses of the ascending aorta is also shown in FIG. 11, and those of skill in the art will understand that it is important not to occlude the two coronary ostia with the prosthetic valve 250.

FIG. 11 shows the THV 250 in its contracted or unexpanded state crimped around the balloon 232. When the clinician is satisfied of the proper positioning and rotational orientation of the valve 250, the balloon 232 is expanded to engage the support stent 10 as seen in FIG. 12. The engagement of the support stent 10 to the exterior of the THV 250 pinches the leaflets of the aortic valve between the support stent and the THV 250, and thereby secures the THV within the annulus of the aortic valve. Once secured into this position, the inner catheter 118 of the delivery system 100 can be retracted, thereby causing the prongs of the inner fork 138 to become disengaged from the retaining arms of the support stent 10. Once the prongs of the inner fork 138 are disengaged, the prongs of the outer fork 140 can be disengaged from the retaining arms by retracting the stent delivery catheter 108. Once disengaged from the support stent, the delivery system 100 can be retracted from the aortic arch and removed from the patient.

It should be noted that the valve 250 can take a variety of different forms and may comprise an expandable stent portion that supports a valve structure. The stent portion desirably has sufficient radial strength to hold the valve at the treatment site and to securely engage the support stent 10. Additional details regarding balloon expandable valve embodiments that can be used in connection with the disclosed technology are described in U.S. Pat. Nos. 6,730,118 and 6,893,460, both of which are hereby expressly incorporated herein by reference.

Once the valve 250 is properly implanted, as seen in FIG. 13, the balloon 232 is deflated, and the entire delivery system including the balloon catheter 230 is withdrawn over the guidewire 224. The guidewire 224 can then be withdrawn, followed by the introducer sheath 220. Ultimately, purse-string sutures 260 at the left ventricular apex can be cinched tight and tied to close the puncture.

Figure 14:
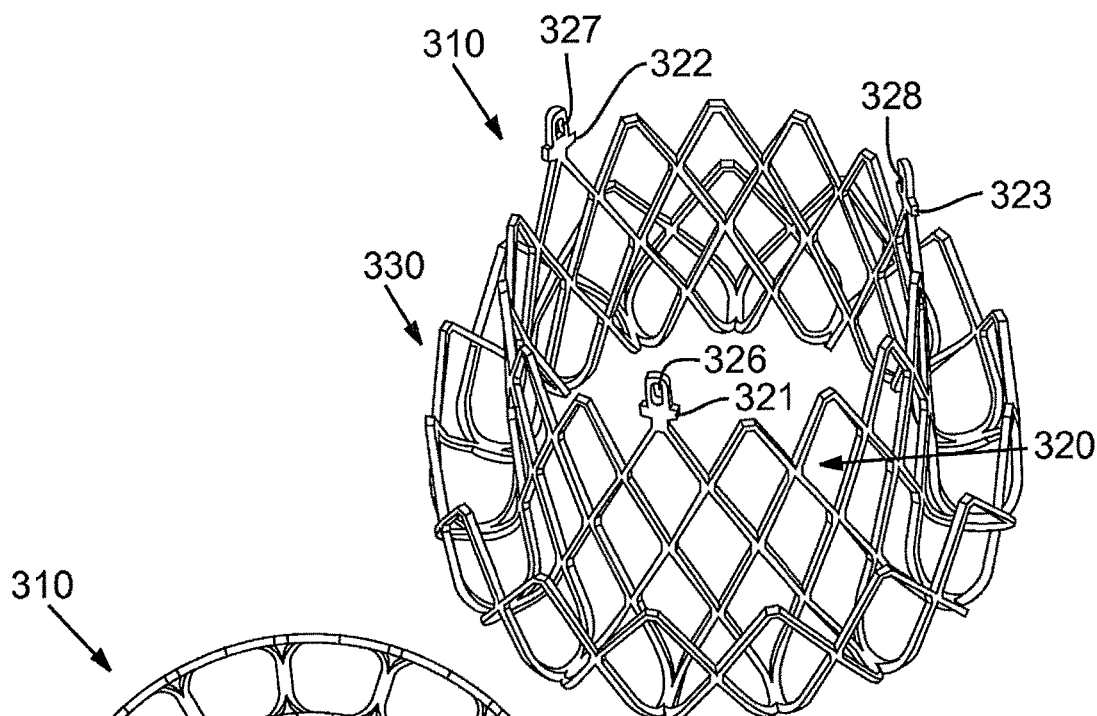
FIG. 14 is a perspective view of another exemplary embodiment of a support structure according to the disclosed technology.
Figure 15:
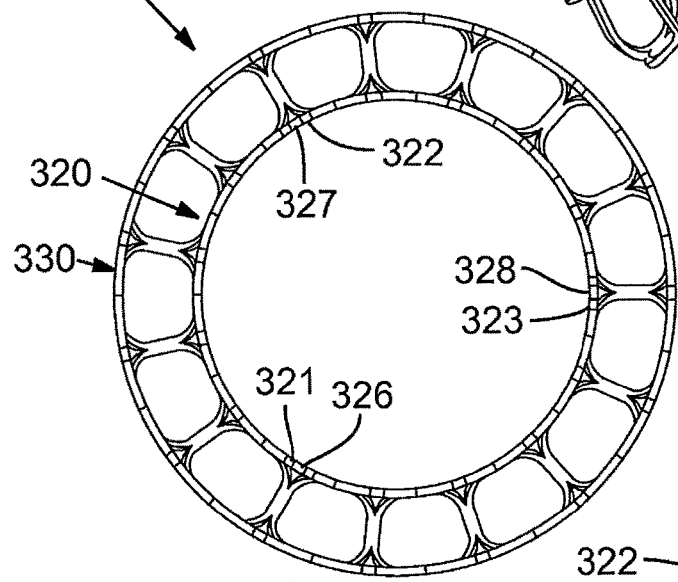
FIG. 15 is a top view of the support structure embodiment shown in FIG. 14
Figure 16:
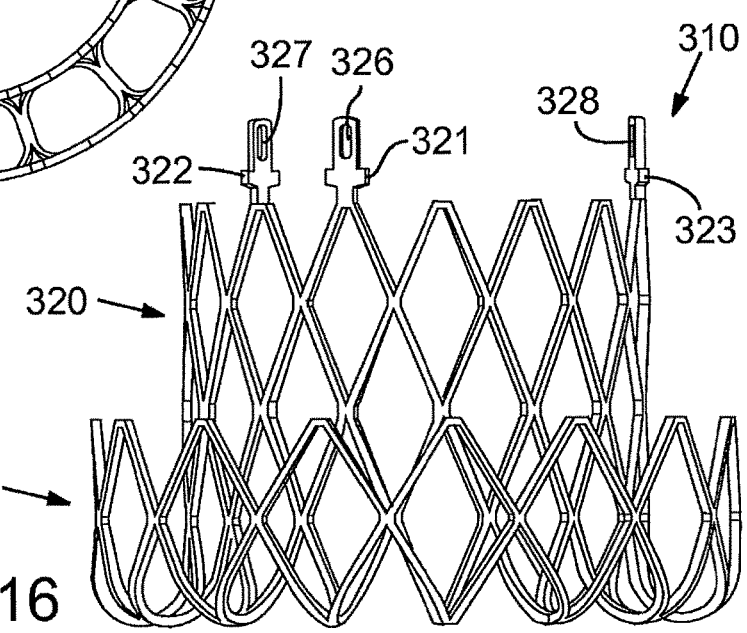
FIG. 16 is a side view of the support structure embodiment shown in FIG. 14.

FIGS. 14-16 shows another embodiment of a support stent or frame 310 that can be used to help secure a THV into the interior of a native heart valve, such as the aortic valve. In particular, FIG. 14 is a perspective view of the support stent 310, FIG. 15 is a top view of the support stent 310, and FIG. 16 is a side view of the support stent 310. Like support stent 10, support stent 310 has a generally annular or toroidal body formed from a suitable shape-memory metal or alloy, such as spring steel, cobalt-chromium alloy (Elgiloy®), or nitinol. The support stent 310 is also radially compressible to a smaller profile and can self expand when deployed into its functional size and shape. In other embodiments, however, the support stent 310 is not self expanding.

The support stent 310 includes a generally cylindrical main body portion 320 and a rim portion 330. The support stent 310 can be a mesh structure, which can be formed, for example, from multiple elements in which approximately half of the elements are angled in a first direction and approximately half of the elements are angled in a second direction, thereby creating a criss-cross or diamond-shaped pattern. In the illustrated embodiment, the rim portion 330 has a greater diameter than the main body portion 320 and is formed as an extension at a bottom region of the main body portion that is folded outwardly from the main body portion and back toward a top region of the main body portion. The rim portion 330 thus forms a U-shaped rim or lip around the bottom region of the support stent 310. In general, the rim portion 330 is designed to have a diameter that is slightly larger than the walls of the aortic arch that surround the aortic valve. Thus, when the support stent 310 is delivered to the aortic valve and deployed at the aorta, the rim portion 330 expands to engage the surrounding aorta wall and frictionally secures the support stent 310. At the same time, the main body portion 320 defines an interior into which an expandable THV can be expanded and which further engages the native leaflets of the aortic valve. Thus, the main body portion 320 operates in the same manner as the support stent 10 described above and illustrated in FIGS. 1-12, whereas the rim portion 330 of the support stent 310 operates to secure the support stent in place by engaging the walls of the aorta that surround the aortic valve.

As best seen in FIGS. 14 and 16, the support stent 310 further includes retaining arms 321, 322, 323 that can be used to help position and deploy the support stent 310 into its proper location relative to the native aortic valve. The retaining arms 321, 322, 323 can have respective apertures 326, 327, 328. In general, the retaining arms 321, 322, 323 are constructed and function in a similar manner as retaining arms 21, 23, 25 described above in the embodiment illustrated in FIGS. 1-12.

Figure 17:
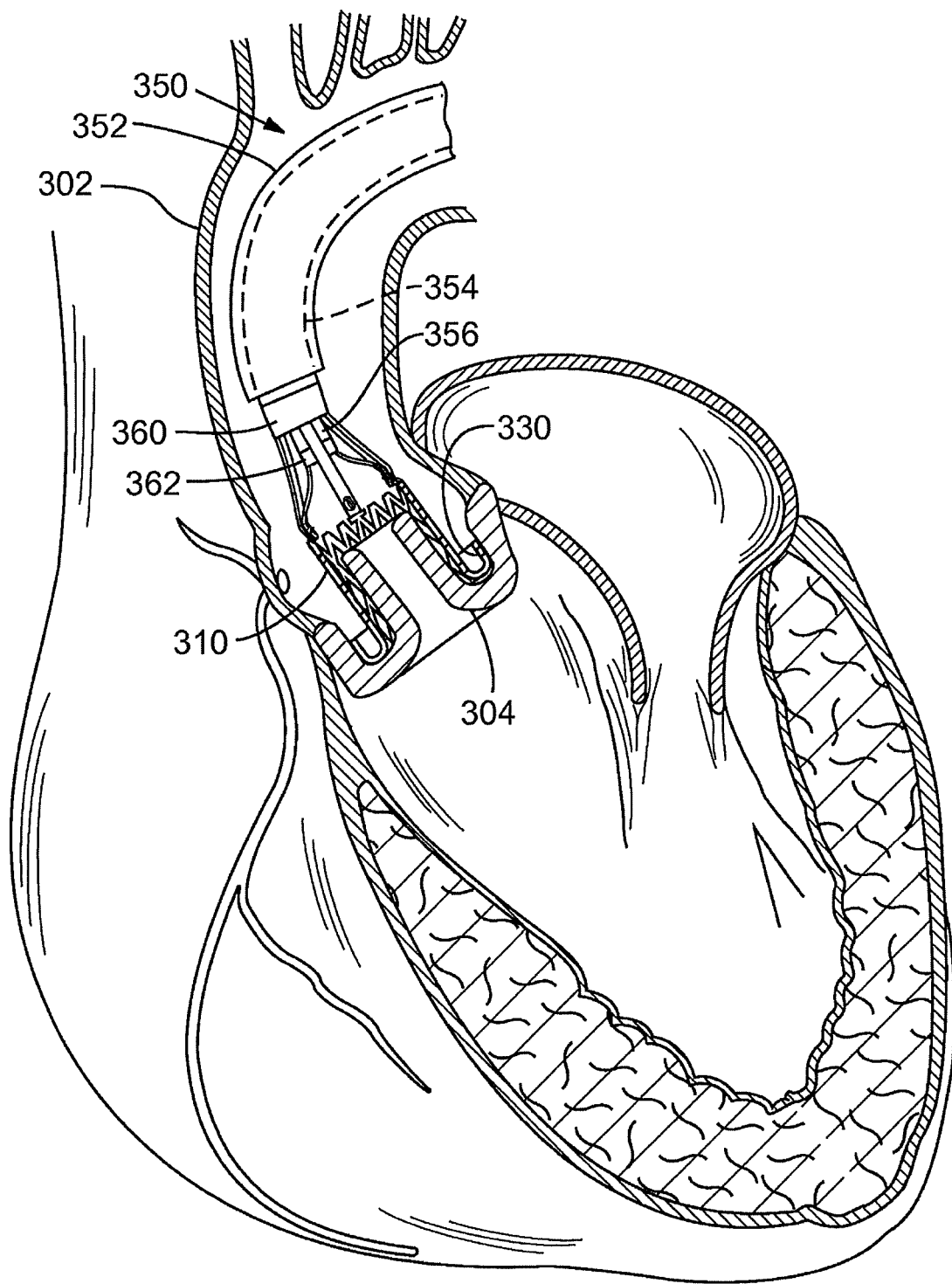
FIG. 17 is a cross-sectional view of a patient's heart illustrating how a delivery system can operate to deploy the support structure of FIG. 14 to a desired position on the patient's aortic valve.
Figure 18:
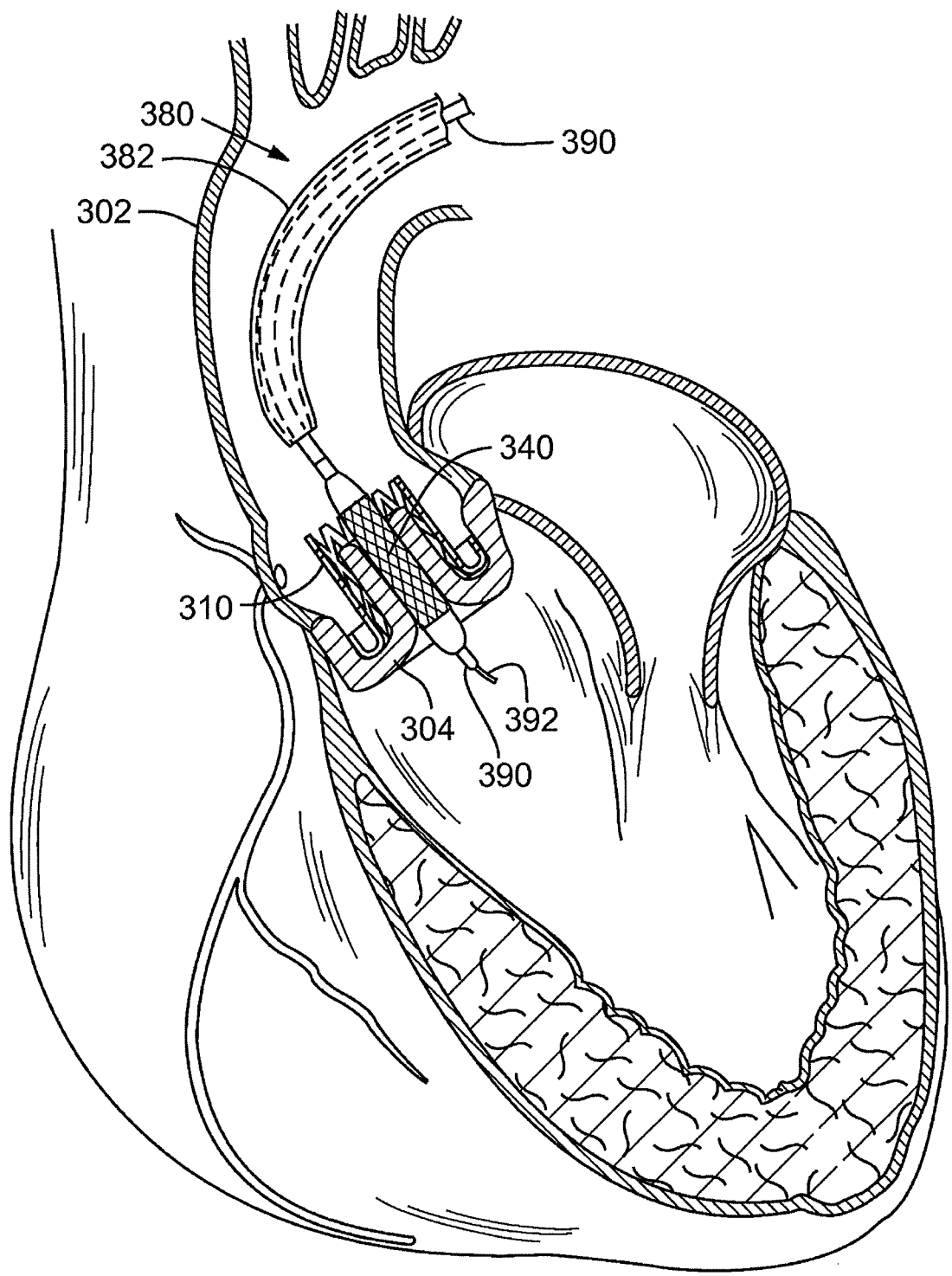
FIG. 18 is a cross-sectional view of a patient's heart illustrating how an exemplary THV can be deployed through the aortic arch and into the patient's aortic valve, where it can be frictionally secured to the native leaflets using the support structure of FIG. 14.

FIGS. 17-18 illustrate one exemplary procedure for deploying the support stent 310 and securing a THV 340 within an interior of the support stent. In particular, FIGS. 17-18 are cross-sectional views through the left side of a patient's heart showing the acts performed in delivering the support stent 310 through the aortic arch to the aortic valve. For the sake of brevity, certain details concerning the delivery system of the THV 340 are omitted. Additional details and alternative embodiments of the delivery system for the THV 340 that may be used with the support stent described herein are discussed in U.S. Patent Application Publication No. 2008/0065011 (U.S. application Ser. No. 11/852,977) and U.S. Patent Application Publication No. 2007/0005131 (U.S. application Ser. No. 11/152,288), which are hereby expressly incorporated herein by reference.

FIG. 17 shows an outer catheter 352 (which can be a guide catheter) of a delivery system 350 as it is advanced through the aortic arch 302 into a position near the surface of the outflow side of the aortic valve 304. The delivery system 350 can be inserted through the femoral artery of the patient and advanced into the aorta in the retrograde direction. FIG. 17 also shows a stent delivery catheter 354, an inner catheter 356, and the support stent 310. Also seen in FIG. 17 are the outer fork 360 and the inner fork 362, which couple the support stent 310 to the distal ends of the stent delivery catheter 354 and the inner catheter 356, respectively.

More specifically, FIG. 17 shows the support stent 310 after it has been advanced through the distal end of the guide catheter 352 and assumes its final, uncompressed shape in a position adjacent to the aortic valve 304. In order to better illustrate the components of the delivery system for the THV, FIGS. 17-18 do not show the entire front side of the support stent 310 or the corresponding valve leaflet that would be secured by the front side of the support stent 310. It is to be understood, however, that in practice the entire support stent 310 would exist and engage a corresponding leaflet of the native heart valve.

The support stent 310 can be positioned adjacent to the aortic valve 304 so that the rim portion 330 of the support stent engages the walls surrounding the aortic valve 304 and exerts an outward force against those walls, thereby securing the support stent 310 within the aorta. This positioning can be achieved, for example, by advancing the guide catheter 352 to a position directly adjacent the aortic valve 304 while the stent delivery catheter 354 and the inner catheter 356 are undeployed and while the support stent 310 remains in its compressed state. The guide catheter 352 can then be retracted while the stent delivery catheter 354 and the inner catheter 356 are held in place, thereby allowing the support stent 310 to expand toward its natural shape. As with the delivery system 100 described above, the position of the guide catheter 352 and the support stent 310 relative to the aortic valve 304, as well as the position of other elements of the system, can be monitored using radiopaque markers and fluoroscopy, or using other imaging systems such as transesophageal echo, transthoracic echo, IVUS, or an injectable dye that is radiopaque.

Once the support stent 310 is positioned into the desired location adjacent the aortic valve 304, the prongs of the inner fork 362 can be disengaged from the corresponding apertures of the retaining arms of the support stent 310. For example, the inner catheter 356 can be retracted into the interior of the stent delivery catheter 354, thereby releasing the support stent 310 from the outer fork 360 and the inner fork 362. The delivery system 350 can then be retracted from the aorta and removed from the patient's body.

With the support stent 310 secured to the aortic valve, a THV (such as any of the THVs discussed above) can be introduced. In contrast to the procedure illustrated in FIGS. 7-13, a delivery system having a delivery catheter that is advanced through the patient's aorta can be used to deliver the THV. In other words, a transfemoral approach can be used. For instance, any of the exemplary systems and methods described in U.S. Patent Application Publication No. 2008/0065011 (U.S. application Ser. No. 11/852,977) or U.S. Patent Application Publication No. 2007/0005131 (U.S. application Ser. No. 11/152,288) can be used with the support stent 310. Alternatively, the transapical approach shown in FIGS. 7-13 can be used.

FIG. 18 shows delivery system 380 comprising an outer catheter 382 (which can be a guide catheter) and a balloon catheter 390 extending through the guide catheter. The balloon catheter 390 has a balloon at its distal end on which the THV is mounted. As with the delivery system 350, the delivery system 380 can be inserted through the femoral artery of the patient and advanced into the aorta in the retrograde direction. FIG. 18 further shows a guidewire 392 that has been first inserted into the patient's vasculature and advanced into the left ventricle. The delivery system can then be inserted into the body and advanced over the guidewire 392 until the THV is positioned within the interior of the aortic valve. As shown, the THV is not only in the interior of the aortic valve 304 but also in the interior of the main body portion of the support stent 310.

FIG. 18 shows the THV 340 in its contracted (or unexpanded) state crimped around the balloon portion of the balloon catheter 390. When the clinician is satisfied of the proper positioning, the balloon of the balloon catheter 390 can be expanded such that the THV 340 expands and urges the native leaflets of the aortic valve against the support stent 310, thereby securing the THV within the annulus of the aortic valve. Once the THV 340 is properly implanted, the balloon of the balloon catheter 390 is deflated, and the entire delivery system 380 including the balloon catheter is withdrawn over the guidewire 392. The guidewire 392 can then be withdrawn.

Other methods of delivering a support stent and THV to the aortic valve or any other heart valve are also possible. For example, in certain embodiments, the support stent and the THV are delivered surgically to the desired heart valve (e.g., in an open-heart surgical procedure). Furthermore, in certain embodiments in which the support stent and THV are delivered surgically, non-compressible support stents and/or THVs are used.

Exemplary Embodiments for Treating Valve Insufficiency and Vessel Aneurysms

Aortic insufficiency (AI) can cause dilatation of the ascending aorta, causing aneurisms, as well as the aortic annulus. In order to prevent further dilatation, embodiments of the present invention provide for anchoring of a deflector that directs blood away from the aneurysm while at the same time treating the insufficient heart valve.

Figure 19:
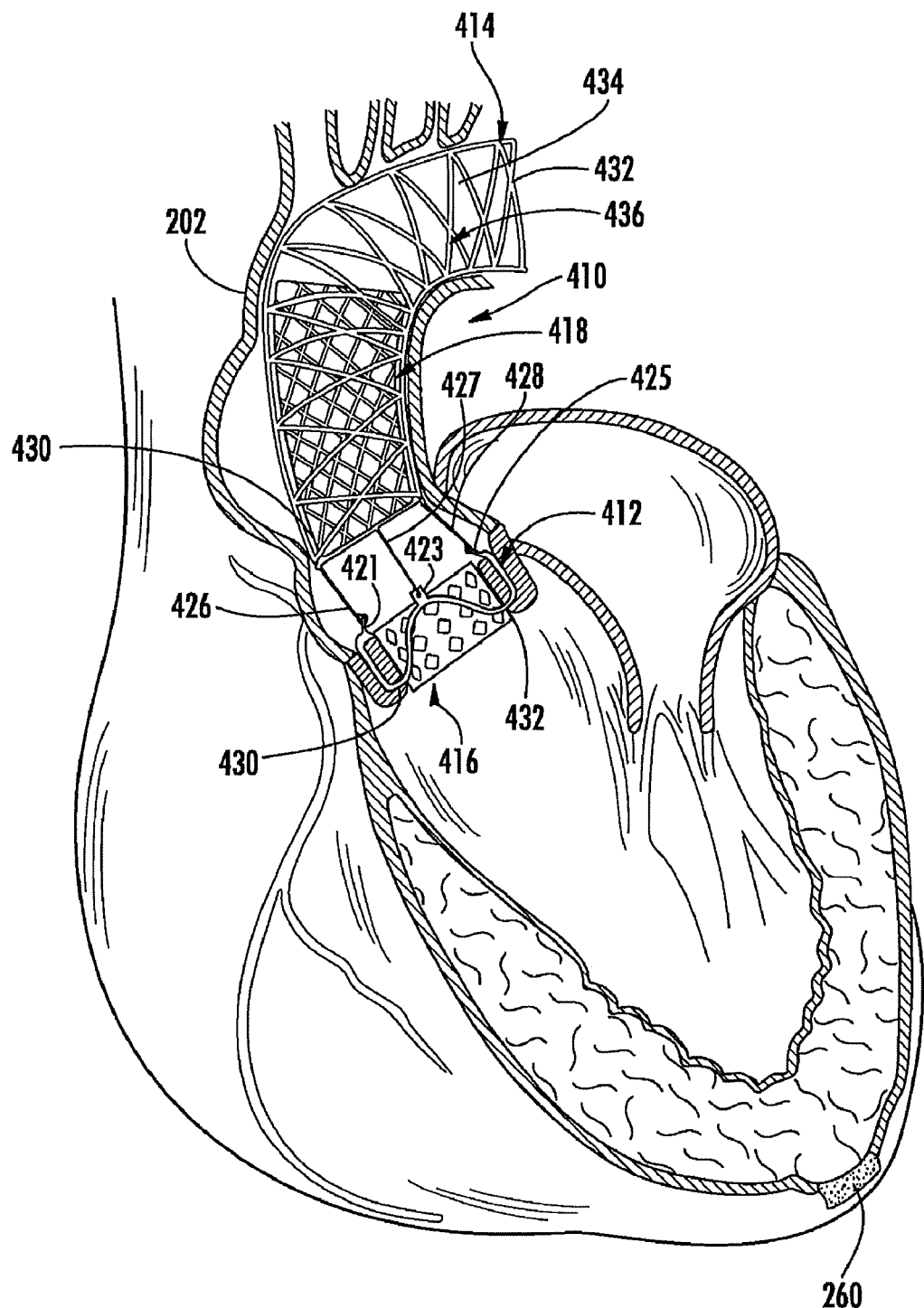
FIG. 19 is a cross-sectional view of a patient's heart showing a medical device of another embodiment of the present invention including a stent that supports a deflector for treating vessel aneurysms.

As shown in FIG. 19, one embodiment of a medical device 410 for treating AI (or aneurism(s) or defects of any other vessel associated with a valve) includes a support structure 412, a stent 414, a prosthetic valve 416 and a deflector 418. The support structure 412 is configured, similar or the same as the support structures described hereinabove, to cooperate with the prosthetic valve 416 to pinch the native valve therebetween and provide an anchor for the stent 414 which extends into the aorta and supports the deflector 418 which is positioned to abate blood flow against the aneurysm.

The support structure 412 (stent or frame) includes, for example in FIG. 19, peaks 420, 422, 424 and valleys 430, 432, 434 and retaining arms 421, 423, 425 defining apertures 426, 427, 428. Similar to the other embodiments of the support structures disclosed herein, a range of variations are possible for anchoring the both the stent 414 and the prosthetic valve 416 and the deflector 418.

As noted above, it should be understood that the shape of the support stent or frame 410 can vary from implementation to implementation. For example, in some embodiments, the support stent is not sinusoidal or otherwise shaped in the z-plane. In other embodiments, the support stent is shaped as a cylindrical band or sleeve. In general, the support stent or frame can be any shape that defines an interior through which a THV can be inserted, thereby causing the native leaflets of the aortic valve (or other heart valve) to be pinched or securely held between the support stent and the THV. Furthermore, the support stent can have a more complex structure. For example, although the support stent illustrated in FIG. 19 is formed from a single annular member (or strut), the support stent can comprise multiple annular elements that interlock or are otherwise connected to one another (e.g., via multiple longitudinal members).

The prosthetic valve 416 of the embodiment illustrated in FIG. 19 is a THV that is similar to the one illustrated in FIG. 1. As noted above, it should be understood, however, that this particular usage is for illustrative purposes only and should not be construed as limiting. Instead, embodiments of the disclosed support structure can be used to secure a wide variety of THVs delivered through a variety of mechanisms (e.g., self-expanding heart valves, other balloon-expanding heart valves, and the like). For instance, any of the embodiments described in U.S. Pat. No. 6,730,118 can be used with embodiments of the disclosed support structure.

As shown in FIG. 19, the stent 414 is a scaffold that is coupled to the support structure 412 and extends from the support structure into the aorta (and over the insufficient portions of the aorta). The stent 414 has a proximal end 430, a distal end 432, and a plurality of interconnected struts 434 defining a plurality of cells 436.

In FIG. 19, the proximal (with respect to the heart) end 430 of the stent 414 is connected or coupled to the support structure 412 by being formed therewith or attachment by wires or other supports. For example, the support structure 412 and stent 414, including the plurality of interconnected struts 434, may be laser cut from a single metal tube. As described hereinbelow, coupling may also be by assembly after separate formation, include assembly in vivo as each portion of the medical device 410 is delivered.

Figure 20:
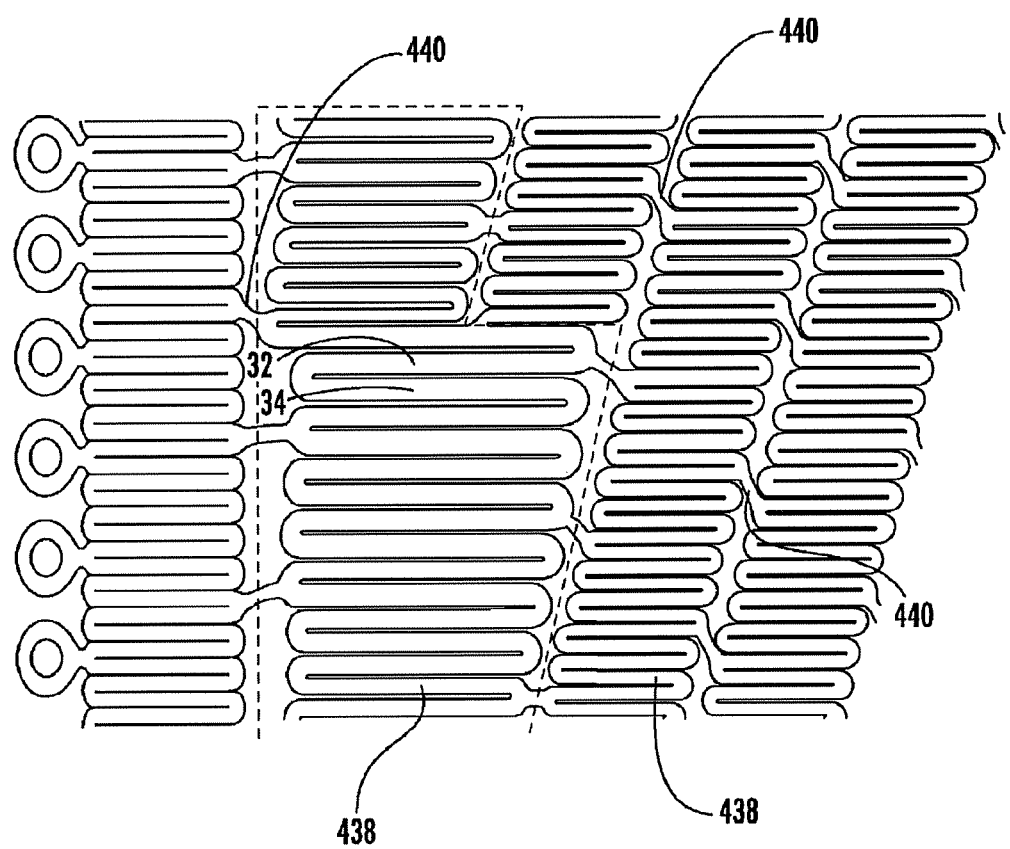
FIG. 20 is a plan view of a portion of a scaffold of the stent of FIG. 19.

Extending from the proximal end 430 in the distal direction is the body of the stent 414 that is formed by the interconnected struts 434 that define between them the cells 436. Preferably, the interconnected struts 434 are formed to promote flexibility and facilitate delivery through tortuous paths and extension over the aortic arch. For example, the strut pattern may be as shown (as a flattened portion of a laser-cut blank prior to expansion) in FIG. 20 and include a plurality of rings 438 formed by sinusoidal struts connected end-to-end, wherein the rings are connected by a plurality of angled, flexible connectors 440. Also, the rings 438 may be formed to have variable lengths and the connectors 440 selectively located to promote directional preferences in flexibility and/or variations in cell sizes between them.

An example of a flexible stent structure is the LIFESTENT manufactured by C.R. BARD, INC. which has a multi-dimensional helical structure that facilitates its use in tortuous paths of peripheral vasculature. Aspects of the LIFESTENT are described in U.S. Pat. No. 6,878,162 entitled "Helical Stent Having Improved Flexibility and Expandability" by Bales et al.

Such flexibility is advantageous for treatment of AI in that the stent 414, when extending along the aortic arch, has a tightly curved configuration with an external, long curvature 442 and an internal curvature 444. Along the external curvature 442 the cell sizes may be larger to allow for the longer path length. These cell sizes may be programmed into the stent by selective cutting and formation of the struts and cells and/or may appear due to the mechanical application of insertion and delivery into the aortic arch. Similarly, the internal curvature 444 may be programmed through selection of the strut structure and/or due to delivery.

In addition, the stent 414 may include structure that facilitates engagement, frictional or mechanical, of the surrounding lumen (e.g., the aorta) where the lumen is in adjacent contact with the stent. For instance, the struts 434 and cells 436 may have a pattern that facilitates frictional engagement, or may have barbs or hooks or micro-anchors or flared portions formed thereon to mechanically engage the lumen and facilitate the support structure 412's role of securing the medical device 410.

The distal end 432 of the stent 414 is positioned within the aortic arch distal the branch (e.g., brachiocephalic, common carotid and left subclavian) arteries extending off of the aorta. The distal end 432 may be a termination of the last row of the rings 438 or may include its own retaining arms 446 defining apertures 448. Use of the retaining arms 446 and apertures 448 enables use of the delivery apparatus 110 shown in FIGS. 3 and 4 and described hereinabove. The distal end 432 may also include structure configured to engage the surrounding lumen walls for additional security of the medical device 410. For example, it may include hooks or barbs or micro anchors.

In another aspect, the cells 436 may include a relatively large cell structure positioned over and near the branch arteries. This facilitates perfusion of the branch arteries, such as by being located over the branch arteries at the aortic arch or closer to the valve for communication with the coronary arteries. The cell structure is relatively large in comparison to the remaining cells configured to support the lumen walls or abate blood flow against aneurysms or further vascular dilatation. In another aspect, the cell size may be selected to guard the branch arteries against embolic debris, so as to act as a partial deflector of such debris.

Figure 21:
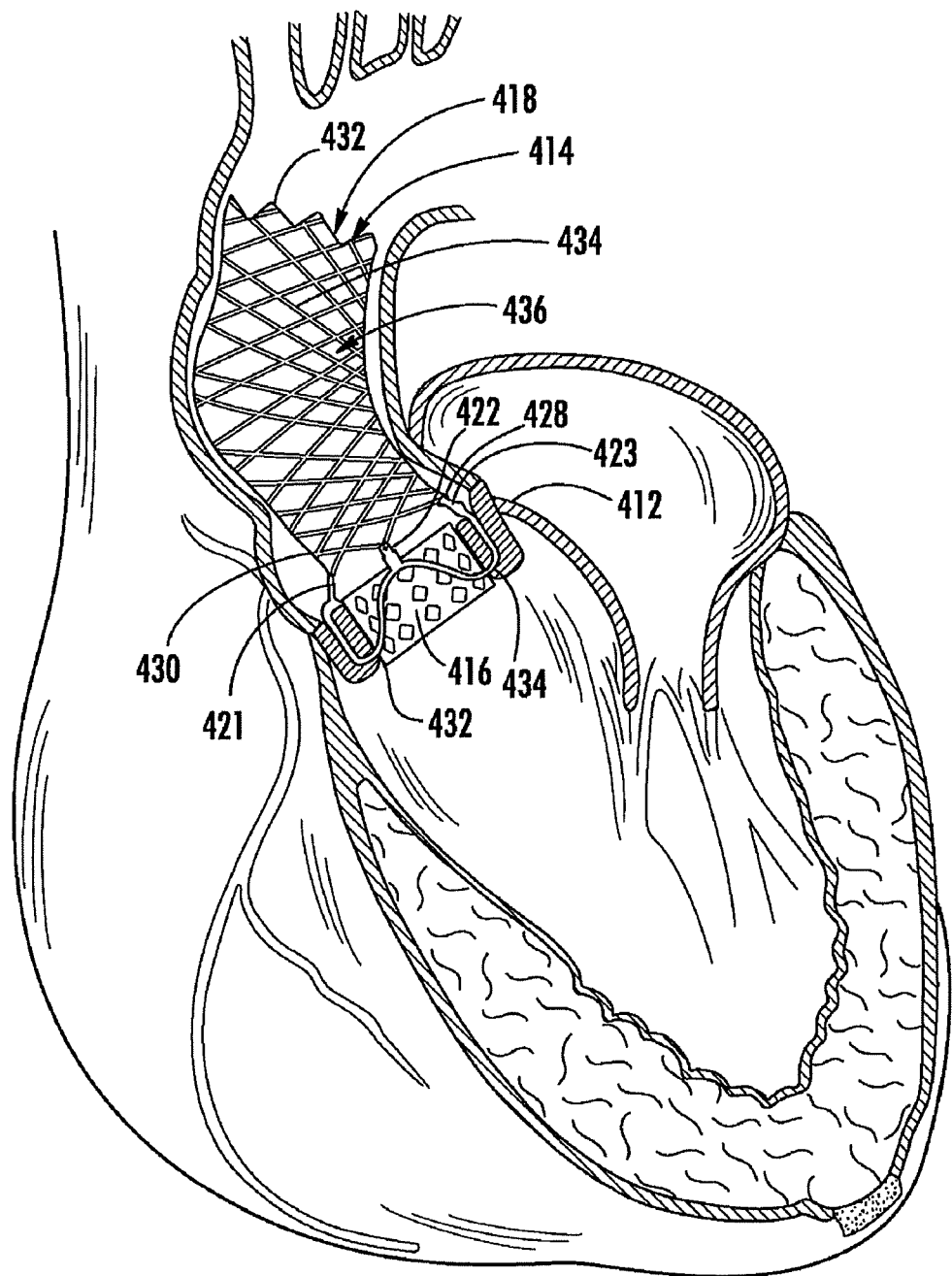
FIG. 21 is a cross-sectional view of a patient's heart showing a medical device of another embodiment wherein a stent is covered with a deflector and is tapered.

The length of the device 410, including the support structure 412 and stent 414, may be enough to extend from the native leaflets, through the sinus of valsalva, into the ascending aorta, over the aortic arch and potentially into the descending aorta. For example, the length of the device 410 may be 30 mm to 100 mm or longer. The stent 414 may also be tapered, small at the annulus to larger at the ascending aorta, columnar or have ends that are a larger diameter for sealing and anchoring, as shown in FIG. 21.

Once this support structure 412 and stent 414 are deployed they act like a scaffold or anchoring device for other devices to be deployed inside of it, such as the prosthetic valve 416, which is delivered and anchored as described above, and one or more deflectors 418.

In FIG. 19, the deflector 418 is a covered stent or graft that is relatively impermeable (e.g. to blood flow and is configured for positioning over an aneurysm in the aortic arch so as to direct blood flow away from the aneurysm. The deflector 418 of the embodiment of FIG. 19 includes a deflector stent 450 supporting a tubular graft material 452 extending around the deflector stent. The deflector 450 is mounted within the stent 414 as would a graft being fit within a vessel without the stent 414. For example, the deflector 450 may be delivered by a catheter extending retrograde to blood flow within the aorta, or extending from the heart chamber and through the aortic valve, and then expanded (or allowed to expand) once the desired location is reached.

Advantageously, the stent 414 guards the aneurysm against the expansion pressure of the deflector 418 and the deflector can have a much smaller expanded diameter than the aneurysm and still is assured of a firm anchor.

Deployment of the medical device 410 of FIG. 19 may include first deploying the support structure 412 and the stent 414 (if they're integrally attached to each other). Then, through the support structure 412 and the sent 414 the THV prosthetic valve 416 is delivered, anchoring it into the proximal end of the device (either the support structure 412 or the stent 414). The covered stent or graft deflector 418 is deployed in the stent 414, covering the area that has the aneurysm and avoiding the branch arteries and associated larger cells 436 of the stent 414. The deflector 418 would then redirect the pulsating blood away from the aneurysm so as to prevent dissection, and the new valve prosthesis 416 would ensure that correct blood flow is restored.

Although the deflector 418 is shown in FIG. 19 as being a single graft or covered stent, the term "deflector" should be construed broadly herein to include any structure that serves to abate (reduce) blood flow against the selected portion of the vessel wall. For example, multiple deflectors 418 in the form of grafts or covered stents could be delivered and positioned to address anatomical variations in size and positioning of the aneurysm(s). Also, the deflector 418 need not be a tubular structure but could be a sheet or shield of material anchored to one side of the stent 414. Also, the deflector 418 need not be separately attached, but could be a portion of the stent 414 with reduced permeability, such as through a polymeric coating. FIG. 21 shows another example wherein the stent 414 is covered with a deflector 418 at the time of delivery.

Figure 22:
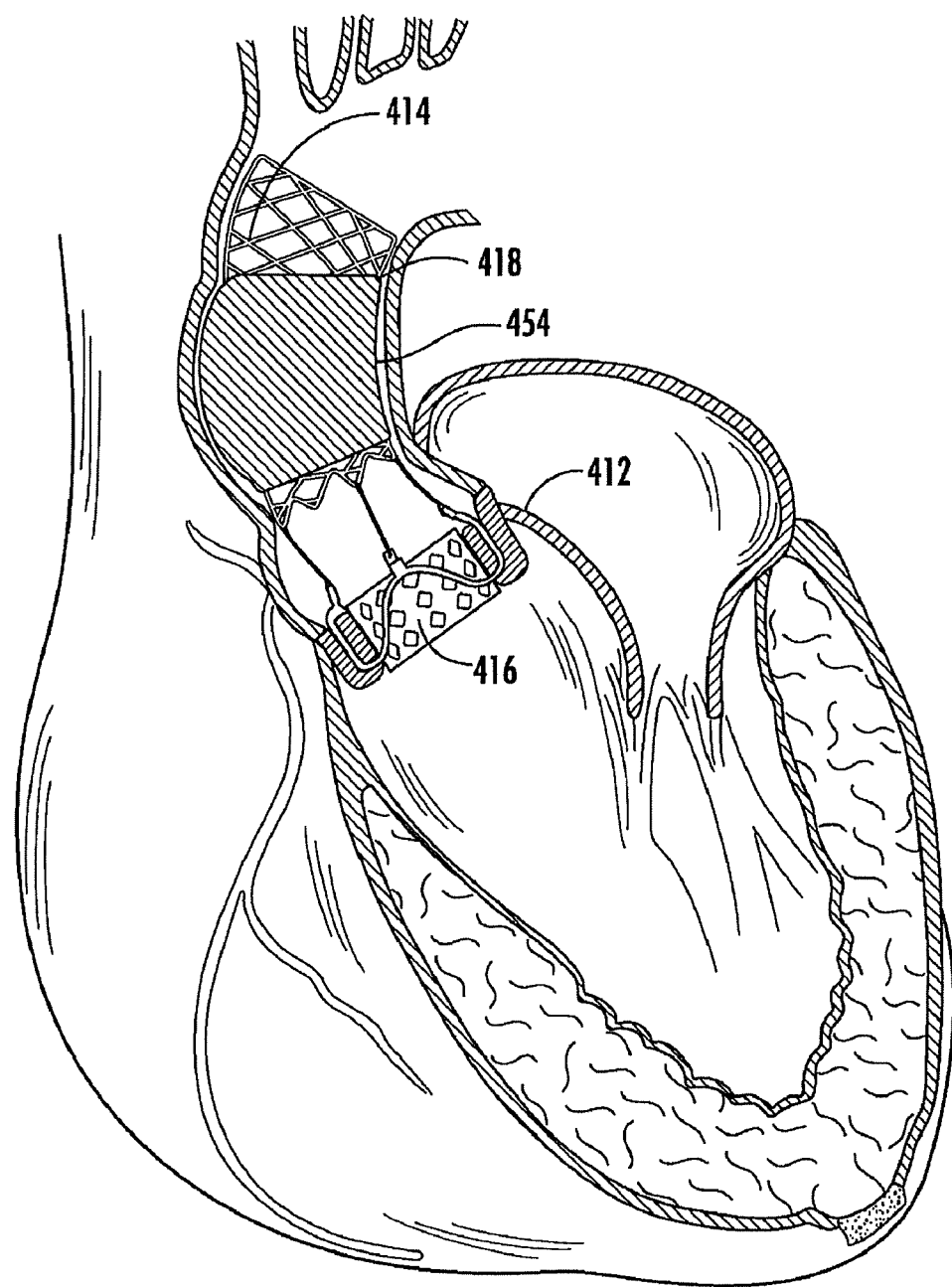
FIG. 22 is a cross-sectional view of a patient's heart showing a medical device of another embodiment wherein a stent is covered with a balloon configured to fill an aneurysm in the insufficient vessel.

FIG. 22 shows another example wherein the stent 414 is covered with a deflector 418 in the form of a balloon 454. The balloon not only deflects blood flow, but also can be inflated so as to expand into and fill the space between the stent 414 and the aneurysm wall. Inflation may be by fluid, such as saline wherein the balloon may include a one-way check valve that stops outflow of the saline after detachment of the inflation lumen. Also, inflation may be by a polymer or other fluid that sets or cures or thickens and can therefore maintain the fill shape after intervention is complete. Preferably, the expansion forces of the balloon 454 are sufficiently low so as to not further expanded the aneurysm but at the same time cause the balloon to take the shape of the aneurysm space. The balloon, therefore, may be comprised of a very pliable material such as a silicone that expands under low pressure and/or may even include a woven material. For woven materials, another advantage is that the woven material may have a limit to expansion and will protect the aneurysm from dissection if the woven balloon is fashioned to fit the aneurysm.

Figure 23:
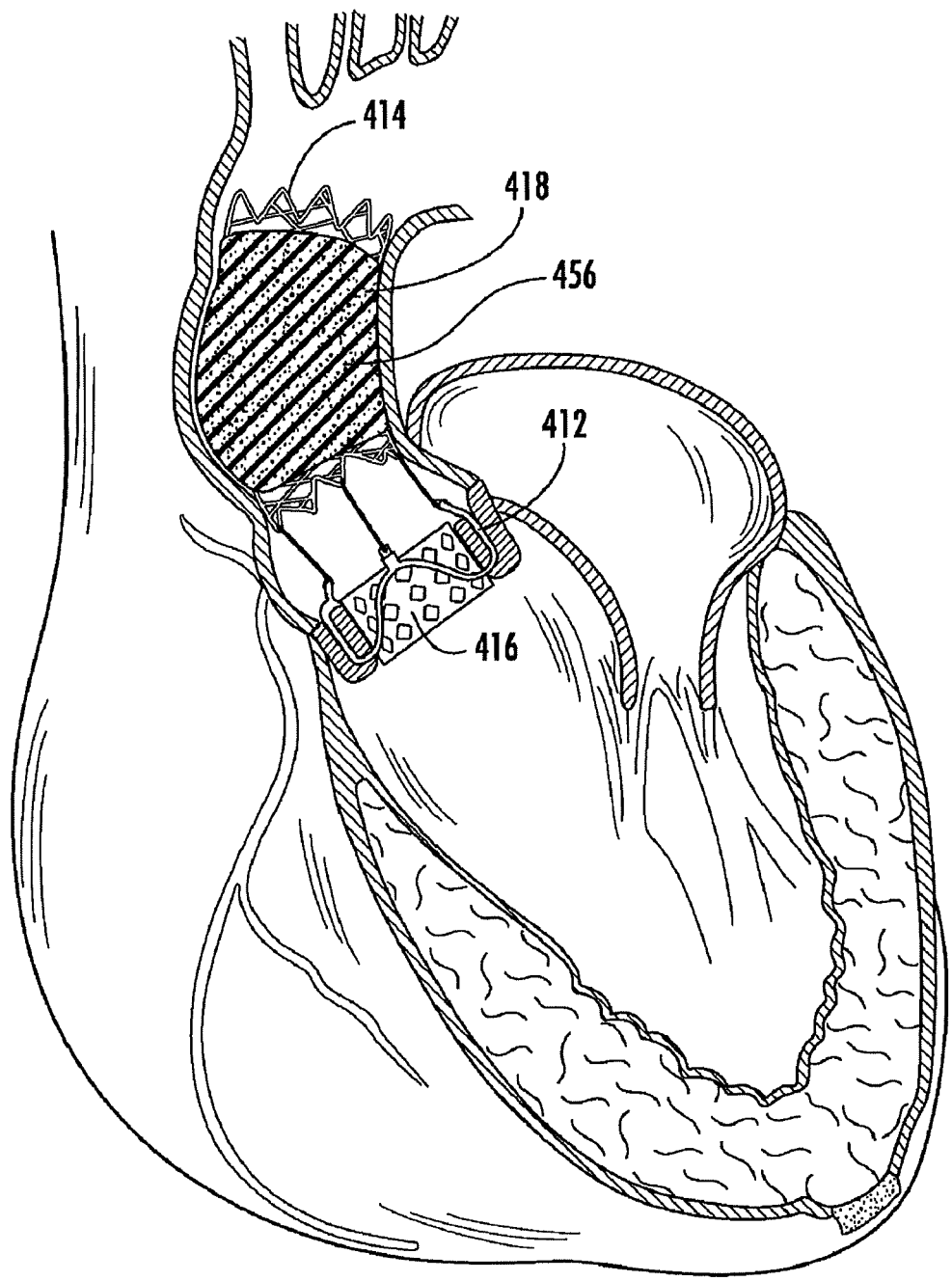
FIG. 23 is a cross-sectional view of a medical device of another embodiment wherein a stent is covered with a foam sleeve deflector.

FIG. 23 shows another example wherein the stent 414 is covered with a deflector 418 in the form of a foam sleeve 456. The foam may be an open celled foam or a closed-cell foam that promotes friction with the surrounding lumen at initial implantation. If open celled the blood will in-grow and create a barrier for the blood not to pass along the aortic wall. The foam may be configured for up to 300% compression.

Also, the foam may be configured, such as by being hydrophilic, to absorb and expand in blood and fill the space between the stent 414 and the lumen. A skin or impermeable layer can be also applied to the stent 414 or foam sleeve 456 so that the foam does not peel/break off and cause an embolism. The skin or impermeable layer inhibits seep of the passing blood through the foam to the aortic wall. For example, an inner surface of the foam sleeve 456 may have a relatively impermeable skin (such as a closed cell foam) to promote passage of blood therethrough while the outer surface is open celled and permeable for expansion.

The foam may also have coagulation properties that promote buildup of clots to help secure the medical device 410 and fill the aneurismal space. The foam may include, for example, a flexible ester polyurethane, reticulated open cell, felted foam with a pore size of 80-100 ppi, a density of 5.4-6.3 pcf. Also, thick woven sleeves may be used that expand in response to absorbing blood, such as a hydrophilic weave or foam.

During delivery, the foam sleeve 456 is crimped down with the stent 414 and then placed in the aorta of the patient. Upon expansion, the stent 414 expands and maintains its more rigid shape, whereas the foam can also expand and take up the current shape of the aorta. The foam advantageously fills the void between the stent 414 and the aneurysm wall, preventing blood (the continued pulse force) from reaching the aneurysm. The foam sleeve 456 creates a seal within the aorta forcing blood to be passed through the stent 414 diameter. It also has effective friction or outward forces on the aortic wall so as to restrict movement.

Figure 24:
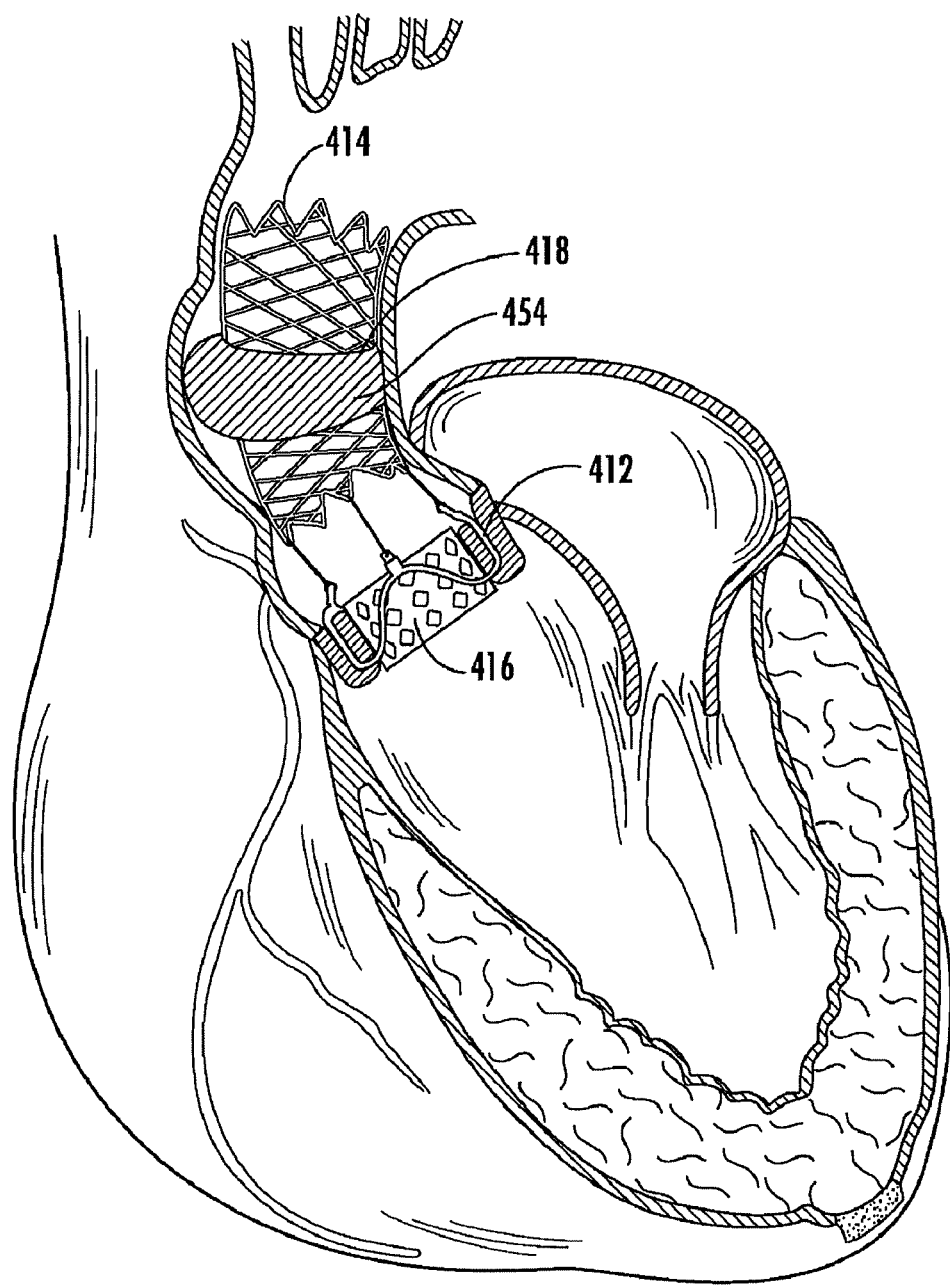
FIG. 24 is a cross-sectional view of a patient's heart showing a medical device of another embodiment including a deflector with an annulus shape.

FIG. 24 shows another example wherein the deflector 418 has an annulus or donut shape, such as a foam or balloon annulus. With its reduced length, the donut may be positioned at the location of the aneurysm, thereby blocking the flow of blood to this particular section of the aortic wall.

Figure 25:
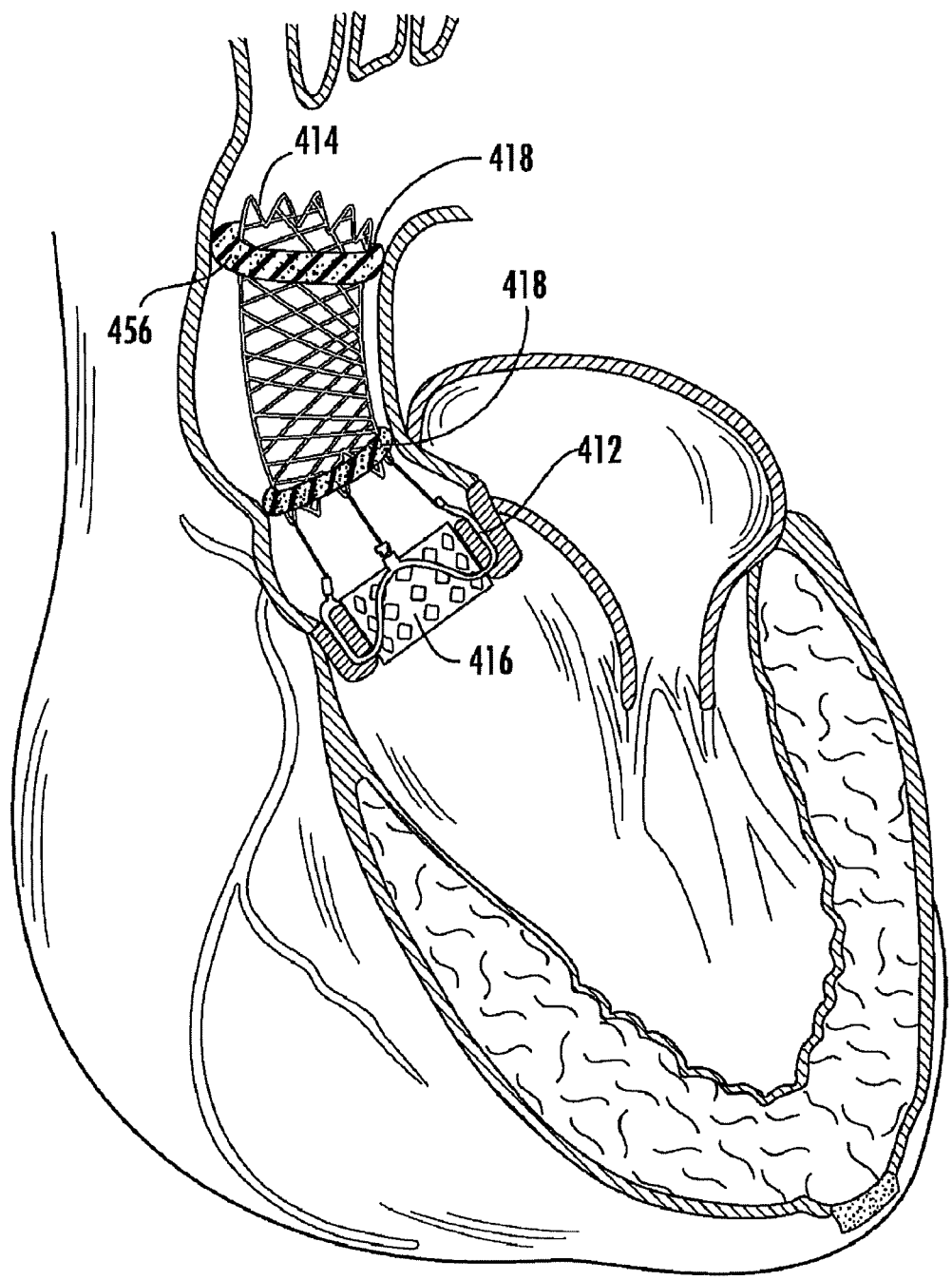
FIG. 25 is a cross-sectional view of a patient's heart showing a medical device of another embodiment including a pair of annulus shaped deflectors.

FIG. 25 shows another example including two donut or annulus shaped deflectors 418 on the stent 414 which aid in retention of the device within the aorta. In this variation, donuts may be placed on opposite sides of the aneurysm and seal the aneurysm against blood flow. The donuts may be foam, balloons or other expansion members. There may be several (more than two) of the annulus deflectors depending up the number and positioning and size of the aneurysms.

Figure 28:
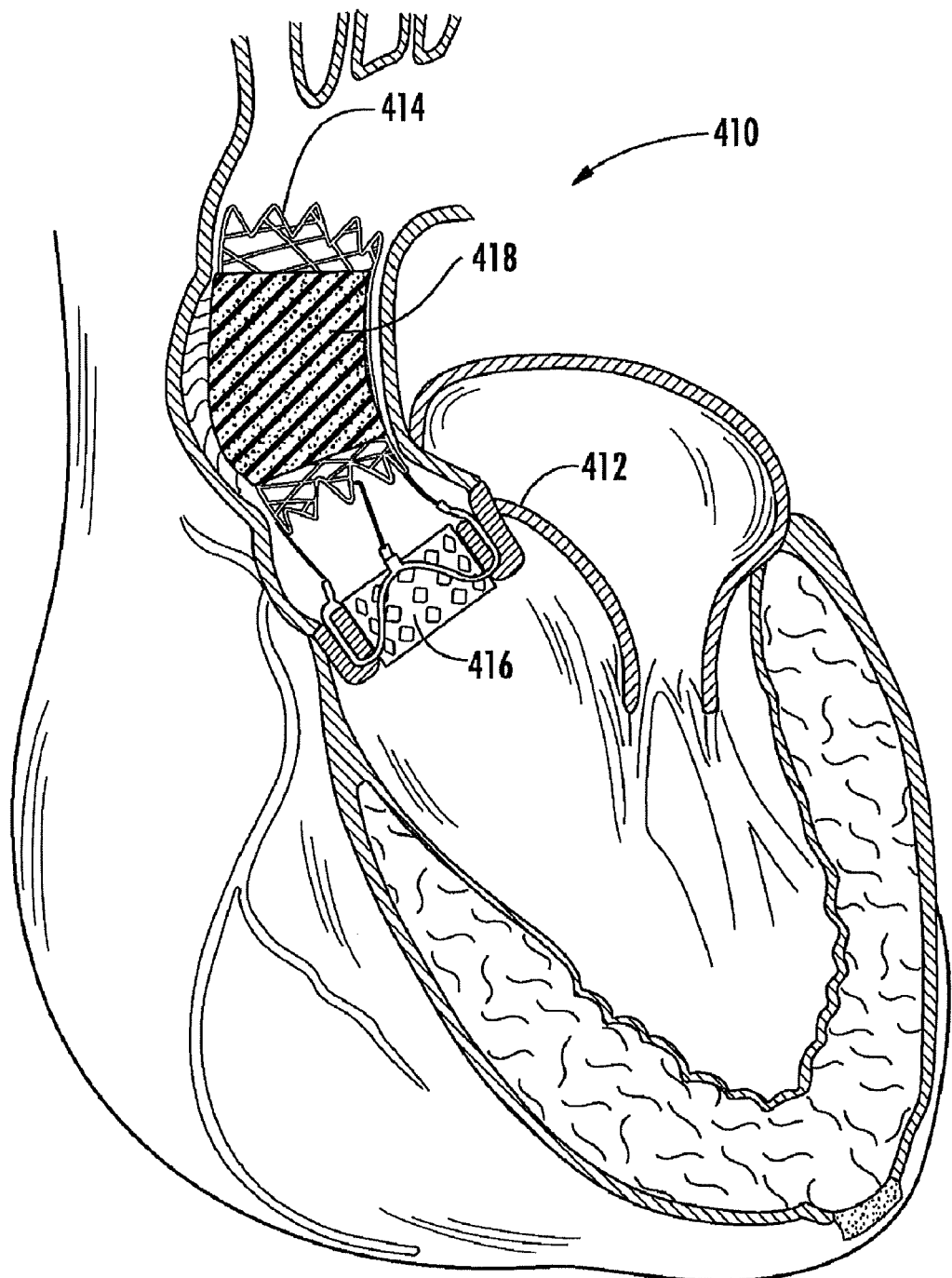
FIG. 28 is a cross-sectional view of a patient's heart showing a medical device of another embodiment including anchors on a foam deflector supported by a stent.

As shown in FIG. 28, the deflector 418 may include micro anchors attached to the foam or balloon section to aid in retention if the expansion force of the foam or balloon is not suitable in larger aortas.

In another aspect, the deflector 418 may include mechanical clot facilitators such as wires, coils or springs that fill the space between the stent 414 and the aneurysm walls to promote embolization therebetween.

Figure 26:
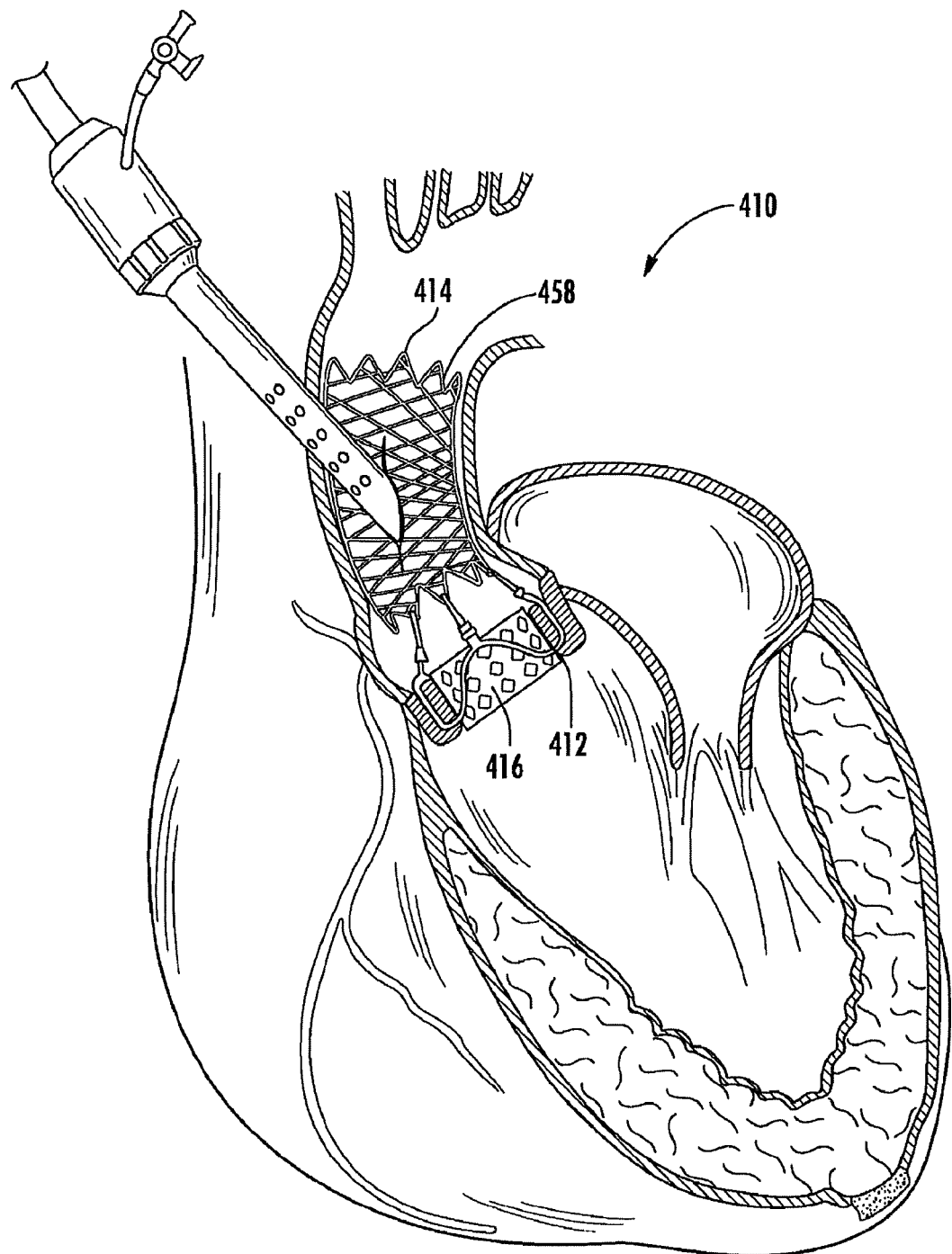
FIG. 26 is a cross-sectional view of a patient's heart showing a medical device of another embodiment including a deflector with a seal allowing passage of THV delivery device.

FIG. 26 shows another embodiment of the present invention wherein the deflector 418 (in the form of a graft) may include a seal 458 in the form of a slit configured to allow passage into the interior of the stent 414. For example, the seal 458 may include overlapping portions or lips of the graft material that self-seal by closing up after removal of delivery tool. Or, the seal may be a valve, such as a duckbill valve.

The graft 418 with the seal 458 may be used in a during a "trans-aortic" THV implantation wherein the graft is first deployed in a percutaneous delivery. The THV is then delivered through the chest wall with a delivery tool (e.g., a catheter) and through a slit in the aorta (aortotomy) and finally through the slit or seal 458 in the graft. The slit then seals around the delivery tool to prevent blood loss. The THV is expanded into place within the support structure 412 or stent 414. The seal 458 closes when the delivery tool is removed, allowing the aorta to be sutured without blood escaping. The graft 418 could be left behind—or it could be retrieved after completion of the procedure. Such a seal 458 may be employed in a range of embodiments with the deflector 418, including the embodiments disclosed herein.

Figure 27:
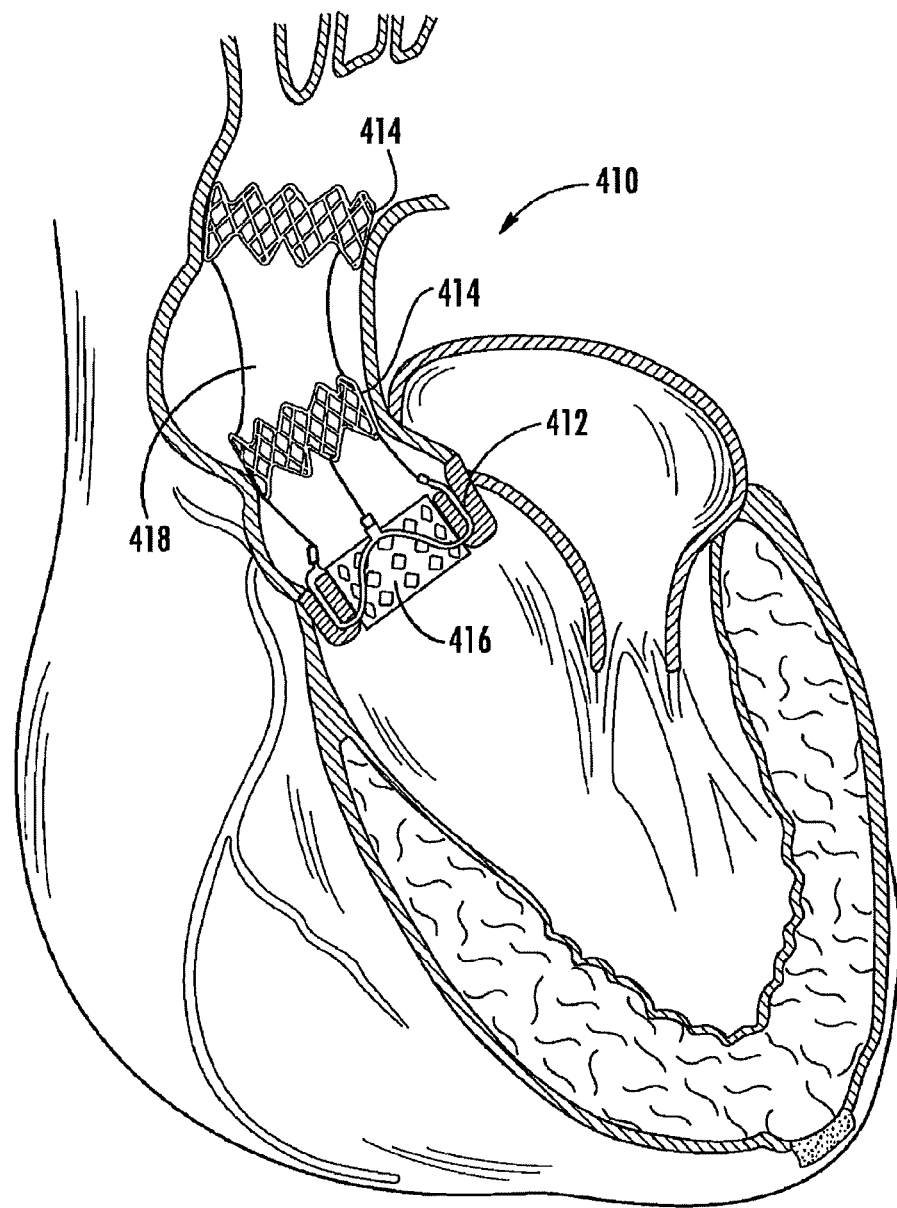
FIG. 27 is cross-sectional view of a patient's heart showing a medical device of another embodiment including a deflector with a resilient hourglass shape configured to resiliently aid in the pumping of blood.

FIG. 27 shows another embodiment wherein the deflector 418 has an hourglass shape and is constructed of a resilient material that deflects in response to increased blood pressure of a heart beat and adds additional pumping action as the arterial pressure drops. For example, the hourglass shape is formed of resilient walls that deflect under pressure and spring back into shape as the pressure drops. In another aspect, the walls of the graft may be relatively thick for an increased resiliency and additional pumping action.

In another embodiment, two anchoring stents may be connected by an elastic tube (e.g., made out of silicone). One of the anchors is deployed in the STJ (right above the native valve) and the other anchor is deployed on the other end of the aneurysm somewhere in the ascending aorta prior to the branches. The elasticity of the tube would aid the heart's pumping action.

Preferably, each of the medical devices 410 described herein is capable of a large amount of compression. For example the device 410, including the embodiment of the stent 414 and its foam sleeve 456, can be compressed or crimped to a diameter that is 8 mm or less. Uncompressed, the diameter may be 50 mm to 90 mm.

A method of using the medical device 410 disclosed herein includes delivering the support structure 412 to a position on or adjacent to the surface of the outflow side of the native heart valve of the patient, wherein the support structure defines a support-structure interior. The expandable prosthetic heart valve 416 is delivered into the native heart valve and into the support-structure interior. The expandable prosthetic heart valve 416 is expanded while it is in the support-structure interior and while the support structure is at the position on or adjacent to the surface of the outflow side of the native heart valve. This causes one or more of the native heart valve leaflets to be frictionally secured between the support structure 412 and the expanded prosthetic heart valve 416.

The stent 414, which is coupled to the support structure 412 either by co-formation or later attachment, is extended into a vessel (such as the aorta) extending from the native heart valve. The deflector 418 is already present on the stent 414 and/or is delivered into and attached to the stent 414. Blood flow against the vessel is abated by the deflector 418.

The method also may include delivering the stent 414 (or portions thereof) to a position adjacent the support structure 412 and coupling it to the support structure prior to extending the stent into the vessel. Also, the deflector 418 may be delivered to a support position on the stent 414 and coupled to the stent in vivo. Further, in the case where the stent 414 has a plurality of portions, the portions could be individually delivered and coupled to each other in vivo. Preferably, the method includes avoiding arteries extending from the vessel when positioning the deflector.

Also, the method may include expanding the deflector 418 to fill at least a portion of the space between an external surface of the stent 414 and the vessel.

Figure 29:
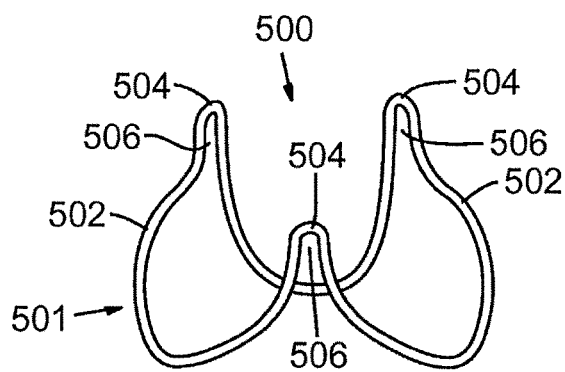
FIG. 29 is a perspective view of another embodiment of a support frame.
Figure 30:
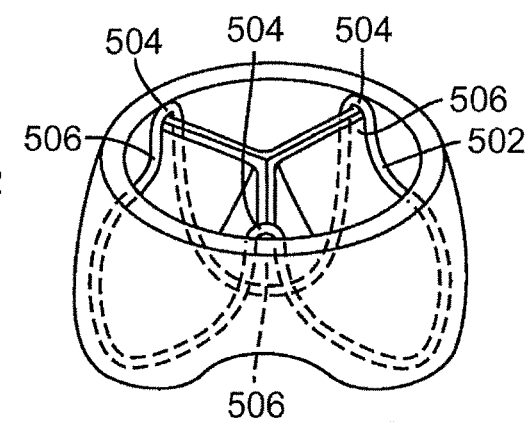
FIG. 30 is a cross-sectional perspective view of the support frame of FIG. 29 implanted in a native heart valve.

FIG. 29 shows another embodiment of a support stent or frame 500 that can be used to treat valve insufficiency (e.g., aortic insufficiency, mitral insufficiency, etc.), or to help secure a THV within the interior of a native heart valve. The support stent 500 comprises an annular main body 501 formed by a plurality of angled struts 502 arranged in a zig-zag pattern and having one or more apices 504 formed by the intersection of two adjacent struts. The struts 502 can be configured such that there is a gap 506 between adjacent struts underneath the apices 506 that receives portions of two adjacent leaflets forming a commissure of a native valve, as shown in FIG. 30. In particular embodiments, the support stent has a gap 506 for each commissure of the native valve where the support stent is to be implanted. Thus, as shown in FIGS. 29 and 30, when the support stent 500 is intended to be implanted at the aortic valve or the pulmonary valve, the support stent 500 desirably has three, angularly spaced gaps 506, with each gap being positioned at a commissure of the native valve when the support stent 500 is implanted. The gaps 506 can be dimensioned to pinch or clamp adjacent leaflets to each other at respective commissures. Similarly, if the support stent is configured to be implanted at the native mitral valve, the support stent desirably has two gaps 504. In this manner, the support stent 500 can retain or clamp the native valve leaflets together, thereby reducing the effective orifice area of the valve which, in turn, can reduce regurgitation through the valve.

If the stent 500 alone does not sufficiently reduce regurgitation or if the native valve further deteriorates over time after implantation of the stent 500, a THV can be deployed within the native valve, using a stent 500 as dock as shown in FIGS. 10-13. In some embodiments, the stent 500 and the THV can be implanted in the same procedure, using the stent 500 as the dock for the THV. As can appreciated, as compared to the implantation steps shown FIGS. 1-13, use of the stent 500 simplifies the procedure since the stent 500 can "clip" onto the commissures of the native leaflets and retain its position once deployed, which obviates the need to hold the stent in place using one catheter while the THV implanted using another catheter as is shown in FIG. 12.

Figure 31:
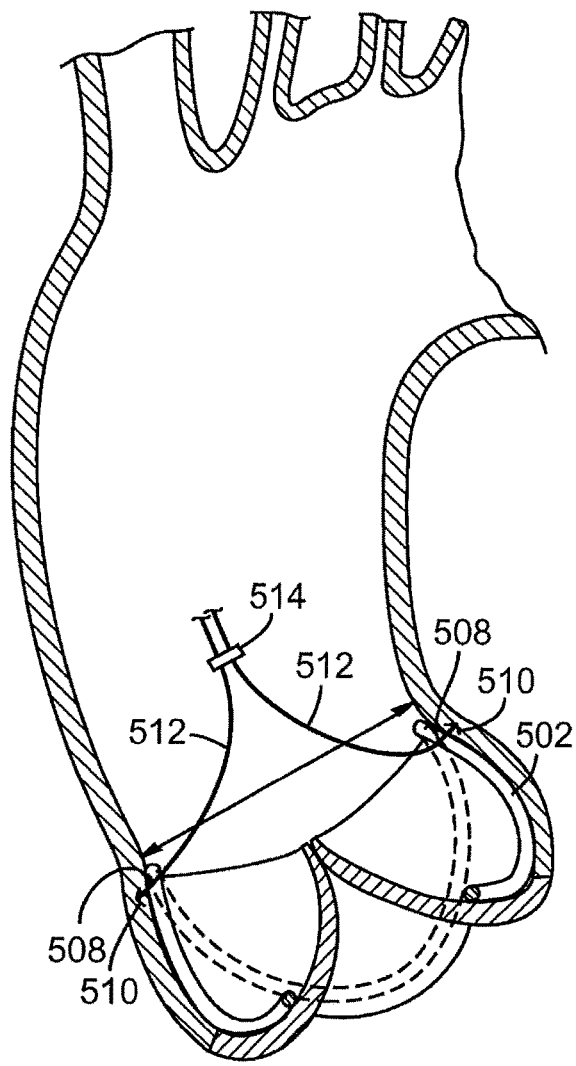
FIG. 31 is a cross-sectional view of the support frame of FIG. 29 implanted in a partial cross-section of the aorta.
Figure 32:
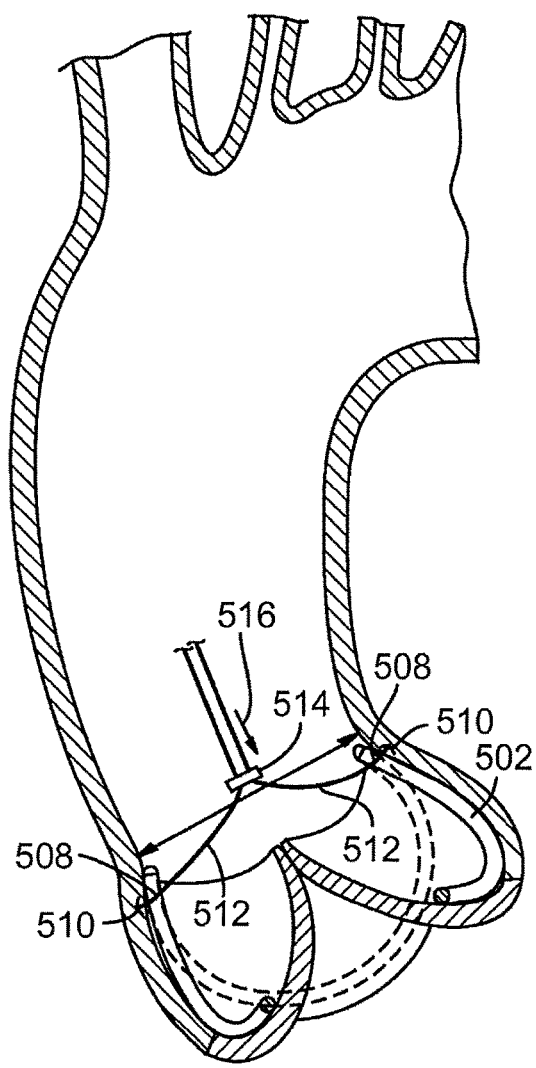
FIG. 32 is another cross-sectional view of the support frame of FIG. 29 implanted in a partial cross-section of the aorta.

Referring to FIGS. 31 and 32, the support stent 500 can also be used to treat native valve insufficiency by reducing the diameter of the valve annulus. The support stent 500 can be anchored in the valve annulus by one or more microanchors 508 comprising one or more sets of barbs 510. Exemplary embodiments of microanchors that can be used with the disclosed technology can be found in U.S. patent application Ser. No. 13/910,975 (U.S. Publication No. 2013/

0331930), which is incorporated herein by reference. As shown in FIG. 31, the microanchors 508 can be positioned in the gaps 506 adjacent the apices 504 of the support stent and can be embedded in the tissue of the valve annulus. One or more sutures 512 coupled to the microanchors 508 can extend upwardly toward a delivery system (not shown) and can comprise one or more suture securement devices, such as a suture clip 514. The suture clip 514 can be configured to travel along the sutures 512 in the direction indicated by arrow 516 (i.e., toward the microanchors 508). As tension is applied to the sutures 512 (by pulling upwardly on sutures and/or pushing downwardly on the suture clip) the suture clip can resist travel of the sutures 512 through the suture clip 514 in the opposite direction (i.e., the suture clip can resist downward travel of the sutures relative to the clip). Exemplary embodiments of suture securement devices that can be used with this technology can be found in U.S. patent application Ser. No. 13/938,071 (U.S. Publication No. 2014/0031864), which is incorporated herein by reference.

Once the microanchors 508 are implanted in the tissue of the valve annulus, tension can be applied to the sutures 512 such that the microanchors 508 are drawn toward one another, thereby reducing the diameter of the valve annulus (FIG. 32). The suture clip 514 retains tension on the sutures 512, thereby retaining the support stent and the surrounding tissue in the reduced diameter state after implantation. In this manner, the support stent 500 can be used to reduce the diameter of the valve annulus.

In other embodiments, the support stent 500 can be implanted in a procedure in which the microanchors 508 are deployed adjacent the commissures of the native valve with each microanchor 508 being provided with a suture 512 that can extend to a delivery apparatus and/or outside the body. When implanting at the native aortic valve, three microanchors 508 (each having a respective suture) can be implanted. The sutures 512 can be threaded through openings in the apices 504 of the support stent 500, which can then be advanced along the sutures until it is placed against the aortic surface of the native leaflets. A suture clip 514 can be advanced down the sutures 512 to tension the sutures and draw the surrounding tissue inwardly to reduce the diameter of the native annulus (as depicted in FIGS. 31-32).

In alternative embodiments, the support stent 500 can be made of a self-expanding material (e.g., Nitinol) and is delivered and deployed using an expansion mechanism (e.g., a balloon catheter). When the support stent 500 is adjacent the native valve, the expansion mechanism over expands the support stent (i.e., expands the support stent radially beyond its functional size) (such as by inflating the balloon of the balloon catheter) and places the support stent against the aortic surface of the native valve. The support stent 500 can have barbs or anchors 508 can that engage, penetrate and/or grab adjacent tissue as the support stent 500 is placed against the native tissue. In lieu of or in addition to barbs or anchors, the support stent 500 can be configured to clip onto commissures of the native valve when the commissures are placed in gaps 506. The expansion mechanism then releases the support stent 500 (such as by deflating the balloon), allowing the support stent to shrink/return to its natural or functional size, pulling the surrounding tissue inwardly to reduce the size of the native annulus.

Alternatively, the aortic annulus can be reduced in size by suturing the support stent 500 in its functional size to the aortic valve.

Figure 33:
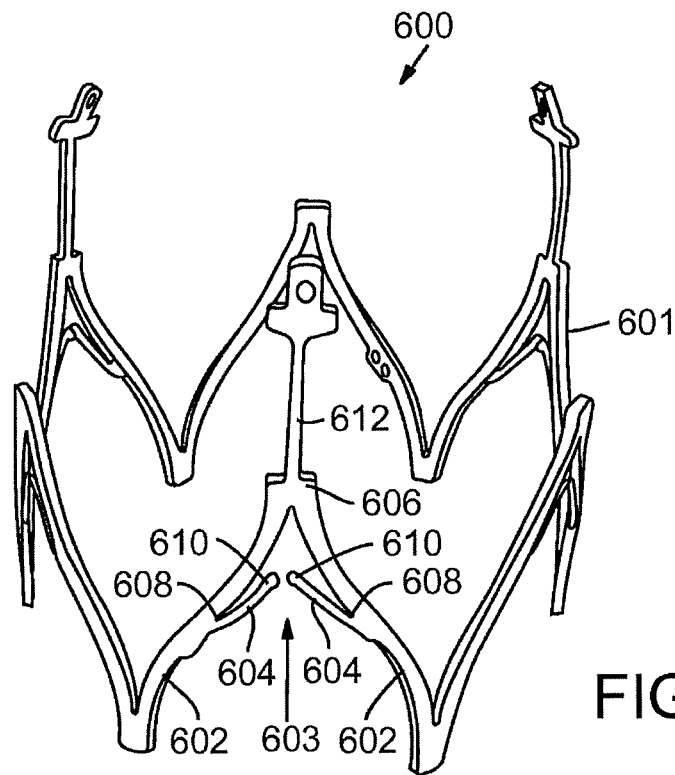
FIG. 33 is a perspective view of another embodiment of a support frame including one or more pairs of leaflet-engaging members.

FIG. 33 shows another embodiment of a support stent or frame 600 that can be used to treat heart valve insufficiency or help secure a THV within the interior of a native heart valve, such as the aortic valve. The support stent 600 comprises an annular main body 601 formed by a plurality of angled struts 602 arranged in zig-zag pattern. The support frame 600 can include one or more leaflet-engaging mechanisms 603. The leaflet-engaging mechanisms 603 can comprise pairs of leaflet-engaging members 604 secured to respective struts 602 below one or more apices 606 formed by the intersection of the two adjacent struts 602. Each leaflet-engaging member 604 has a fixed end portion 608 secured to a respective strut and a free end portion 610. The leaflet-engaging members 604 extend upwardly toward the apex 606 and toward each other. In their normal, unbiased (i.e., non-deflected) state, the leaflet-engaging members 604 can be configured such that there is a small gap between respective free end portions 610 that receives portions of two adjacent leaflets 616 forming a commissure of a native valve, as further described below. The struts 602 and the leaflet-engaging members 604 can be laser cut (or otherwise machined or formed) from a single piece of material (e.g., a tubular piece of metal) such that the leaflet-engaging members 604 are integral to the support stent. In other embodiments, the leaf springs 604 can be separately formed and welded to the struts 602.

In particular embodiments, the support stent has a pair of leaflet-engaging members 604 for each commissure of the native valve where the support stent is to be implanted. Thus, as shown in FIG. 33, when the support stent 600 is intended to be implanted at the aortic valve or the pulmonary valve, the support stent 600 desirably has three, angularly spaced pairs of leaflet-engaging members 604, with each pair being positioned underneath an apex 606 that is positioned at a commissure of the native valve when the support stent 600 is implanted. If the support stent is configured to be implanted at the native mitral valve, the support stent desirably has two pairs of leaflet-engaging members 604. Although less desirable, in some embodiments, the number of pairs of leaf springs can be less than the number of commissures of the native valve where the support stent is to be implanted. Similar to the support stent 310, the support stent 600 can have retaining arms 612 for releasably securing the support stent 600 to a delivery apparatus (e.g., delivery apparatus 350).

Figure 34:
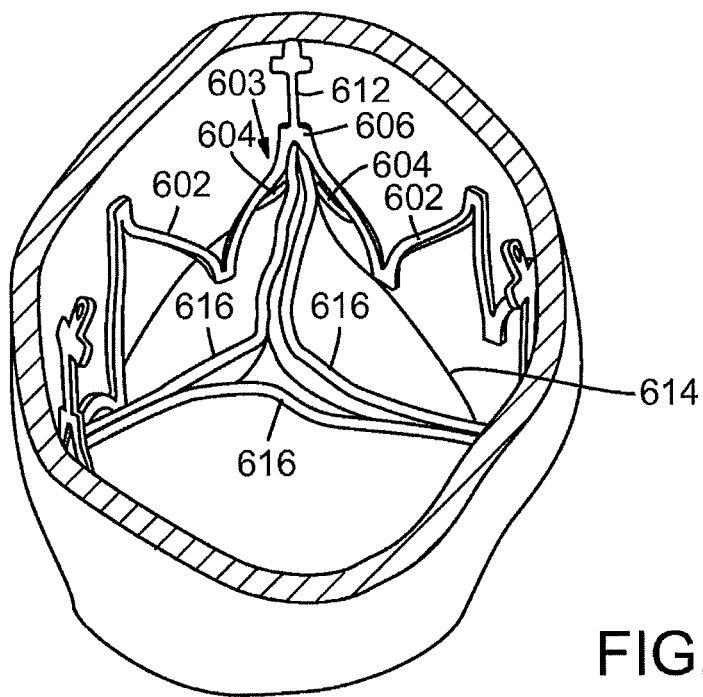
FIG. 34 is a perspective view of the support frame of FIG. 33 implanted in a partial section of an aorta.

FIG. 34 shows the support stent 600 implanted in the aortic root behind the leaflets 616 of an aortic valve 614. To deliver and deploy the support stent at the implantation site, the support stent 600 can be mounted in a compressed state on a delivery apparatus 350 (FIG. 17) and delivered to the vicinity of the native aortic valve, as described in detail above. When the support stent 600 is adjacent the aortic valve 614 (e.g., within or just above the aortic root), the support stent 600 can be deployed from the catheter 352, allowing the support stent to expand to its functional size. Each pair of leaflet-engaging members 604 is rotationally aligned within one of the commissures of the aortic valve. Thereafter, the delivery apparatus 350 is further advanced toward the aortic valve, causing each pair of leaflet-engaging members 604 to slide over a pair of native leaflets 616 of one the commissures of the aortic valve. The gap between the free end portions 610 of the leaf springs is such that insertion of the native leaflets 616 can place the leaf springs in tension and pinch the native leaflets between the leaf springs. Once the native leaflets are captured by the support stent 600, the support stent can be released from the delivery apparatus 350. The compressive force of the leaflet-engaging members 604 against the native leaflets 616 is sufficient to hold the support stent 600 in place against the flow of blood. Thereafter, if desired, a THV can be implanted within the interior of the aortic valve 614 (as shown in FIG. 18) and expanded against the native leaflets 614, which in turn are pressed radially outwardly against the support stent.

Figure 35:
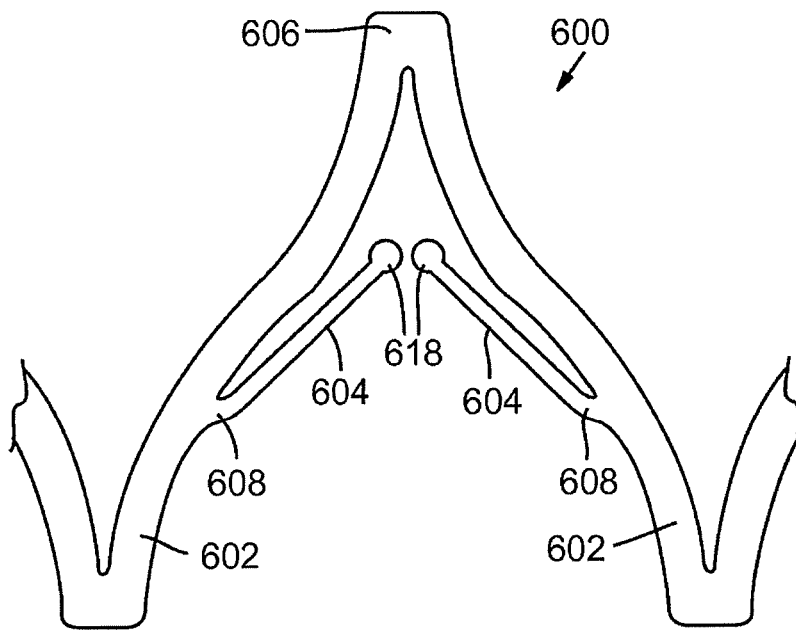
FIG. 35 is a partial side elevation view of another embodiment of the support frame of FIG. 33 in which free end portions of the leaflet-engaging members are spherical.

FIG. 35 shows a modification of the support stent 600 having leaflet-engaging members 604 with spherical free end portions 618 that are configured to contact each other in their normal, unbiased (non-deflected) state. The curved outer surfaces of the spherical free end portions 610 can help to engage the native leaflets placed between the spherical free end portions 618 without damaging the leaflets. During insertion of native leaflets between the leaflet-engaging members 604, the leaflet-engaging members 604 can flex such that the spherical free end portions 618 move upwardly and away from each other to allow the leaflets to slide between the spherical free end portions 618 (as depicted in FIG. 35).

Figure 36:
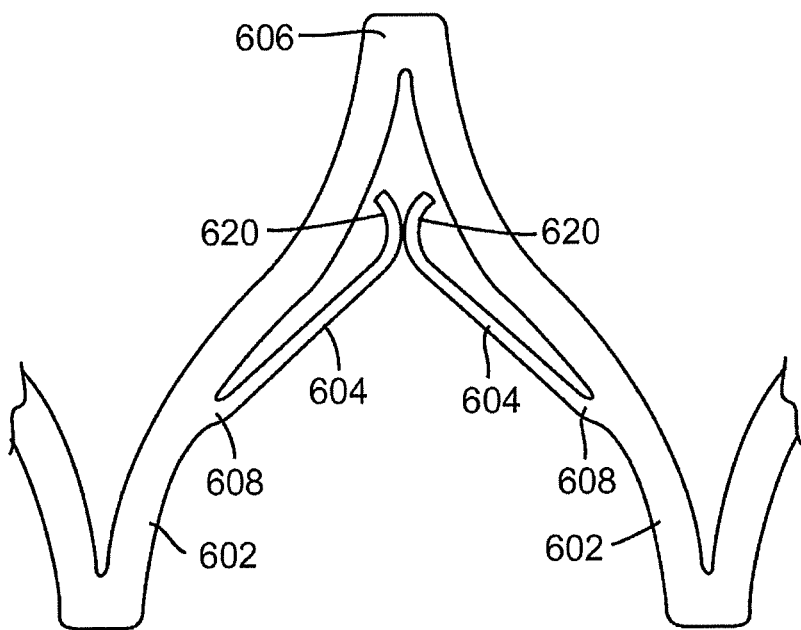
FIG. 36 is a partial side elevation view of another embodiment of the support frame of FIG. 33 in which free end portions of the leaflet-engaging members are curved.
Figure 37:
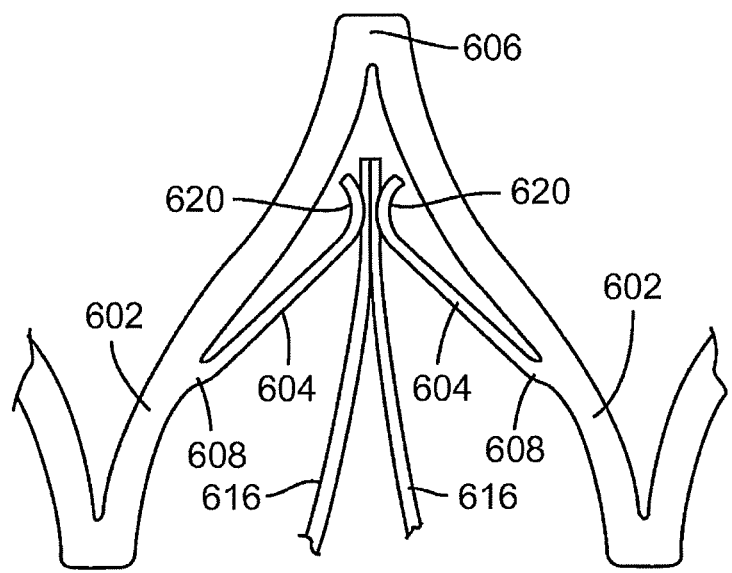
FIG. 37 is a partial side elevation view of the support frame of FIG. 36 illustrating native leaflets engaged between the leaflet-engaging members.

FIG. 36 shows another modification of the support stent 600 having leaflet-engaging members 604 with curved free end portions 620, which can enhance the retention force against the leaflets while minimizing bulkiness of the leaflet-engaging members 604. FIG. 37 shows the support stent of FIG. 36 implanted within the aortic root with a pair of leaflets 616 captured between the free end portions 620 of the leaflet-engaging members 604.

Figure 38:
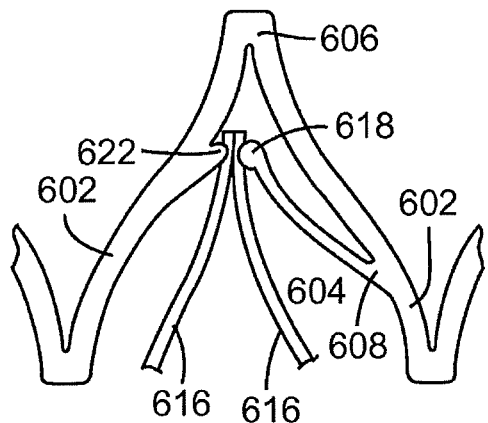
FIG. 38 is a partial side elevation view of another embodiment of the support frame of FIG. 33 having a single leaflet-engaging member.

FIG. 38 shows another modification of the support stent 600 having a single leaflet-engaging member 604 below one or more selected apices 606. In this embodiment, the leaflet-engaging member 604 is configured to capture a pair of leaflets 616 between a spherical free end portion 618 of the leaflet-engaging member 604 a protrusion 622 extending toward the leaflet-engaging member 604. In the embodiment shown, the protrusion 622 is shaped to snag or bind against the adjacent leaflet 616 to help retain the leaflets 616 in place between the leaflet-engaging member 604 and the protrusion. In alternative embodiments, the leaflets 616 can be captured between the spherical free end portion 618 of the leaflet-engaging member 604 and the surface of an adjacent strut 602.

Figure 39:
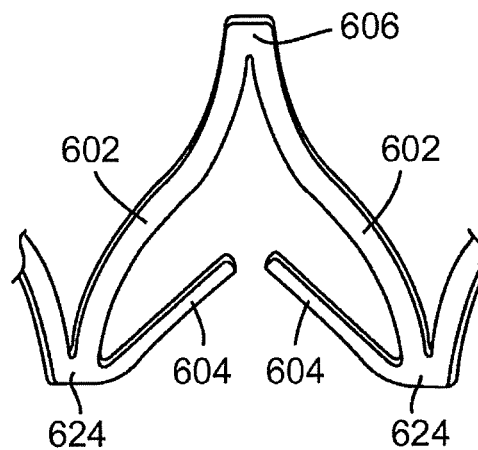
FIG. 39 is a partial side elevation view of another embodiment of the support frame of FIG. 33 having leaflet-engagement members extending from distal apices of the support frame.

FIG. 39 illustrates another modification of the support frame 600, wherein the leaflet-engaging members 604 are configured to extend from distal apices 624 formed by the intersection of two adjacent struts 602 at the outflow end of the support frame 600.

Figure 40:
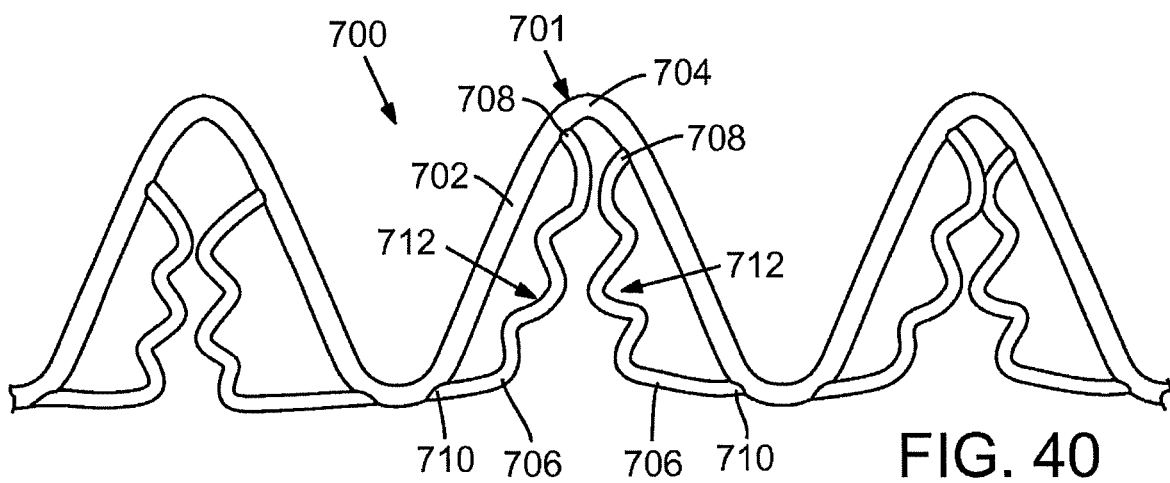
FIG. 40 is a side elevation view of another embodiment of a support frame in a flattened state including pairs of leaflet-engaging members having curved sections.

FIG. 40 shows another embodiment of support stent 700 comprising an annular main body 701 (shown flattened) formed by a plurality of struts 702. Positioned beneath one or more selected apices 704 of the support stent are leaflet-engaging mechanisms 705 comprising pairs of leaflet-engaging members 706 configured to capture a respective pair of native leaflets. In the illustrated embodiment, each leaflet-engaging member 706 has a first end 708 secured to a strut 702 and a second end 710 secured to the same strut 702. Each leaflet-engaging member 706 can have a plurality of curved sections 712 extending between the first and second ends 708, 710, respectively, allowing adjacent leaflet-engaging members 706 of a pair to deflect away from each other while a pair of native leaflets are inserted therebetween. Each pair of leaflet-engaging members 706 can also apply sufficient compressive force against the leaflets once they are in place between the leaflet-engaging members 706 such that the leaflets are retained between the leaflet-engaging members 706. In the embodiment shown, the leaflet-engaging members 706 can be configured to define a small gap between the curved sections 712 of adjacent members 706. In alternative embodiments, the curved sections 712 can define points of contact that can contact corresponding contact points of an adjacent member 706 when the members 706 are in their non-deflected state.

Figure 41:
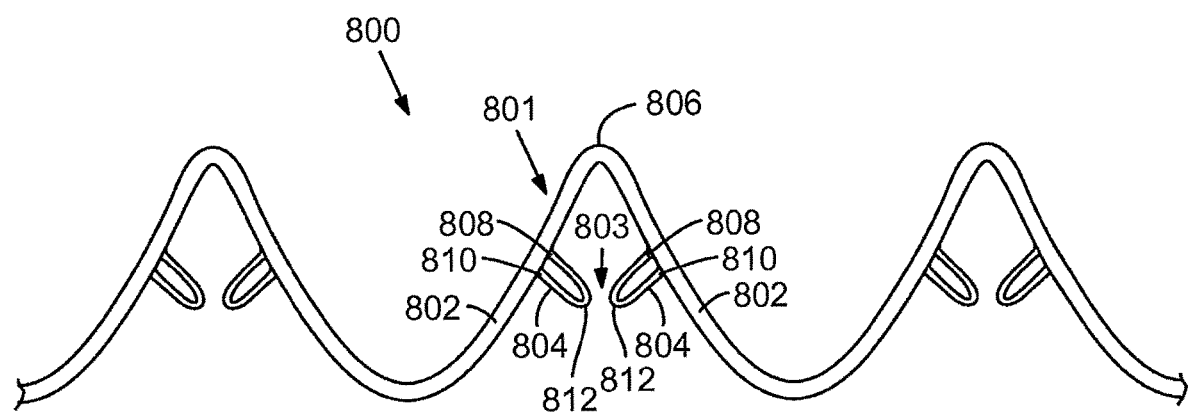
FIG. 41 is a side elevation view of another embodiment of a support frame in a flattened state including pairs of semi-annular leaflet-engaging members.
Figure 42:
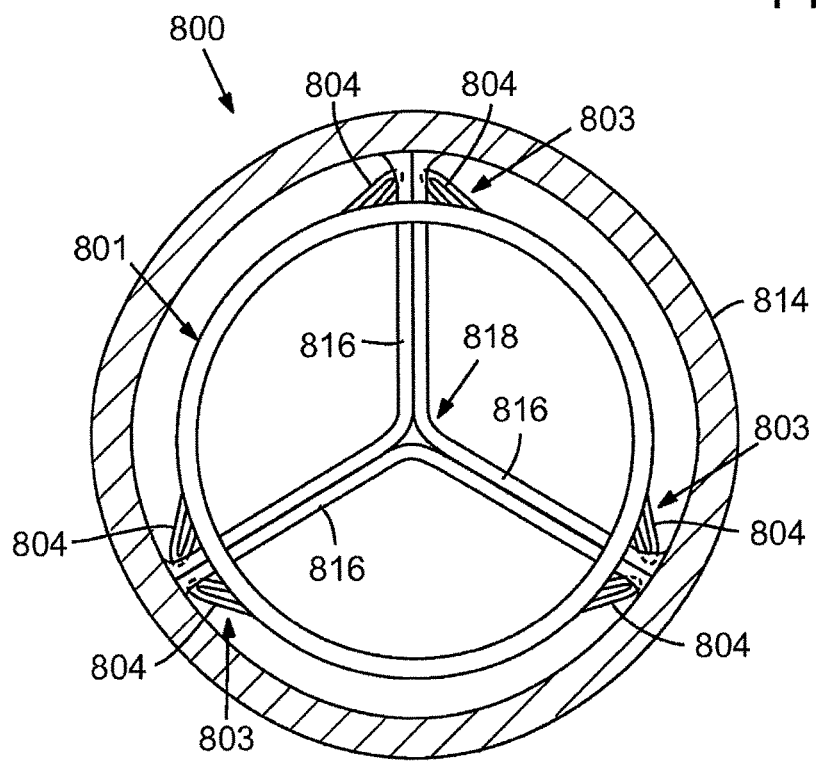
FIG. 42 is a plan view of the support frame of FIG. 41 implanted in the aortic root.

FIG. 41 illustrates another embodiment of a support frame 800 shown in a flattened or unrolled state for purposes of illustration. The support frame 800 comprises an annular main body 801 formed by a plurality of struts 802, and one or more leaflet-engaging mechanisms 803. The leaflet-engaging mechanisms 803 can comprise pairs of semi-annular leaflet-engaging members 804 positioned beneath respective apices 806 of the support frame. Each leaflet-engaging member 804 in the illustrated embodiment comprises first and second fixed end portions 808, 810 secured to a respective strut 802 and a peak 812 formed by a portion of the leaflet-engaging member 804 intermediate the two fixed end portions 808, 810. In the embodiment shown, the leaflet-engaging members 804 can extend generally in the direction of the outflow end of the support frame 800 such that the first fixed end portion 808 is closer to the apex 806 than is the peak 812. FIG. 42 shows the support frame 800 implanted in the aortic root 814 with the native leaflets 816 of the aortic valve 818 captured between respective pairs of leaflet-engaging members 804.

FIG. 43 shows another embodiment of a support stent 900 comprising a plurality of struts 902 and a plurality of leaflet-engaging mechanisms 903. The leaflet-engaging mechanisms 903 can comprise clipping members 904 secured to distal apices 916 of the struts 902 at the inflow end of the support stent 900. FIG. 44 shows a clipping member 904 apart from the support stent 900. Each clipping member 904 comprises two leg portions 906 secured to each other at an apex 908. Each leg portion 906 has a free end portion 910 that can be angled inwardly toward the other free end portion 910 as shown. Each clipping member 904 can be secured to the support frame 900 with a section of fabric cloth 912 that extends around the apex 908 of the clipping member 904 and an adjacent distal apex 916 of the support frame 900 at the inflow end of the support frame. Sutures can be used to secure the cloth 912 in place around the clipping member 904 and the adjacent distal apex 916 of the support frame 900. As can be seen in FIGS. 43 and 45, two leg portions 906 of adjacent clipping members 904 can extend toward each other for capturing a pair of native leaflets 914.

In some embodiments, the clipping members 904 can be separately formed from the support frame 900, and can be fabricated from metal wire having a diameter that is smaller than the diameter of the struts 902. For example, in some embodiments, the diameter of the clipping members 904 can be from about 0.010 inch to about 0.023 inch. Each leg portion 906 of the clipping members 904 can also have a length L of, for example, 5 mm or greater (FIG. 46). In this manner, the clipping members 904 can be configured to apply an inward retaining force $F_{in}$ on the aortic valve leaflets, as shown in FIGS. 45 and 46. In some embodiments, the retaining force $F_{in}$ can be about 3 N. The clipping members 904 can also have a removal force $F_R$ needed to remove or reposition the device 900 along the leaflets 914, and a buckling force $F_B$ oriented axially with respect to struts 902. The removal force $F_R$ and the buckling force $F_B$ can be configured such that the application of the required removal force $F_R$ can result in a buckling force $F_B$ sufficient to cause the clipping members 904 to bend or buckle, thus reducing the risk of tearing the native valve leaflets 914 when repositioning or removing the support frame 900. In some embodiments, the removal force $F_R$ can be about 6 N. In alternative embodiments, the clipping members 904 can be integrally formed with the support frame 900.

FIG. 47 shows another embodiment of support stent 1000 comprising an annular main body formed by a plurality of struts 1002. Positioned beneath one or more selected apices 1004 of the support stent 1000 are leaflet-engaging mechanisms 1003 comprising horseshoe-shaped leaflet-engaging members 1006 configured as clips corresponding to each of the three commissure locations of the native aortic valve. Each of the leaflet-engaging members 1006 can be configured to capture a respective pair of native leaflets at each commissure of the aorta. The leaflet-engaging members 1006 and support frame 1000 can be integrally manufactured or separately manufactured and subsequently assembled using any suitable method or combination of, for example, welding, tying with suture or wire, adhesive, mechanically fastening, and the like. In this application, the phrases "integrally manufactured," "integrally formed," and "integral to" all refer to a construction that does not include any adhesive, fasteners, or other means for securing separately formed pieces of material to each other.

FIGS. 48 and 49 illustrates fragmentary views of another embodiment of a support frame 1100 comprising an annular main body formed by a plurality of struts 1102. The support frame 1100 can comprise one or more leaflet-engaging mechanisms 1103 including a pair of integrated leaflet-engagement members 1104. The leaflet-engaging members 1104 can be positioned beneath selected apices 1106 and can be configured to capture respective pairs of native leaflets. In the illustrated embodiment, each leaflet-engaging member 1104 has a first end 1108 secured to a strut 1102 and a second end 1110 secured to the same strut 1102. Each leaflet-engaging member 1104 can be spring-biased, allowing adjacent leaflet-engaging members 1104 of a pair to deflect away from each other when a pair of native leaflets are inserted between the leaflet-engaging members 1104. The leaflet-engaging members 1104 can be configured to apply force against the leaflets such that the leaflets are retained between the leaflet-engaging members 1104.

In the embodiment of FIG. 48, the curved leaflet-engaging members 1104 can define points of contact that contact corresponding contact points of an adjacent member 1104 when the members 1104 are in their non-deflected state. Alternatively, the members 1104 can be configured to define a small gap between the curved sections of adjacent members 1104, as shown in FIG. 49. The members 1104 can also have diameters greater than, equal to (FIG. 49), or less than (FIG. 48) the diameter of the struts 1102 depending on, for example, the degree of spring-bias desired.

FIGS. 50 and 51 illustrate a fragmentary view of another embodiment of a support stent 1200 comprising an annular main body formed by a plurality of struts 1202. Beneath one or more selected apices 1204, the struts 1202 can be curved or otherwise shaped such that adjacent struts define a leaflet-engaging mechanism 1203 having a narrow leaflet-engagement region 1206 between the struts 1202. The leaflet-engagement region 1206 can comprise a gap dimensioned to grip the native aortic valve leaflets. The struts 1202 can be spring-biased, allowing adjacent pairs of struts 1202 to deflect away from each other when a pair of native leaflets are inserted between the struts 1202, and causing the struts 1202 to apply force against the leaflets sufficient to retain the leaflets in place between the struts 1202. In some embodiments, the leaflet-engagement region 1206 can include teeth or serrations 1208 configured to engage the native leaflets, thereby helping to keep the frame 1200 in place after implantation.

FIG. 52 shows another embodiment of a stent 1300 comprising an annular main body formed by a plurality of struts 1302. The support frame 1300 can include leaflet-engaging mechanisms 1303 located beneath select apices 1304 and defined by the struts 1302. The struts 1302 can be separated by narrow leaflet-engagement regions 1306. The leaflet-engagement regions 1306 can comprise serrations 1308 configured to engage native leaflets when they are inserted between the struts 1302. In this manner, the stent 1300 can be held in place after implantation.

Figure 55:
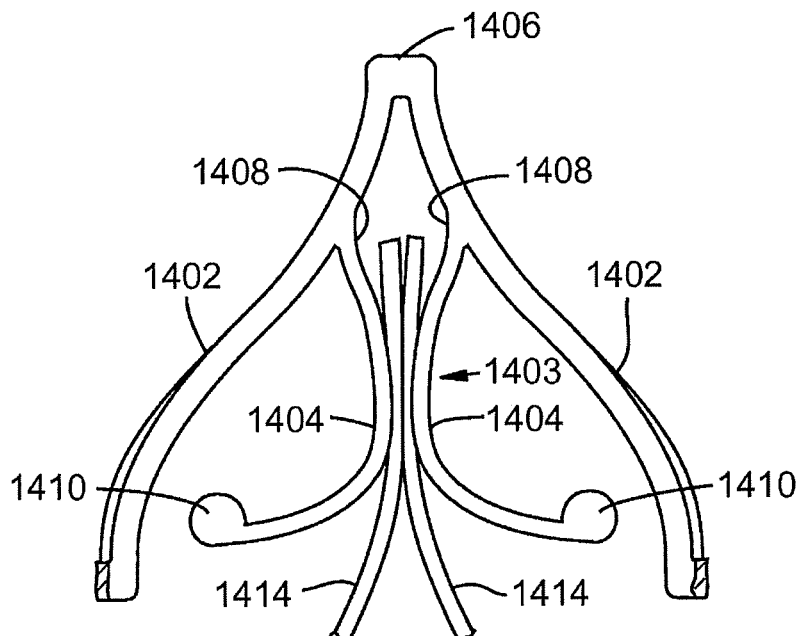
FIG. 55 is a partial side elevation view of the support frame of FIG. 53 with native valve leaflets engaged between the spring members.

Referring to FIGS. 53-55 there is shown another embodiment of a support frame 1400 comprising an annular main body 1401 (shown flattened in FIG. 53) formed by a plurality of struts 1402. The support frame 1400 can comprise one or more leaflet-engaging mechanisms 1403, which can include a pair of leaflet-engaging members 1404 secured to respective struts 1402 below one or more apices 1406 formed by the intersection of two adjacent struts 1402. Each leaflet-engaging member 1404 can have a fixed end portion 1408 secured to a respective strut 1402 and a free end portion 1410. The leaflet-engaging members 1404 can extend downwardly from near the apices 1406 at the outflow end of the support frame 1400 and toward each other, defining a narrow leaflet-engaging region 1405, before curving toward the struts 1402 near the inflow end of the frame 1400. As best shown in FIG. 54, in their normal, unbiased (non-deflected) state, the leaflet-engaging members 1404 can be configured such that there is a small gap between free end portions 1410 and the struts 1402. In this manner the leaflet-engaging members 1404 can deflect toward adjacent struts 1402 when the leaflets 1414 of a native valve are inserted therebetween, as shown in FIG. 55. As with embodiments previously described, the struts 1402 and the leaflet-engaging members 1404 can be laser cut (or otherwise machined or formed) from a single piece of material (e.g., a tubular piece of metal) such that the leaflet-engaging members 1404 are integral to the support stent. Alternatively, the leaflet-engaging members 1404 can be separately formed and welded to the struts 1402.

In the embodiment shown, the support frame 1400 can comprise a pair of leaflet-engaging members 1404 located beneath each apex 1406 of the frame. This can make implantation of the support frame 1400 easier by reducing the amount by which the frame 1400 must be rotated in order to line up the pairs of leaflet-engaging members with the commissures of the native valve. Alternatively, the support frame 1400 can have a pair of leaflet-engaging members 1404 for each commissure of the native valve where the support frame is to be implanted. Thus, similar to the embodiment of FIG. 33 above, when the support frame 1400 is intended to be implanted at the aortic valve or the pulmonary valve, the support frame 1400 desirably has three, angularly spaced pairs of leaflet-engaging members 1404, with each pair being positioned underneath an apex 1406 that is positioned at a commissure of the native valve when the support frame 1400 is implanted. Similarly, if the support frame 1400 is configured to be implanted at the native mitral valve, the support frame 1400 desirably can have two pairs of leaflet-engaging members 1404. Although less desirable, in some embodiments, the number of pairs of leaflet-engaging members 1404 can be less than the number of commissures of the native valve where the support stent is to be implanted. Similar to the support stent 310, the support stent 1400 can also have retaining arms 1412 (FIG. 53) for releasably securing the support stent 1400 to a delivery apparatus (e.g., delivery apparatus 350).

Figure 56:
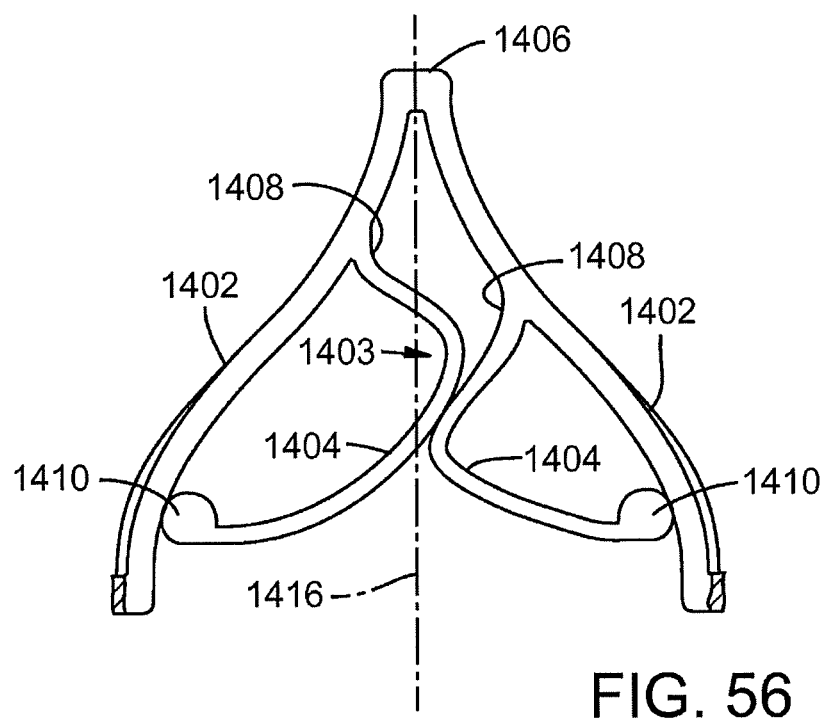
FIG. 56 is a partial side elevation view of an alternative embodiment of the support frame of FIG. 53 including spring members configured to overlap one another.

FIG. 56 shows a modification of the support stent 1400 having leaflet-engaging members 1404 that overlap one another in their normal (non-deflected) state. In this manner, the leaflet-engaging members 1404 can be configured to retain the native valve leaflets 1414 by applying a preload to the leaflets 1414 once they are captured between the leaflet-engaging members 1404. In the embodiment shown, the overlapping region of the leaflet-engaging members 1404 is offset from a central axis 1416 extending though apex 1406, and the respective fixed end portions 1408 of the leaf springs are vertically offset from one another. Alternatively, the respective leaflet-engaging members 1404 can overlap symmetrically about the central axis 1416 of the stent, and the fixed end portions 1408 can be fixed to the respective struts 1402 at the same vertical position. In the embodiment shown, the free end portions 1410 of the leaflet-engaging members 1404 contact the struts 1402 when the leaflet-engaging members 1404 are in their non-deflected state. Alternatively, the free end portions 1410 can be spaced from the struts 1402 such that there is a gap between the free end portions 1410 and the struts 1402, depending upon the degree of spring bias desired in the leaflet-engaging members 1404.

Figure 57:
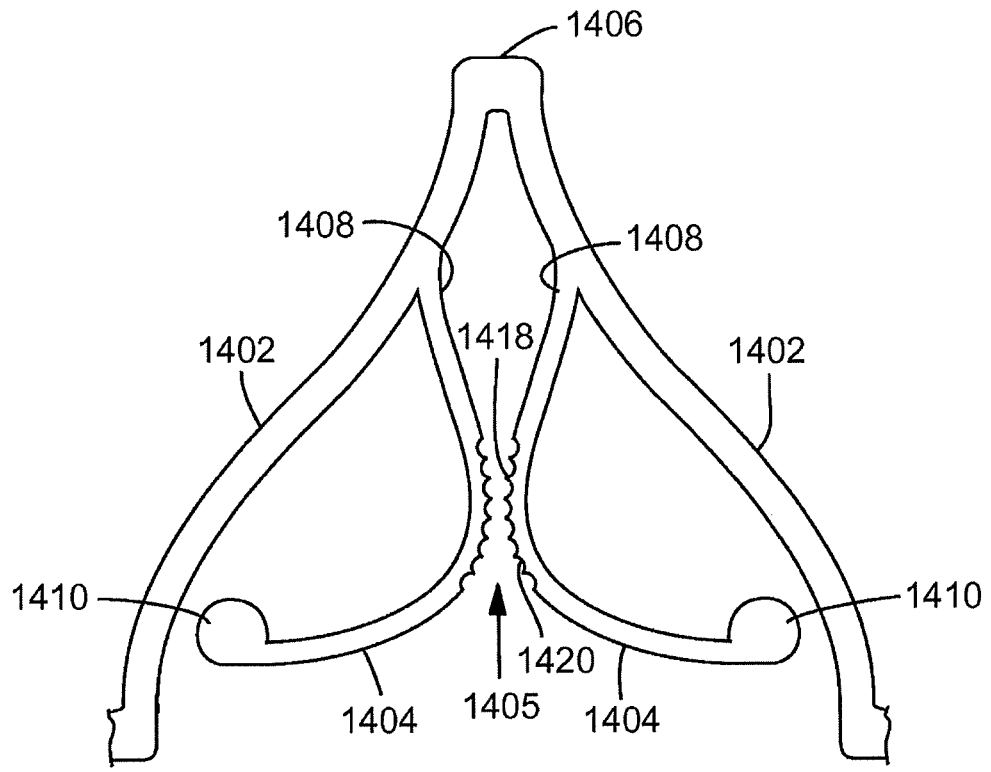
FIG. 57 is a partial side elevation view of another embodiment of the support frame of FIG. 53 including spring members having serrations orthogonal to the surfaces of the spring members.
Figure 58:
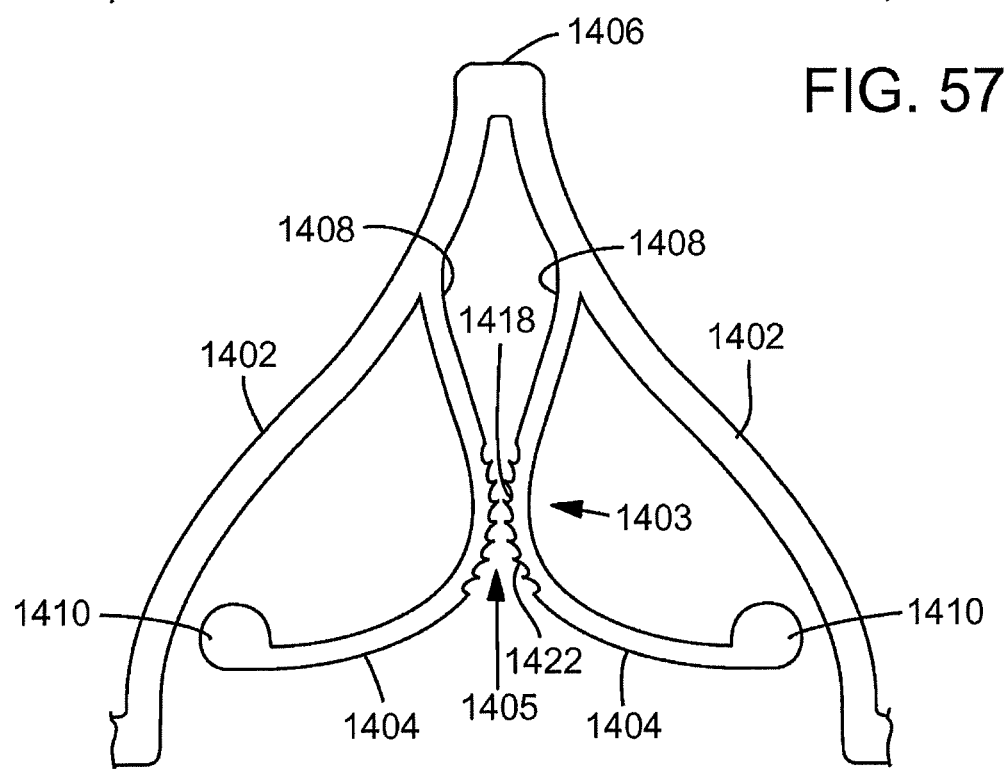
FIG. 58 is a partial side elevation view of another embodiment of the support frame of FIG. 53 including spring members having serrations oriented in the direction of the outflow end of the support frame.

FIGS. 57 and 58 show another modification of the support frame 1400 having leaflet-engaging members 1404 that comprise or serrations 1418 located in the leaflet engagement region 1405. The serrations 1418 can be defined by circular cutouts 1420 such that the serrations 1418 extend outwardly from the leaflet-engaging members 1404 in a direction generally orthogonal to the surface of the leaflet-engaging members 1404, as shown in FIG. 57. The serrations 1418 can aid in retaining the native leaflets between the leaflet-engaging members 1404 after insertion. Alternatively, the leaflet-engaging members 1404 can comprise angled cutouts 1422 such that the serrations 1418 are oriented generally in the direction of the outflow end of the support frame 1400, as shown in FIG. 58. In this manner, the serrations 1418 can allow smooth insertion of the native leaflets between the leaflet-engaging members 1404 (i.e., the orientation of the serrations 1418 can minimize damage to the leaflets caused by the serrations 1418 during insertion) while retaining the native leaflets after insertion between the leaflet-engaging members 1404. In further alternative embodiments, the leaflet-engaging members 1404 can comprise surface roughness in the leaflet-engagement region 1405 to increase retention of the native valve leaflets.

Figure 59A:
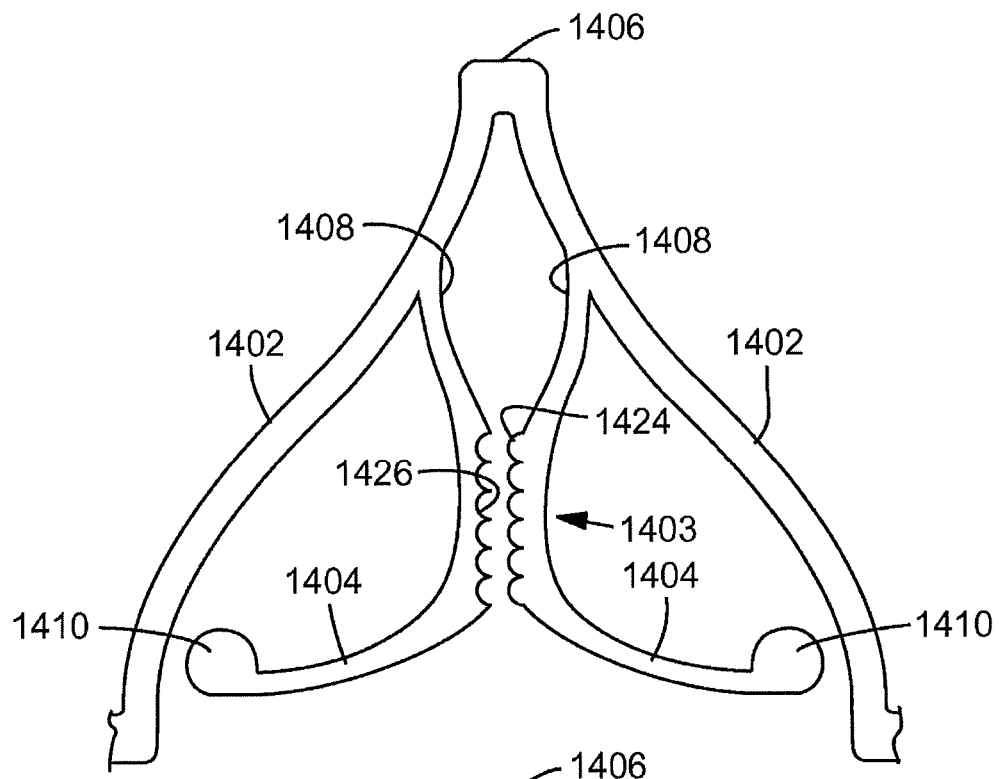
FIG. 59A is a partial side elevation view of another embodiment of the support frame of FIG. 53 wherein one spring member of each pair of spring members has circular protrusions and one spring member has circular cutouts.
Figure 59B:
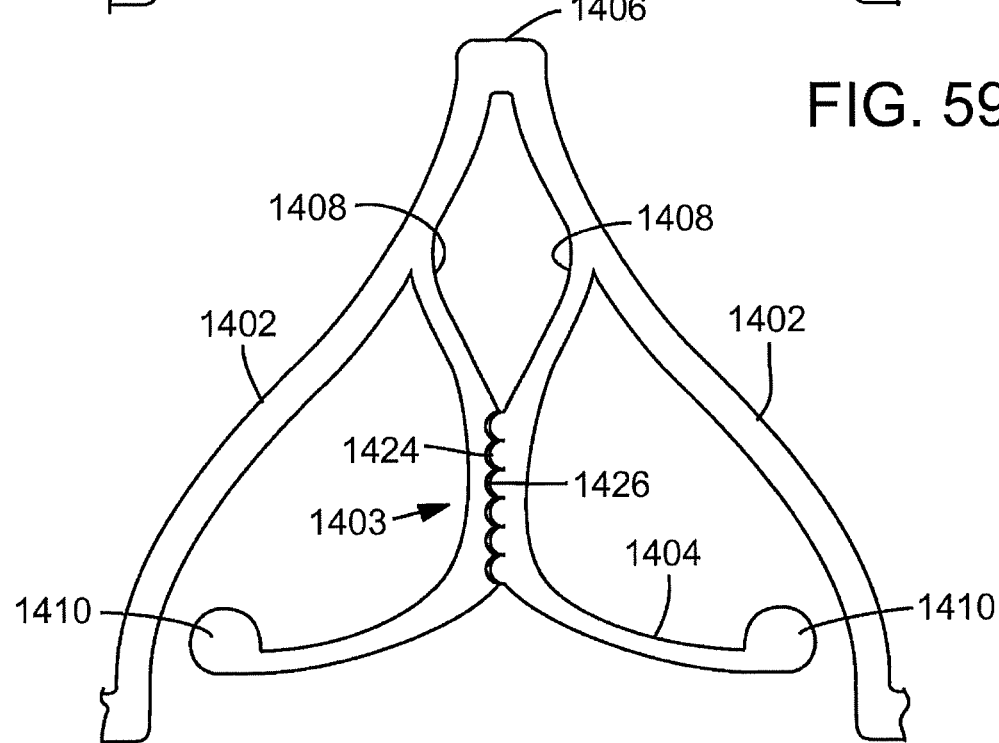
FIG. 59B is a partial side elevation view of the support frame of FIG. 59A illustrating the circular protrusions of one respective spring member received in the circular cutouts of the other respective spring member.

FIGS. 59A and 59B show another modification of the support stent 1400 wherein respective leaflet-engaging members 1404 of each pair comprise protrusions 1424 and corresponding cutouts or recesses 1426 configured to receive the protrusions 1424. In some embodiments, the leaflet-engaging members 1404 can be spring-biased to move between an open position (FIG. 59A), wherein the respective leaf springs define a gap therebetween, and a closed position (FIG. 59B), wherein the recesses 1426 receive the protrusions 1424 of the corresponding leaflet-engaging member 1404. In this manner, native valve leaflets inserted between the leaflet-engaging members 1404 when the leaflet-engaging members 1404 are in the open position can be engaged and retained between the protrusions 1424 and the recesses 1426 of the respective leaflet-engaging members 1404 when the leaflet-engaging members 1404 are in the closed position.

Figure 60:
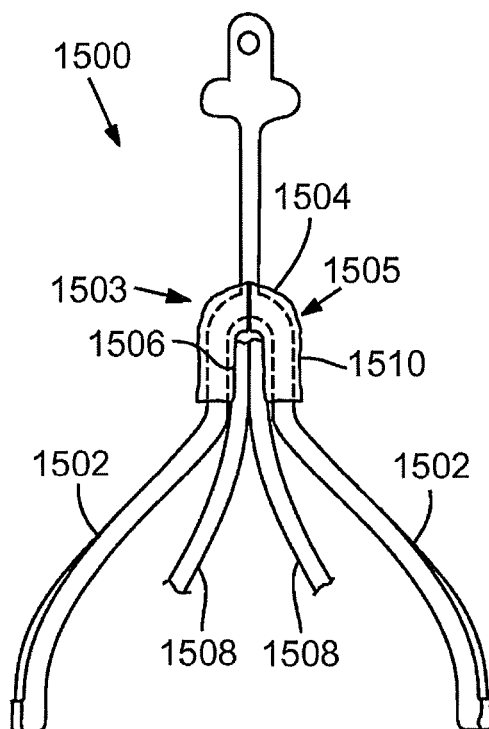
FIG. 60 is a partial side elevation view of another embodiment of a support frame including a leaflet-engaging portion.

FIG. 60 shows a detail view of another embodiment of a stent 1500 comprising an annular main body formed by a plurality of struts 1502. Beneath apices 1504, the support frame 1500 can comprise a leaflet-engaging mechanism 1503 in the form of a leaflet-engaging portion 1505 defined by the struts 1502. The leaflet-engaging portion 1505 can define a gap 1506 configured to engage and retain native valve leaflets 1508 after insertion of the leaflets into the gap 1506. The leaflet-engagement portion 1505 can include a cloth or fabric covering 1510 surrounding the respective struts 1502 and extending over the apex 1504. The fabric covering 1510 can be configured to engage the native leaflets 1508 when the leaflets are inserted into the gap 1506. The fabric covering 1510 can be configured to reduce wear and/or damage to the native leaflets, as well as to accommodate different leaflet thicknesses. Cloth or fabric is optionally included in any embodiment of the support frames disclosed herein at any location where tissue damage or wear is likely to occur.

Figure 61:
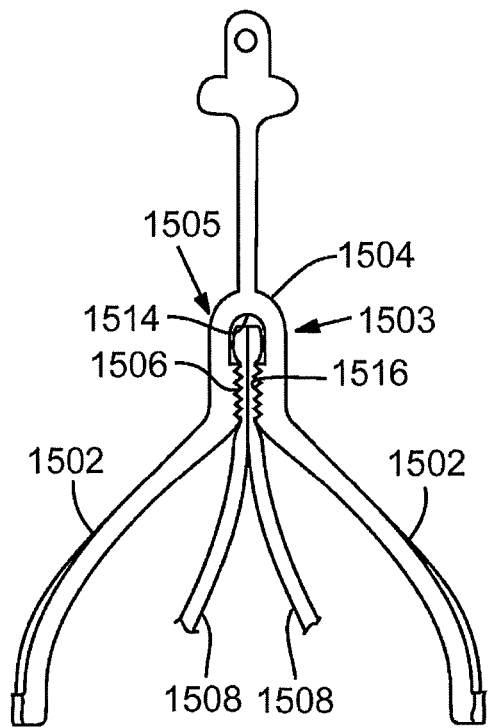
FIG. 61 is a partial side elevation view of another embodiment of the support frame of FIG. 60 in which the leaflet-engaging portion includes two gaps defined by differences in thickness of the struts.
Figure 62:
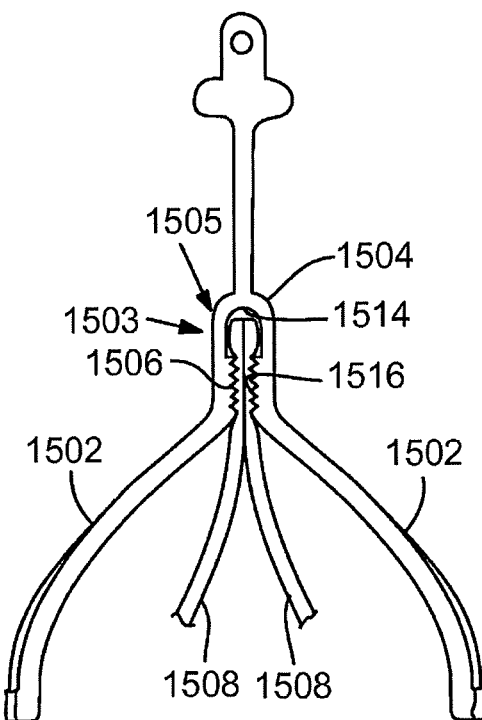
FIG. 62 is a partial side elevation view of another embodiment of the support frame of FIG. 61, in which the leaflet-engaging portion includes barbs.

FIG. 61 shows a modification of the stent 1500 having a leaflet-engagement portion 1505 that defines a first gap 1506 and a second gap 1514, with the first gap 1506 being narrower than the second gap 1514. The first gap 1506 can be defined by an increase in thickness of the respective struts 1502 in the region of the first gap 1506, and can comprise serrations 1516 on the respective struts 1502. The first gap 1506, together with the serrations 1516, can aid in retaining the native leaflets 1508 after insertion into the leaflet-engaging portion 1505. In some embodiments, the struts 1502 can have a uniform first thickness except for the portion of the respective struts 1502 that define the first gap 1506, where the thickness of the struts 1502 can increase to a second thickness that is greater than the first thickness before returning to the first thickness in the region defining the second gap 1514. In alternative embodiments, the struts 1502 can have a third thickness in the region defining the second gap 1514 that is less than the first thickness, as shown in FIG. 62.

Figure 63:
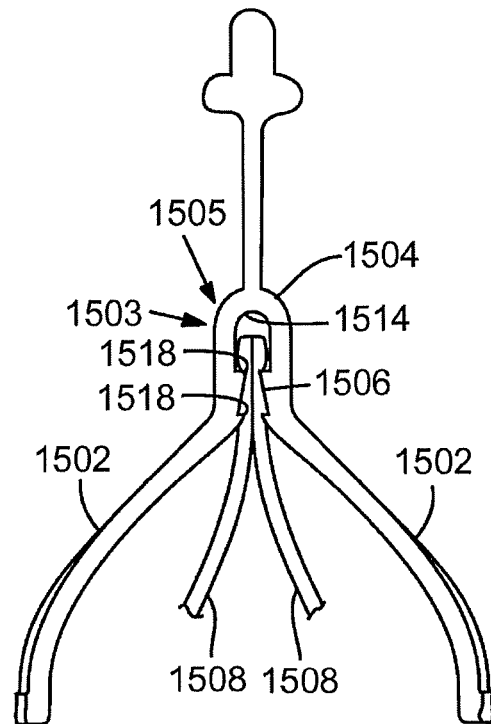
FIG. 63 is a partial side elevation view of another embodiment of the support frame of FIG. 61, wherein a gap of the leaflet-engaging portion comprises a tapered shape and one or more barbs.

FIG. 63 shows another modification of the stent 1500 wherein the first gap 1506 has a tapered shape, with the distance between respective struts 1502 decreasing from the inflow end of the first gap 1506 to the outflow end of the first gap 1506. The leaflet-engaging portion 1505 can also include one or more projections or barbs 1518 located on respective struts 1502 and extending into the first gap 1506 and or the second gap 1514. For example, as shown in FIG. 63, the leaflet-engaging portion 1505 can include barbs 1518 located on respective struts 1502 at the inflow end of the first gap 1506, and barbs 1518 located on the outflow end of the first gap 1506 and oriented generally in the direction of the second gap 1514. In this manner, the support frame 1500 can be retained in place after insertion of the native leaflets 1508 in the leaflet-engaging portion 1505. In alternative embodiments, the leaflet-engaging portion 1505 need not include barbs, or the barbs may be smooth projections rather than pointed projections.

Figure 64:
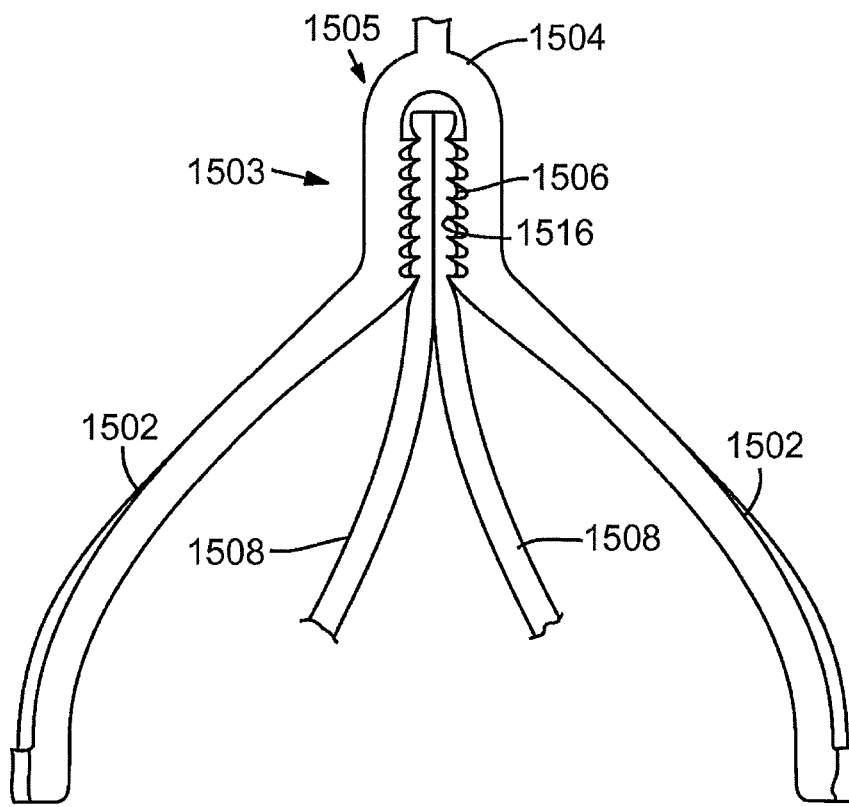
FIG. 64 is a partial side elevation view of another embodiment of the support frame of FIG. 60 comprising serrations.

In another alternative embodiment of the support frame 1500, the struts 1502 can define a single gap 1506 in the leaflet-engaging portion 1505, as shown in FIG. 64. The gap 1506 can comprise cutouts or serrations 1516 extending from the distal end of the gap 1506 to the proximal end, or any suitable length therebetween.

Figure 65:
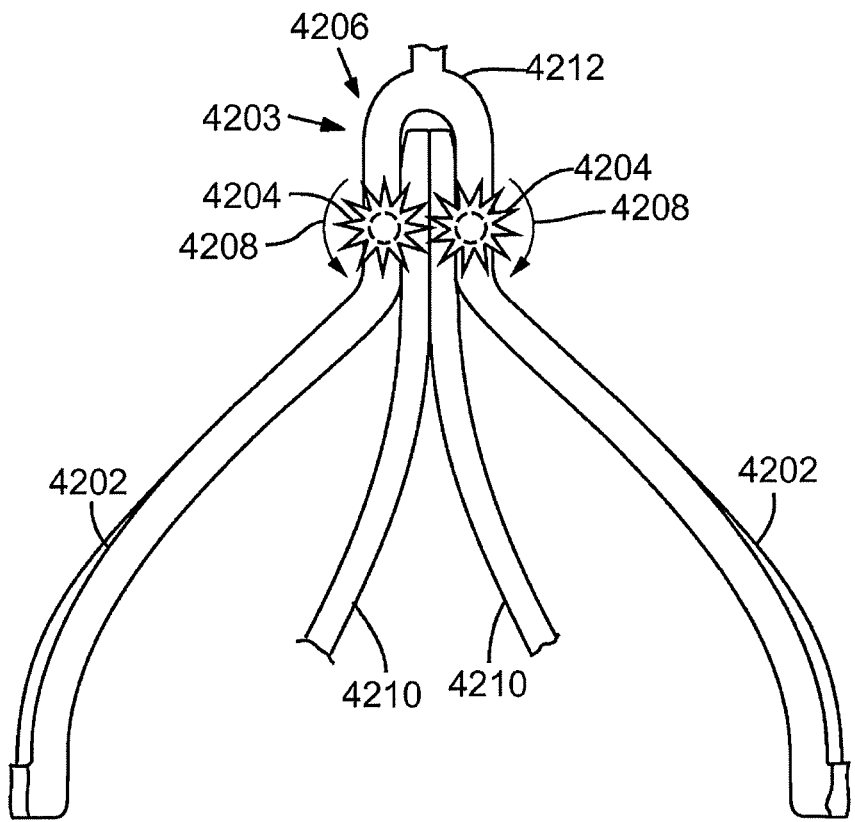
FIG. 65 is a partial side elevation view of another embodiment of the support frame of FIG. 60 comprising a pair of leaflet-engaging wheels.

FIG. 65 is a detail view of another embodiment of a support frame 4200 comprising an annular main body formed by a plurality of angled struts 4202. The support frame 4200 can include a leaflet-engaging mechanism 4203 comprising a pair of toothed or notched wheels 4204 rotatably secured to a leaflet-engaging portion 4206 of the frame 4200 below an apex 4212 defined by the intersection of the struts 4202. In the illustrated embodiment, each wheel 4204 can have an easy direction of rotation (indicated by arrows 4208), which permits native leaflets 4210 to easily enter the leaflet-engaging portion 4206 of the support frame 4200. Rotating each wheel 4204 in an opposite direction is more difficult, thereby tending to keep the leaflets 4210 engaged in the leaflet-engaging portion 4206. Some embodiments of the wheels 4204 can comprise a soft or elastomeric material contacting the leaflets 4210, thereby reducing wear or damage thereto. Some embodiments can include only one wheel 4204, which can engage the leaflets 4210 between the wheel 4204 and a strut 4202 of the leaflet-engaging portion 4206.

Figure 66A:
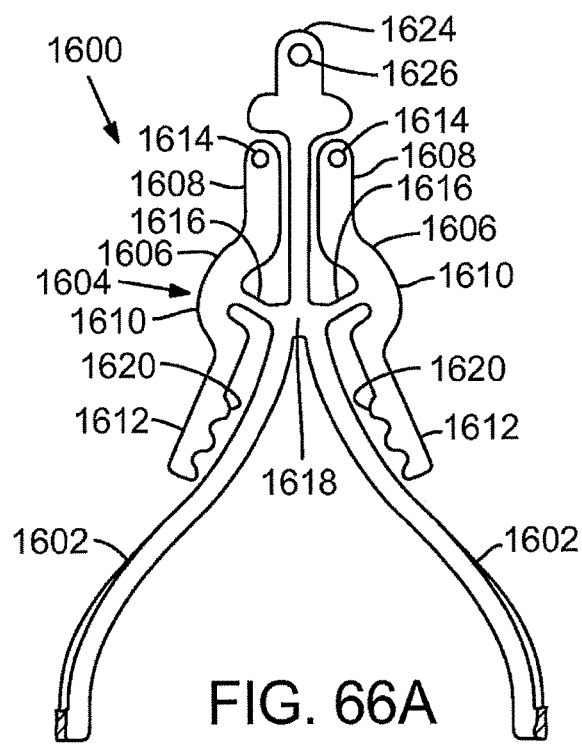
FIG. 66A is a partial side elevation view of another embodiment of a support frame including a leaflet-clipping mechanism configured as a pair of clipping arms.
Figure 66B:
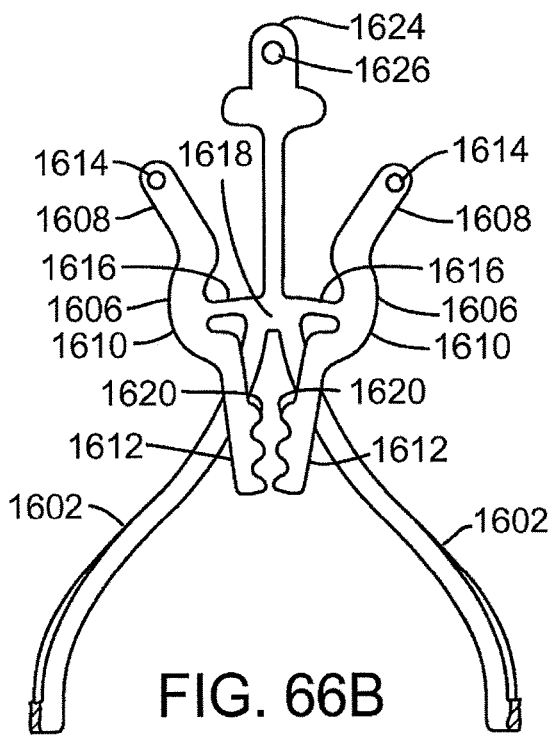
FIG. 66B is a partial side elevation view of the support frame of FIG. 66A illustrating the leaflet-clipping mechanism in the closed position.

FIGS. 66A-66D are detail views of another embodiment of a support frame 1600 comprising an annular main body formed by a plurality of struts 1602. The frame 1600 can include one or more active leaflet-clipping mechanisms 1604 comprising two clipping arms 1606 movable between an open position (FIG. 66A) and a closed position (FIG. 66B). In some embodiments, the clipping arms 1606 can be biased towards the closed position. The clipping arms 1606 can comprise respective proximal end portions 1608, intermediate portions 1610, and distal leaflet-engaging portions 1612. In the embodiment shown, the proximal end portions 1608 include holes or eyelets 1614 configured to receive wires or flexible prongs (e.g., flexible prongs 141 of the delivery system 350). In this manner, the clipping arms 1606 can be held in the open position when mounted on a delivery apparatus prior to implantation, as further described below.

The intermediate portions 1610 can include connecting members 1616 coupled to the struts 1602 of the stent 1600. In the embodiment shown, the connecting members 1616 can be coupled to the struts on or adjacent to the apices 1618 of the struts 1602. However, the connecting members 1616 can be coupled to the struts 1602 at any suitable location along the length of the struts. The connecting members 1616 can act as fulcrums about which the clipping arms 1606 pivot when moving between the open and closed positions.

Figure 66C:
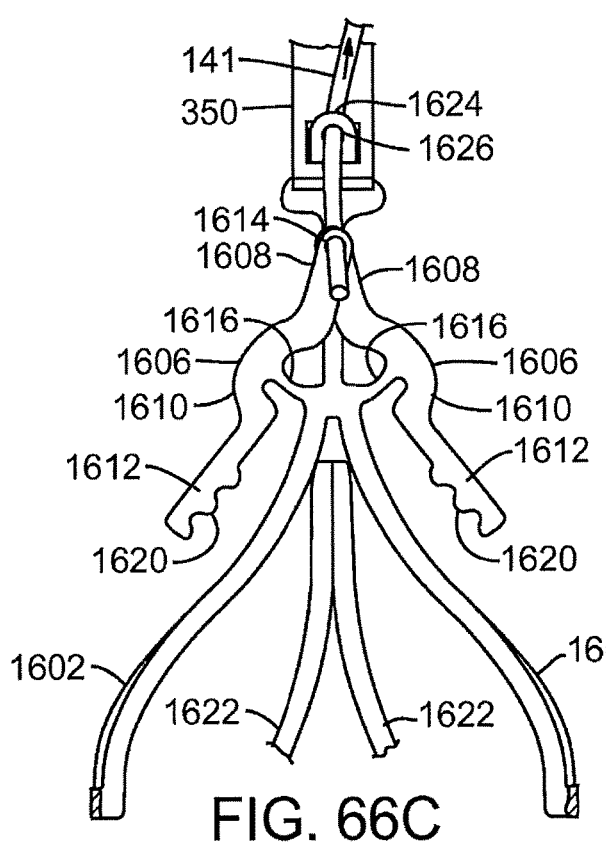
FIG. 66C is a partial side elevation view of the support frame of FIG. 66A illustrating the leaflet-clipping mechanism held in the open position by a delivery device.
Figure 66D:
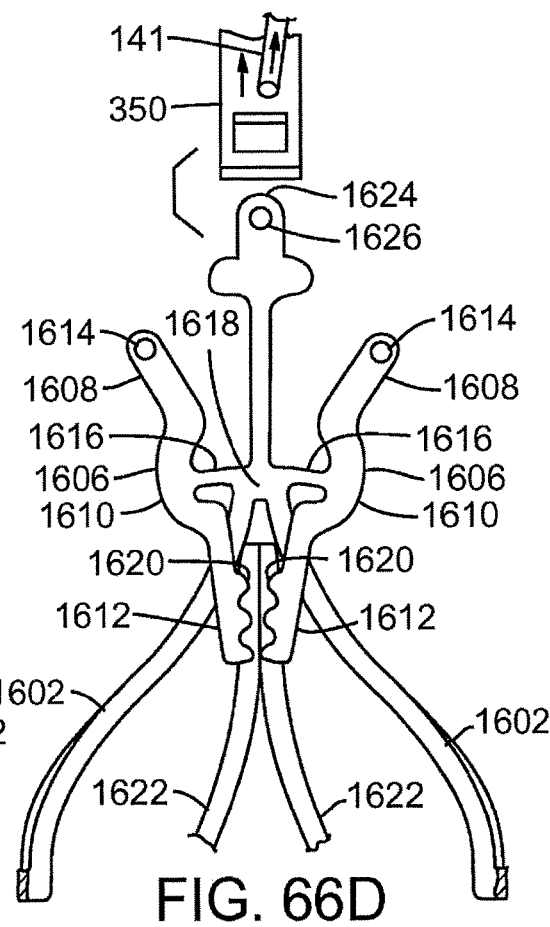
FIG. 66D is a partial side elevation view of the support frame of FIG. 66A illustrating the leaflet-clipping mechanism engaging a pair of native valve leaflets.

The leaflet-engaging portions 1612 can be configured to engage the native leaflets 1622 when the clipping arms 1606 are in the closed position, as shown in FIGS. 66C and 66D. In the embodiment shown, the leaflet-engaging portions 1612 include projections 1620 configured to engage and retain the native leaflets 1622 between the clipping arms 1606. Alternatively, the leaflet-engaging portions 1612 can include any suitable type of surface treatment to aid in retaining the leaflets 1622 between the clipping arms 1606 such as cutouts, serrations, surface roughness, etc. In further alternative embodiments, the leaflet-engaging portions 1612 may not include any surface treatment.

The struts 1602 and the one or more leaflet-engaging mechanisms 1604 can be laser cut (or otherwise machined or formed) from a single piece of material (e.g., a tubular piece of metal) such that the leaflet-engaging mechanisms 1604 are integral to the support stent. In other embodiments, the leaflet-engaging mechanisms 1604 can be separately formed and welded or otherwise coupled to the struts 1602. In some embodiments, the leaflet-engaging mechanisms 1604 can be located on the interior of the stent annulus. Alternatively, the leaflet-engaging mechanisms 1604 can be located on the exterior of the stent annulus.

[Advantages?]

After fabrication of the stent, the clipping arms 1606 can be arranged on respective sides of the struts 1602, with the connecting members coupled to the struts, as shown in FIG. 66A. The clipping arms 1606 can then be shape set such that the clipping arms are biased toward the closed position, as shown in FIG. 66B. Prior to insertion into a patient, the flexible prongs 141 of the delivery system 350 can be threaded through the apertures 1626 of the retaining arms 1624 and through the holes 1614 of the clipping arms such that the clipping arms 1606 are held in the open position, as shown in FIG. 66C. After positioning the stent over and around the valve leaflets 1622, the flexible prongs 141 can be retracted through the holes 1614, releasing the clipping arms 1606. The clipping arms 1606 can then move to the closed position, capturing the leaflets 1622 between respective leaflet-engaging portions 1612 of the clipping arms, as shown in FIG. 66D. The flexible prongs 141 can then be retracted through the apertures 1626 of the retaining arms 1624, and the delivery system 350 can be withdrawn, leaving the stent secured to the leaflets 1622 in the native valve.

FIGS. 67A, 67B, 68A, and 68B illustrate another embodiment of a support frame 1700 comprising an annular main body 1701 formed by a plurality of struts 1702. The stent 1700 can include one or more active leaflet-engaging mechanisms 1704 comprising an elongated member 1706 configured to move between an open position (FIG. 67A) and a closed position (FIG. 67B), in a direction indicated by arrow 1724. In the embodiment shown, the elongated member 1706 can comprise a proximal end portion 1708 having an eyelet or hole 1710, and a distal end portion 1712 coupled to an apex 1714 of the stent and/or the base of a retaining arm 1716. In the embodiment shown, the elongated member 1706 can be disposed in an opening 1726 defined by the retaining arm 1716 when the elongated member 1706 is in the open position, and can move out of the opening 1726 when moving to the closed position.

Figures 67A, 67B:
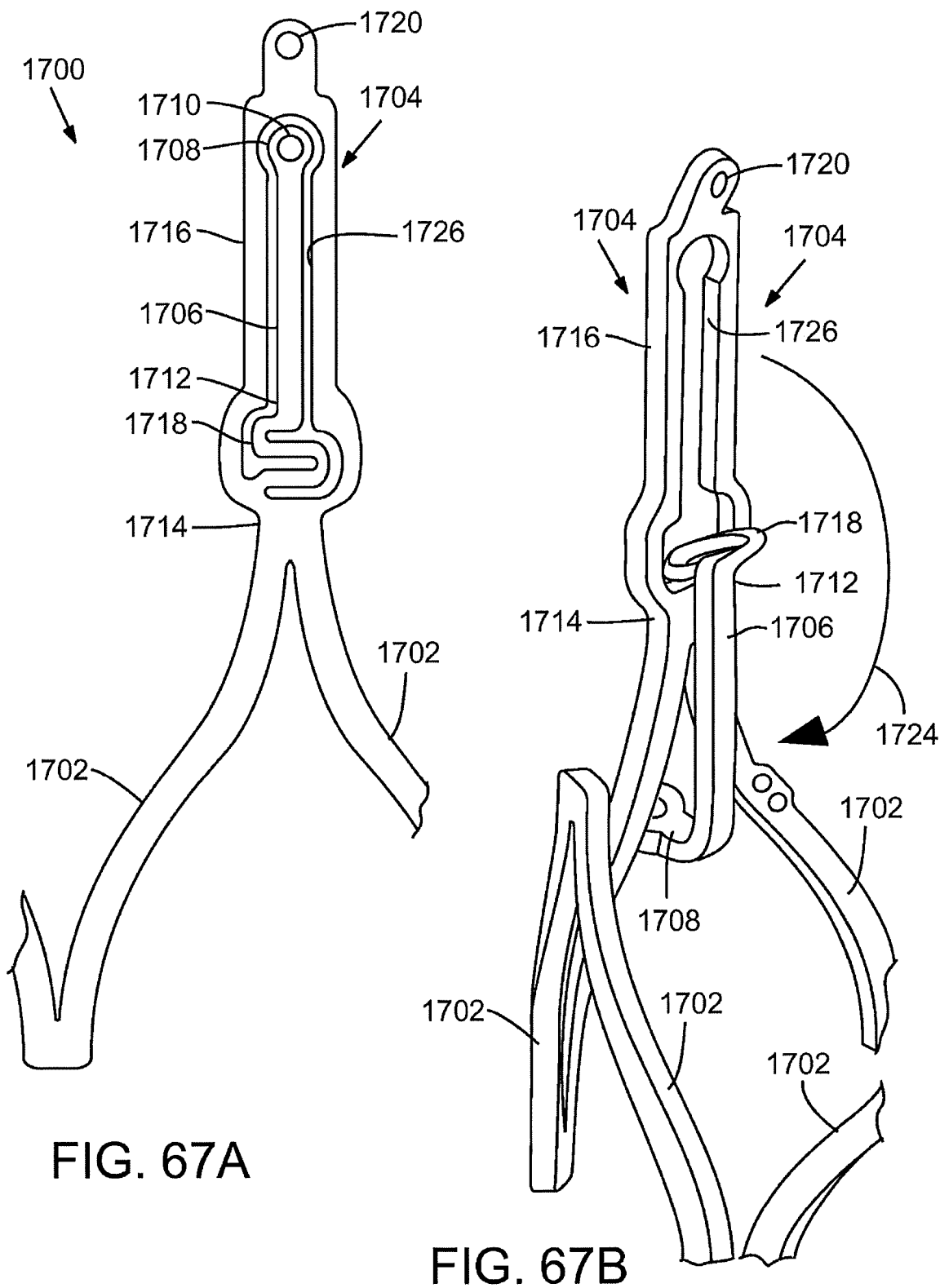
FIG. 67A is a partial side elevation view of another embodiment of a support frame including an elongated member configured as a leaflet-engaging mechanism.
FIG. 67B is a partial side elevation view of the support frame of FIG. 67A illustrating the leaflet-engaging mechanism in the closed position.

In some embodiments, the proximal end portion 1708 of the elongated member 1706 can be curved radially inward (i.e., curved in a direction toward the center of the valve annulus), as shown in FIG. 67B. Alternatively, the proximal end portion 1708 can be straight or otherwise conform to the vertical profile of the retaining arms 1714, as shown in FIG. 67A. The distal end portion 1712 can comprise a spring portion 1718, which can be shape set such that the elongated member 1706 is biased toward the closed position, as shown in FIG. 67B.

Figure 68A:
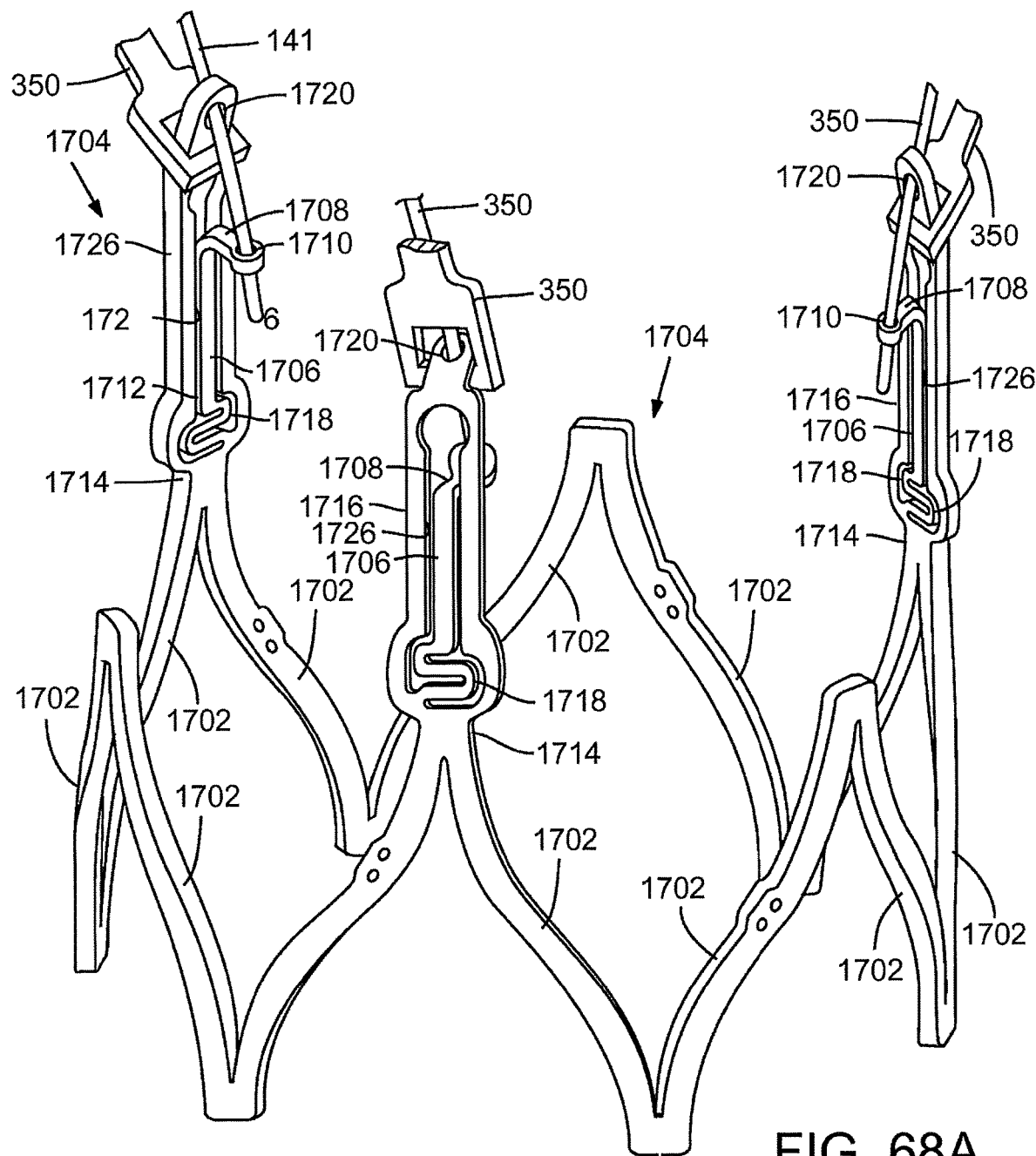
FIG. 68A is a perspective view of the support frame of FIG. 67A illustrating the leaflet-engaging mechanisms held in the open position by a delivery device.
Figure 68B:
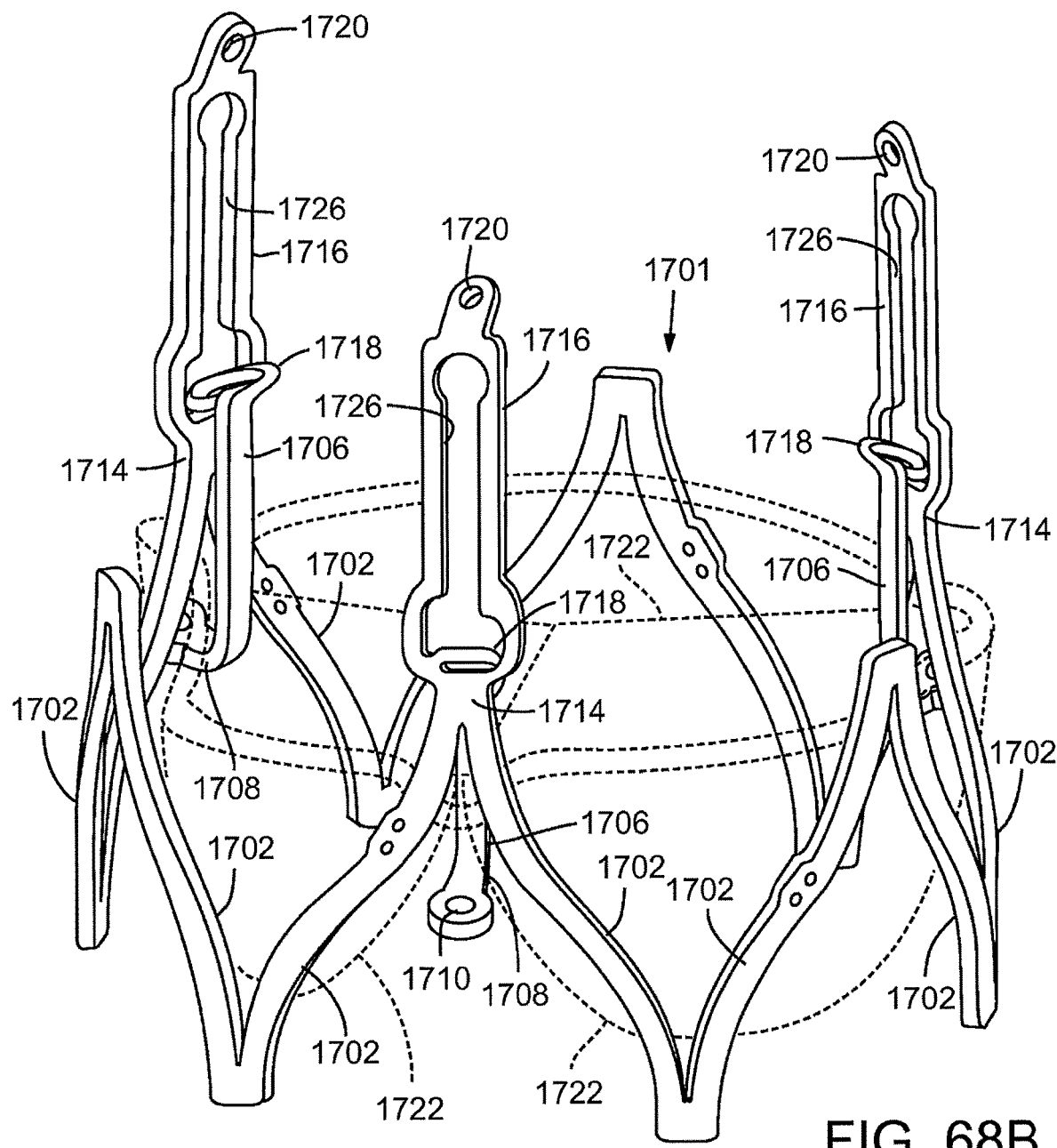
FIG. 68B is a perspective view of the support frame of FIG. 67A illustrating the leaflet-engaging mechanisms engaging native valve leaflets.

The leaflet-engaging mechanisms 1704 can be integrally formed (e.g., by laser cutting, machining, or forming) with the stent 1700 from a single piece of material (e.g., a piece of metal). Alternatively, the leaflet-engaging mechanisms 1704 can be separately formed and welded or otherwise coupled to the stent 1700. When the support frame 1700 is intended to be implanted at the aortic valve or the pulmonary valve, the support stent 1700 desirably has three, angularly spaced leaflet-engaging mechanisms 1704, with each mechanism being positioned at a commissure of the native valve when the support stent 1700 is implanted, as shown in FIGS. 68A and 68B. Similarly, if the support stent is configured to be implanted at the native mitral valve, the support stent desirably has two leaflet-engaging mechanisms 1704.

Prior to implantation, the elongated member 1706 can be shape set such that it is biased toward the closed position, as described above. The flexible prongs 141 of the delivery system 350 can be threaded through the apertures 1720 of the retaining arms 1716 and through the holes 1710 of the elongated member 1706 such that the elongated member is held in the open position, as shown in FIG. 68A. Referring to FIG. 68B, after positioning the stent over and around the valve leaflets 1722 (shown in phantom), the prongs 141 can be retracted through the holes 1710, releasing the elongated members 1706. The elongated members 1706 can then move to the closed position, engaging and retaining the leaflets 1722 between struts 1702, as shown in FIG. 66D. The prongs 141 can then be retracted through the apertures 1720 of the retaining arms 1716, and the delivery system 350 can be withdrawn, leaving the stent secured to the leaflets 1722 in the native valve.

Figure 69A:
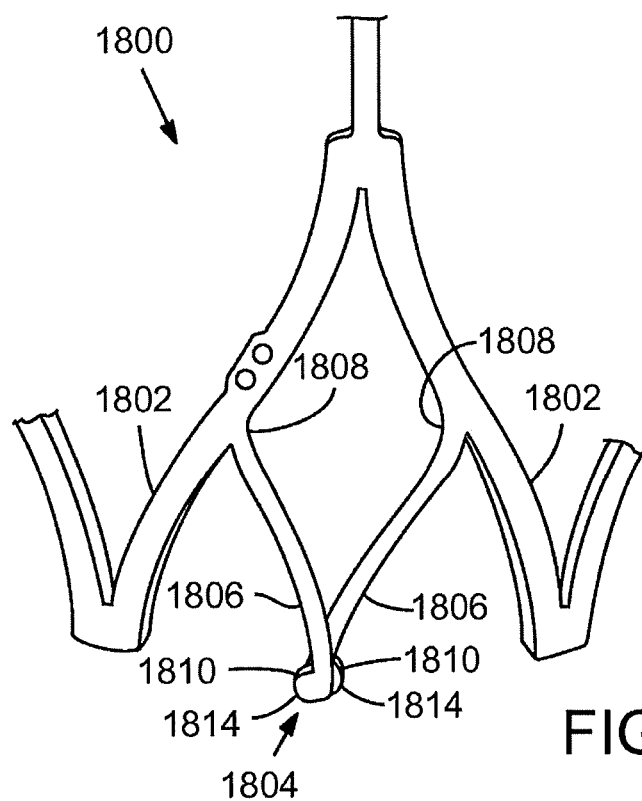
FIG. 69A is a partial side elevation view of another embodiment of a support frame including a leaflet-engaging mechanism configured as a pair of leaflet-engaging members.
Figure 69B:
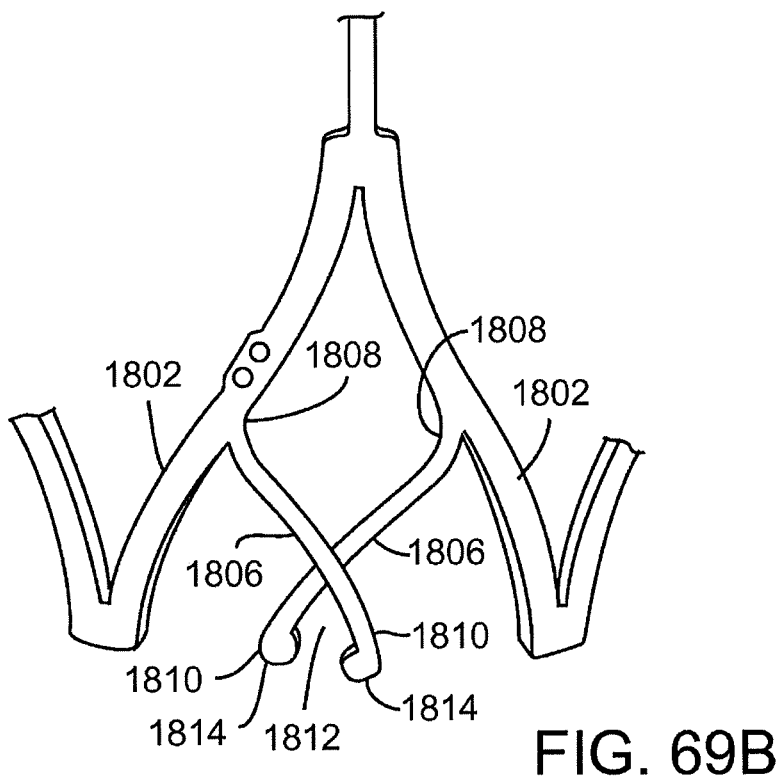
FIG. 69B is a partial side elevation view of the support frame of FIG. 69A illustrating the leaflet-engaging mechanism in the open position.

FIGS. 69A and 69B show a detail view of another embodiment of a support frame 1800 comprising an annular main body formed by a plurality of struts 1802. The stent 1800 can include one or more active leaflet-engaging mechanisms 1804 comprising a pair of leaflet-engaging members 1806 secured to respective struts 1802. The leaflet-engaging members 1806 can be movable between an open position, as shown in FIG. 69B, and a closed position, as shown in FIG. 69A. Each leaflet-engaging member 1806 can have a fixed end portion 1808 secured to a respective strut 1802 and a free end portion 1810. The leaflet-engaging members 1806 can extend distally from the struts 1802 toward the inflow end of the frame 1800 and toward one another, such that the free end portions 1810 are substantially coincident when the leaflet-engaging members 1806 are in the closed position. In the embodiment shown, the fixed end portions 1808 of the leaflet-engaging members 1806 are secured to the struts 1802 at the midpoint of the struts. However, in alternative embodiments, the leaflet-engaging members 1806 can be secured to the struts 1802 at any suitable location. In the illustrated embodiment, the free end portion 1810 of each leaflet-engaging member 1806 comprises a foot 1814 that can be directed towards the received leaflets (not shown), which can aid in retaining the leaflets between the leaflet-engaging members 1806. In alternative embodiments, the free end portions 1810 can comprise other leaflet-engaging features such as barbs, serrations, cutouts, hooks, surface roughness, etc.

The open and closed positions can correspond to a radially collapsed state and a radially expanded state of the frame 1800, respectively. For example, when the frame 1800 is in a radially collapsed state, such as when loaded or partially deployed from a delivery catheter, the struts 1802 can be circumferentially displaced toward one another, as shown in FIG. 69B. Circumferential displacement of the struts 1802 toward one another can cause the free end portions 1810 of the leaflet-engaging members 1806 to be circumferentially displaced away from one another, thereby defining a leaflet-engagement region 1812 between the free end portions 1810 of the respective leaflet-engaging members 1806. During implantation, the frame 1800 can be partially deployed from the delivery catheter and positioned such that the native valve leaflets (not shown) are located in the leaflet-engagement regions 1812 of the respective leaflet-engaging mechanisms 1804. The frame 1800 can then be fully deployed from the delivery catheter, causing the frame 1800 to expand to its functional size and causing the leaflet-engaging members 1806 to be circumferentially displaced to the closed position (causing the end portion 1810 to move toward each other, FIG. 69A), thereby engaging the leaflets at or near their commissures between the free end portions 1810 of the members 1806.

Figure 70A:
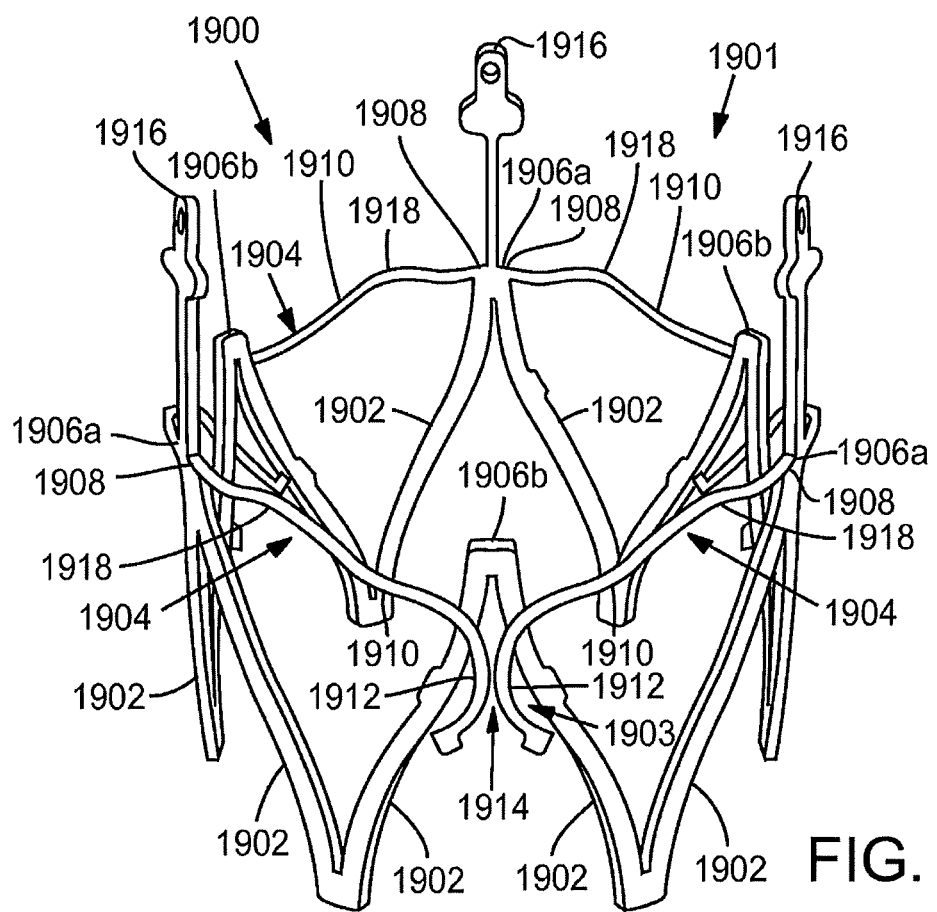
FIG. 70A is a perspective view of another embodiment of support frame including leaflet-engaging mechanisms configured as pairs of leaflet-engaging members.
Figure 70B:
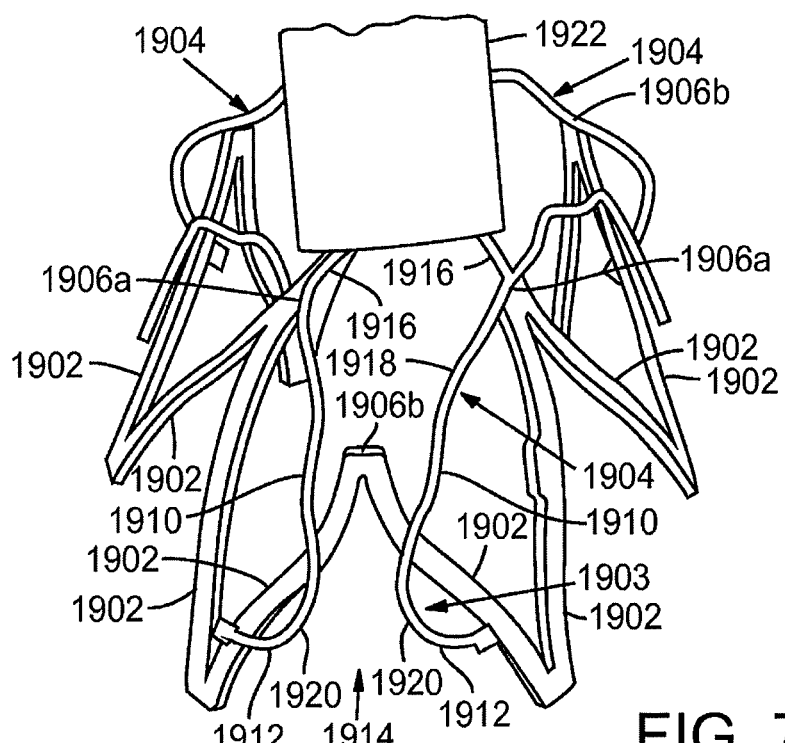
FIG. 70B is a perspective view of the support frame of FIG. 70A illustrating the leaflet-engaging mechanisms in the open position when the support frame is partially deployed from a delivery device.

FIGS. 70A and 70B show a perspective view of another embodiment of a support frame 1900 comprising an annular main body 1901 formed by a plurality of struts 1902. The frame 1900 can comprise one or more leaflet-engaging mechanisms 1903 comprising pairs of leaflet-engaging members 1904 extending circumferentially between alternating first and second apices 1906*a*, 1906*b*. Each leaflet-engaging member 1904 can comprise a fixed end portion 1908 coupled to a first apex 1906*a*, an intermediate portion 1910 coupled to an adjacent second apex 1906*b*, or to the struts 1902 immediately below the second apex 1906*b*, and a free end portion 1912 disposed beneath the second apex 1906*b*. The pairs of leaflet-engaging members 1904 can be configured to move between an open position (FIG. 70B) and a closed position (FIG. 70A) corresponding to a partially deployed (i.e., a partially radially collapsed) configuration and a fully deployed configuration of the stent 1900, respectively.

In the illustrated embodiment, the intermediate portions 1910 of the leaflet-engaging members 1904 can comprise peaks 1918 located approximately equidistant between the first and second apices 1906*a*, 1906*b*. The peaks 1918, along with the relatively long length of the intermediate portions 1910, can provide the leaflet-engaging members 1904 with some resiliency or flexibility which, in concert with the curved contact area, can reduce the risk of damage to the leaflets. The free end portions 1912 of the leaflet-engaging members 1904 of each respective pair can define a leaflet-engaging region or gap 1914 dimensioned to engage and retain the leaflets (not shown) of a native heart valve. In the embodiment shown, the free end portions 1912 of the leaflet-engaging members 1904 can define a curved leaflet contact area 1920, which can reduce the risk of damage to the leaflets. In some embodiments, the leaflet contact areas 1920 can include surface treatment such as projections, cutouts, surface roughness, etc., to aid in retaining the leaflets between the leaflet-engaging members.

In the embodiment shown, the first apices 1906*a* can comprise retaining arms 1916. In this manner, as the stent is deployed from a delivery catheter 1922, the second apices 1906*b* can emerge from the delivery catheter 1922 first, while the retaining arms 1916 of the first apices 1906*a* remain within the lumen of the delivery catheter 1922, as shown in FIG. 70B. This can cause the retaining arms 1916 and the associated first apices 1906*a* to flex radially inward, in turn drawing the struts 1902 of the second apices 1906*b* apart. This can cause the free end portions 1912 of the leaflet-engaging members 1904 to be drawn into the open position, allowing the leaflets to be inserted in the leaflet-engaging region 1914. Once situated about the leaflets, the retaining arms 1916 can be fully deployed from the delivery catheter 1922, allowing the frame 1900 to expand to its functional size and causing the leaflet-engaging members 1904 to move into the closed position, engaging and retaining the native leaflets. In some embodiments, the curved free end portions 1912 of the leaflet-engaging members 1904 can be configured to contact the leaflets in both the open and closed configurations, which can permit the leaflet-engaging members 1904 to roll into place as the support frame expands to the closed configuration, thereby reducing the risk of damage to the native leaflets.

The leaflet-engaging members 1904 can be integrally formed with the stent 1900, or can be separately formed and secured to the stent by, e.g., welding, brazing, adhesive, etc. In the embodiment shown, the fixed-end portions 1908 are integrally formed with the first apices 1906*a*, while the intermediate portions 1910 are welded to the radially outward-facing surfaces of the struts 1902 of the second apices 1906*b*. In alternative embodiments, the fixed-end portions 1908 and the intermediate portions 1910 can both be integrally formed with the respective first and second apices 1906*a*, 1906*b*, or the fixed end portions 1908 and the intermediate portions 1910 can be separately formed and secured to the respective apices 1906*a*, 1906*b* as described above.

FIGS. 71, 72A, 72B, and 73 illustrate another embodiment of a support frame 2000 comprising an annular main body 2001 having a plurality of leaflet-engaging mechanisms configured as frame subunits 2002 formed by a corresponding number of branching members 2004. The frame subunits 2002 can comprise an actuator portion 2006 and a leaflet-engaging portion 2008. The leaflet-engaging portion 2008 can comprise two leaflet-clipping subunits 2010 movable between an open position (FIG. 72A) and a closed position (FIGS. 71 and 72B) by actuation of the actuator portion 2006. In the embodiment shown, the frame 2000 includes three frame subunits 2002 formed by three respective branching members 2004, and interconnected by connecting members 2012.

Referring to the frame subunit 2002 shown fully in FIG. 71, the actuator portion 2006 can comprise a peak 2014 and a valley 2016. The peak 2014 can be formed by the intersection of a first branch 2018 and a second branch 2020 of the branching member 2004 at a proximal end of the actuator portion 2006. The first and second branches 2018, 2020 of the branching member 2004 can be arcuate, and can further branch into third and fourth branches 2022, 2024, and fifth and sixth branches 2026, 2028, respectively. The valley 2016 can be defined by the convergence of the fourth and fifth branches 2024, 2026 of the branching member 2004 near a proximal end of the leaflet-engaging portion 2008. In the embodiment shown, the fourth and fifth branches 2024, 2026 converge toward one another, but do not intersect to form a single integral member. However, in alternative embodiments, the fourth and fifth branches 2024, 2026 can intersect to form an integral member, as desired. In the embodiment shown, the peak 2010 can further comprise a retaining arm 2011.

Figure 73:
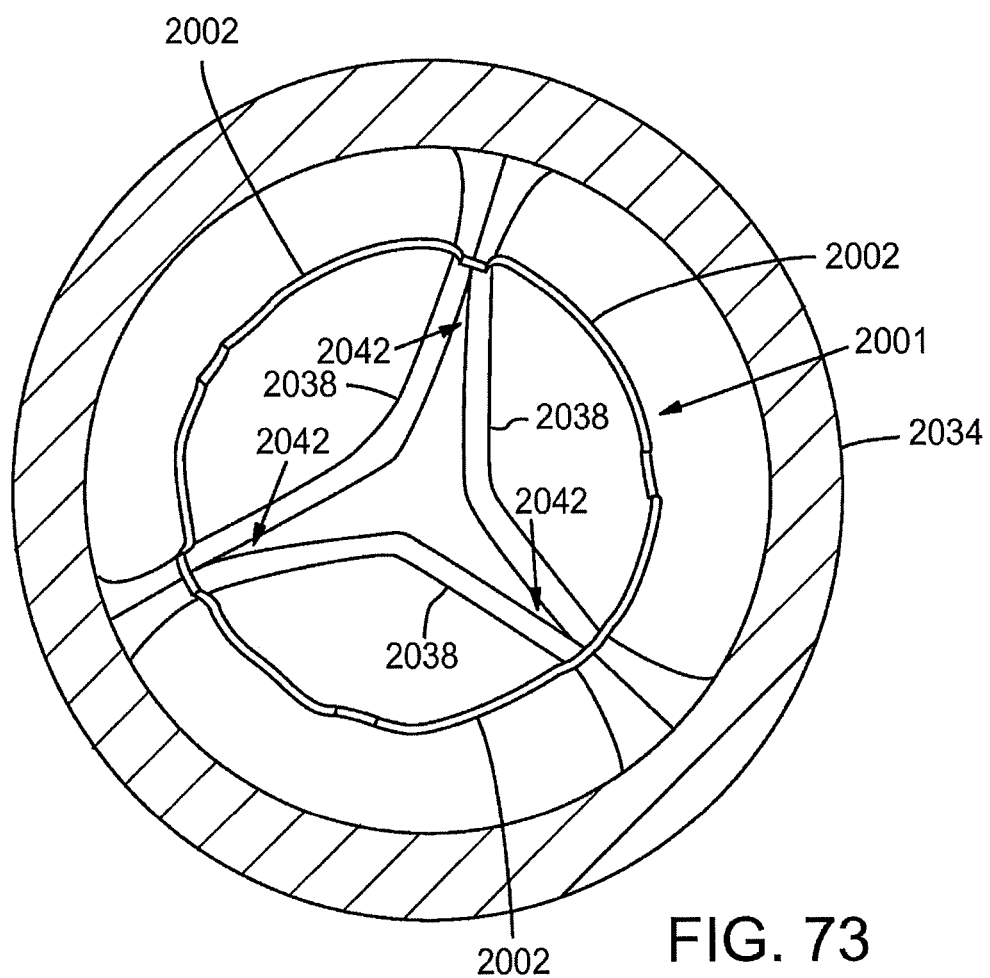
FIG. 73 is a plan view of the support frame of FIG. 71 implanted in an aortic valve.

The leaflet-clipping subunits 2010 can each have a peak 2030 and a valley 2032. The peaks 2030 can be formed by the respective proximal intersections of the third and fourth branches 2022, 2024, and the fifth and sixth branches 2026, 2028, respectively, of the branching member 2002. Similarly, the valleys 2032 can be formed by the respective distal intersections of the third and fourth branches 2022, 2024, and the fifth and sixth branches 2026, 2028, respectively. The respective peaks 2030 of the leaflet-clipping subunits 2010 can be angled away from one another such that the leaflet-clipping subunits 2010 are biased toward the closed position when the frame is in the fully expanded configuration. In this manner, the leaflet-clipping subunits 2010 can be configured to engage and retain native leaflets 2038 between the respective leaflet-clipping subunits 2010 when the frame 2000 is deployed in a native valve 2034, as shown in FIG. 73. The fourth and fifth branches 2024, 2026 can also be interconnected by a spring member 2036, which can aid in biasing the leaflet-clipping subunits 2010 toward the closed position.

The support frame 2000 can be configured such that when partially deployed from the end of a delivery catheter 2040 with the actuator portions 2006 of the respective frame subunits 2002 within the catheter and the leaflet-clipping subunits 2010 outside the catheter, radial compression of the actuator portions 2006 can actuate or lever the leaflet-clipping subunits 2010 into the open position, as shown in FIG. 72A. In this manner, a user can position the support frame 2000 over the commissures 2042 of the native valve leaflets 2038 such that the leaflets are located between respective leaflet-clipping subunits 2010 of the leaflet-engaging portions 2008. As the support frame 2000 is more fully deployed, the radial compression of the actuator portions 2006 can be released, causing the leaflet-clipping subunits 2010 to close, capturing the leaflets 2038 of the native valve 2034 therebetween, as shown in FIG. 73. Partially retracting the support frame 2000 back into the catheter 2040 can reopen the leaflet-clipping subunits 2010 by applying radial compression to the actuator portion 2006, permitting the user to reposition the device. FIG. 72B is an illustration of the support frame partially deployed from the delivery catheter 2040 with the leaflet-clipping subunits 2010 intermediate the open and closed positions. FIG. 73 is a top view of the support frame fully deployed in an aortic valve 2034.

The branching members 2004 of the support frame can be laser cut (or otherwise machined or formed) from a single piece of material (e.g., a tubular piece of metal) such that the frame subunits 2002 are integral to the support stent. In other embodiments, the various branches of the branching members 2004 can be separately formed and welded or otherwise coupled together to form the frame subunits 2002. In further alternative embodiments, respective frame subunits can be integrally formed and then joined together by, for example, welding, brazing, adhesives, etc.

Figure 74B:
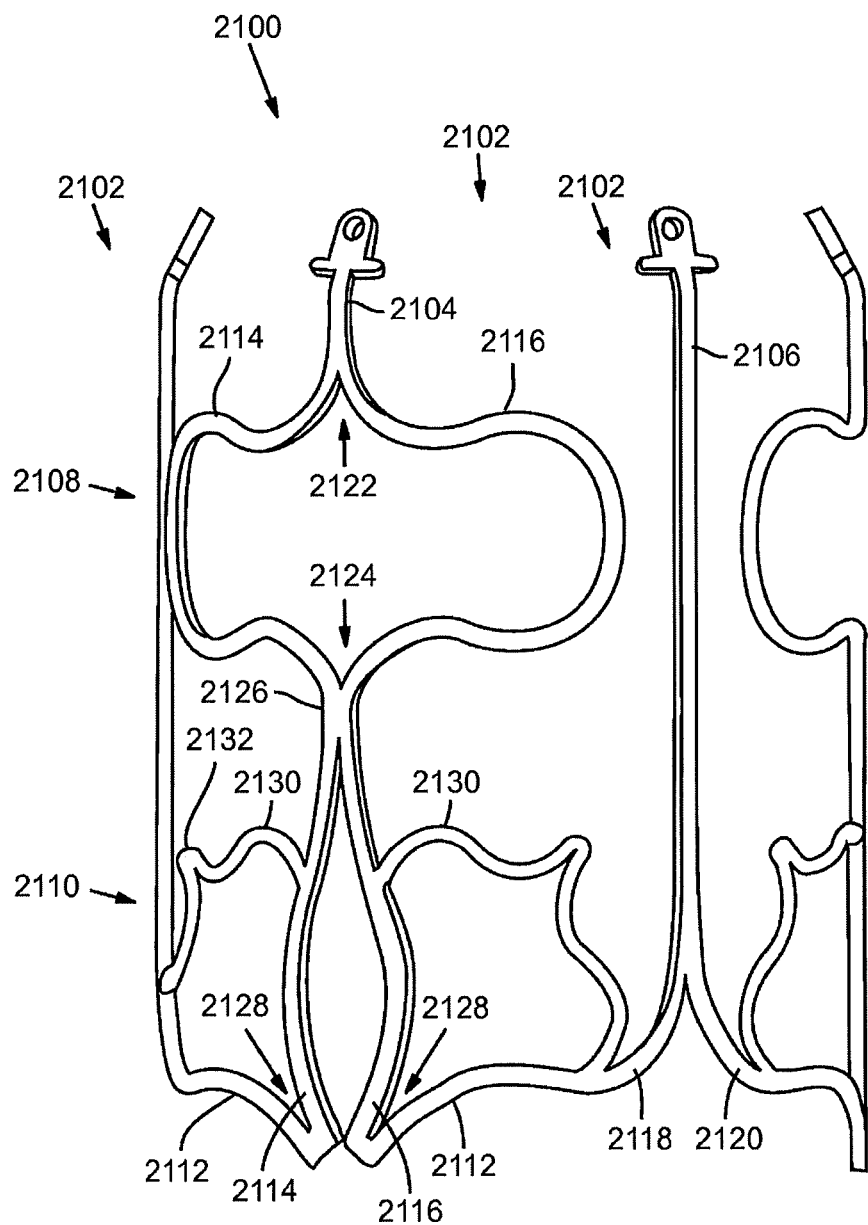
FIG. 74B is a side elevation view of the support frame of FIG. 74A in a fully expanded configuration.

FIGS. 74A and 74B illustrate another embodiment of a support frame 2100 comprising an annular main body 2101 including a plurality of leaflet-engaging mechanisms configured as frame subunits 2102. The frame subunits 2102 can be formed by a plurality of first and second frame members 2104, 2106 configured as retaining arms. FIG. 74A is a side elevation view of a flattened layout pattern of the support frame 2100, while FIG. 74B illustrates the support frame 2100 in a fully expanded configuration. The frame subunits 2102 can comprise an actuator portion 2108 and a leaflet-engaging portion 2110. The leaflet-engaging portion 2110 can comprise two leaflet-clipping subunits 2112 movable between an open position and a closed position by actuation of the actuator portion 2108, similar to the embodiment of FIG. 71. In the embodiment shown, the frame 2100 includes three frame subunits 2102, although the frame can include any suitable number of frame subunits depending upon the valve structure into which the frame is to be implanted.

Each of the first frame members 2104 can comprise first and second internal branches 2114, 2116, which can define the actuator portions 2108 of the respective frame subunits 2102, as further described below. Each of the second frame members 2106 can comprise first and second external branches 2118, 2120, which can define respective boundaries of the leaflet-engaging portions 2110. In the embodiment shown, the frame subunits 2102 can be bounded by respective second frame members 2106.

The actuator portion 2108 can comprise a peak 2122 and a valley 2124. The peak 2122 can be formed by the intersection of the first internal branch 2114 and the second internal branch 2116 of the first frame member 2104 at a proximal end of the first frame member 2104. The first and second internal branches 2114, 2116 of the first frame member 2104 can be symmetrically arcuate, and can intersect one another at an intersection 2126 located at a distal end of the actuator portion 2108, thereby defining the valley 2124 of the actuator portion 2108. In the embodiment shown, the intersection 2126 can act as a lever, causing the leaflet-clipping subunits 2112 to move to the open position when radial compression is applied to the first and second internal branches 2114, 2116 of the actuator portion 2106. In alternative embodiments, the first and second internal branches 2114, 2116 of the first frame member 2104 need not intersect.

Referring to the leaflet-engaging portion 2110, the first and second internal branches 2114, 2116 of the first frame member 2104 can continue to extend distally from the intersection 2126 to a distal end of the leaflet-engaging portion 2110 where they can intersect the first and second external branches 2118, 2120 of the second frame member 2106 to form valleys 2128 of the respective leaflet-clipping subunits 2110. The first internal branches 2114 and the second external branches 2120, and the second internal branches 2116 and the first external branches 2118, can be interconnected by respective interconnecting members 2130. The interconnecting members 2130 can define peaks 2132, which can be angled away from one another. In this manner, the interconnecting members 2130 can act as springs biasing the leaflet-clipping subunits 2112 toward the closed position when the stent 2100 is in the fully expanded configuration. In this manner, the leaflet-clipping subunits 2112 can be configured to engage and retain native valve leaflets between the respective leaflet-clipping subunits when the frame is deployed in a native valve.

The support frame 2100 can be configured such that when partially deployed from the end of a catheter with the actuator portions 2108 of the respective frame subunits 2102 within the catheter and the leaflet-clipping subunits 2112 outside the catheter, radial compression of the actuator portions 2108 can actuate or lever the leaflet-clipping subunits 2112 into the open position, similar to the embodiment of FIG. 71. In this manner, a user can position the support frame 2100 over the commissures of the native valve leaflets such that the leaflets are located between respective leaflet-clipping subunits 2112 of the leaflet-engaging portions 2110. As the support frame 2100 is more fully deployed, the radial compression of the actuator portions 2108 can be released, causing the leaflet-clipping subunits 2112 to move to the closed position, capturing the leaflets of the native valve therebetween. Partially retracting the support frame 2100 back into the catheter can reopen the leaflet-clipping subunits 2112 by reapplying radial compression to the actuator portions 2108, permitting the user to reposition the device.

The first and second frame members 2104, 2106 of the support frame 2100 can be laser cut (or otherwise machined or formed) from a single piece of material (e.g., a tubular piece of metal) such that the frame subunits 2102 are integral to the support stent. In other embodiments, the various branches of the first and second frame members 2104, 2106 can be separately formed and welded or otherwise coupled together to form the frame subunits 2102.

Figure 75A:
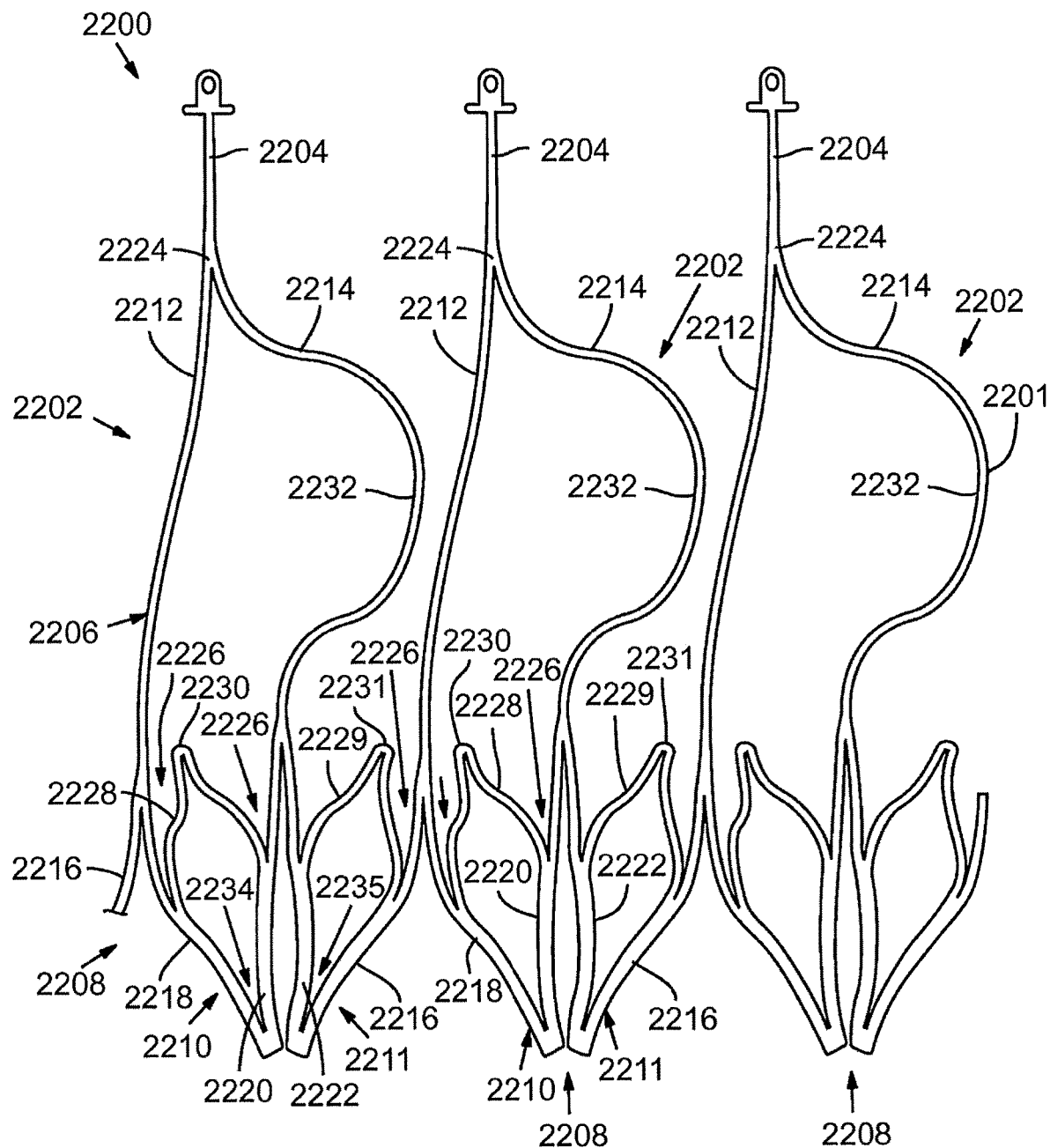
FIG. 75A is a side elevation view of another embodiment of a support frame in a flattened state and comprising a plurality of subunits, the subunits defining leaflet-engaging mechanisms.
Figure 75B:
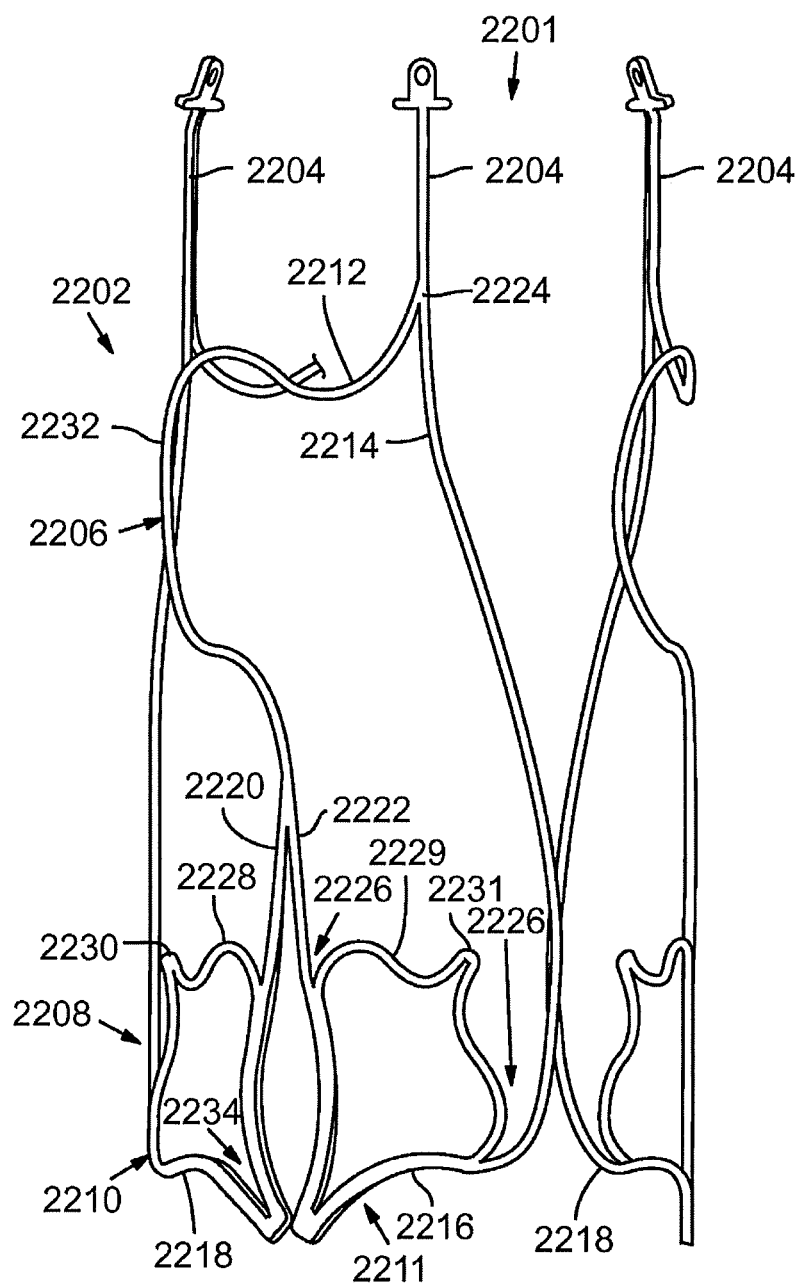
FIG. 75B is a side elevation view of the support frame of FIG. 75A in a fully expanded configuration.

FIGS. 75A and 75B illustrate another embodiment of a support frame 2200 comprising an annular main body 2201 including a plurality of leaflet-engaging mechanisms configured as frame subunits 2202. The frame subunits 2202 can be formed by a plurality of frame members 2204 configured as retaining arms, similar to the embodiment of FIGS. 74A and 74B. FIG. 75A is a side elevation view of a flattened layout pattern of the support frame 2200, while FIG. 75B illustrates the support frame 2200 in a fully expanded configuration. The frame subunits 2202 can comprise an actuator portion 2206 and a leaflet-engaging portion 2208. The leaflet-engaging portion 2208 can comprise two leaflet-clipping subunits 2210, 2211 movable between an open position and a closed position by actuation of the actuator portion 2206, similar to the embodiment of FIG. 71. In the embodiment shown, the frame 2200 includes three frame subunits 2202, although the frame can include any suitable number of frame subunits depending upon the valve structure into which the frame is to be implanted.

Each of the frame members 2204 can comprise first and second branches 2212, 2214, which can define the actuator portions 2206 of respective frame subunits 2202, as further described below. Each respective first branch 2212 can further divide into third and fourth branches 2216, 2218, which can define respective boundaries of the leaflet-clipping subunits 2210, 2211. Similarly, each respective second branch 2214 can further divide into fifth and sixth branches 2220, 2222.

Referring to the frame subunits 2202 generally, the actuator portion 2206 can comprise a peak 2224 and two valleys 2226. The peak 2224 can be formed by the intersection of the first branch 2212 and the second branch 2214 of the frame member 2204 at a proximal end of the frame member 2204. The valleys 2226 can be defined by the fourth and fifth branches 2218, 2220, and an interconnecting member 2228, which can extend between the fourth and fifth branches 2218, 2220. In the embodiment shown, the second branch 2214 can have an arcuate portion 2232 extending laterally with respect to a longitudinal axis of the support frame 2200. In this manner, radial compression of the actuator portion 2206, and particularly of the second branch 2214, can cause the leaflet-clipping subunits 2210, 2211 to move to the open position.

Referring to the leaflet-engaging portion 2208, the third and fourth branches 2216, 2218 of the frame member 2204 can extend distally from the first branch 2212 to a distal end of the leaflet-engaging portion 2208 where they can intersect the sixth and fifth branches 2222, 2220, respectively. In this manner, the third and sixth branches 2216, 2222 of the frame member 2204 can define a valley 2235 of the leaflet-clipping subunit 2210, and the fourth and fifth branches 2218, 2220 can define a valley 2234 of the leaflet-clipping subunit 2211. The sixth branch 2222 and the third branch 2216 can also be interconnected by an interconnecting member 2229, similar to the interconnecting member 2228. The interconnecting members 2228, 2229 can comprise central peaks 2230, 2231, respectively, and can be angled away from one another. In this manner, the interconnecting members 2228, 2229 can act as springs, biasing the leaflet-clipping subunits 2210, 2211 toward the closed position when the stent 2200 is in the fully expanded configuration. In this manner, the leaflet-clipping subunits 2210, 2211 can be configured to engage and retain the native leaflets of a heart valve between the respective leaflet-clipping subunits when the frame is deployed in a native valve.

The support frame 2200 can be configured such that when partially deployed from the end of a catheter with the actuator portions 2206 of the respective frame subunits 2202 within the catheter and the leaflet-clipping subunits 2210, 2211 outside the catheter, radial compression of the actuator portions 2206 can actuate or lever the leaflet-clipping subunits 2210, 2211 into the open position, similar to the embodiment of FIG. 71. In this manner, a user can position the support frame over the commissures of the native valve leaflets such that the leaflets are located between respective leaflet-clipping subunits 2210, 2211 of the leaflet-engaging portions 2208. As the support frame 2200 is more fully deployed, the radial compression of the actuator portions 2206 can be released, causing the leaflet-clipping subunits 2210, 2211 to move to the closed position, capturing the leaflets of the native valve therebetween. Partially retracting the support frame 2200 back into the catheter can reopen the leaflet-clipping subunits 2210, 2211 by reapplying radial compression to the actuator portions 2206, permitting the user to reposition the device.

Figure 76A:
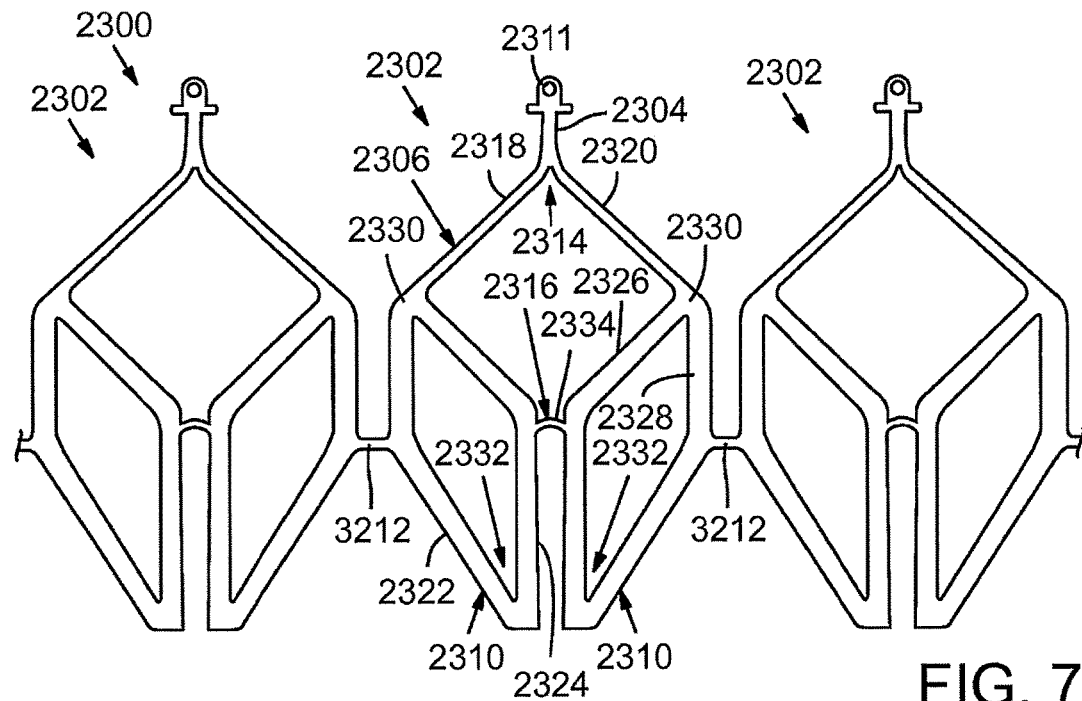
FIG. 76A is a side elevation view of another embodiment of a support frame in a flattened state and comprising a plurality of subunits, the subunits defining leaflet-engaging mechanisms.
Figure 76B:
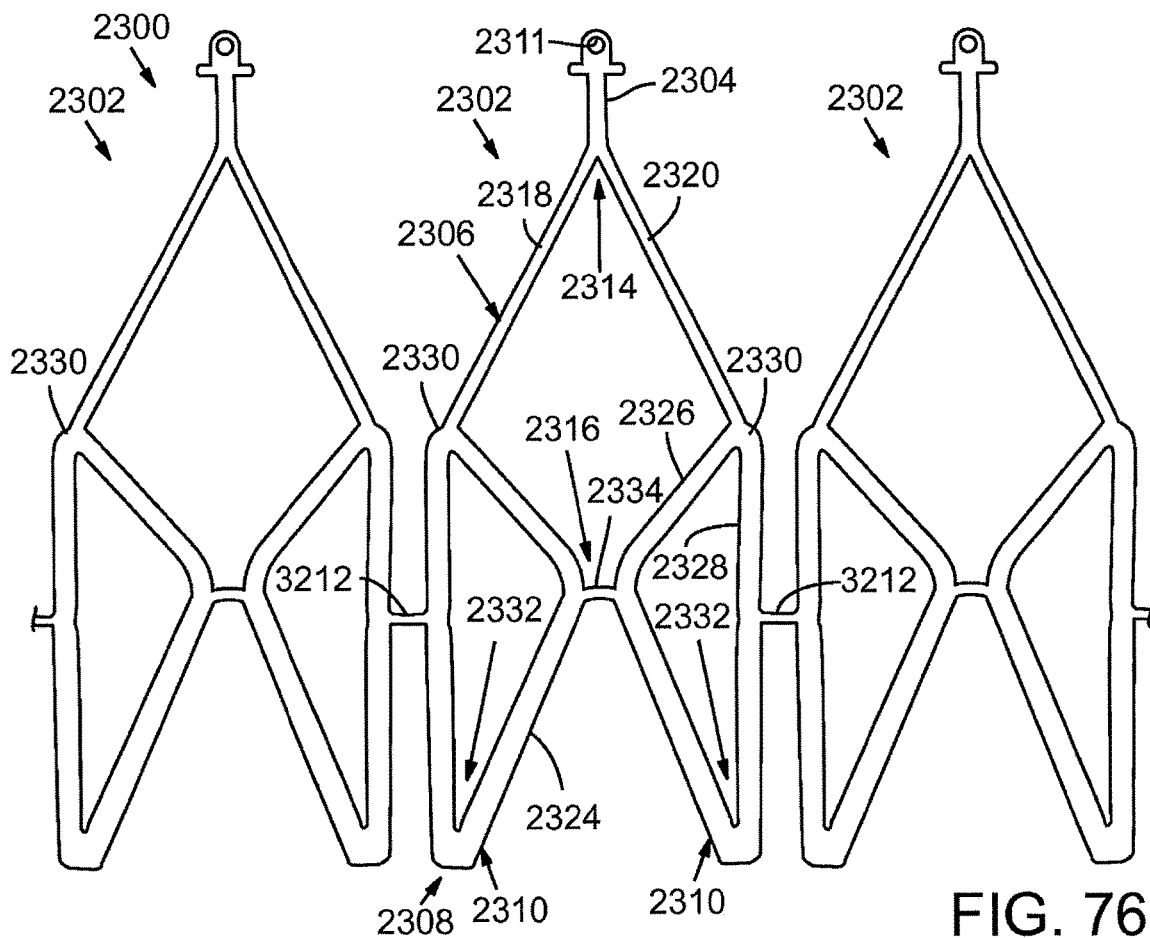
FIG. 76B is a side elevation view of the support frame of FIG. 76A in a flattened state illustrating the leaflet-engaging mechanisms in the open position.

FIGS. 76A and 76B illustrate another embodiment of a support frame 2300 comprising an annular main body including a plurality of leaflet-engaging mechanisms configured as frame subunits 2302. The plurality of frame subunits 2302 can be formed by a corresponding number of branching members 2304, similar to the embodiment of FIG. 71. The frame subunits 2302 can comprise an actuator portion 2306 and a leaflet-engaging portion 2308. The leaflet-engaging portion 2308 can comprise two leaflet-clipping subunits 2310 movable between an open position (FIG. 76B) and a closed position (FIG. 76A) by actuation of the actuator portion 2306. In the embodiment shown, the frame 2300 includes three frame subunits 2302 formed by three respective branching members 2304, and interconnected by connecting members 2312.

Referring to the frame subunits 2302 generally, the actuator portion 2306 can comprise a peak 2314 and a valley 2316. The peak 2314 can be formed by the intersection of a first branch 2318 and a second branch 2320 of the branching member 2004 at a proximal end of the actuator portion 2306. The first and second branches 2318, 2320 of the branching member 2304 can be angular, and can further branch into third and fourth branches 2322, 2324, and fifth and sixth branches 2326, 2328, respectively. In the embodiment shown, the third, fourth, fifth, and sixth branches 2322, 2324, 2326, 2328 are thicker than the first and second branches 2318, 2320 from which they originate. In this manner, the first and second branches 2318, 2320 can be configured to deform to a greater degree than the leaflet-clipping subunits 2310 when the when the support frame is in the open configuration. However, in alternative embodiments, all branches of the branching member 2304 can have the same thickness.

The valley 2316 can be defined by the convergence of the fourth and fifth branches 2324, 2326 of the branching member 2304 near a proximal end of the leaflet-engaging portion 2308, where the fourth and fifth branches 2324, 2326 can be interconnected by a spring member 2334. In the embodiment shown, the fourth and fifth branches 2324, 2326 converge, but do not intersect to form a single integral member. However, in alternative embodiments, the fourth and fifth branches 2324, 2326 can intersect to form an integral member, as desired. In the embodiment shown, the peak 2314 can further comprise a retaining arm 2311.

The leaflet-clipping subunits 2310 can each have a peak 2330 and a valley 2332. The peaks 2330 can be formed by the respective proximal intersections of the third and fourth branches 2322, 2324, and the fifth and sixth branches 2326, 2328, respectively, of the branching member 2302. Similarly, the valleys 2332 can be formed by the respective distal intersections of the third and fourth branches 2322, 2324, and the fifth and sixth branches 2326, 2328, respectively. The respective peaks 2330 of the leaflet-clipping subunits 2310 can be angled away from one another such that the leaflet-clipping subunits are biased toward the closed position when the frame is in the fully expanded configuration. In this manner, the leaflet-clipping subunits 2310 can be configured to engage and retain the native leaflets between the respective leaflet-clipping subunits 2310 when the frame 2300 is deployed in a native valve. As noted above, the fourth and fifth branches 2324, 2326 can also be interconnected by a spring member 2334, which can aid in biasing the leaflet-clipping subunits 2310 toward the closed position.

The support frame 2300 can be configured such that when partially deployed from the end of a catheter with the actuator portions 2306 of the respective frame subunits 2302 within the catheter and the leaflet-clipping subunits 2310 outside the catheter, radial compression of the actuator portions 2306 can actuate or lever the leaflet-clipping subunits 2310 into the open position (FIG. 76B), as described above with respect to the embodiment of FIG. 71. In this manner, a user can position the support frame 2300 over the commissures of the native valve such that the leaflets are located between respective leaflet-clipping subunits 2310 of the leaflet-engaging portions 2308. As the support frame 2300 is more fully deployed, the radial compression of the actuator portions 2306 can be released, causing the leaflet-clipping subunits 2310 to close (FIG. 76A), capturing the leaflets of the native valve therebetween. Partially retracting the support frame back into the catheter can reopen the leaflet-clipping subunits 2310 by reapplying radial compression to the actuator portion 2306, permitting the user to reposition the device.

The branching members 2304 of the support frame can be laser cut (or otherwise machined or formed) from a single piece of material (e.g., a tubular piece of metal) such that the frame subunits 2302 are integral to the support stent. In other embodiments, the various branches of the branching members 2304 can be separately formed and welded or otherwise coupled together to form the frame subunits 2302. In further alternative embodiments, respective frame subunits can be integrally formed and then joined together by, for example, welding, brazing, adhesives, etc.

Figure 77A:
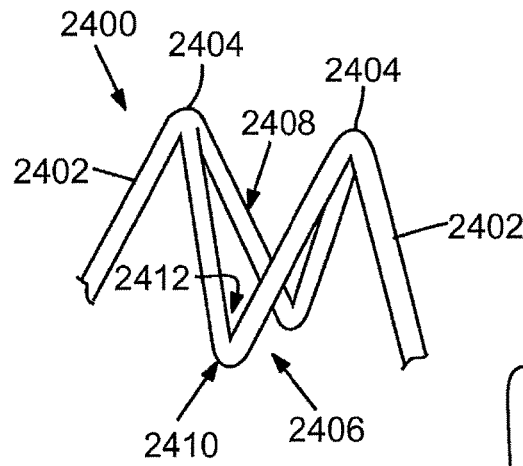
FIG. 77A is a partial perspective view of another embodiment of a support frame comprising one or more leaflet-engaging mechanisms including pairs of struts.
Figure 77B:
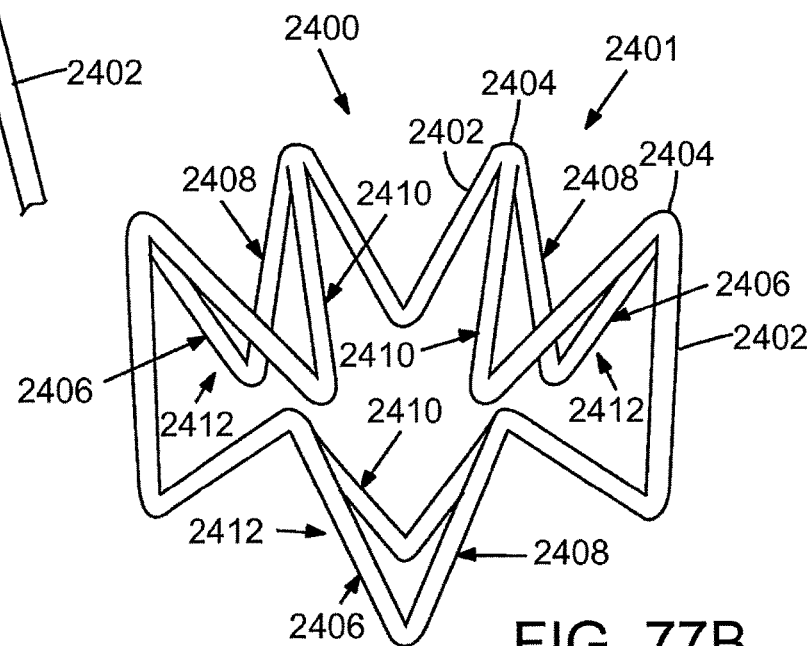
FIG. 77B is a perspective view of the support frame of FIG. 77A.

FIGS. 77A and 77B illustrate another embodiment of a support frame 2400 comprising an annular main body 2401 (FIG. 77B) formed by a plurality of struts 2402, which can include a plurality of apices 2404 formed by the intersection of two adjacent struts 2402. The support frame can further include one or more leaflet-engaging mechanisms 2406 comprising first and second pairs 2408, 2410 of struts 2402 extending distally from respective apices 2404. The struts 2402 of each respective pair 2408, 2410 can be angled away from one another such that the pairs 2408, 2410 of struts 2402 define a leaflet capture region 2412 therebetween. The pairs 2408, 2410 of struts 2402 of each leaflet-engaging portion 2406 can also be angled away from one another such that the leaflet capture region 2412 defined therebetween narrows toward the proximal end of the support frame 2400 before terminating at the respective apices 2404.

For example, in the embodiment shown in FIGS. 77A and 77B, the first pair 2408 of struts 2402 can be angled such that the struts 2402 extend radially inward from the respective apices 2404. Similarly, the second pair 2410 of struts 2402 can be angled such that the struts 2402 extend radially outward from the respective apices 2404. In this manner, the leaflet-engaging portions 2406 can be slipped over the native leaflets of the aorta like paperclips. In some embodiments, the distal end portions of the struts 2402 of the first and second pairs 2408, 2410 can include surface treatments such as threads, grooves, surface roughness, etc., to aid in retaining the native leaflets 2414 after implantation.

Figure 77C:
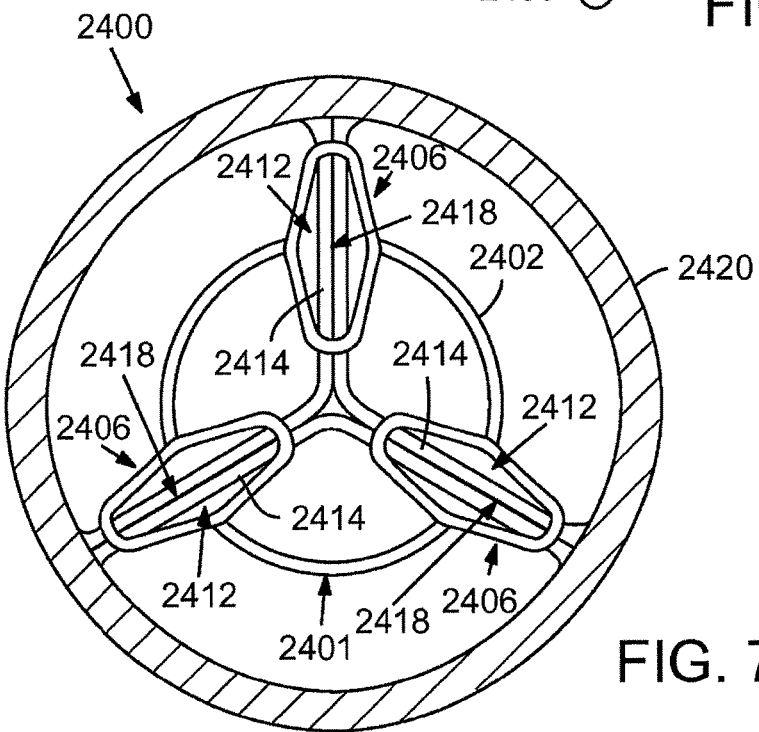
FIG. 77C is a plan view illustrating an alternative embodiment of the support frame of FIG. 77A located in a native heart valve.

In an alternative embodiment shown in FIG. 77C, the leaflet-engaging mechanisms 2406 can be oriented at right angles to the annular main body 2401. In this manner, the leaflet-engaging mechanisms 2406 can be slipped over the commissures 2418 formed by the native leaflets 2414 of the aorta 2420. In this manner, the support frame 2400 can reduce the valvular orifice area of the aorta 2420 by restricting the degree to which the native leaflets 2414 are allowed to open.

Figure 78:
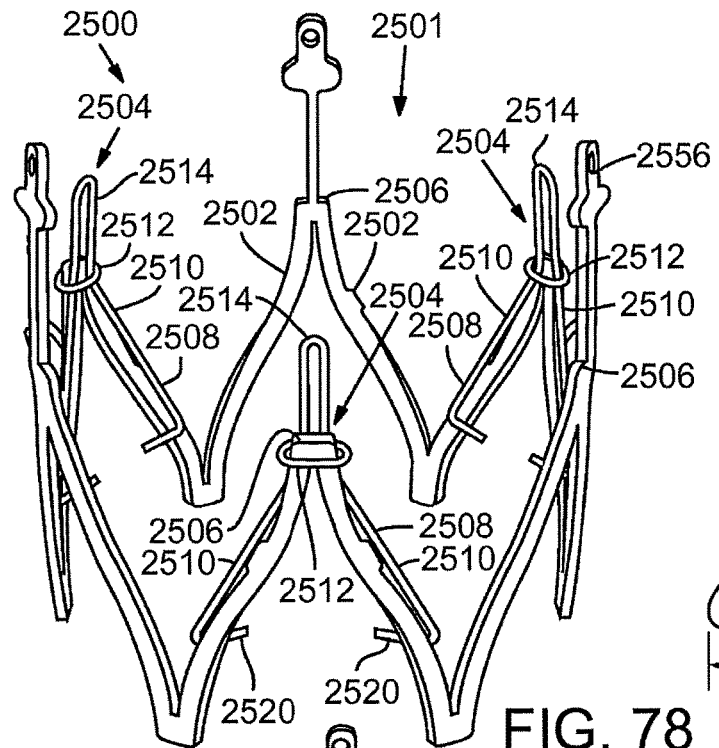
FIG. 78 is a perspective view of another embodiment of support frame comprising leaflet-clipping mechanisms configured as clipping arms located on the interior of the support frame.
Figure 79:
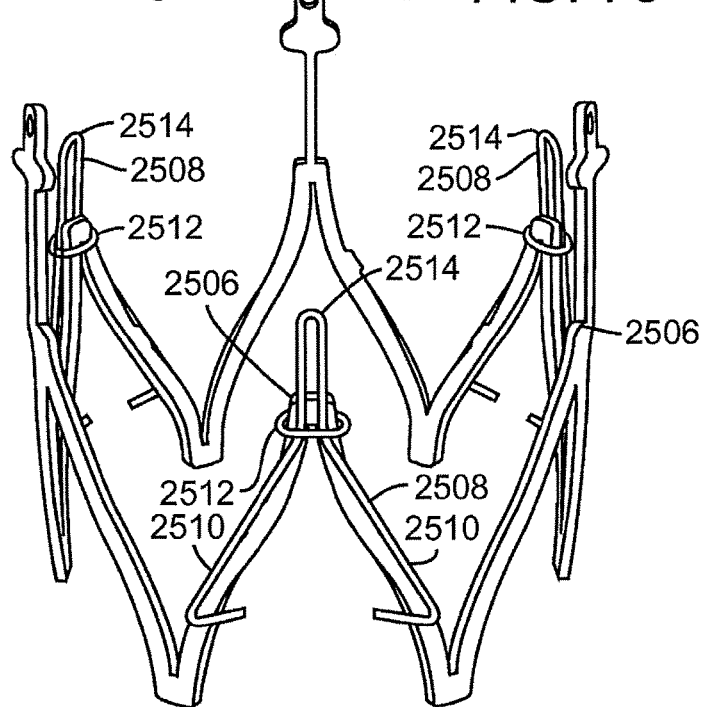
FIG. 79 is a perspective view of another embodiment of a support frame comprising leaflet-clipping mechanisms configured as clipping arms located on the exterior of the support frame.

FIGS. 78-89 illustrate another embodiment of a stent 2500 comprising an annular main body 2501 formed by a plurality of struts 2502. The stent 2500 can include one or more active leaflet-engaging mechanisms 2504 situated on three respective apices 2506 formed by the intersection of two adjacent struts 2502. The leaflet-engaging mechanisms 2504 can comprise leaflet clips 2508 having two clipping arms 2510 slidably disposed in an annular constraint 2512. The clipping arms 2510 of the leaflet clips 2508 can be movable between an open position (see, e.g., FIG. 78) and a closed position (see, e.g., FIG. 89) as the leaflet clip 2508 is drawn distally and proximally, respectively, through the annular constraint 2512. In this manner, the leaflet-engaging mechanisms 2504 can permit a user to position the support frame 2500 in a first step and clip the leaflets of a native valve in a second step, thereby providing improved control on both positioning and clipping force. The leaflet-engaging mechanisms 2504 can be disposed on the interior of the support frame 2500, as shown in FIG. 78, or on the exterior of the support frame, as shown in FIG. 79.

Figure 80:
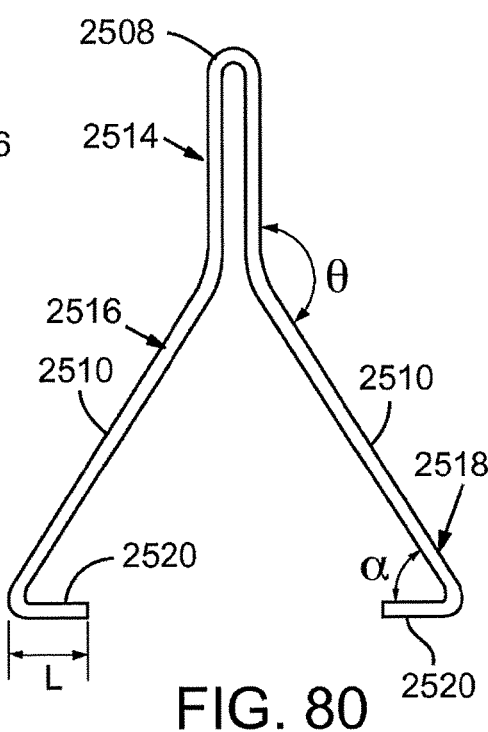
FIG. 80 is a side elevation view of a clipping arm.

Referring to FIG. 80, the leaflet clips 2508 can comprise a proximal hairpin portion 2514 formed by parallel sections of the clipping arms 2510, an intermediate portion 2516 in which the clipping arms 2510 diverge, and a leaflet-engaging portion 2518 in which end portions 2520 of the respective clipping arms 2510 are oriented toward one another. In some embodiments, the hairpin portions 2514 of the leaflet clips 2508 can extend above the respective apices 2506 of the stent such that proximal movement of the leaflet clips 2508 through the annular constraints 2512 can cause the annular constraints 2512 to apply force to the clipping arms 2510. Application of force to the clipping arms 2510 by the annular constraint 2512 can cause the end portions 2520 of the clipping arms 2510 to move toward one another. The distance between the respective end portions 2520 of the clipping arms 2510, and the resultant force applied to the native leaflets therebetween, can be controlled by appropriate vertical positioning of the leaflet clips 2508 in the annular constraints 2512.

In some embodiments, the leaflet clips 2508 can be configured to match the geometric profile of the struts 2502 of the support frame 2500 such that the potential for the leaflet clips 2508 to interfere with positioning of the stent is reduced. For example, the clipping arms 2510 can define an angle θ between the hairpin portion 2514 and the intermediate portion 2516. The angle θ can be configured such that the diverging portions of the clipping arms 2510 approximate the profile of the struts 2502 of the support frame 2500. Similarly, the end portions 2520 of the clipping arms 2510 can be oriented at an angle α with the diverging portions of the clipping arms 2510 of the intermediate portion 2516. The end portions 2520 of the clipping arms 2510 can also have a length L. The angle α and the length L of the end portions 2520 can be selected to reduce the tendency of the leaflet clips 2508 to interfere with placement of the stent 2500 during implantation, while allowing the end portions 2520 to engage and retain the native leaflets. In some embodiments, the angle θ can be from about 130 degrees to about 170 degrees. In some embodiments, the angle θ can be about 147 degrees. In some embodiments, the angle α can be from about 45 degrees to about 60 degrees.

In some embodiments, the clipping arms 2510 of the leaflet clips 2508 can have a rectangular cross-sectional shape. This can increase the torsional stiffness of the clipping arms 2510, reducing the tendency of the end portions 2520 to rotate inwardly or outwardly when the clipping arms are forced together by the annular constraint 2512. In alternative embodiments, the clipping arms 2510 can have a round cross-sectional shape, or any other suitable cross-sectional shape.

The annular constraints 2512 can be configured as, for example, tubular members, suture loops, or folding tabs. In the embodiment shown, the annular constraints 2512 are configured as suture loops encircling each respective apex 2506 to which a leaflet-engaging mechanism 2504 is mounted. The annular constraints 2506 can also be configured as one or more suture loops that encircle each strut 2502 below the apex 2506 to which a leaflet-engaging mechanism 2504 is mounted. The annular constraints 2512 can be integral to the support frame 2500, or can be separately attached.

Figure 81:
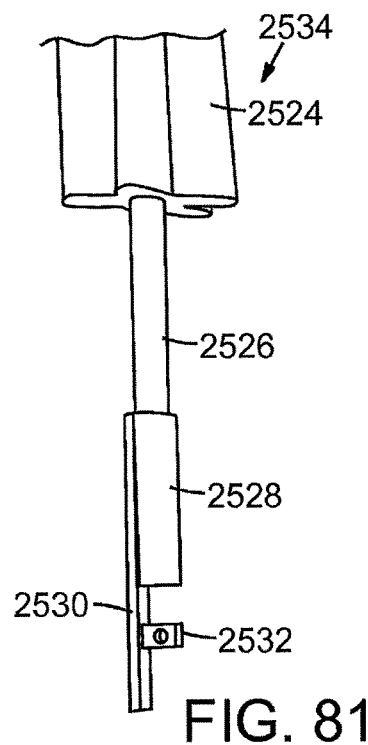
FIG. 81 is a side elevation view of a portion of an actuation assembly of a delivery device.
Figure 82A:
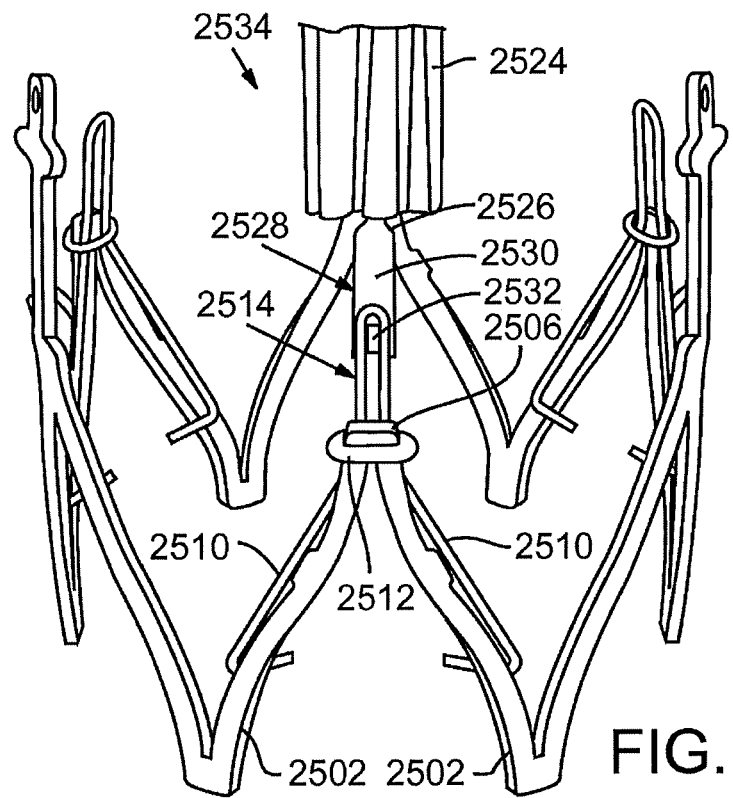
FIG. 82A is a perspective view of the support frame of FIG. 78 illustrating a portion of an actuator assembly engaged with a clipping mechanism and showing an actuator assembly catheter in a retracted position.
Figure 82B:
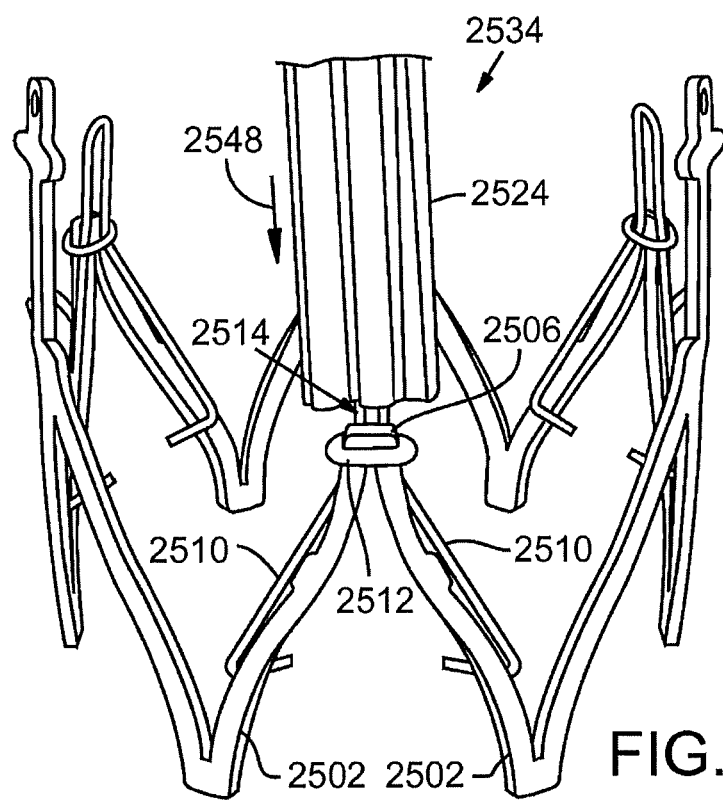
FIG. 82B is a perspective view of the support frame of FIG. 78 illustrating a portion of an actuator assembly engaged with a clipping mechanism and showing an actuator assembly catheter in an advanced position.
Figure 86:
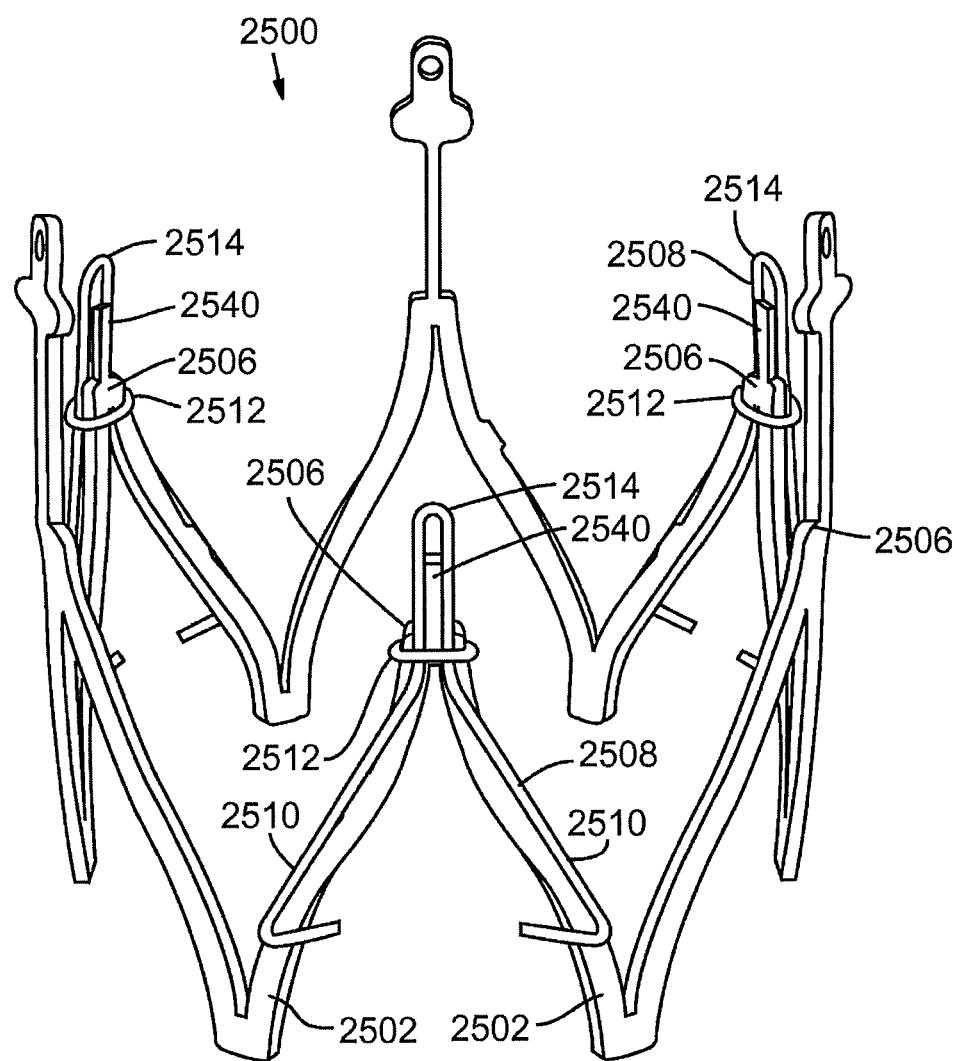
FIG. 86 is a perspective view of another embodiment of the support frame of FIG. 78 intended for use with the actuator member of FIG. 85.

FIG. 81 illustrates a portion of an actuation assembly 2534 of a deployment device 2522 (FIG. 83) for actuating the leaflet-engaging mechanisms 2504. The actuation assembly 2534 can comprise an actuator member catheter 2524 dimensioned to receive the proximal hairpin portion 2514 of a leaflet clip 2508, and an actuator member 2526 slidably disposed in the actuator member catheter 2524. A distal end portion 2528 of the actuator member 2526 can comprise a tab 2530 including a pin 2532. The pin 2532 can be dimensioned to engage the proximal end of the hairpin portion 2514, as shown in FIG. 82A. The actuator member catheter 2524 can then be moved over the distal end portion 2528 of the actuator member 2526 and the engaged hairpin portion 2514 in the direction of arrow 2548, thereby securing the leaflet clip 2508 to the actuator member 2526, as shown in FIG. 82B. In this manner, longitudinal movement of the actuator member 2526 in the actuator member catheter 2524 can cause corresponding movement of the leaflet clip 2508 through the annular constraint 2512. This, in turn, can cause the clipping arms 2510 of the leaflet clip 2508 to move between the open and closed positions. The leaflet clip 2508 can be released by retracting the actuator member catheter 2524, exposing the distal end portion 2528 of the actuator member 2526 and allowing the hairpin portion 2514 to disengage from the pin 2532. The deployment device 2522 can comprise a corresponding actuation assembly 2534 for each leaflet-clipping mechanism 2504 of the support frame 2500, as shown in FIG. 83.

FIGS. 84 and 85 illustrate alternative embodiments of the distal end portions 2528 of the actuator members 2526. FIG. 84 shows distal end portions 2528 of the actuator member 2526 comprising hooks 2536 configured to engage the hairpin portions 2514 of the leaflet clips 2508. The actuator member of FIG. 84 can be used in conjunction with the frame of FIG. 86, which includes integral tabs 2540 extending from respective apices 2506 and located radially inward of the leaflet-clipping mechanisms 2504. FIG. 85 shows another embodiment of a distal end portion 2528 of the actuator member 2526 having a circular protrusion 2538 located toward a proximal end of the tab 2530. The round shape of the protrusion 2538, along with its location toward the proximal end of the tab 2530 can reduce the tendency of the leaflet clips 2508 to prematurely disengage from the actuator member 2526.

Figures 87, 88, 89A, 89B:
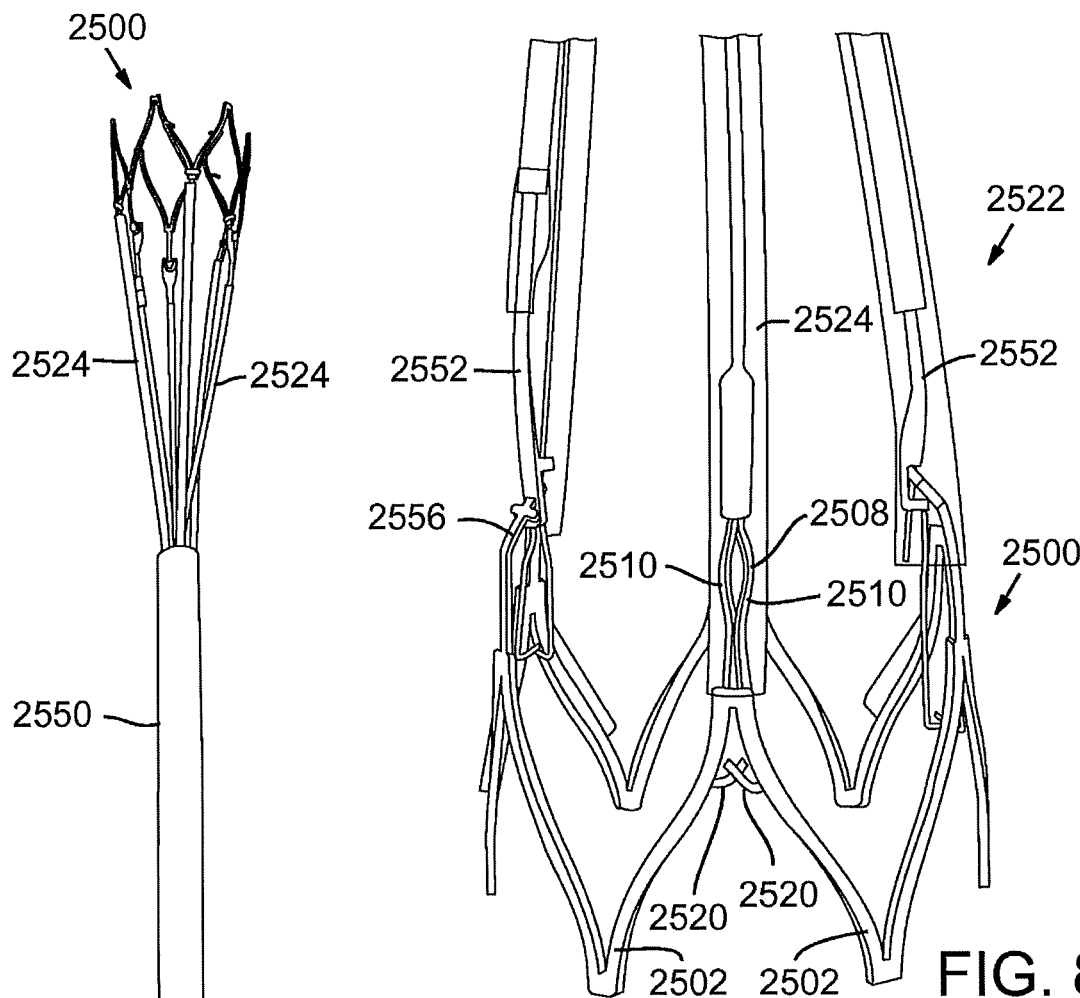
FIG. 87 is a side elevation view of an embodiment of a delivery device for use with the support frame of FIG. 78.
FIG. 88 is a perspective view of the support frame of FIG. 78 engaged with the delivery device and illustrating the clipping members in the closed position.
FIG. 89A is a perspective view of another embodiment of an outer sheath of a delivery device for use with the support frame of FIG. 78.
FIG. 89B is a perspective view of an inner sheath of the delivery device of FIG. 88A.

FIG. 87 is a perspective view of the deployment device 2522 coupled to the support frame 2500. The deployment device can comprise an outer sheath 2550. The actuator member catheters 2524 and associated actuator members 2526 can engage the respective leaflet clipping mechanisms 2504, and can pass through the outer sheath 2550. Similarly, retaining-arm-engaging members 2552 can pass through the outer sheath 2550 and can engage the respective retaining arms 2556 of the support frame. In this manner, the various actuator member catheters 2524, actuator members 2525, retaining-arm-engaging members 2552, and retaining member catheters 2556 can be actuated independently of one another. FIG. 88 illustrates the support frame 2500 engaged to the deployment device 2522 with the actuator members 2526 retracted and the leaflet clips 2508 of the leaflet-clipping mechanisms 2504 in the closed position.

FIGS. 89A and 89B illustrate perspective views of one embodiment of an outer sheath 2540 for use with the support frame 2500. The outer sheath 2540 can comprise an outer proximal catheter 2542, and three distal catheters 2544 extending from and in communication with the outer proximal catheter 2542. The outer sheath 2540 can further comprise an inner proximal catheter 2546, shown in FIG. 88B, which can configured to be contained within the outer proximal catheter 2542. The actuator members 2526 of the respective actuator assemblies 2534 can be configured to travel in the lumens of the respective distal catheters 2544.

The following description concerns various embodiments of support frames that are configured to be self-retaining in the native valve through application of pressure to various anatomical structures of the native valve, such as via one or more frame-retaining mechanisms configured to engage portions of the aortic root and/or the aorta. Any of the embodiments described herein having leaflet-engaging mechanisms can be provided with one or more frame-retaining mechanisms described in detail below, unless the context suggests otherwise. Similarly, any of the embodiments described herein having one or more frame-retaining mechanisms can be provided with one or more leaflet-engaging mechanisms, unless the context suggests otherwise.

Figure 90:
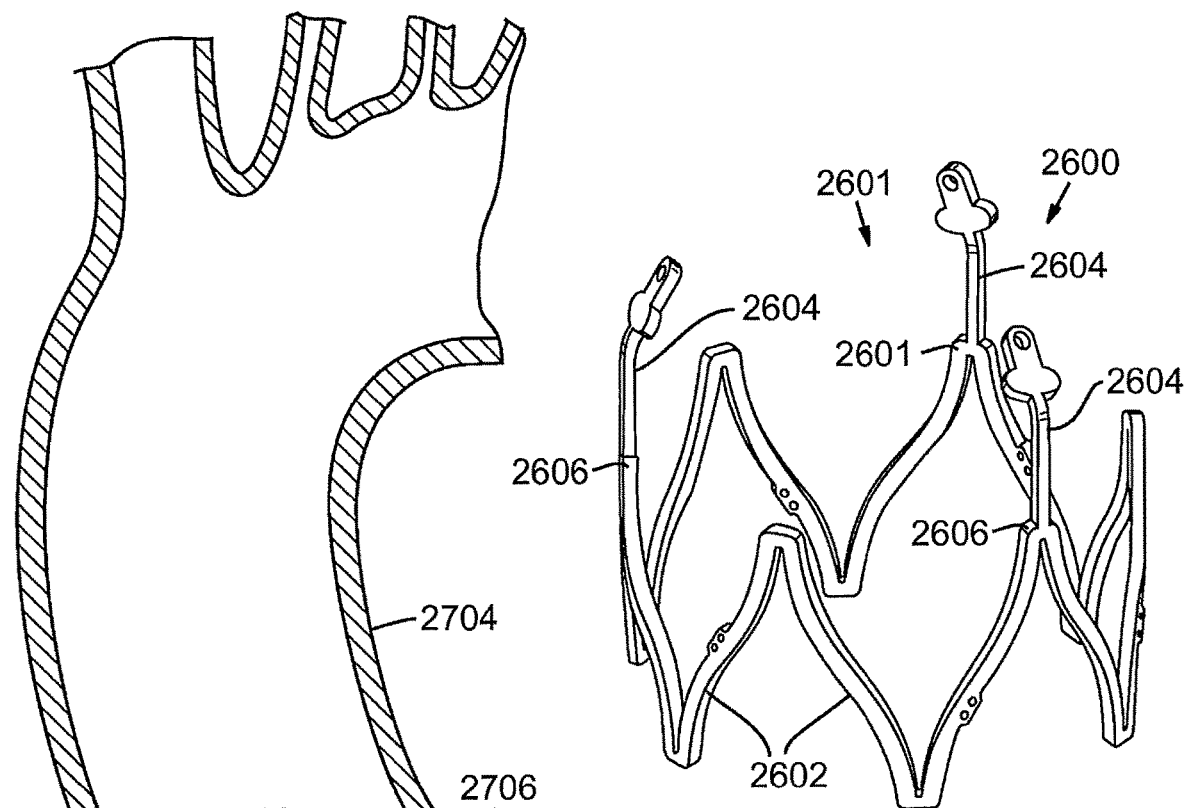
FIG. 90 is a perspective view of another embodiment of a support frame.

The following embodiments can be used for treating valve insufficiency by, for example, reducing the valvular circumference or reducing the valvular orifice area. The following embodiments can also be used for supporting a transcatheter heart valve (THV), and can be used in combination with any of the support frames described herein. Referring to FIG. 90, a support frame or stent 2600 can comprise an annular main body 2601 formed by a plurality of angled struts 2602. The support stent 2600 can include one or more retaining arms 2604 (e.g., three equally spaced retaining arms 2604) extending proximally from the apices 2606 of the struts 2602. The retaining arms 2604 can be used to form a releasable connection with the distal end of a delivery apparatus, as previously described. In some embodiments, the support stent 2600 can include one or more projections or protrusions (not shown) that can assist in retaining a THV in the implanted position within the interior of the support stent 2600, as further described in U.S. Patent Application No. 61/729,109 and WIPO Publication No. 2014/081796, which are incorporated herein by reference.

Figure 91:
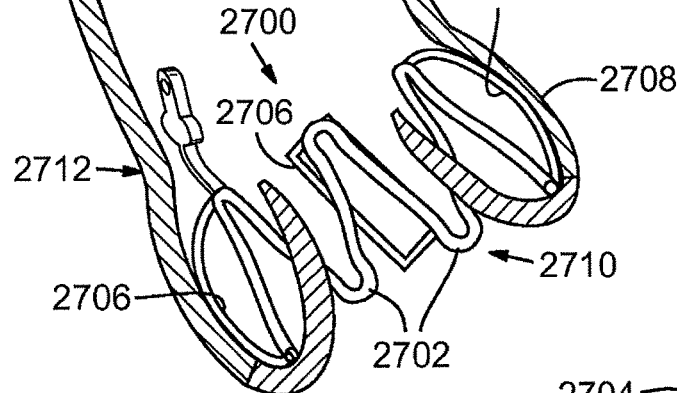
FIG. 91 is a cross-sectional side elevation view of another embodiment of a support frame comprising one or more arcuate members implanted in the aortic root.
Figure 92:
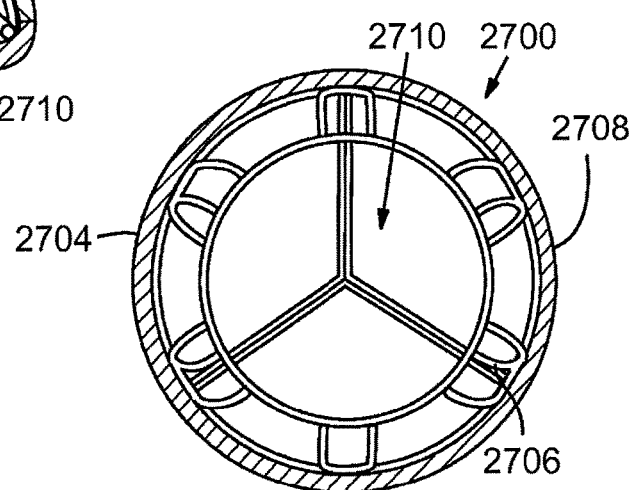
FIG. 92 is a plan view illustrating the support frame of FIG. 91 implanted in a cross-section of the aorta.

FIGS. 91 and 92 show another embodiment of a support frame 2700 comprising an annular main body formed by a plurality of angled struts 2702, similar to the embodiment of FIG. 90. FIG. 91 shows the support frame 2700 located in a partial cross-section of an aorta 2704. The support frame 2700 can further comprise one or more frame-retaining mechanisms configured as arcuate members 2706. The arcuate members can be configured to extend radially outwardly from the support frame and contact the walls of the aortic root 2708. For purposes of illustration, the front half of the support frame is not shown. FIG. 92 is a cross-sectional plan view of the support frame 2700 located in the aorta 2704.

The arcuate members 2706 can comprise metal or polymer strips or hoops. In the embodiment shown, the arcuate members 2706 can contact the walls of the aortic root 2708 from substantially the aortic valve 2710 to substantially the sinotubular junction 2712. In this manner, the arcuate members 2706 can retain the support frame 2700 in place after implantation. In alternative embodiments, the height of the arcuate members 2706 can be configured such that the arcuate members 2708 contact any suitable portion of the walls of the aortic root 2708.

FIGS. 93-96 show various embodiments of another support frame 2800 located in a partial cross-section of the aorta 2802. The support stent 2800 can comprise an annular main body formed by a plurality of angled struts 2804 similar to the embodiment of FIG. 90 above. The support stent 2800 can further include one or more elongated frame-retaining mechanisms configured as vertical members 2806 extending proximally from apices 2808 formed by the intersection of respective adjacent struts 2804. The one or more vertical members 2806, in turn, can comprise one or more elongated horizontal members 2810 configured to contact the walls of the ascending aorta 2812, thereby retaining the support stent 2800 in place after implantation.

In some embodiments, the vertical members 2806 can be shape set such that they are biased against the walls of the ascending aorta 2812 when the support stent 2800 is expanded to its fully expanded configuration. Similarly, the one or more horizontal members 2810 can be shape set to have a radius larger than the radius of the ascending aorta 2812 such that the horizontal members 2810 are biased against the walls of the ascending aorta 2812 when the support stent is fully expanded. The vertical and horizontal members 2806, 2810 can thereby work in concert to retain the support frame 2800 in position after implantation. The vertical and horizontal members 2806, 2810 can be fabricated from suitable shape-memory metals or alloys, such as spring steel, cobalt-chromium alloy (Elgiloy®), or nitinol, or from various polymeric materials.

Figure 93:
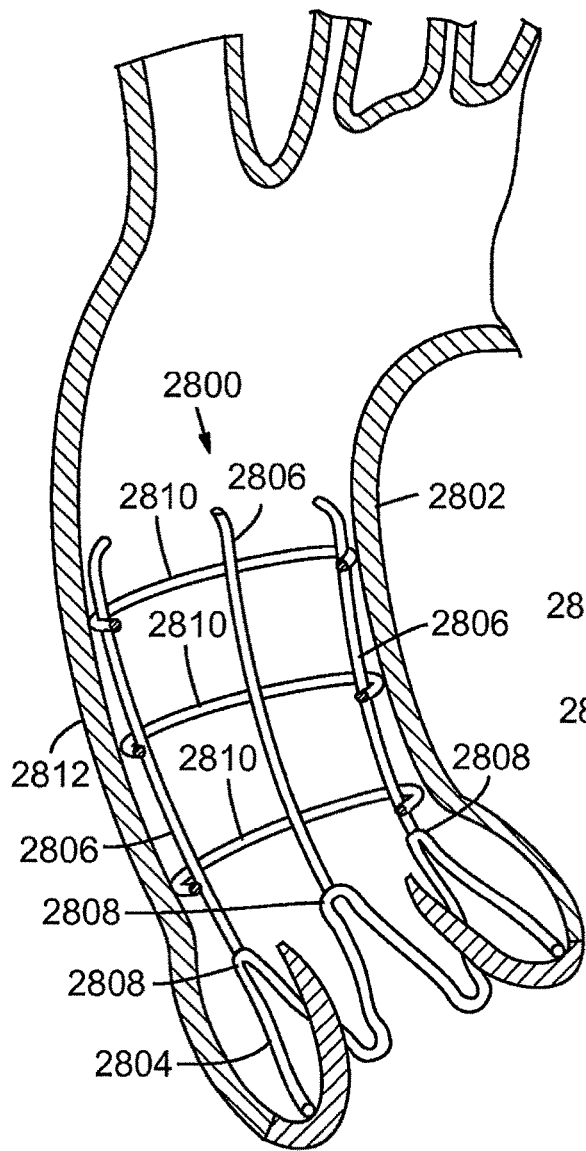
FIG. 93 is a cross-sectional side elevation view of another embodiment of a support frame comprising one or more vertical and horizontal members extending into the ascending aorta.

The number, size, and position of the vertical and horizontal members 2806, 2810 can vary from implementation to implementation. For example, as shown in FIG. 93, the support stent 2800 can include vertical members 2806 extending from each apex 2808 and horizontal members 2810 located at intervals along the length of the vertical members 2806. The horizontal members 2810 can be further configured to extend around substantially the entire circumference of the ascending aorta 2812. In some embodiments, the horizontal members 2810 can be coupled to each of the vertical members 2806. Alternatively, the horizontal members 2810 can be coupled to a single vertical member 2806, or any other suitable number of vertical members 2806.

Figure 94:
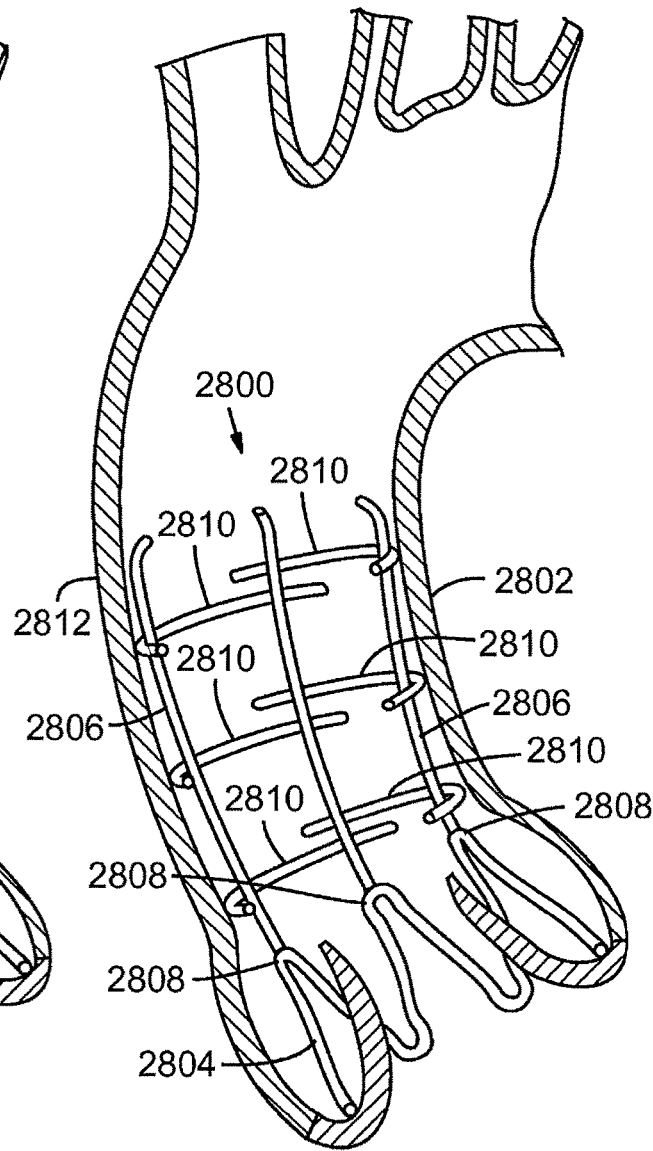
FIG. 94 is a cross-sectional side elevation view of an alternative embodiment of the support frame of FIG. 93 having horizontal members that extend around the two adjacent vertical members.
Figure 96:
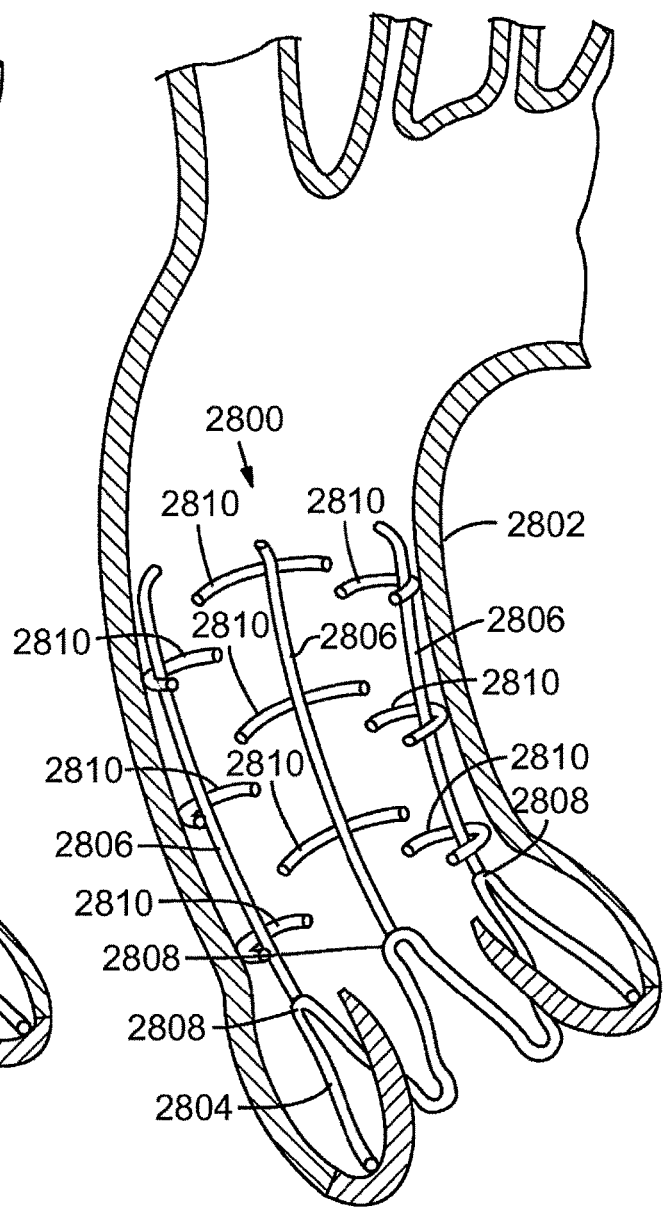
FIG. 96 is a cross-sectional side elevation view of another alternative embodiment of the support frame of FIG. 93 having horizontal members that are centered about respective vertical members without extending around adjacent vertical members.

In further alternative embodiments, the horizontal members 2810 can extend around less than the entire circumference of the ascending aorta 2812, and can be vertically offset from one another, as shown in FIGS. 94 and 96. More specifically, as shown in FIG. 94, each of the horizontal members 2810 can be centered about a single vertical member 2806, and can extend around the two adjacent vertical members 2806 without extending around the entire circumference of the ascending aorta 2812. Alternatively, each of the horizontal members 2810 can be centered about a single vertical member 2806 without extending around the adjacent vertical members, as shown in FIG. 96.

Figure 95:
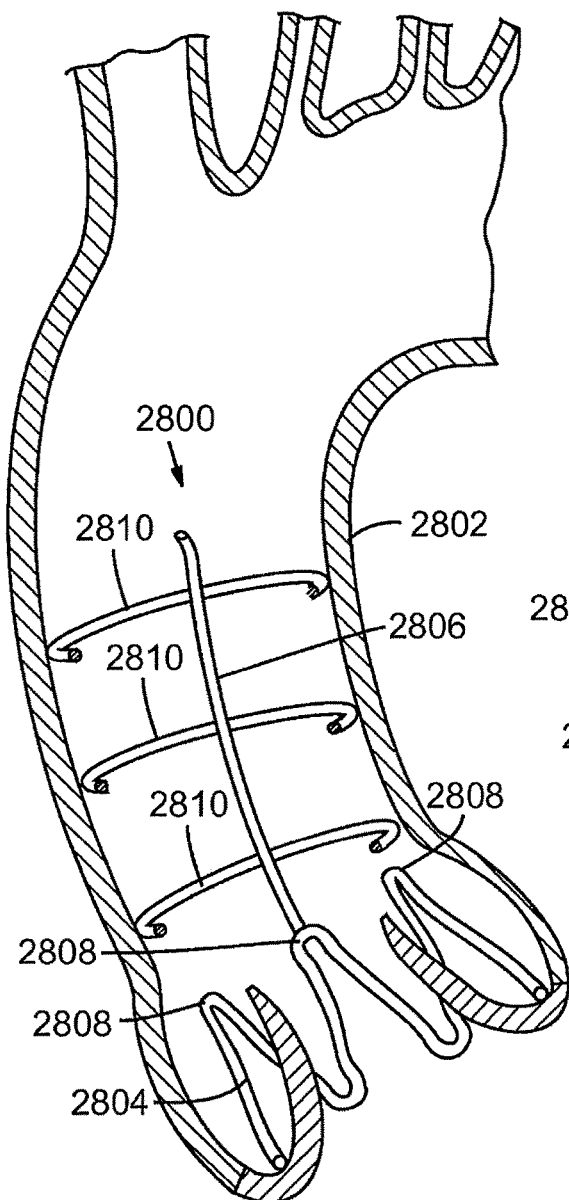
FIG. 95 is a cross-sectional side elevation view of another alternative embodiment of the support frame of FIG. 93 having a single vertical member.

In another alternative embodiment shown in FIG. 95, the support stent 2800 can comprise a frame-retaining mechanism configured as a single vertical member 2806 extending from a single apex 2808. The vertical member 2806 can further include one or more horizontal members 2810 centered about and coupled to the vertical member 2806. The horizontal members 2810 can be configured to extend around substantially the entire circumference of the ascending aorta 2812, or any portion thereof, as desired. The vertical and horizontal members 2806, 2810 can be shape set or otherwise configured to contact the walls of the ascending aorta 2812 to retain the support frame 2800 in position after implantation, as described above. The vertical and horizontal members 2806, 2810 can be integrally formed with the support frame 2800, or can be separately formed and secured to the support frame and/or to one another by, for example, welding, brazing, suture, adhesives, etc.

Figure 97:
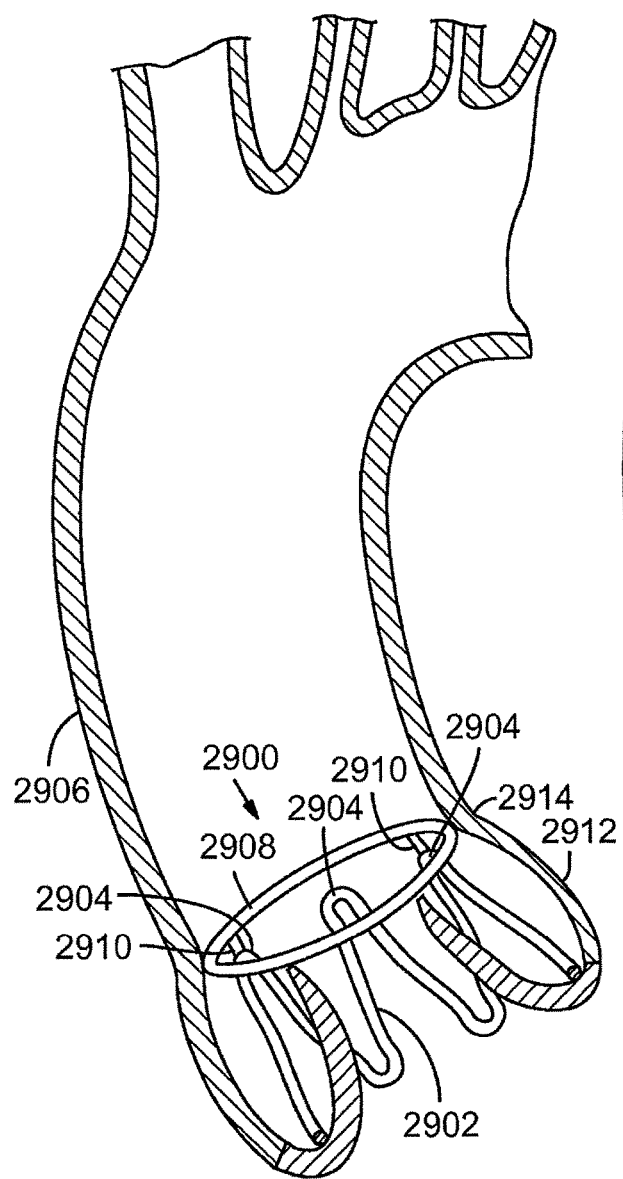
FIG. 97 is a cross-sectional side elevation view of another embodiment of a support frame implanted in the aortic root and including an annular member located at the sinotubular junction.

Referring now to FIG. 97, there is shown another embodiment of a support frame 2900 comprising an annular main body formed by a plurality of angled struts 2902 and having a plurality of apices 2904 formed by the intersection of two adjacent struts 2902, similar to the embodiment of FIG. 90 above. The support frame 2900 is shown located in a partial cross-section of an aorta 2906. The support frame 2900 can further comprise frame-retaining mechanism configured as an annular member 2908 coupled to the support frame 2900 by one or more rigid, or semi-rigid, vertical members 2910 extending from respective apices 2904. The annular member 2908 can be located in the aortic root 2912 and can be configured to contact the walls of the aortic root 2912 substantially beneath the sinotubular junction 2914. In this manner, the annular member 2908 in combination with the one or more vertical members 2910 can restrain upward movement of the support frame 2900 in the aortic root 2912.

In the embodiment shown, the support frame 2900 can comprise two vertical members 2910 on the portion of the support frame located in the dorsal half of the aorta 2906, and two vertical members 2910 on the portion of the support frame located in the ventral half of the aorta 2906 (not shown). However, in alternative embodiments, the support frame 2900 can include any suitable number of vertical members 2910 located on any suitable portion of the support frame 2900. The vertical members 2910 can be integrally formed with the support frame 2900, or can be separately formed and secured to the support frame by, for example, welding, brazing, suture, adhesives, etc.

Figure 98:
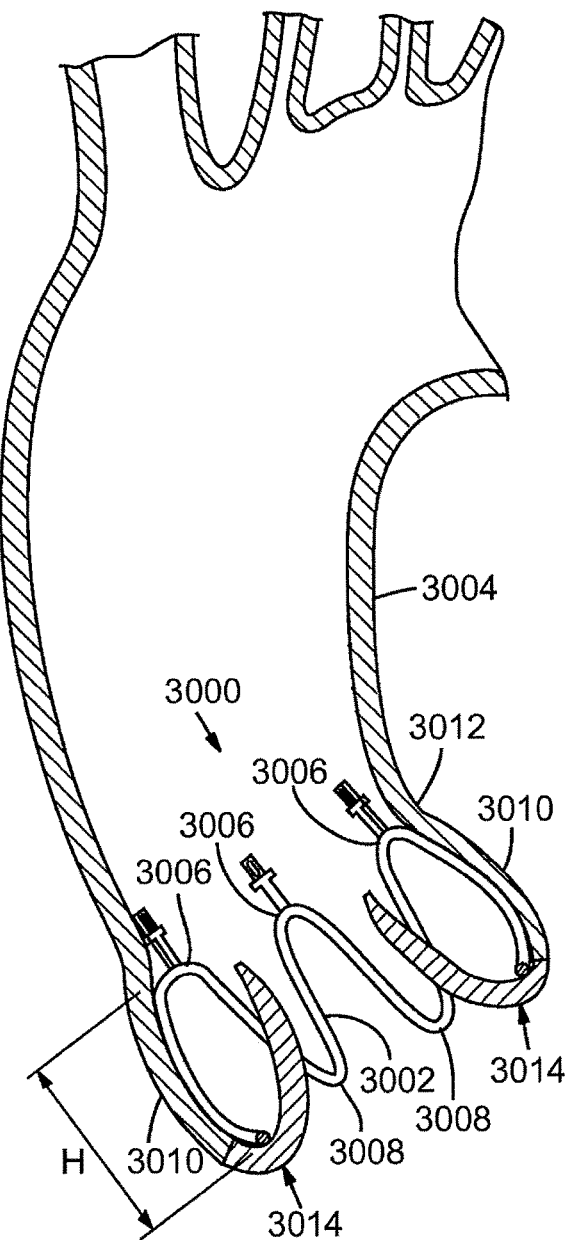
FIG. 98 is a cross-sectional side elevation view of another embodiment of a support frame implanted in the aortic root and including a plurality of struts configured to conform to the contours of the aortic sinuses.

FIG. 98 shows another embodiment of a support frame 3000 comprising an annular main body formed by a plurality of angled struts 3002 similar to the embodiment of FIG. 90 above. The support frame 3000 is shown located in a partial cross-section of an aorta 3004. The support frame 3000 can have a plurality of proximal apices 3006 and distal apices 3008 formed by the intersections of two adjacent struts 3002 at respective proximal and distal ends of the support frame. The struts 3002 can thereby define a height H extending from the proximal apices 3006 to the distal apices 3008. The struts 3002 can also be configured to conform to the contours of the aortic root 3010 such that the struts contact the walls of the aortic root 3010. For example, the support frame 3000 can be shape set to have a diameter greater than the diameter of the aortic root 3010, causing the struts 3002 to contact the walls of the aortic root 3010 to retain the support stent in place after implantation.

In the embodiment shown, the height H can be configured such that the proximal apices 3004 are located adjacent the sinotubular junction 3012 and the distal apices 3008 are located adjacent the aortic valve 3014. In this manner, the struts 3002 can operate as a frame-retaining mechanism by contacting and exerting force against the walls of the aortic root 3010 along substantially the entire length of the aortic root 3010 from adjacent the sinotubular junction 3014 to adjacent the aortic valve leaflets 3014. Alternatively, the height H can be configured such that the struts 3002 contact any suitable portion of the walls of the aortic root 3010. In further alternative embodiments, the proximal apices 3006 can be configured to contact the sinotubular junction 3012 and the distal apices 3008 can be configured to contact the aortic valve leaflets 3014.

Figure 99A:
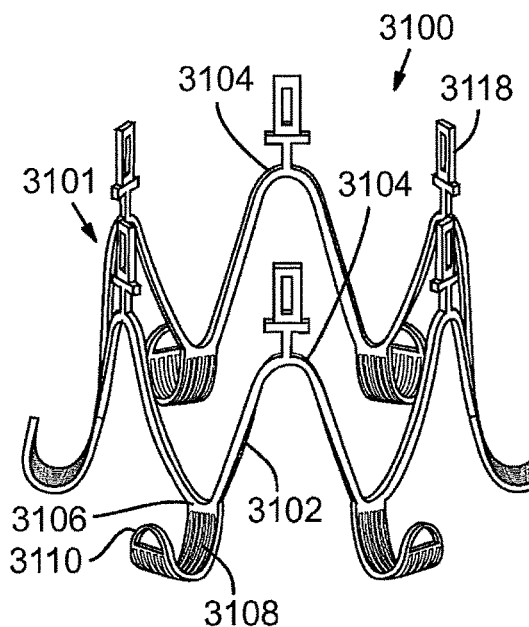
FIG. 99A is a perspective view of another embodiment of a support frame comprising a plurality of distally-extending arcuate members.
Figure 99B:
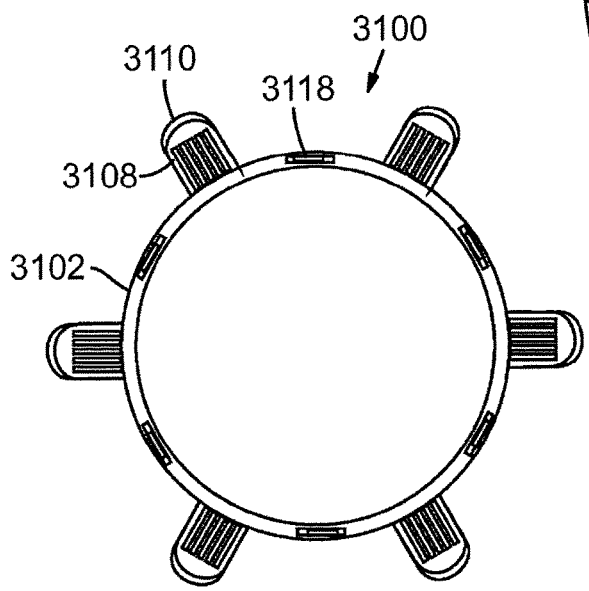
FIG. 99B is a plan view of the support frame of FIG. 99A.
Figure 100:
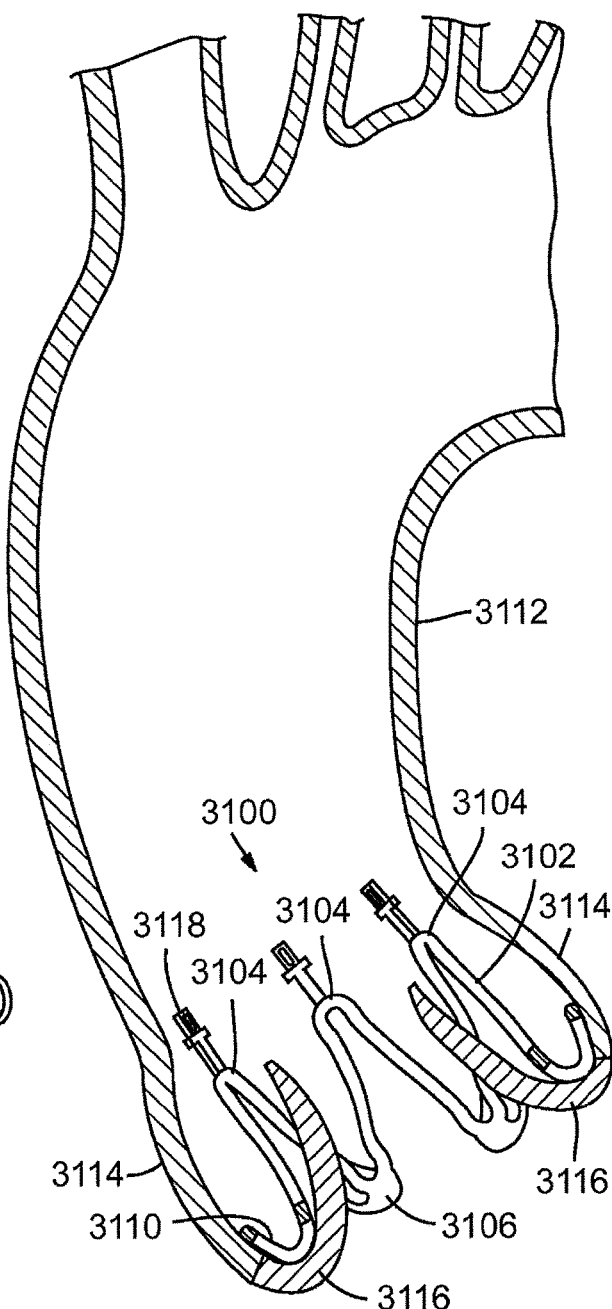
FIG. 100 is a cross-sectional side elevation view of the support frame of FIG. 99A implanted in the aortic root.

FIGS. 99A, 99B, and 100 illustrate another embodiment of a support frame 3100 comprising an annular main body formed by a plurality of angled struts 3102, similar to the embodiment of FIG. 90 above. The support frame 3100 can have a plurality of proximal apices 3104 and distal apices 3106 formed by the intersections of two adjacent struts 3102 at respective proximal and distal ends of the support frame. In the embodiment shown, the proximal apices 3104 can comprise retaining arms 3118 extending proximally therefrom. The support frame 3100 can further comprise a plurality of frame-retaining mechanisms configured as arcuate members 3108. The arcuate members 3108 can extend distally from respective distal apices 3106 before curving radially outward and ending at rounded distal end portions 3110. In the embodiment shown, the distal end portions 3110 can be oriented generally proximally with respect to the support frame 3100. Referring to FIG. 100, when implanted in the aorta 3112, the arcuate members 3108 can be configured to contact and apply pressure to the walls of the aortic root 3114, thereby retaining the support frame 3100 in place after implantation. In some embodiments, the arcuate members 3108 can also be configured to contact the bases of the aortic valve leaflets 3116, as shown in FIG. 100. The arcuate members 3108 can be integrally formed with the support frame 3100, or can be separately formed and secured to the support frame 3100 by, for example, welding, brazing, suture, adhesives, etc.

Figures 101, 102:
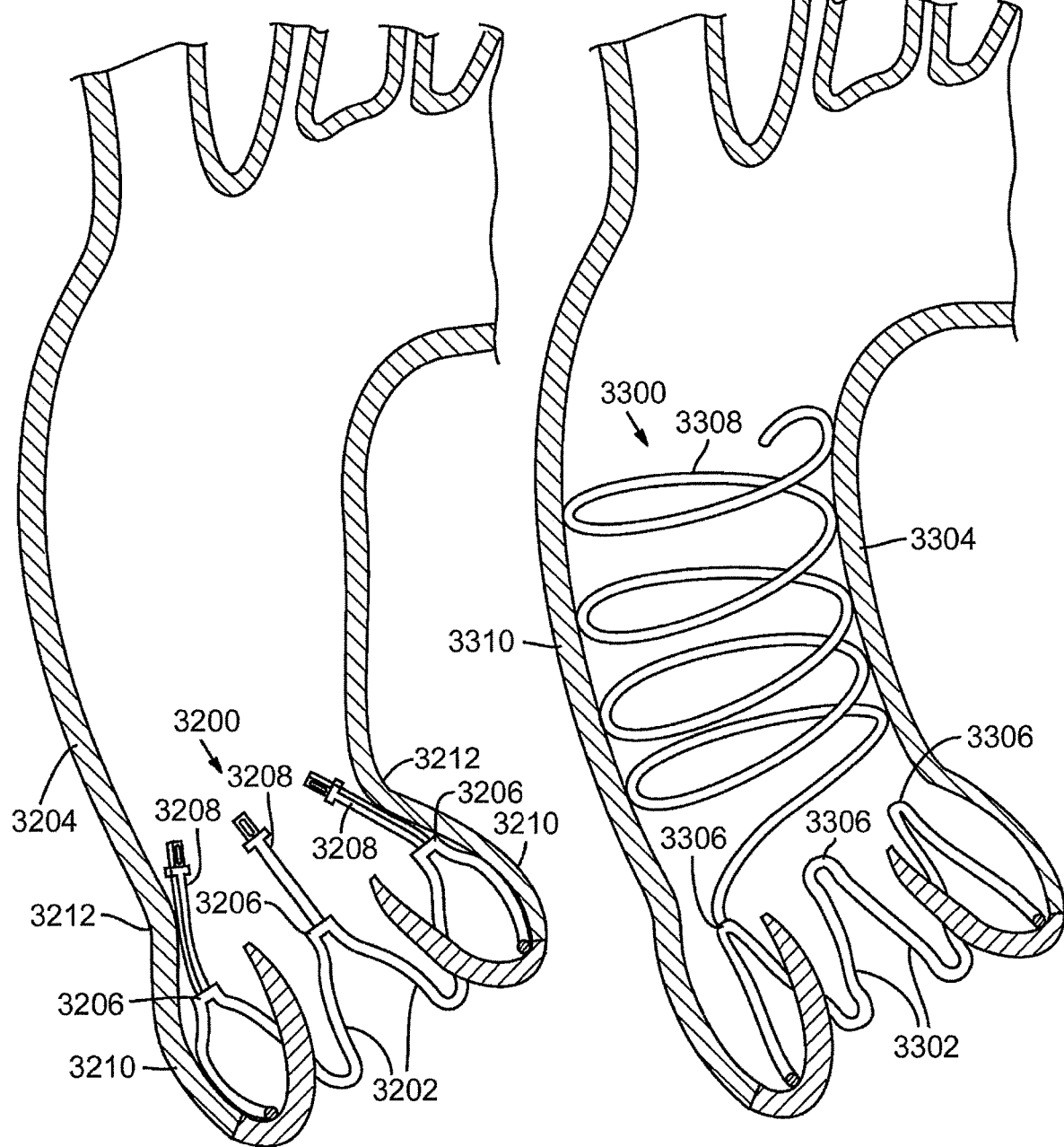
FIG. 101 is a cross-sectional side elevation view of another embodiment of a support frame including a plurality of retaining arms configured to exert pressure against the sinotubular junction and the walls of the aortic sinuses.
FIG. 102 is a cross-sectional side elevation view of another embodiment of a support frame located in the aortic root and comprising a spring member extending into the ascending aorta.

FIG. 101 illustrates another embodiment of a support frame 3200 comprising an annular main body formed by a plurality of angled struts 3202. The support frame 3200 is shown located in a partial cross-section of an aorta 3204, and can further comprise a plurality of apices 3206 formed by the intersection of two adjacent struts 3202. The support frame can include one or more frame-retaining mechanisms configured as retaining arms 3208 extending proximally from the apices 3206. The retaining arms 3208 can be configured to contact and exert pressure against the walls of the aortic root 3210 and/or the sinotubular junction 3212, thereby urging the support frame 3200 downward and aiding in retaining the support frame in place after implantation. In the embodiment shown, the retaining arms 3208 can be flexible such that they deflect radially inward upon contacting the walls of the aortic root 3210 and/or the sinotubular junction 3212. The retaining arms 3208 can be made from metal (e.g., nitinol) or suitable biocompatible polymers, and can be integrally formed with the support frame 3200 or separately formed and secured to the support frame by, for example, welding, brazing, suture, adhesives, etc.

Figures 103, 104:
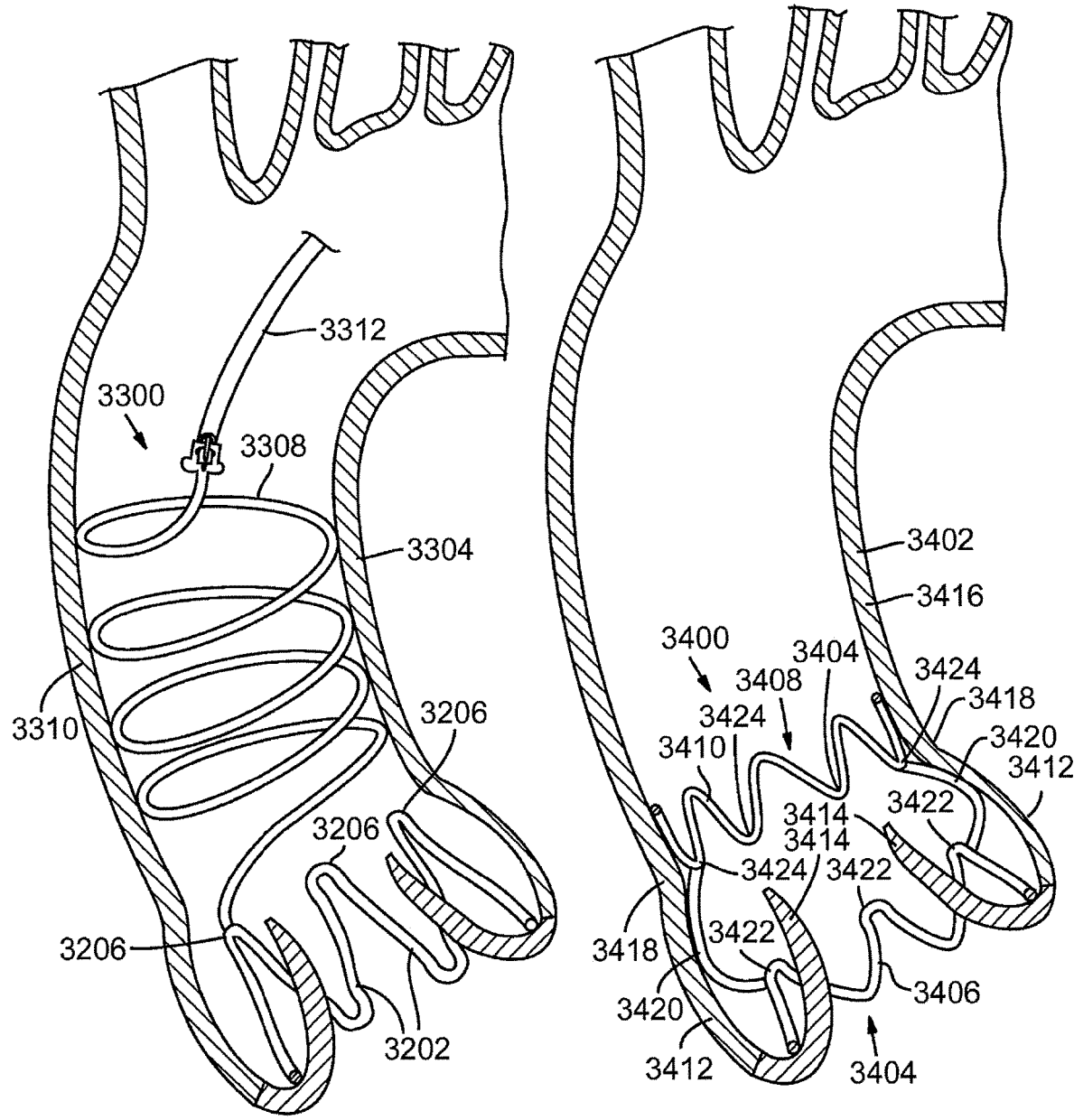
FIG. 103 is a cross-sectional side elevation view of the support frame of FIG. 102 illustrating the spring member connected to the distal end of a delivery device.
FIG. 104 is a cross-sectional side elevation view of another embodiment of a support frame located in the aorta including a first frame and a second frame interconnected by one or more elongated members.

FIG. 102 illustrates another embodiment of a support frame 3300 comprising an annular main body formed by a plurality of angled struts 3302. The support frame 3300 is shown located in a partial cross-section of an aorta 3304, and can further comprise a plurality of apices 3306 formed by the intersection of two adjacent struts 3302. The support frame 3300 can further comprise a frame-retaining mechanism configured as a spring member 3308 extending proximally from an apex 3306 of the support frame 2300 into the ascending aorta 3310. The spring member 3308 can be helically wound or coiled, and can be shape set to have a diameter greater than the ascending aorta 3310 such that the spring member 3308 contacts and exerts a force against the walls of the ascending aorta 3310. This, in turn, can urge the support frame 3300 downward, helping to retain the support frame in place after implantation. In the embodiment shown, the spring member 3308 can originate from a single apex 3306. However, in alternative embodiments, the spring member 3308 can originate from any suitable number of apices 3306, including all of the apices 3306. In some embodiments, the spring member 3308 can be configured as a retaining arm, which can engage with a delivery device 3312, as shown in FIG. 103. The spring member 3308 can be made from metal (e.g., nitinol) or suitable biocompatible polymers, and can be integrally formed with the support frame 3300 or separately formed and secured to the support frame by, for example, welding, brazing, suture, adhesives, etc.

FIG. 104 illustrates another embodiment of a support frame 3400 located in a partial cross-section of an aorta 3402. The support frame 3400 can comprise a first annular frame 3404 formed by a plurality of angled struts 3406, and a second annular frame 3408 formed by a plurality of angled struts 3410. The first annular frame 3404 can be situated in the aortic root 3412 proximate the aortic valve leaflets 3414, while the second annular frame 3408 can be situated in the ascending aorta 3416 proximate the sinotubular junction 3418. In some embodiments, the second annular frame 3408 can be configured to have a diameter greater than the diameter of the ascending aorta 3416 such that the second annular frame 3408 exerts a radial force against the walls of the ascending aorta 3416. This can allow the second annular frame 3408 to resist proximal and/or distal motion within the ascending aorta 3416.

The first and second annular frames 3404, 3408 can be interconnected by one or more frame-retaining mechanisms configured as interconnecting members 3420. The one or more interconnecting members 3420 can be coupled to proximal apices 3422 of the first annular frame 3404 and to distal apices 3424 of the second annular frame 3408, and can be spring-biased. In this manner, the interconnecting members 3420 can urge the first annular frame 3404 downwardly, thereby helping to retain the support frame 3400 in place after implantation. In the embodiment shown, the interconnecting members 3420 can be configured to deflect and contact the walls of the aortic root and/or the sinotubular junction 3418, further increasing the stability of the support frame 3400 after implantation. In some embodiments, the interconnecting members 3420 can be made from metal (e.g., nitinol) or suitable biocompatible polymers, and can be integrally formed with the first and second annular frames 3404, 3408. Alternatively, the interconnecting members 3420 and the first and second annular frames 3404, 3408 can be separately formed and secured together by, for example, welding, brazing, suture, adhesives, etc.

Figure 105:
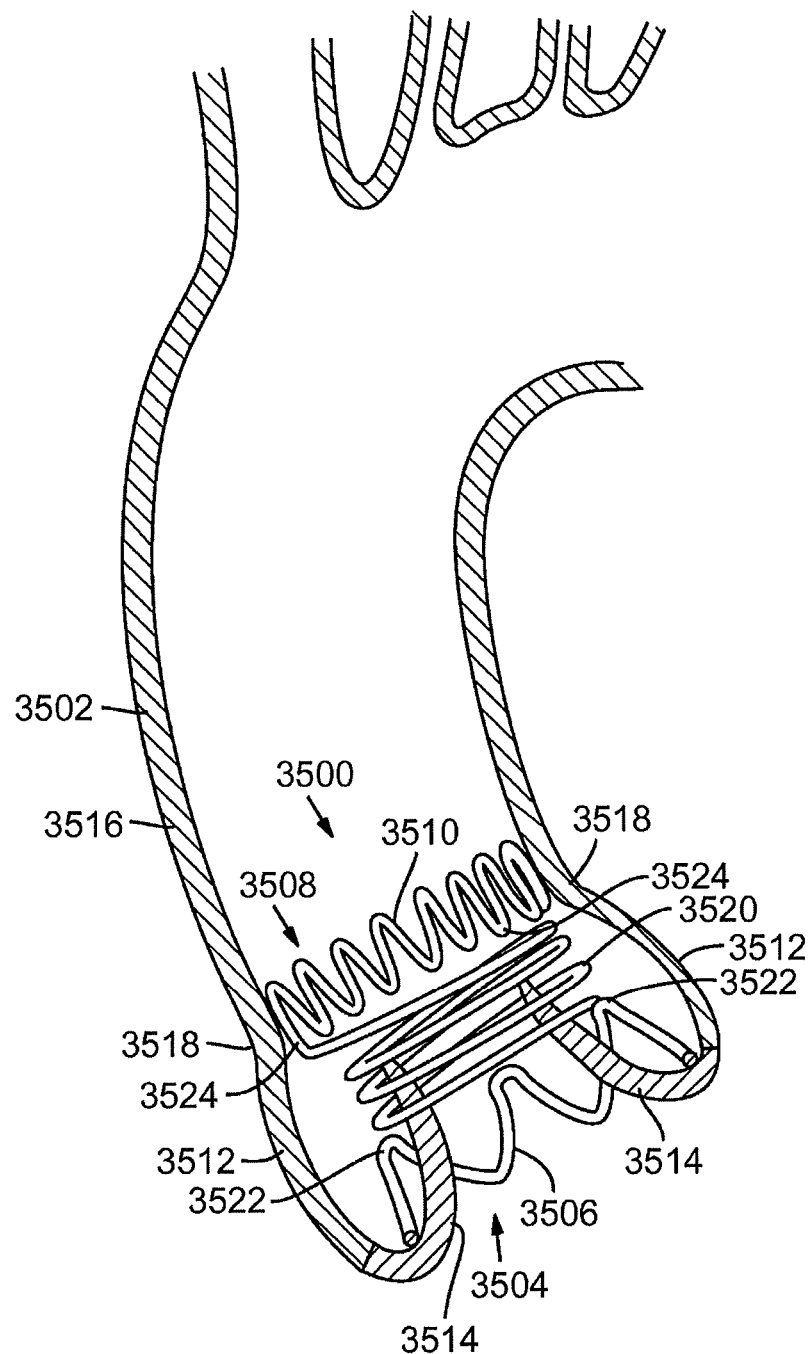
FIG. 105 is a cross-sectional side elevation view of another embodiment of a support frame located in the aorta and including a first frame and a second frame interconnected by a spring member.

FIG. 105 illustrates another embodiment of a support frame 3500 located in a partial cross-section of an aorta 3502. The support frame 3500 can comprise a first annular frame 3504 formed by a plurality of angled struts 3506, and a second annular frame 3508 formed by a plurality of angled struts 3510, similar to the embodiment of FIG. 104. The first annular frame 3504 can be situated in the aortic root 3512 proximate the aortic valve leaflets 3514, while the second annular frame 3508 can be situated in the ascending aorta 3516 proximate the sinotubular junction 3518. In some embodiments, the second annular frame 3508 can be configured to have a diameter greater than the diameter of the ascending aorta 3516 such that the second annular frame 3508 exerts a radial force against the walls of the ascending aorta 3502. This can allow the second annular frame 3508 to resist proximal and/or distal motion within the ascending aorta 3516.

The first and second annular frames 3504, 3508 can be interconnected by a frame-retaining mechanism configured as a spring member 3520. The spring member 3520 can be coupled to a respective proximal apex 3522 of the first annular frame 3504 and to a respective distal apex 3524 of the second annular frame 3508, and can be helically coiled. In this manner, the spring member 3520 can urge the first annular frame 3504 downwardly, thereby helping to retain the support frame 3500 in place after implantation. In the embodiment shown, the spring member 3520 is coupled to a single proximal apex 3522 of the first annular frame 3504 and a single distal apex 3524 of the second annular frame 3508. Alternatively, the spring member 3520 can be coupled to multiple proximal apices 3522 and/or multiple distal apices 3524 of the first and second annular frames 3504, 3508, respectively. In further alternative embodiments, the support frame 3500 can comprise multiple spring members 3520. In some embodiments, the spring member 3520 can be made from metal (e.g., nitinol) or suitable biocompatible polymers, and can be integrally formed with the first and second annular frames 3504, 3508. Alternatively, the spring member 3520 and the first and second annular frames 3504, 3508 can be separately formed and secured together by, for example, welding, brazing, suture, adhesives, etc.

Figure 106:
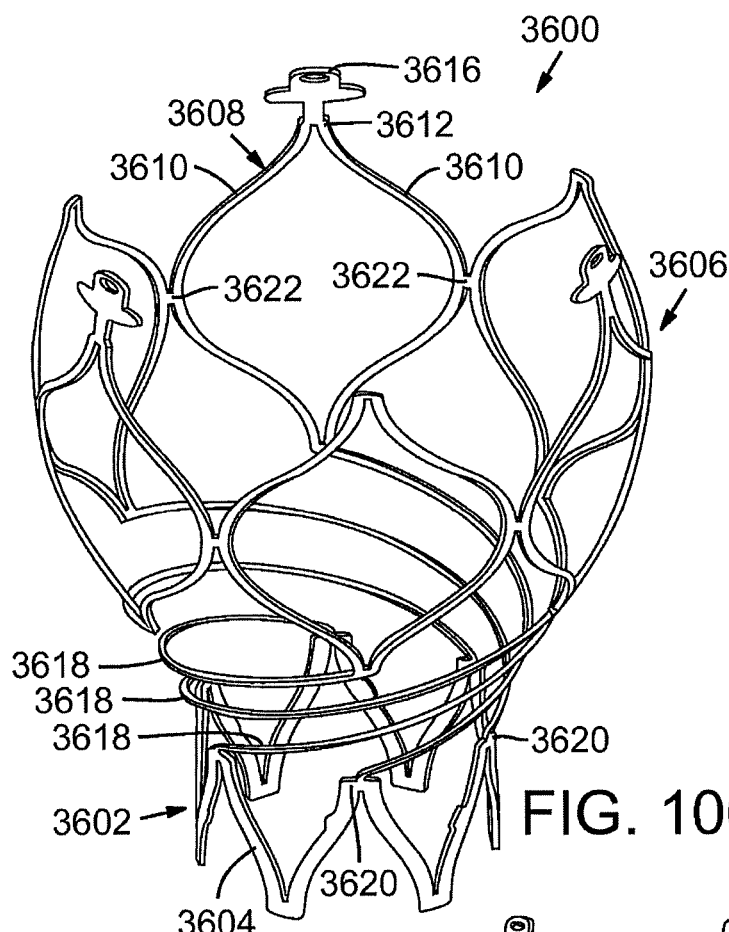
FIG. 106 is a perspective view of another embodiment of a support frame including a first frame and a second frame interconnected by a plurality of interconnecting members.
Figure 107:
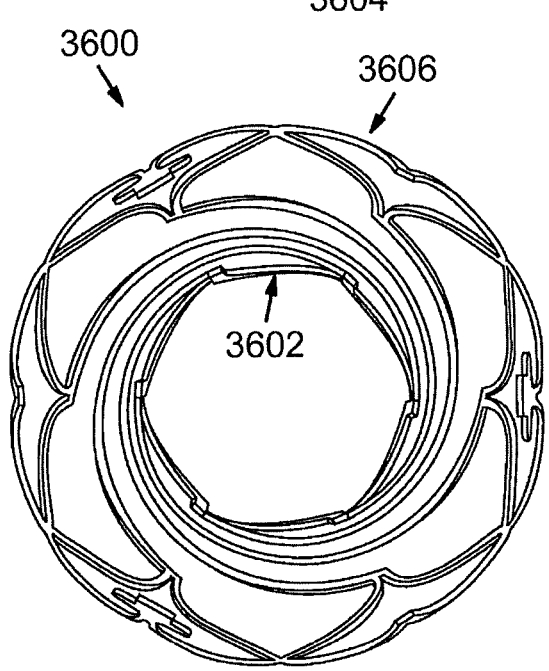
FIG. 107 is a plan view of the support frame of FIG. 106.
Figure 108:
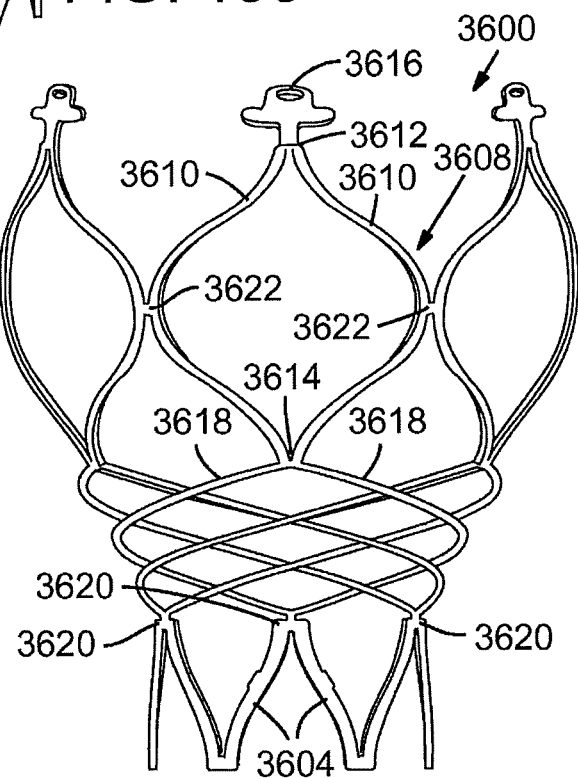
FIG. 108 is a side elevation view of the support frame of FIG. 106.
Figure 109:
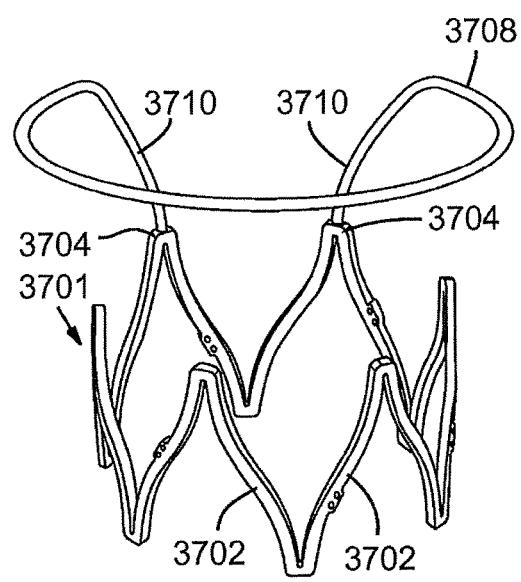

FIGS. 106-108 illustrate another embodiment of a support frame 3600 comprising a first annular frame 3602 formed by a plurality of angled struts 3604, and a second annular frame 3606 comprising a plurality of frame subunits 3608 formed by a corresponding number of branching members 3610. The first annular frame 3602 can be configured to be located in the aortic root, while the second annular frame 3606 can be configured to be located in the ascending aorta, similar to the embodiments of FIGS. 104 and 105. The frame subunits 3608 of the second annular frame 3606 can comprise proximal apices 3612 formed by the proximal intersection of two respective branching members 3610 and distal apices 3614 formed by corresponding distal intersections of the branching members 3610. In the embodiment shown, alternating proximal apices 3612 can comprise retaining arms 3616 extending therefrom. The second annular frame 3606 can be configured to have a diameter greater than the diameter of the ascending aorta such that the second annular frame 3608 exerts a radial force against the walls of the ascending aorta. This can allow the second annular frame 3606 to resist proximal and/or distal motion within the ascending aorta. The frame subunits 3608 can be optionally coupled by short coupling members 3622, which can increase the rigidity of the second frame 3606.

The first and second annular frames 3602, 3606 can be interconnected by one or more frame-retaining mechanisms configured as interconnecting members 3618. The one or more interconnecting members 3618 can be coupled to respective proximal apices 3620 of the first annular frame 3602 and to respective distal apices 3614 of the second annular frame 3606, and can be helically coiled. In this manner, the interconnecting members 3618 can urge the first annular frame 3602 downwardly, thereby helping to retain the support frame 3600 in place after implantation. In the embodiment shown, an interconnecting member 3618 interconnects each proximal apex 3620 of the first annular frame 3602 with each distal apex 3614 of the second annular frame 3606. Alternatively, interconnecting members 3618 can interconnect every other proximal apex 3620 of the first annular frame 3602 with every other distal apex 3614 of the second annular frame 3606. In further alternative embodiments, each proximal apex 3620 of the first annular frame 3602 can be interconnected with each distal apex 3614 of the second annular frame 3606 by pairs of interconnecting members 3618, as shown in FIG. 108. In the embodiment of FIG. 108, the interconnecting members 3618 of each respective pair can extend in opposite radial directions around the support frame 3600 from the respective proximal apices 3620 of the first annular frame 3602 to the distal apices 3614 of the second annular frame (i.e., one interconnecting member 3618 can extend in a clockwise direction while the other interconnecting member can extend in a counterclockwise direction before coupling to the respective distal apex 3614 of the second frame 3606). Additionally, in some embodiments the support frame 3600, and particularly the second frame 3608, can be configured to be axially compliant such that the geometry of the support frame 3600 can change to accommodate variations in the shape of the ascending aorta.

Figure 110:
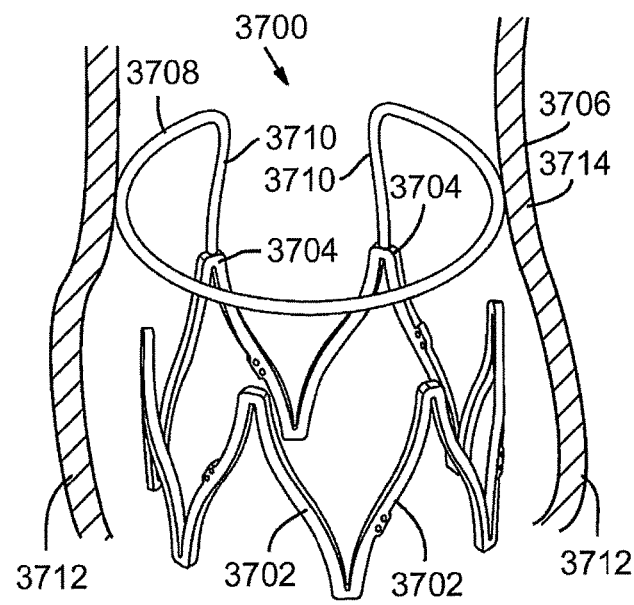
Figure 111:
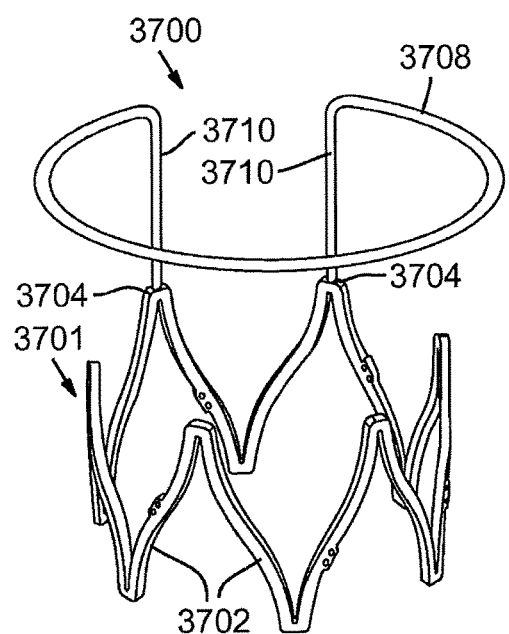
Figure 112:
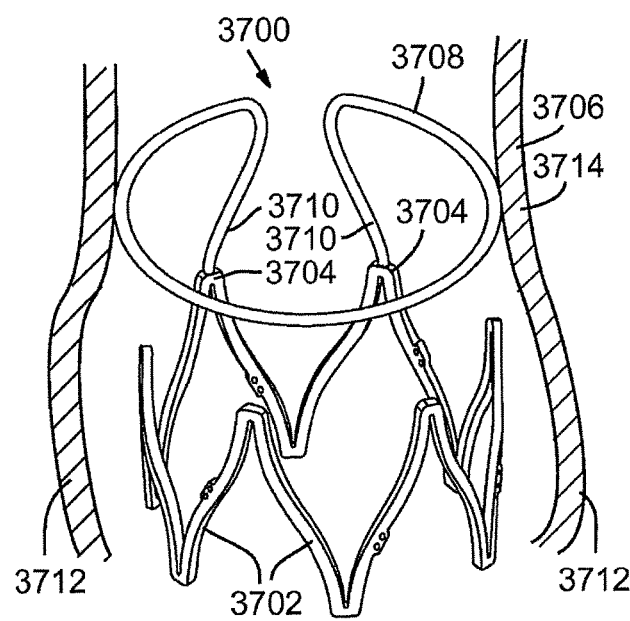

FIGS. 109-112 illustrate another embodiment of a support frame 3700 comprising an annular main body 3701 formed by a plurality of angled struts 3702 and having a plurality of apices 3704 formed by the intersection of two adjacent struts 3702. In FIGS. 110 and 112, the support frame 3700 is shown located in a partial cross-section of an aorta 3706. The support frame 3700 can further comprise a frame-retaining mechanism configured as a semi-annular member 3708 coupled to the support frame 3700 by two rigid, or semi-rigid, vertical members 3710 extending from respective apices 3704, similar to the embodiment of FIG. 97. The support frame 3700 can be located in the aortic root 3712, while the semi-annular member 3708 can be located in the ascending aorta 3714, as shown in FIGS. 110 and 112.

In the embodiment shown, the vertical members 3710 can be integral with the semi-annular member 3708, and can be shape set such that the semi-annular member 3708 has a diameter greater than the ascending aorta 3714. In this manner, the semi-annular member 3708 can be configured to exert radial force against the walls of the ascending aorta 3714 which, in combination with the two vertical members 3710, can restrain upward movement of the support frame 3700 in the aortic root 3712. For example, in the embodiment of FIG. 109, the vertical members 3710 can be shape set such that they extend away from one another at an angle in the proximal direction, thereby urging the semi-annular member 3708 radially outward. In this manner, the semi-annular member 3708 can have a diameter greater than the diameter of the ascending aorta 3714 when the support frame is in the fully expanded configuration. Alternatively, the vertical members 3710 can be shape set such that they are oriented substantially parallel to a longitudinal axis of the support frame 3700 when the support frame is in the expanded configuration, and the semi-annular member 3708 can be configured to have a diameter greater than the diameter of the ascending aorta 3714 without urging by the vertical members 3710, as shown in FIG. 111. In this manner, the vertical members 3710 can be urged toward one another by radial compression of the semi-annular member 3708 imposed by the walls of the ascending aorta 3714, as shown in FIGS. 110 and 112, respectively, which can aid in retaining the support frame 3700 in place after implantation.

The vertical members 3710 and the semi-annular member 3708 can be made from metal (e.g., nitinol) or from suitable biocompatible polymers, and can be integrally formed with the support frame 3700. Alternatively, the vertical members 3710 and the semi-annular member 3708 can be separately formed and secured to the support frame 3700 by, for example, welding, brazing, suture, adhesives, etc.

Figure 114:
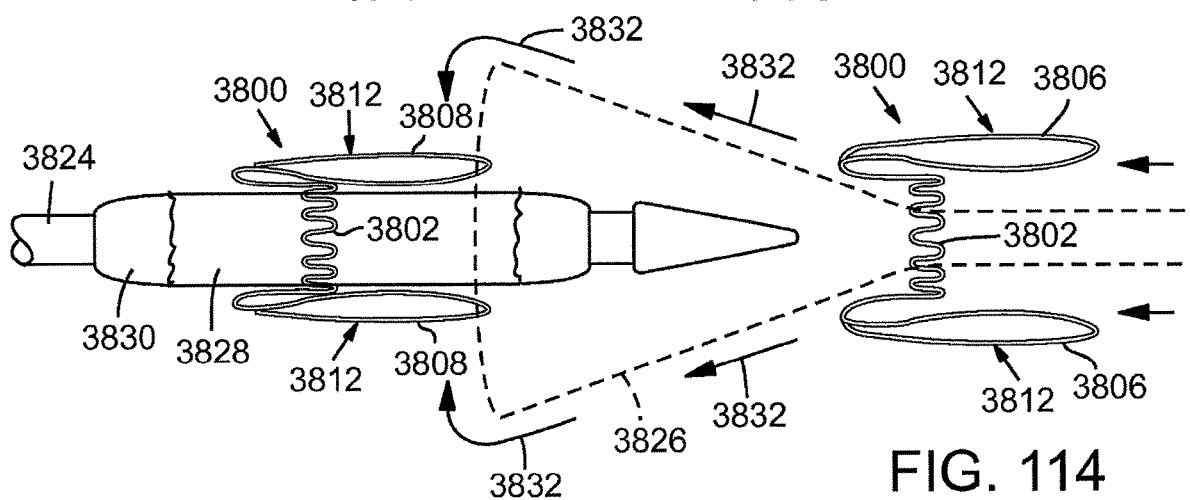
Figure 115:
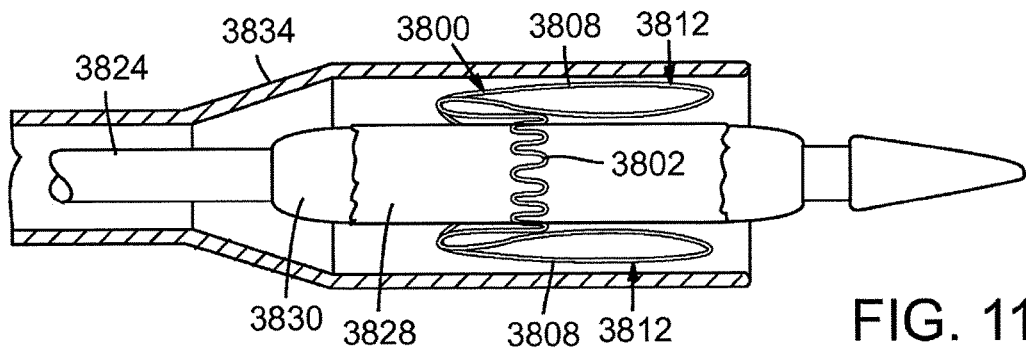

FIGS. 113-115 illustrate another embodiment of a support frame 3800 comprising an annular main body 3801 formed by a plurality of angled struts 3802 and having a plurality of apices 3804 formed by the intersection of two adjacent struts 3802. The support frame 3800 can include a plurality of frame retaining members 3806 configured as retaining loops 3808. The retaining loops 3808 can be located in the aortic root 3818 behind the native leaflets 3820 (see, e.g., FIGS. 117 and 118), and can be configured to exert radial force against the walls of the aortic root 3818 to aid in retaining the support frame 3800 in place after implantation.

Each retaining member 3806 can comprise a proximal portion 3810 and a distal portion 3812. The proximal portion 3810 can be formed by respective end portions 3814 of loop or wire 3808, which can extend proximally from respective apices 3804, before curving distally. In this manner, the proximal portion 3810 can define a leaflet-engaging region 3822 configured to receive the native leaflets 3820, and the respective end portions 3814 of the loops 3808 can extend over the native valve leaflets 3820 when the support frame is implanted (see, e.g., FIGS. 117 and 118). The distal portion 3812 of the retaining member 3806 can be defined by an intermediate portion 3816 of the loop or wire 3808, and can have a radiused profile to distribute force against the walls of the aortic root 3818 (e.g., during the period of maximum pressure differential during the cardiac cycle).

In some embodiments, the loop or wire 3808 can extend proximally from the apices 3804 of the support frame 3800 for a distance of from about 5 mm to about 10 mm before curving distally. In some embodiments, the distal portions 3812 of the retaining members 3806 can have a height of from about 12 mm to about 18 mm. In this manner, the height of the retaining members 3806 can be approximately equal to the height of the native valve leaflets 3820, which can reduce the likelihood of damage to the leaflets 3820 during and after implantation.

Referring to FIGS. 114 and 115, the support frame 3800 can be radially collapsible such that it can be loaded onto a delivery apparatus 3824 in the direction of arrows 3832 via a loading device such as the funnel loader 3826, shown in phantom in FIG. 114. Alternatively, the support frame 3800 can be loaded on to the delivery device 3824 with any of various other loading devices, including reverse crimpers and circular spreaders. In some embodiments, the support frame 3800 can be radially collapsed around a transcatheter heart valve ("THV") 3828, which can itself be radially collapsed around a balloon catheter 3830. The THV 3828 can have a balloon-expandable metal frame supporting a valve member, such as multiple tissue leaflets supported by the frame.

Figure 119:
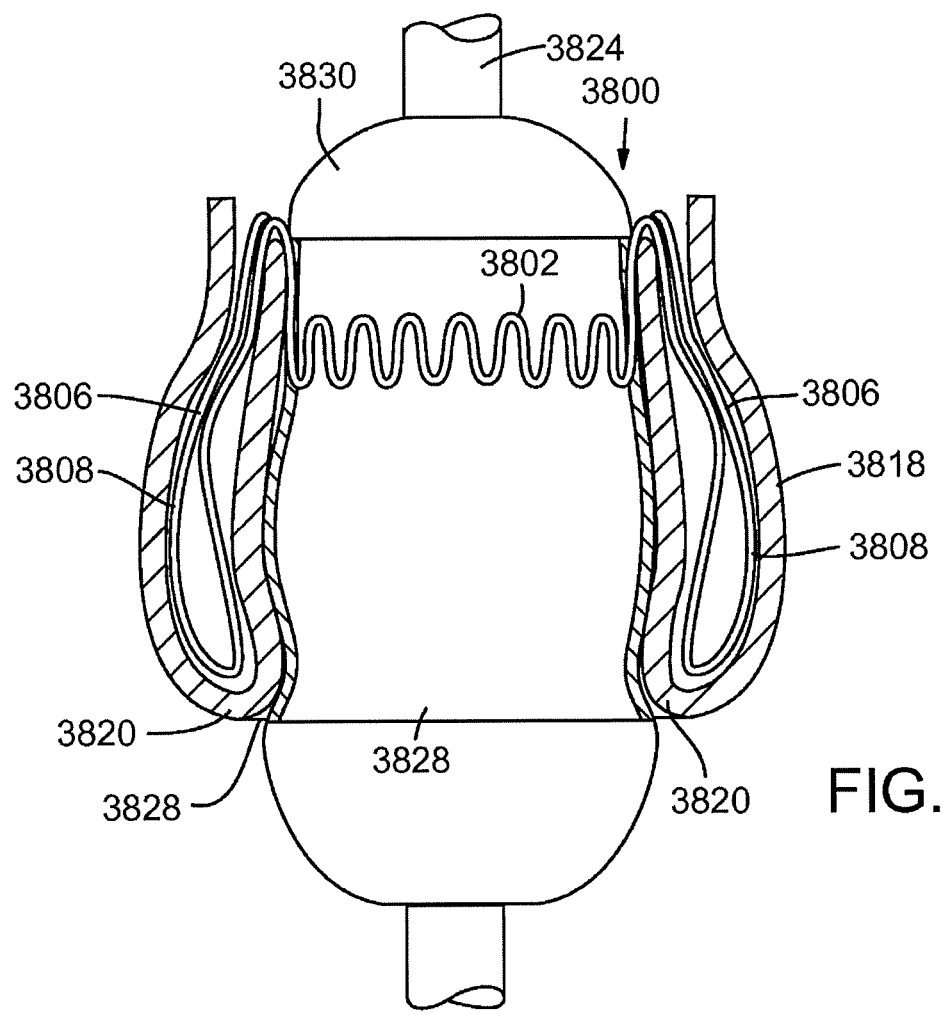
Figure 120:
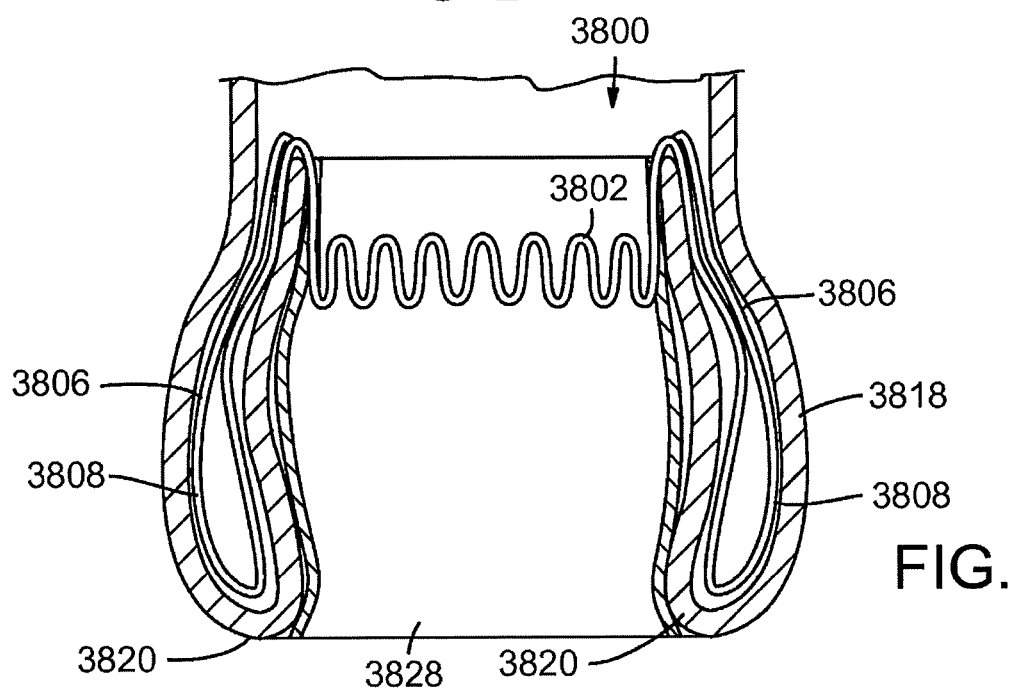

As shown in FIG. 115, the support frame 3800 can be held in place by an external sheath 3834. Retracting the external sheath 3834 can allow the retaining loops 3808 to expand radially into the aortic root 3818 behind the native valve leaflets 3820, as shown in FIGS. 117 and 118. With the retaining loops 3808 in place behind the leaflets 3820, the balloon catheter 3830 can be inflated, thereby radially expanding the THV 3828 into its fully expanded configuration, and capturing the leaflets 3820 between the THV 3828 and the support frame 3800, as shown in FIG. 119. With the THV 3828 anchored in place, the balloon catheter 3830 can be deflated, and the delivery device 3824 can be retracted, leaving the support frame 3800 and the THV 3828 implanted in the aortic root 3818, as shown in FIG. 120.

The support frame 3800 can be configured such that as the THV 3828 and the support frame 3800 are radially expanded by the balloon catheter 3830, the support frame 3800 exerts a constant or nearly constant radial force on the THV 3828. For example, as shown in the stress-strain plot of FIG. 116, the THV 3828 can be configured to have a diameter of about 6 mm when radially collapsed around the delivery device 3824, and a diameter of about 30 mm when fully expanded. The support frame 3800, which can be collapsed onto the delivery device 3824 over the THV 3828, can have corresponding diameters when radially collapsed and expanded. As the support frame 3800 and the THV 3828 are expanded from the radially collapsed state to the fully expanded state, the radial force exerted on the THV 3828 by the support frame 3800 can remain constant or increase only slightly. This is illustrated by the area 3836 between the curves 3838 and 3840 of FIG. 116, indicating that the support frame 3800 absorbs a nearly constant amount of strain energy as the support frame and THV 3828 are expanded. In this manner, the rate and degree of expansion of the THV 3828 with the balloon catheter 3830 can be precisely controlled. In alternative embodiments, any of the support frames/stents described herein can be implanted with a THV using the delivery apparatus 3824 and the delivery technique described above.

In an alternative embodiment shown in FIG. 121, the retaining loops 3808 can comprise planar members 3840 coupled to and suspended from a pair of coupling members 3842. The coupling members 3842 can extend proximally from respective apices 3804 before curving distally and coupling to the planar members 3840, thereby defining leaflet-engaging regions 3844 similar to the leaflet-engaging regions 3822. In some embodiments, the planar members 3840 can comprise thin sheets of material (e.g., metals such as nitinol, polymeric materials, etc.), and can have a radiused profile. In some embodiments, the planar members 3840 and/or the coupling members 3842 can be covered in a cloth material to cushion the load applied to the walls of the aortic sinuses 3818 and to promote ingrowth of the surrounding tissue. In further alternative embodiments, the delivery device 3824 need not include a THV 3828. Rather, the support frame 3800 can be implanted in the aorta and positioned so as to reshape the leaflets 3820 to address, for example, aortic insufficiency.

FIGS. 122-126 illustrate another embodiment of a support frame 3900 comprising an annular main body 3901 formed by a plurality of first and second struts 3902, 3904. Respective pairs of first struts 3902 can intersect at first proximal apices 3906 and define leaflet-engaging mechanisms 3908. Similarly, respective pairs of second struts 3904 can intersect at second proximal apices 3910, thereby defining actuator mechanisms 3912. The leaflet-engaging mechanisms 3908 can be movable between an open position (FIG. 124) and a closed position (FIG. 125) by action of a delivery device 3914, the relevant portion of which is shown in FIGS. 124-126.

The delivery device 3914 can comprise a plurality of first and second actuator members 3922, 3924 configured to engage the first and second apices 3906, 3910 of the leaflet-engaging mechanisms 3908 and the actuator mechanisms 3912, respectively. The first actuator members 3922 can be configured to apply compressive axial force to the first apices 3906 of the leaflet-engaging mechanisms 3908 in the direction indicated by arrows 3928 (i.e., the first actuator members 3922 can be configured to push downwardly on the first apices 3906 of the leaflet-engaging mechanisms 3908). Meanwhile, the second actuator members 3924 can be configured to apply tensile force to the second apices 3910 of the actuator mechanisms 3912 in the direction indicated by arrows 3930 (i.e., the second actuator members 3924 can be configured to pull upwardly on the second apices 3910 of the actuator mechanisms 3912). In this manner, the combined action of the first and second actuator members 3922, 3924 can cause the second struts 3904 of the actuator mechanisms 3912 to be drawn together while the first struts 3902 of the respective leaflet-engaging mechanisms 3908 are drawn apart, thereby moving the leaflet-engaging mechanisms 3908 into the open position, as shown in FIG. 124. When the respective compressive and tensile forces applied to the leaflet-engaging mechanisms 3908 and actuator mechanisms 3912 are released, the leaflet-engaging mechanisms 3908 can return to the closed position (FIG. 125). In this manner, the leaflet-engaging mechanisms 3908 can engage and retain native valve leaflets 3944 when the support frame 3900 is implanted in the aorta 3946, as shown in FIG. 126.

FIG. 123 illustrates a detail view of a representative leaflet-engaging mechanism 3908. Each leaflet-engaging mechanism 3908 can comprise a proximal portion 3916, a spring portion 3918, and a leaflet-engaging portion 3920. The proximal portion 3916 can include an aperture 3926 configured to engage a respective first actuator member 3922 of the delivery device 3914 (FIG. 124). The spring portion 3918 can comprise two spring subunits 3932, one spring subunit 3932 being located on each respective first strut 3902 of the leaflet-engaging mechanism 3908. Each spring subunit 3932 can comprise a spring member 3934 and a pair of travel-limiting members 3936. Each respective pair of travel-limiting members 3936 can define a gap 3938 therebetween. As axial force is applied to the leaflet-engaging mechanism 3908 and tensile force is applied to the adjacent actuator mechanisms 3912 by respective first and second actuator members 3922, 3924 of the delivery device 3914, the struts 3902 can be drawn apart in the direction of arrows 3948. This can bias the spring members 3934 away from one another. Meanwhile, the respective travel-limiting members 3936 of each pair can be drawn together until the travel-limiting members 3936 make contact, thereby limiting further travel of the spring members 3934 and, consequently, of the first struts 3902.

The leaflet-engaging portion 3920 of the leaflet-engaging mechanism 3908 can define a leaflet-engaging region 3940 between the respective first struts 3902 configured to receive the native leaflets 3944. In some embodiments, the leaflet-engaging region 3940 can extend between the respective spring members 3934 of the spring subunits 3932. In the embodiment shown, the opposing surfaces of the first struts 3902 of the leaflet-engaging portion 3920 can comprise barbs 3942 configured to engage and retain the native leaflets. In alternative embodiments, the opposing surfaces of the first struts 3902 of the leaflet-engaging portion 3920 can comprise any suitable surface treatment such as projections, cutouts, surface roughness, etc., as desired. In some embodiments, the first and second struts 3902, 3904 can be integrally formed with the support frame 3900. Alternatively, the first and second struts 3902, 3904 can be separately formed and secured together by, for example, welding, brazing, suture, adhesives, etc.

FIGS. 127-129 illustrate another embodiment of a support frame 4000 comprising an annular main body formed by a plurality of curved inner and outer members 4002, 4004, the inner and outer members intersecting at three respective apices or crowns 4006. The support frame 4000 can be configured to have a diameter less than the diameter of a regurgitant native valve such that when implanted, the support frame 4000 can reduce the valve circumference and, thereby, the valvular orifice area. Thus, the support frame 4000 can effectively "re-model" the structure of the regurgitant valve at the base of the leaflets. In some embodiments, the support frame 4000 can pull together the commissures of the native valve, thereby improving leaflet coaptation (improving valve function). The support frame 4000 can also provide a restraint against further progression of valve dilatation.

The inner members 4002 can be arranged to form an inner clover 4008 having three inner apices 4010 formed by the intersection of adjacent inner members 4002. The outer members 4004 can be arranged to form an outer clover 4012 that is concentrically located with the inner clover 4008 and has a diameter greater than the inner clover 4008. The inner apices 4010 of the inner clover 4008 can be coupled to the respective crowns 4006 near the center of the crowns 4006, while the outer members 4004 can be coupled to sides of the respective crowns 4006. In this manner, the inner and outer members 4002, 4004 can define gaps 4014 therebetween extending along each aspect of the support frame 4000.

In the embodiment shown, the inner and outer members 4002, 4004 can be generally parallel, with the inner members 4002 extending radially inward of the outer members 4004. In this manner, the gaps 4014 can be configured to receive the native leaflets 4016 of the aortic valve 4018 (shown in phantom), with the inner members 4002 situated along the ventricular surface of the leaflets 4016 and the outer members 4004 situated along the aortic surface of the leaflets 4016 (when implanted in the native aortic valve). In some embodiments, the inner and outer members 4002, 4004 can be shape set such that they are spring-biased toward one another. In this manner, the inner and outer members 4002, 4004 can pinch and retain the native leaflets 4016 when the leaflets are inserted therebetween, thereby remodeling the aortic valve 4018 by reducing the valve circumference and/or the valvular orifice area. The inner and outer members 4002, 4004 can be made from metal (e.g., nitinol) or from suitable biocompatible polymers, and can be integrally formed with the support frame 4000. Alternatively, the inner and outer members 4002, 4004 can be separately formed and secured to the support frame 4000 by, for example, welding, brazing, suture, adhesives, etc.

Referring to FIG. 128, the support frame 4000 can be configured to be loaded onto a delivery device 4020 in a radially collapsed state. The delivery device 4020 can be configured such that the inner clover 4008 is held in a radially collapsed state by an inner sheath 4022, and the outer clover 4012 is held in a radially collapsed state by an outer sheath 4024. When the delivery device 4020 is located in the aorta, the outer sheath 4024 can be partially retracted in the direction of arrow 4026, thereby exposing the distal aspect of the outer clover 4012. This partial exposure of the outer clover 4012 can cause the outer members 4004 to flare open to a diameter greater than the diameter of the aortic valve. The outer members 4004 can be positioned in the native pockets/sinuses behind the native leaflets. The inner sheath 4022 can then be advanced in the direction of arrow 4028, exposing the inner clover 4008. Because the proximal aspect of the inner clover 4008 is still constrained by the outer sheath 4024, the inner members 4002 can flare outward to a diameter greater than the diameter of the inner clover in its fully expanded configuration.

When the outer members 4004 of the outer clover 4012 are properly located behind the native leaflets (i.e., on the aortic side of the leaflets) and the inner members 4002 of the inner clover 4008 are properly located on the ventricular side of the native leaflets, the outer sheath 4024 can be fully retracted. The inner and outer clovers 4008, 4012 can then return to their respective natural diameters, engaging the native leaflets between the inner and outer clovers 4008, 4012 and drawing the native leaflets together, thereby reducing the circumference of the aortic valve and/or reducing the orifice area of the aortic valve.

In an alternative embodiment shown in FIG. 129, a proximal end portion of the inner sheath 4022 can include a balloon 4032 configured to flare the outer members 4004 of the partially exposed outer clover 4012 when inflated. Alternatively, the inner sheath 4022 can have a region of increased diameter configured to flare the outer members 4004 of the outer clover 4012 when the outer sheath 4024 is retracted.

FIG. 130 illustrates another embodiment of a support frame 4100 comprising an annular main body configured as a clover 4104 formed by a plurality of angled struts 4102. The clover 4104 can have three apices 4106 formed by the intersection of adjacent struts 4102. The support frame 4100 can further include a leaflet-engaging mechanism in the form of clipping members 4108 coupled to each of the respective apices 4106. The clipping members 4108 can comprise retaining arms 4110, which can extend through sleeves 4111 coupled to the apices 4106 of the clover 4104. The retaining arms 4110 can comprise coupling members configured as claws 4122, which can engage a spherical end portion 4124 of an elongated member 4112 of a delivery device 4114, shown in FIG. 130. In this manner, the clipping members 4108 can be movable between a clamped position and an unclamped position by action of the elongated members 4112 of the delivery device 4114.

The clipping members 4108 can be located at the commissures 4118 of the aortic valve 4116 such that when the clipping members 4108 are moved from the unclamped to the clamped position, the native leaflets 4120 can be pinched against the underlying struts 4102 of the clover 4104. In some embodiments, the clover 4104 can be configured to have a diameter less than the natural diameter of the aortic valve 4116. In this manner, when the native leaflets 4120 are clipped against the clover 4104 by the clipping members 4108, the support frame 4100 can remodel the aortic valve 4116 by drawing the native valve leaflets 4120 together. This can reduce the circumference of the aortic valve 4116 and reduce the area of the valve orifice, thereby reducing regurgitation.

The support frame 4100 can be loaded onto the delivery device 4114 with the coupling members 4122 of the clipping members 4108 engaged with spherical end portions 4124 of the elongated members 4112. Initially, the clipping members 4108 can be located above the clover 4104 so as not to interfere with the placement of the clover 4104. The delivery device 4124 can be advanced through a surgical opening in the left ventricle and into the aorta, where the clover 4104 can be positioned such that the apices 4106 are located between the leaflets 4120 at the commissures 4118 of the aortic valve 4116. When the clover 4104 is properly located, the elongated members 4112 can be retracted, thereby moving the clipping members 4108 from the unclamped to the clamped position. This, in turn, can cause the leaflets 4120 to be pinched between the clipping members 4108 and the struts 4102 of the clover 4104. The coupling members 4122 can then be disengaged from the spherical end portions 4124 of the elongated members 4112, and the delivery device 4114 can be retracted.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:
1. A method, comprising:
  implanting a support frame in a native heart valve, the support frame comprising a main body configured as a clover formed by a plurality of angled struts and a leaflet-engaging mechanism coupled to the main body and configured to secure the support frame at the native heart valve, wherein the leaflet-engaging mechanism comprises retaining arms and implanting the support frame further comprises moving the retaining arms between two positions and through sleeves coupled to the main body.

2. The method of claim 1, wherein the clover comprises three apices formed by an intersection of adjacent struts of the plurality of angled struts.

3. The method of claim 1, wherein:
the retaining arms are coupled to elongated members of a delivery device, and
the method further comprises moving the elongated members to move the retaining arms between the two positions.

4. The method of claim 1, wherein:
the leaflet-engaging mechanism comprises clipping members, wherein each clipping member includes one of the retaining arms; and
implanting the support frame further comprises engaging leaflets of the native heart valve with the clipping members.

5. The method claim 4, wherein each clipping member includes a plurality of outer protrusions and implanting the support frame further comprises engaging outflow sides of the leaflets of the native heart valve with the plurality of outer protrusions.

6. The method of claim 1, wherein:
implanting the support frame further comprises advancing the support frame through a patient's body in a radially collapsed state; and
at least partially advancing the support frame from a delivery sheath such that the support frame expands to an expanded state.

7. The method of claim 1, further comprising reducing a valvular orifice area of the native heart valve with the support frame.

8. The method of claim 1, further comprising deploying a prosthetic heart valve in the support frame.

9. The method of claim 1, wherein implanting the support frame further comprises engaging inflow sides of the leaflets of the native heart valve with the plurality of angled struts of the clover.

10. A method, comprising:
delivering a support frame to a native heart valve with a delivery device, the support frame comprising:
a main body configured as an inner clover formed by a plurality of inner, angled struts; and
a leaflet-securing portion coupled to the main body and comprising a plurality of coupling members releasably connected to a plurality of elongated members of the delivery device during delivery of the support frame to the native heart valve;
implanting the support frame in the native heart valve such that each of the plurality of inner, angled struts forming the inner clover is disposed on an inflow side of the leaflets of the native heart valve and the leaflet-securing portion is disposed on an outflow side of the leaflets of the native heart valve to secure the support frame at the native heart valve;
releasing the coupling members from the elongate members of the delivery device after implanting the support frame in the native heart valve; and
deploying a prosthetic heart valve in the support frame, wherein deploying the prosthetic heart valve in the support frame comprises expanding the prosthetic heart valve from a radially compressed state to a radially expanded state in the support frame after implanting the support frame in the native heart valve,
wherein the leaflet-securing portion comprises a plurality of clipping members coupled to apices of the inner clover, and wherein the leaflets of the native heart valve are pinched between the clipping members and the inner clover at commissures of the native heart valve when the support frame is implanted.

11. The method of claim 10, wherein the inner clover comprises three apices formed by an intersection of adjacent struts of the plurality of inner, angled struts.

12. The method of claim 10, wherein:
delivering the support frame further comprises advancing the support frame through a patient's body in a radially collapsed state; and
at least partially advancing the support frame from a delivery sheath of the delivery device such that the support frame expands to an expanded state.

13. The method of claim 10, further comprising reducing a valvular orifice area of the native heart valve with the support frame.

14. The method of claim 10, wherein each clipping member comprises a retaining arm and two outer protrusions.

15. The method of claim 10, wherein the coupling members are configured as claws that are releasably connected to spherical end portions of the elongated members of the delivery device during the act of delivering.

16. A method comprising:
implanting a support frame in a native heart valve, the support frame comprising:
a main body configured as an inner clover formed by a plurality of inner, angled struts; and
a leaflet-securing portion coupled to the main body,
wherein the main body and the leaflet-securing portion are configured to secure the support frame at the native heart valve, and
wherein each of the plurality of inner, angled struts forming the inner clover is disposed on an inflow side of the leaflets of the native heart valve and the leaflet-securing portion is disposed on an outflow side of the leaflets of the native heart valve, wherein:
the leaflet-securing portion is a leaflet-engaging mechanism coupled to the main body and comprises a plurality of clipping members, wherein each clipping member includes a retaining arm and two outer protrusions; and
implanting the support frame further comprises engaging the leaflets of the native heart valve with the plurality of clipping members such that the outer protrusions are located on the outflow side of the leaflets of the native heart valve.

17. The method of claim 16, wherein:
wherein implanting the support frame further comprises moving the retaining arms between two positions and through sleeves coupled to the main body.

18. The method of claim 17, wherein the retaining arms are coupled to elongated members of a delivery device; and
the method further comprises moving the elongated members to move the retaining arms between the two positions.

19. A method, comprising:
delivering a support frame to a native heart valve with a delivery device, the support frame comprising:
a main body configured as an inner clover formed by a plurality of inner, angled struts; and
a leaflet-securing portion coupled to the main body and comprising a plurality of coupling members releasably connected to a plurality of elongated members of the delivery device during delivery of the support frame to the native heart valve, wherein the coupling members are configured as claws that are releasably connected to spherical end portions of the elongated members of the delivery device during the act of delivering;

implanting the support frame in the native heart valve such that each of the plurality of inner, angled struts forming the inner clover is disposed on an inflow side of the leaflets of the native heart valve and the leaflet-securing portion is disposed on an outflow side of the leaflets of the native heart valve to secure the support frame at the native heart valve;

releasing the coupling members from the elongate members of the delivery device after implanting the support frame in the native heart valve; and deploying a prosthetic heart valve in the support frame, wherein deploying the prosthetic heart valve in the support frame comprises expanding the prosthetic heart valve from a radially compressed state to a radially expanded state in the support frame after implanting the support frame in the native heart valve.

20. The method of claim 19, wherein releasing the coupling members from the elongate members of the delivery device comprises disengaging the claws from the spherical end portions.

* * * * *